(12) United States Patent
Guan et al.

(10) Patent No.: US 7,285,703 B2
(45) Date of Patent: Oct. 23, 2007

(54) PLANT LIKE STARCHES AND THE METHOD OF MAKING THEM IN HOSTS

(75) Inventors: Hanping Guan, Chapel Hill, NC (US); Peter Keeling, Ames, IA (US); Angela McKean, Cary, NC (US)

(73) Assignee: BASF Plant Science GmbHNC (US)

( * ) Notice: Subject to any disclaimer, the term of this patent is extended or adjusted under 35 U.S.C. 154(b) by 102 days.

(21) Appl. No.: 11/330,822

(22) Filed: Jan. 11, 2006

(65) Prior Publication Data

US 2006/0150281 A1 Jul. 6, 2006

Related U.S. Application Data

(63) Continuation of application No. 10/336,753, filed on Jan. 6, 2003, now abandoned, which is a continuation of application No. 09/402,254, filed as application No. PCT/US98/06660 on Apr. 3, 1998, now abandoned.

(51) Int. Cl.
*C12N 15/31* (2006.01)
*C12N 15/63* (2006.01)
*C12N 15/82* (2006.01)
*A01H 5/00* (2006.01)

(52) U.S. Cl. .................. 800/288; 800/284; 800/300.1; 800/312; 435/468; 435/320.1; 536/23.1; 536/23.2; 536/23.7

(58) Field of Classification Search ............ None
See application file for complete search history.

(56) References Cited

FOREIGN PATENT DOCUMENTS

| WO | WO93/09237 | 5/1993 |
| WO | WO92/24292 | 10/1994 |
| WO | WO98/10082 | 3/1998 |
| WO | WO98/22601 | 5/1998 |
| WO | WO98/44780 | 10/1998 |
| WO | WO99/07841 | 2/1999 |
| WO | WO99/58698 | 11/1999 |

OTHER PUBLICATIONS

Shewmaker, C.K. et al., Expression of *Escherichia coli* Glycogen Synthase in the Tubers of Transgenic Potatoes(*Solanum tuberosum*) Results in a Highly Branched Starch, Plant Physiology, 1994, pp. 1159-1166 vol. 104.
Guan, H. et al. Maize branching enzyme catalyzes synthesis of glycogen-like polysaccharide in glgB-deficient *Escherichia coli*. Plant Biology 1995, pp. 964-967 vol. 92.
Kortstee, A.J. et al. Expression of *Escherichia coli* branching enzyme in tubers of amylose-free transgenic potatoe leads to an increased branching degree of the amylopeclin. The Plant Journal, 1996, pp. 83-90 vol. 10(1).
Sweetlove et al., "Characterization of transgenic potato (*Solanum tuberosum*) tubers with increased ADPglucose pyrophosphorylase," Biochem. J., 1990, 487-492, vol. 320.
Meyer et al., "Cloning, Expression, and Sequence of an Allosteric Mutant ADPglucose Pyrophosphorylase from *Escherichia coli*B," Arch Biochem, Apr. 1993, 64-71, 302(1).
Govons et al., "Biosynthesis of Bacterial Glycogen—XI: Kinetic Characterization of an Altered Adenosine . . . " The Journal of Biological Chemistry, Mar. 10, 1973, 1731-1740, 248(5).
Sweetlove et al., "Starch metabolism in tubers of transgenic potato (*Solanum tuberosum*) with increased ADPglucose pyrophosphorylase" Biochem. J., 1996, 493-498, 320.
Stark et al., "Regulation of the Amount of Starch in Plant Tissues by ADP Glucose Pyrophosphorylase" Science, Oct. 9, 1992, 287-292, 258.

*Primary Examiner*—Phuong Bui
*Assistant Examiner*—Brent T Page
(74) *Attorney, Agent, or Firm*—Patricia A. McDaniels

(57) ABSTRACT

The invention relates to hosts containing constructs with genes from the starch pathway. More typically the present invention relates to bacterial hosts that form plant like starches. Additionally the present invention relates to plant hosts that have genes from the starch pathway. The invention further relates to the starches produced by said hosts.

8 Claims, 101 Drawing Sheets

WAXY = MAIZE GRANULE BOUND STARCH SYNTHASE

Fig. 43

```
*** INPUT INFORMATION ***

FILE NAME    : ECGLGA1.SEQ      SEQUENCE : NORMAL    1488 BP

CODON TABLE  : UNIV.TCN

SEQUENCE     REGION :      1 -  1488

TRANSLATION  REGION :      1 -  1488

*** DNA TRANSLATION ***

1   ATG CAG GTT TTA CAT GTA TGT TCA GAG ATG TTC CCG CTG CTT AAA ACC    48
  1    M   Q   V   L   H   V   C   S   E   M   F   P   L   L   K   T    16

49   GGC GGT CTG GCT GAT GTT ATT GGG GCA TTA CCC GCA CAA ATC GCA        96
 17    G   G   L   A   D   V   I   G   A   L   P   A   Q   I   A        32

97   GAC GGC GTT GAC GCT CGC GTA CTG TTG CCT GCA TTT CCC GAC ATT CGC   144
 33    D   G   V   D   A   R   V   L   L   P   A   F   P   D   I   R    48

145   CGT GGC GTG ACC GAT GCG CAG GTA TCC CGT GAT ACC TCC GCC           192
 49    R   G   V   T   D   A   Q   V   S   R   D   T   S   A            64

193   GGA CAT ATC ACG CTG TTG CAT TAC GAT CGT AAC GGG GTT GGC ATT TAC   240
 65    G   H   I   T   L   L   H   Y   D   R   N   G   V   G   I   Y    80

241   CTG ATT GAC GCG CCG CAT CTC TAT GAT CGT CCG GGA AGT CCG TAT CAC   288
 81    L   I   D   A   P   H   L   Y   D   R   P   G   S   P   Y   H    96

289   GAT ACC AAC TTA TTT GTC CAT ACC GAC AAC GTA TTG CGT TTT GCG CTG   336
 97    D   T   N   L   F   V   H   T   D   N   V   L   R   F   A   L   112

337   CTG GGG TGG GTT GGG GCA GAA ATG GCC AGC GGG CTT GAC CCA TTC TGG   384
113    L   G   W   V   G   A   E   M   A   S   G   L   D   P   F   W   128
```

Fig. 43 continued

| | | | | | | | | | | | | | | | | |
|---|---|---|---|---|---|---|---|---|---|---|---|---|---|---|---|---|
| 385 | CGT | CCT | GAT | GTG | GTG | CAT | GCG | CAC | GAC | TGG | CAT | GCA | GGC | CTT | GCG | CCT | 432 |
| 129 | R | P | D | V | V | H | A | H | D | W | H | A | G | L | A | P | 144 |
| 433 | GCG | TAT | CTG | GCG | GCG | CGC | GGG | CCG | GCG | AAG | CCG | GTG | TTT | ACT | GTG | 480 |
| 145 | A | Y | L | A | A | R | G | P | A | K | P | V | F | T | V | 160 |
| 481 | CAC | AAC | CTA | GCC | TAT | CAA | GGC | TTC | ATG | TAT | GCA | CAT | CAC | ATG | AAT | GAC | 528 |
| 161 | H | N | L | A | Y | Q | G | F | M | Y | A | H | H | M | N | D | 176 |
| 529 | ATC | CAA | TTG | CCA | TCA | TTT | AAT | ATT | CTG | TAC | ATT | CAT | GGG | CTG | GAA | TTC | 576 |
| 177 | I | Q | L | P | S | F | N | I | L | Y | I | H | G | L | E | F | 192 |
| 577 | GGA | CAA | ATC | TCT | TTC | CTG | AAG | GCC | GCC | TTT | TTT | TAT | GCC | GAT | CAC | ATT | 624 |
| 193 | G | Q | I | S | F | L | K | A | A | F | F | Y | A | D | H | I | 208 |
| 625 | ACG | GCG | GTC | AGT | CCA | ACC | TAC | GCT | CGC | GAG | ATC | ACC | GAA | CCG | CAG | TTT | 672 |
| 209 | T | A | V | S | P | T | Y | A | R | E | I | T | E | P | Q | F | 224 |
| 673 | GCC | TAC | GGT | ATG | GAA | GGT | CTG | TTG | CAA | CAG | CGT | CAC | CGC | GAA | GGG | CGT | 720 |
| 225 | A | Y | G | M | E | G | L | L | Q | Q | R | H | R | E | G | R | 240 |
| 721 | CTT | TCC | GGC | GTA | CCG | AAC | GGC | GTG | GAC | GAG | AAA | ATC | TGG | AGT | CCA | GAG | 768 |
| 241 | L | S | G | V | P | N | G | V | D | E | K | I | W | S | P | E | 256 |
| 769 | ACG | GAC | TTA | CTG | GAA | AAT | GTG | CCG | TCG | CAG | CGC | TAC | CAA | ATC | GCA | ATG | GAT | 816 |
| 257 | T | D | L | L | E | N | V | P | S | Q | R | Y | Q | I | A | M | D | 272 |
| 817 | AAA | GCG | GAT | AAA | AAG | CTT | TTT | GCA | GAA | GCC | GAT | ACG | TTG | AAG | GTT | 864 |
| 273 | K | A | D | K | K | L | F | A | E | A | D | T | L | K | V | 288 |
| 865 | GAC | GAT | GTG | CCG | CGC | CTT | TTT | GAA | GCC | TCA | CCG | GGT | CTG | TCC | GAG | CAG | 912 |
| 289 | D | D | V | P | R | L | F | E | A | S | P | G | L | S | E | Q | 304 |
| 913 | AAA | GGT | CTC | GAT | TCG | GTG | CTG | CTA | CTC | GGC | GCG | CCG | GTG | TCG | CAG | CAG | 960 |
| 305 | K | G | L | D | S | V | L | L | L | G | A | P | V | S | Q | Q | 320 |
| 961 | GGC | GGG | CAG | CTG | GCG | CTA | CTC | GGC | GCG | GCG | CCG | GTG | CTG | CAG | GAA | 1008 |
| 321 | G | G | Q | L | A | L | L | G | A | A | P | V | L | Q | E | 336 |

Fig. 43 continued

| | | | | | | | | | | | | |
|---|---|---|---|---|---|---|---|---|---|---|---|---|
| 1009 337 | GGT G | TTC F | CTT L | GCG A | GCA A | GAA E | TAC Y | CCC P | GGT G | CAG Q | GTG V | GGC G | GTT V | CAG Q | 1056 352 |
| 1057 353 | ATT I | GGC G | TAT Y | CAC H | GAA E | GCA A | TTT F | TCG S | CAT H | CGC R | ATT I | ATG M | GGC G | GCG A | GAC D | 1104 368 |
| 1105 369 | GTC V | ATT I | CTG L | GTG V | CCC P | AGC S | CGT R | TTC F | GAA E | TTC F | CCG P | TTA L | ACG T | GGC G | CAA Q | CTT L | 1152 384 |
| 1153 385 | TAT Y | GGA G | TCG S | AAG K | TAC Y | GGT G | ACG T | GAC D | TGC C | CCG P | TTA L | GTG V | CGA R | ACC T | CGC R | GGT G | GGG G | 1200 400 |
| 1201 401 | CTT L | GCT A | GAT D | ACG T | GTT V | TCT S | CTC L | TGT C | GAA E | CTG L | CCG P | TTA L | GTG V | CGA R | AAC N | CTT L | GCA A | GAT D | GGC G | 1248 416 |
| 1249 417 | GTC V | GCC A | AAT N | GGG G | TTT F | ATC I | TTC F | GCT A | TTT F | GAA E | GAT D | AGT S | CTG L | TGG W | AAT N | GCC A | CTT L | TGG W | TCG S | TTA L | 1296 432 |
| 1297 433 | CGG R | ACT T | ATT I | CGA R | CGT R | CGT R | GCT A | CAG Q | TTT F | TTT F | GTA V | CTG L | TGG W | TCC S | TGT C | TTT F | CCT P | CCA P | CTG L | TGG W | 1344 448 |
| 1345 449 | CGG R | TTT F | GTG V | CAA Q | CGT R | TAC Y | CGT R | GAG E | CAG Q | GCT A | TTT F | ATG M | GCA A | TAT Y | TAC Y | GAT D | CGC R | TGG W | CAG Q | GTC V | 1392 464 |
| 1393 465 | GCG A | AAG K | TCG S | TAC Y | CGT R | TAC Y | CGT R | GAG E | CTT L | TTT F | TAT Y | TAT Y | TAG * | TTT F | AAA K | TAG * | TTT F | TCA S | 1440 480 |
| 1441 481 | GGA G | AAC N | GCC A | TAC Y | ATG M | AAT N | GCT A | CCG P | TTT F | CCG P | ACA T | TAT Y | TCA S | TCG S | ACG T | CCC P | ACG T | CTT L | 1488 496 |

Fig. 44

```
*** INPUT INFORMATION ***

FILE NAME    : ECGLGB.SEQ        SEQUENCE : NORMAL    2361 BP
    CODON TABLE  : UNIV.TCN

SEQUENCE     REGION :    1 -  2361
    TRANSLATION  REGION :    1 -  2361

*** DNA TRANSLATION ***

1  ATG TCC GAT CGT ATC GAT AGA GAC GTG ATT AAC GCG CTA ATT GCA GGC    48
   1   M   S   D   R   I   D   R   D   V   I   N   A   L   I   A   G    16

49  CAT TTT GCG GAT CCT TTT TCC GTA CTG GGA ATG CAT AAA ACC ACC GCG    96
  17   H   F   A   D   P   F   S   V   L   G   M   H   K   T   T   A    32

97  GGA CTG GAA GTC CGT GCC CTT TTA CCC GAC GCT ACC GAT GTG TGG GTG   144
  33   G   L   E   V   R   A   L   L   P   D   A   T   D   V   W   V    48

145  ATT GAA CCG AAA ACC GGG CGC AAA CTC GCA AAA CTG GAG TGT CTC GAC   192
  49   I   E   P   K   T   G   R   K   L   A   K   L   E   C   L   D    64

193  TCA CGG GGA TTC TTT AGC GTC ATT GGC GTC AAG AAT TTT TTC           240
  65   S   R   G   F   F   S   V   I   G   V   K   N   F   F            80

241  CGC TAT CAG TTG GCT GTT CAT TGG CCG CTA ATC CAG CTG ATT GAT       288
  81   R   Y   Q   L   A   V   H   W   P   L   I   Q   L   I   D        96

289  GAT CCT TAC CGT TTT GGT CAG GAA ATG GAT GCC TGG CTA                336
  97   D   P   Y   R   F   G   Q   E   M   D   A   W   L               112

337  TTA TCT GAA GGT ACT CAC CTG CGC CCG TAT GAA ACC TTA GGC GCG CAT   384
 113   L   S   E   G   T   H   L   R   P   Y   E   T   L   G   A   H   128
```

Fig. 44 continued

| Pos/AA# | 1 | 2 | 3 | 4 | 5 | 6 | 7 | 8 | 9 | 10 | 11 | 12 | 13 | 14 | 15 | 16 | End |
|---|---|---|---|---|---|---|---|---|---|---|---|---|---|---|---|---|---|
| 385 / 129 | GCA A | GAT D | ACT T | ATG M | GAT D | GGC G | GTC V | ACA T | GGT G | ACG T | CGT R | TTC F | TCT S | GTC V | TGG W | GCT A | 432 / 144 |
| 433 / 145 | CCA P | AAC N | GCC A | CGT R | CGG R | GTC V | TCG S | GTG V | GTT V | GGG G | CAA Q | TTC F | AAC N | TAC Y | TGG W | GAC D | 480 / 160 |
| 481 / 161 | GGT G | CGC R | CGT R | CAC H | CCG P | ATG M | CAC H | AAC N | CGC R | AAA K | GAG E | AGC S | GGC G | ATC I | TGG W | GAA E | 528 / 176 |
| 529 / 177 | CTG L | TTT F | ATC I | CCT P | GGG G | GCG A | AAC N | CTG L | AAA K | CAG Q | CTC L | TAT Y | AAA K | TAC Y | GAG E | ATG M | 576 / 192 |
| 577 / 193 | ATT I | GAT D | AAT N | GAT D | GGG G | GGC G | GAA E | AAT N | GGT G | CTG L | TCC S | GAC D | CCT P | TAT Y | GCC A | TTT F | 624 / 208 |
| 625 / 209 | GAA E | GCG A | CAA Q | ATG M | CGC R | CCG P | GAA E | ACC T | CTG L | TCC S | CTT L | ATT I | TGC C | GGG G | CTG L | CCG P | 672 / 224 |
| 673 / 225 | GAA E | AAG K | GTT V | GTA V | CAG Q | ACT T | GAG E | CGC R | TCT S | GCG A | AAA K | GCG A | AAT N | CAG Q | TTT F | GAT D | 720 / 240 |
| 721 / 241 | GCG A | CCA P | ATC I | TCT S | ATT I | TAT Y | GAA E | GTT V | CAC H | CTG L | CGC R | TCC S | TGG W | CGT R | CAA Q | CAC H | 768 / 256 |
| 769 / 257 | ACC T | GAC D | AAC N | AAT N | TTC F | TGG W | TTG L | AGC S | CAC H | CTG L | CAC H | CTG L | GAG E | GAT D | CTG L | CTG L | 816 / 272 |
| 817 / 273 | GTG V | CCT P | TAT Y | CAT H | AAA K | ATG M | TAC Y | GGC G | TAC Y | TAC Y | GAG E | GCC A | GAT D | CAA Q | CTA L | CCC P | 864 / 288 |
| 865 / 289 | ATT I | AAC N | GAG E | CCC P | CCC P | TTC F | GAT D | GGC G | TTT F | ACC T | CAC H | CTC L | TAT Y | CCA P | ACC T | GGC G | 912 / 304 |
| 913 / 305 | CTG L | TAT Y | GCG A | CCA P | ACC T | CGC R | CGT R | TTT F | AGT S | TGG W | CTC L | TAT Y | GAC D | TTC F | CGT R | TAT Y | 960 / 320 |

Fig. 44 continued

| Pos | 1 | 2 | 3 | 4 | 5 | 6 | 7 | 8 | 9 | 10 | 11 | 12 | 13 | 14 | 15 | 16 | Pos |
|---|---|---|---|---|---|---|---|---|---|---|---|---|---|---|---|---|---|
| 961 | TTC | ATT | GAT | GCC | GCA | CAC | GCA | GCT | GGT | CTG | AAC | GTG | ATT | CTC | GAC | TGG | 1008 |
| 321 | F | I | D | A | A | H | A | G | G | L | N | V | I | L | D | W | 336 |
| 1009 | GTG | CCA | GGC | CAC | TTC | TAT | GAA | CCG | ACT | GAT | GAC | TTT | CTT | GAA | TTT | GAT | 1056 |
| 337 | V | P | G | H | F | Y | E | P | T | D | D | F | L | E | F | D | 352 |
| 1057 | GGC | ACG | AAC | TTG | TAT | CAC | AGC | GAT | CCG | GAA | CGT | GAA | GGC | TAT | CAT | CAG | 1104 |
| 353 | G | T | N | L | Y | H | S | D | P | E | R | E | G | Y | H | Q | 1104 |
| 1105 | GAC | TGG | AAC | ACG | CTG | TAC | AAC | TAT | GGT | CGC | GAA | GTC | AGT | AAC | 1152 |
| 369 | D | W | N | T | L | Y | N | Y | G | R | E | V | S | N | 384 |
| 1153 | TTC | CTC | GGT | AAC | GCG | CTT | TAC | GTG | ATT | ATG | GAA | CGT | TTT | ATT | GAT | 1200 |
| 385 | F | L | G | N | A | L | Y | V | I | M | E | R | F | I | D | 400 |
| 1201 | GCG | CTG | GTC | CGC | GAT | GCG | GCG | TCA | ACC | ATC | CCG | TTG | CGT | ATG | AGC | 1248 |
| 401 | A | L | V | R | D | A | A | S | T | I | P | L | R | M | S | 416 |
| 1249 | CGT | AAA | GAG | GGG | ATT | GAA | TTC | TTG | ACA | GAT | GAT | TAT | TTT | GGC | CGC | AAT | 1296 |
| 417 | R | K | E | G | I | E | F | L | T | D | D | Y | F | G | R | N | 432 |
| 1297 | CTT | GAA | GCG | TCC | CGT | CCG | CCG | ATG | GCT | GAG | GGG | ATT | CTT | GGT | GAG | 1344 |
| 433 | L | E | A | S | R | P | P | M | A | E | G | I | L | G | E | 448 |
| 1345 | CAG | GTT | TAT | CGT | GGT | GCG | CCG | TGG | ATG | GGC | ACC | TTG | GAC | TAC | TTC | AAG | 1392 |
| 449 | Q | V | Y | R | G | A | P | W | M | G | T | L | D | Y | F | K | 464 |
| 1393 | GGC | GTT | GGG | GCG | CAG | TAT | CAT | CAC | GAT | AAA | CTG | ACC | TTC | GAT | CTC | GAC | 1440 |
| 465 | G | V | G | A | Q | Y | H | D | K | L | T | F | D | L | D | 480 |
| 1441 | TGG | AAC | CTC | GGC | TGG | ATG | CAG | TAT | CAC | CAT | CAG | TAC | GAT | AAG | ATG | 1488 |
| 481 | W | N | L | G | W | M | Q | Y | H | H | Q | Y | D | K | M | 496 |
| 1489 | CCG | GTT | TAT | CGT | CAG | TAT | CGT | CAC | CAC | TTG | TCG | CAT | GGG | ATT | CTC | GAC | 1536 |
| 497 | P | V | Y | R | Q | Y | R | H | H | L | S | H | G | I | L | D | 512 |
| 1537 | TAC | AAC | TAC | ACT | GAA | AAC | TTC | GTC | CTG | CCG | TTG | TCG | CAT | GAT | GAA | GTG | 1584 |
| 513 | Y | N | Y | T | E | N | F | V | L | P | L | S | H | D | E | V | 528 |

Fig. 44 continued

| nt/aa | 1 | 2 | 3 | 4 | 5 | 6 | 7 | 8 | 9 | 10 | 11 | 12 | 13 | 14 | 15 | 16 | nt/aa |
|---|---|---|---|---|---|---|---|---|---|---|---|---|---|---|---|---|---|
| 1585 / 529 | GTC V | CAC H | GGT G | AAA K | TCG S | ATT I | CTC L | GAC D | CGC R | ATG M | CCG P | GGC G | GAC D | GCA A | TGG W | | 1632 / 544 |
| 1633 / 545 | CAG Q | AAA K | TTC F | GCG A | AAC N | CTG L | TAC Y | GCC A | CGC R | TAT Y | GGC G | ATG M | TGG W | GCA A | TTC F | | 1680 / 560 |
| 1681 / 561 | CCG P | GGC G | AAG K | AAA K | CTA L | CTG L | TTC F | ATG M | GGT G | AAC N | GAA E | TTT F | GCC A | CAG Q | GGC G | CGC R | 1728 / 576 |
| 1729 / 577 | GAG E | TGG W | AAC N | CAT H | GAC D | GCC A | AGC S | TAT Y | GAC D | TGG W | CTG L | CAT H | ATG M | TTG L | GAA E | GGC G | 1776 / 592 |
| 1777 / 593 | GAT D | AAC N | CGC R | CAC H | CAT H | CAC H | GTC V | CAG Q | CGT R | ATG M | CAT H | GAT D | TTT F | CTG L | TAC Y | CTC L | 1824 / 608 |
| 1825 / 609 | ACC T | TAC Y | CGC R | CAC H | AAA K | GCA A | ATG M | GCA A | CAT H | AAA K | GAA E | CTG L | CGC R | GAT D | TAC Y | | 1872 / 624 |
| 1873 / 625 | GGC G | TTT F | GAA E | TGG W | CTG L | GTG V | GAT D | AAC N | GAA E | CGC R | GAA E | TTT F | GAC D | CTG L | TAC Y | GGC G | 1920 / 640 |
| 1921 / 641 | TTT F | GTG V | CGT R | CGC R | GAT D | AAA K | ATG M | GAA E | AAA K | GAA E | ATC I | CGC R | TCC S | GTT V | GCC A | ATC I | 1968 / 656 |
| 1969 / 657 | TTT F | ACG T | CCG P | GTA V | CCG P | CGT R | CGT R | GAA E | CGC R | ATC I | TTC F | GGC G | ATG M | CTG L | AAC N | CCG P | 2016 / 672 |
| 2017 / 673 | GGC G | AAA K | TGG W | CGT R | GAA E | ATC I | CTC L | GAT D | ACC T | GAA E | CGC R | TTC F | TCC S | ATG M | TAT Y | GGC G | 2064 / 688 |
| 2065 / 689 | AGT S | AAT N | GCA A | GGC G | AAT N | CAT H | GAT D | GTA V | CAC H | TAT Y | ATC I | GGC G | GAT D | GAG E | ATT I | GCC A | 2112 / 704 |
| 2113 / 705 | CAC H | GGT G | CGT R | CAG Q | CAT H | TCA S | AGC S | ACG T | CTG L | CAC H | TAT Y | CAC H | AGC S | GAT D | CTG L | CCG P | 2160 / 720 |
| 2161 / 721 | ATC I | TGG W | CTG L | GTT V | CGG R | GAG E | GCA A | GAA E | TGA * | CAC H | AAC N | CCG P | CCA P | TTG L | GCA A | AAC N | 2208 / 736 |

| 2209 | CCG | CTC | CCC | TCG | GCG | CGC | ATT | ACG | ACG | GTC | AGG | GCG | TCA | ACT | TCA | CAC | 2256 |
| 737  | P   | L   | P   | S   | A   | R   | I   | T   | T   | V   | R   | A   | S   | T   | S   | H   | 752  |

| 2257 | TTT | TCT | CCG | CTC | ATG | CCG | AGC | GGG | TAG | AAC | TGT | GTG | TCT | TTG | ACG | CCA | 2304 |
| 753  | F   | S   | P   | L   | M   | P   | S   | G   | *   | N   | C   | V   | S   | L   | T   | P   | 768  |

| 2305 | ATG | GCC | AGG | AAC | ATC | GCT | ATG | ACT | TGC | CAG | GGC | ACA | GTG | GCG | ACA | TTT | 2352 |
| 769  | M   | A   | R   | N   | I   | A   | M   | T   | C   | Q   | G   | T   | V   | A   | T   | F   | 784  |

| 2353 | GGC | ACG | GTT |     |     |     |     |     |     |     |     |     |     |     |     |     | 2361 |
| 785  | G   | T   | V   |     |     |     |     |     |     |     |     |     |     |     |     |     | 787  |

Fig. 45a

```
LOCUS       MZEZEIN10K   2562 bp   DNA              PLN      19-J
UL-1994
DEFINITION  Zea mays 10-kDa zein gene, complete cds.
ACCESSION   M23537
NID         g340933
KEYWORDS    methionine-rich protein; seed storage protein; zein pr
otein.
SOURCE      Zea mays 3-week old seedling leaf DNA.
  ORGANISM  Zea mays
            Eukaryota; Plantae; Embryobionta; Magnoliophyta; Lilio
psida;
            Commelinidae; Cyperales; Poaceae.
REFERENCE   1 (bases 1 to 2562)
  AUTHORS   Kirihara,J.A., Petri,J.B. and Messing,J.
  TITLE     Isolation and sequence of a gene encoding a methionine
-rich 10-kDa zein protein from maize
  JOURNAL   Gene 71, 359-370 (1988)
  MEDLINE   89138012
COMMENT     NCBI gi: 340933
FEATURES             Location/Qualifiers
     source          1..2562
                     /organism="Zea mays"
                     /cell_line="inbred BSSS-53"
                     /dev_stage="3-week old seedling"
                     /sequenced_mol="DNA"
                     /tissue_type="leaf"
     TATA_signal     1044..1050
     mRNA            1082..1685
     CDS             1137..1589
                     /note="10 kDa;          NCBI gi: 511870"
                     /codon_start=1
                     /product="zein protein"
                     /db_xref="PID:g511870"
                     /translation="MAAKMLALFALLALCASATSATHIPGHLPPV
MPLGTMNPCMQYC
```

Fig. 45a continued

```
         MMQQGLASLMACPSLMLQQLLALPLQTMPVMPQMMTPNMMSPLM
MPSMMSPMVLPSM
AAF"
         MSQIMMPQCHCDAVSQIMLQQQLPFMFNPMAMTIPPMFLQQPFVG
sig_peptide    1137..1199
               /codon_start=1
mat_peptide    1200..1586
               /note="10 kDa"
               /codon_start=1
               /product="zein protein"
polyA_signal   1655..1660
BASE COUNT    782 a    506 c    471 g    803 t
ORIGIN
8 ..
MZEZEIN10K  Length: 2562  May 29, 1996 15:41  Type: N  Check: 840

1 AAGCTTGCTA CTTTCTTTCC TTAATGTTGA TTTCCCCTTT GTTAGATGTT
   51 CTTTGTGTTA TATACACTCT GTATACAAGG ATGCGATACA CACATCAGCT
  101 AGTCCTAATG ATGCCACCGA CTTTACTTGA GGAAAAGGAA ACAAATATGA
  151 TGTGGCCATC ACATTCTCAA TAACAATGAC CATGTGCGCA ATGACATACC
  201 ATCATATTTG ATATCATAAA AATAAATTTA TTATCAAAGT AAACATATAG
  251 TTCATATATC AGATATTAAA GTGATAAGAA CAAATATTAC ATTTTATCTT
  301 ATATAAAATG ACGAAAAAGG TACGAGTTGA AAAGGAGTCC AACCCCTTTT
  351 TTATAGCTTG TTCGGTTGCT TGTTCTCTTC GGCTAGCGAG GTGGTAGAAT
  401 GTGAGAGTGT TGCGCGTGGA TTCCCGTCGT AGTGTTCTTA GGTGATTTCT
  451 CACGGCCCAT CTGTGATATA GCGACTCATA TGTGGTGTAA TAGCCCATTG
  501 GGAGAAGGGG AGAGATATAG ATCTACGTGA TTTGCACGTG ATGCACGACG
  551 AACGAAACTG GTGGTTTAAA GTAGTAGAGG TTTGTCATTA GAGGTGTAAA
```

Fig. 45a continued

```
 601  TGGTACATAT ATTATCCGTT CATATTCGAA TTTGATCCGT ATAAGAGGGC
 651  TAAGATCTAA TCCGTATACA AGTCCAAGTA TTAAGTATCC GATCCATATC
 701  GGATCTTTAT CCGTATCCGT ATACTCAAAA TTTGATGTTT AAGATTTTAA
 751  TATATATTTA AACTTTATAG GAACTCGATA ATATTTGTAT CTGATTTGAA
 801  TTATGAAAAC AAATATGGAA CGATTAATTT CAGTCTATAT CCGTTCCGAT
 851  ATTTGTCATG CTTTGCTAAA AATACCTTTA CAAGGCATCT TGTGCAGATT
 901  ATATATTAAT CTGAAATCAG TTAGAGAAGC CTACAAATTT GACCAAATGC
 951  CGAGTCATCC GGCTTATCCC CTTTCCAACT TTCAGTTCTG CAAGCGCCAG
1001  AAATCGTTTT TCATCTACAT TGTCTTTGTT GCCTGCATAC ATCTATAAAT
1051  AGGACCTGCT AGATCAATCG CAGTCCATCG GCCTCAGTCG CACATATCTA
1101  CTATACTATA CTCTAGGAAG CAAGGACACC ACCGCCATGG CAGCCAAGAT
1151  GCTTGCATTG TTCGCTCTCC TAGCTCTTTG TGCAAGCGCC ACTAGTGCGA
1201  CCCATATTCC AGGGCACTTG CCACCAGTCA TGCCATTGGG TACCATGAAC
1251  CCATGCATGC AGTACTGCAT GATGCAACAG GGGCTTGCCA GCTTGATGGC
1301  GTGTCCGTCC CTGATGCTGC AGCAACTGTT GGCCTTACCG CTTCAGACGA
1351  TGCCAGTGAT GATGCCACAG ATGATGACGC CTAACATGAT GTCACCATTG
1401  ATGATGCCGA GCATGATGTC ACCAATGGTC TTGCCGAGCA TGATGTCGCA
1451  AATAATGATG CCACAATGTC ACTGCGACGC CGTCTCGCAG ATTATGCTGC
1501  AACAGCAGTT ACCATTCATG TTCAACCCAA TGGCCATGAC GATTCCACCC
1551  ATGTTCTTAC AGCAACCCTT TGTTGGTGCT GCATTCTAGA TAGAAATATT.
```

Fig. 45a continued

```
1601  TGTGTTGTAT CGAATAATGA GTTGACATGC CATCGCGTGT GACTCATTAT
1651  TAACAATAAA ACAAGTTCC  TCTTATTATC TTTTATATC  TCTCCCTATC
1701  CATTTTTGCA AAGCCCATTA TCCCTTACTC CCTAAGTCCC AATATATTTT
1751  AGACCTTAAA TTGTATGTCT ATATTCAAAA GAATGACAAT AAATCTAGAC
1801  ATATATATAA AACACATACA TTAAGTATTG TATGAATCTA TTAAAATGCT
1851  AAAACGACTA ATATTATGGG ACGGAGGGAG TACTTTATTA GTAGATTACA
1901  TTGTTATTTT CTCTATTCCA AATATAAGTC TGGTTTTTCA ATCAATCAAT
1951  ATATATTACC ATGTCCAAAC ATTTTGAATT ATATATCTAG GTGCAGCATC
2001  CGTGCACGAT CGTAAAGAA  GCAGTCACGG TGTTGGTCCC AAAAACTAAT
2051  CGTCCGTTGT CGGTCACCTA TAAAGATTCA GACTCCTCCT TTTGAATTAC CAAAATAAGG
2101  CAATATAATT AATGTAATAT CAAAAAAAGG AGAAGATCAA GGTAAATAAA GGCATTTTGT
2151  CATAAGCAAA GGAAGCATAA GAATGCATAA GTAATGATTT GTGTCTCTTT
2201  GAGAAAACAT TATTCACGTG GCTCCGAGAG GATACCATCG GATGTTCGAT
2251  ATATTTTTT  CTATCAATTG TTCGAAAGTT CTTTGTCTCA TGCATGGGCA
2301  GGTAATACAA TGATGCCTTA ATTTATAGGG ACGGTGCGAC GTACAAATTT GTATAAAATT
2351  AAAAATACTC CTATCAATTG TTCGAAAGTT CTTTGTCTCA TGCATGGGCA
2401  ATGTACCTCT ATTTATAGGG ACGGTGCGAC GTACAAATTT GTATAAAATT
2451  ATATTTTAT  TCCCAAATCC TATGCATATG TGTCGGGGAC CATAATTAGG
2501  GGTACCCTCA AGGCTCCTAA TTCTCAGCTG GTAACCCCAT CAGCATAAAG
2551  CTGCAAAGGC CT
```

Fig. 45b

LOCUS    MZEZEIN10K    2562 bp    DNA    PLN    19-JUL-1994
DEFINITION  Zea mays 10-kDa zein gene, complete cds.
ACCESSION  M23537
NID    g340933
KEYWORDS   methionine-rich protein; seed storage protein; zein protein.
SOURCE    Zea mays 3-week old seedling leaf DNA.
  ORGANISM  Zea mays
            Eukaryota; Plantae; Embryobionta; Magnoliophyta; Liliopsida;
            Commelinidae; Cyperales; Poaceae.
REFERENCE  1  (bases 1 to 2562)
  AUTHORS   Kirihara,J.A., Petri,J.B. and Messing,J.
  TITLE     Isolation and sequence of a gene encoding a methionine-rich 10-kDa
            zein protein from maize
  JOURNAL   Gene 71, 359-370 (1988)
  MEDLINE   89138012
COMMENT    NCBI gi: 340933
FEATURES           Location/Qualifiers
     source          1..2562
                     /organism="Zea mays"
                     /cell_line="inbred BSSS-53"
                     /dev_stage="3-week old seedling"
                     /sequenced_mol="DNA"
                     /tissue_type="leaf"
     TATA_signal     1044..1050
     mRNA            1082..1685
     CDS             1137..1589
                     /note="10 kDa; NCBI gi: 511870"
                     /codon_start=1
                     /product="zein protein"
                     /db_xref="PID:g511870"

/translation="MAAKMLALFALLALCASATSATHIPGHLPPVMPLGTMNPCMQYC

MMQQGLASLMACPSLMLQQLLALPLQTMPVMMPQMMTPNMMSPLMMPSMMSPMVL
PSMMSQIMMPQCHCDAVSQIMLQQQLPFMFNPMAMTIPPMFLQQPFVGAAF"
     sig_peptide     1137..1199
                     /codon_start=1
     mat_peptide     1200..1586
                     /note="10 kDa"
                     /codon_start=1
                     /product="zein protein"
     polyA_signal    1655..1660
BASE COUNT      782 a    506 c    471 g    803 t
ORIGIN

Fig. 45b continued

MZEZEIN10K Length: 2562 May 29, 1996 15:41 Type: N Check: 8408 ..

```
   1 AAGCTTGCTA CTTTCTTTCC TTAATGTTGA TTTCCCCTTT GTTAGATGTT

51 CTTTGTGTTA TATACACTCT GTATACAAGG ATGCGATACA CACATCAGCT

101 AGTCCTAATG ATGCCACCGA CTTTACTTGA GGAAAAGGAA ACAAATATGA

151 TGTGGCCATC ACATTCTCAA TAACAATGAC CATGTGCGCA ATGACATACC

201 ATCATATTTG ATATCATAAA AATAAATTTA TTATCAAAGT AAACATATAG

251 TTCATATATC AGATATTAAA GTGATAAGAA CAAATATTAC ATTTTATCTT

301 ATATAAAATG ACGAAAAAGG TACGAGTTGA AAAGGAGTCC AACCCCTTTT

351 TTATAGCTTG TTCGGTTGCT TGTTCTCTTC GGCTAGCGAG GTGGTAGAAT

401 GTGAGAGTGT TGCGCGTGGA TTCCCGTCGT AGTGTTCTTA GGTGATTTCT

451 CACGGCCCATCTGTGATATAGCGACTCATATATGTGGTGTAATAGCCCATTG

501 GGAGAAGGGG AGAGATATAG ATCTACGTGA TTTGCACGTG ATGCACGACG

551 AACGAAACTG GTGGTTTAAA GTAGTAGAGG TTTGTCATTA GAGGTGTAAA

601 TGGTACATAT ATTATCCGTT CATATTCGAA TTTGATCCGT ATAAGAGGGC

651 TAAGATCTAA TCCGTATACA AGTCCAAGTA TTAAGTATCC GATCCATATC

701 GGATCTTTAT CCGTATCCGT ATACTCAAAA TTTGATGTTT AAGATTTTAA

751 TATATATTTA AACTTTATAG GAACTCGATA ATATTTGTAT CTGATTTGAA

801 TTATGAAAAC AAATATGGAA CGATTAATTT CAGTCTATAT CCGTTCCGAT

851 ATTTGTCATG CTTTGCTAAA AATACCTTTA CAAGGCATCT TGTGCAGATT

901 ATATATTAAT CTGAAATCAG TTAGAGAAGC CTACAAATTT GACCAAATGC

951 CGAGTCATCC GGCTTATCCC CTTTCCAACT TTCAGTTCTG CAAGCGCCAG

1001 AAATCGTTTT TCATCTACAT TGTCTTTGTT GCCTGCATAC ATCTATAAAT

1051 AGGACCTGCT AGATCAATCG CAGTCCATCG GCCTCAGTCG CACATATCTA
1101 CTATACTATA CTCTAGGAAG CAAGGACACC ACCGCCATG
```

Fig. 46

```
*** INPUT INFORMATION ***

FILE NAME    : ECGLGC3.SEQ        SEQUENCE : NORMAL    1328 BP

CODON TABLE  : UNIV.TCN

SEQUENCE REGION    :    1 -   1328

TRANSLATION REGION :    1 -   1326

*** DNA TRANSLATION ***

1  ATG GTT AGT TTA GAG AAG AAC GAT CAC TTA ATG TTG GCG CGC CAG CTG   48
  1   M   V   S   L   E   K   N   D   H   L   M   L   A   R   Q   L   16

49  CCA TTG AAA TCT GTT GCC CTG ATA CTG GCA GGA CGT ACC GGT CGC CGC   96
 17   P   L   K   S   V   A   L   I   L   A   G   R   T   G   R   R   32

97  CTG AAG GAT TTA ACC AAT AAG CGA GCA AAA CCG GCC GTA CAC TTC GGC  144
 33   L   K   D   L   T   N   K   R   A   K   P   A   V   H   F   G   48

145  GGT AAG TTC CGC ATT ATC GAC TTT GCG CTG TCT AAC TGC ATC AAC TCC  192
 49   G   K   F   R   I   I   D   F   A   L   S   N   C   I   N   S   64

193  GGG ATC CGT CGT ATG GGC GTG GGC ATC ACC CAG TAC CAG TCC CAC ACT CTG  240
 65   G   I   R   R   M   G   V   G   I   T   Q   Y   Q   S   H   T   L   80

241  GTG CAG CAC ATT CAG CGC CTG TGG TCA TTC AAT GAA GAA ATG AAC      288
 81   V   Q   H   I   Q   R   L   W   S   F   F   N   E   E   M   N   96

289  GAG TTT GTC GAT CTG CCA GCA CAG CAG AGA ATG AAA GGG GAA AAC      336
 97   E   F   V   D   L   P   A   Q   Q   R   M   K   G   E   N  112

337  TGG TAT CGC GGC ACC GCA GAT GCG GTC ACC CAA AAC CTC GAC ATT ATC  384
113   W   Y   R   G   T   A   D   A   V   T   Q   N   L   D   I   I  128
```

Fig. 46 continued

| Pos | 1 | 2 | 3 | 4 | 5 | 6 | 7 | 8 | 9 | 10 | 11 | 12 | 13 | 14 | 15 | 16 | End | AA# |
|---|---|---|---|---|---|---|---|---|---|---|---|---|---|---|---|---|---|---|
| 385 / 129 | CGT R | CGT R | TAT Y | AAA K | GCG A | GAA E | TAC Y | GTG V | GTG V | ATC I | CTG L | GCG A | GGC G | GAC D | CAT H | ATC I | 432 | 144 |
| 433 / 145 | TAC Y | AAG K | CAA Q | GAC D | TAC Y | TCG S | CGT R | ATG M | CTT L | ATC I | ATC I | GAT D | CAC H | GTC V | GAA E | AAA K | 480 | 160 |
| 481 / 161 | GTA V | CGT R | TGT C | ACC T | TAC Y | GTT V | GTT V | TGT C | ATG M | CCA P | GTA V | ATT I | CCG P | GAA E | GAA E | GCC A | 528 | 176 |
| 529 / 177 | GCA A | TTT F | GGC G | GTT V | ATG M | GCG A | GTT V | GAT D | GAG E | AAC N | GAT D | AAA K | ACT T | ATC I | GAA E | TTC F | 576 | 192 |
| 577 / 193 | GTG V | GAA E | AAA K | CCT P | GCT A | AAC N | CCG P | TCA S | CCG P | ATG M | CCG P | AAC N | CCG P | CCG P | AGC S | AAA K | 624 | 208 |
| 625 / 209 | TCT S | CTG L | GCG A | AGT S | ATG M | GGT G | ATC I | TAC Y | GTC V | TTT F | GAC D | GCC A | TAT Y | CTG L | TAT Y | TAT Y | 672 | 224 |
| 673 / 225 | GAA E | CTG L | GAA E | GAA E | CTG L | GAT D | GAC D | CGC R | GAT D | GAG E | AAC N | TCC S | AGC S | CAC H | GAC D | TTT F | 720 | 240 |
| 721 / 241 | GGC G | AAA K | GAT D | TTG L | ATT I | CCC P | AAG K | ATC I | ACC T | GAA E | GCC A | GGT G | CTG L | GCC A | TAT Y | GCG A | 768 | 256 |
| 769 / 257 | CAC H | CCG P | TTC F | CCG P | CTC L | GAT D | GTG V | CAA Q | TGC C | TCT S | TGG W | CCG P | GAT D | GCC A | GAG E | CCG P | 816 | 272 |
| 817 / 273 | TAC Y | TGG W | CGC R | GAT D | GTG V | TCT S | GCT A | ACG T | TGC C | GTA V | CTG L | GAA E | TAC Y | TAC Y | AAC N | CTC L | 864 | 288 |
| 865 / 289 | GAT D | CTG L | GCC A | TCT S | GTG V | GAC D | GTG V | AAA K | CTG L | AAA K | CCG P | TAC Y | TGG W | ATG M | TAC Y | GAT D | ATG M | TAC Y | CGC R | AAT N | TGG W | 912 | 304 |
| 913 / 305 | CCA P | ATT I | CGC R | ACC T | TAC Y | AAT N | GAA E | TCA S | TTA L | CCG P | CCA P | GCG A | AAA K | TTC F | GTG V | CAG Q | 960 | 320 |

Fig. 46 continued

```
 961  GAT CGC TCC GGT AGC CAC GGG ATG ACC CTT AAC TCA CTG GTT TCC GGC  1008
 321    D   R   S   G   S   H   G   M   T   L   N   S   L   V   S   G   336

1009  GGT TGT GTG ATC TCC GGT GTG TCG GTG GTG CAG TCC GTT CTG TTC TCG  1056
 337    G   C   V   I   S   G   V   S   V   V   Q   S   V   L   F   S   352

1057  CGC GTT CGC GTG AAT TCA GGT GTA TTC TGC AAC ATT GAT TCC GCC GTA TTG TTA  1104
 353    R   V   R   V   N   S   G   V   F   C   N   I   D   S   A   V   L   L   368

1105  CCG GAA GTA TGG GTA GGT ATT GTT CGC TGC CGT CTG CGC TGC GTC ATC  1152
 369    P   E   V   W   V   G   I   V   R   C   R   L   R   C   V   I   384

1153  GAT CGT GCT TGT GCA CGT ATT CCG GAA ATG GGC ATT GGT GAA GAA GCA  1200
 385    D   R   A   C   A   R   I   P   E   M   G   I   G   E   E   A   400

1201  GAG GAA GAT GCA CGT GAA ATG CTA CGG AAG TTA TCA GAA GGC ATC GTG CTG  1248
 401    E   E   D   A   R   E   M   L   R   K   L   S   E   G   I   V   L   416

1249  GTA ACG CGC GAA ATG CTA CGG AAG TTA GGG CAT AAA CAG GAG CGA TAA  1296
 417    V   T   R   E   M   L   R   K   L   G   H   K   Q   E   R   *   432

1297  TGC AGG TTT TAC ATG TAT GTT CAG AGA TGT TT  1328
 433    C   R   F   Y   M   Y   V   Q   R   C       442
```

Fig. 47

```
*** INPUT INFORMATION ***

FILE NAME   : ECGLGC.DNA           SEQUENCE : NORMAL    1328 BP
    CODON TABLE : UNIV.TCN

SEQUENCE     REGION :    1 -  1328
    TRANSLATION  REGION :    1 -  1326

*** DNA TRANSLATION ***

1  ATG GTT AGT TTA GAG AAG AAC GAT CAC TTA ATG TTG GCG CGC CAG CTG    48
    1   M   V   S   L   E   K   N   D   H   L   M   L   A   R   Q   L    16

49  CCA TTG AAA TCT GTT GCC CTG ATA CTG GCG GGA CCG GCC CGT GGT ACC    96
   17   P   L   K   S   V   A   L   I   L   A   G   P   A   R   G   T    32

97  CTG AAG GAT TTA ACC AAT AAG CGA GCA AAA CCG GCC CTG TCT AAC TGC   144
   33   L   K   D   L   T   N   K   R   A   K   P   A   L   S   N   C    48

145  GGT AAG TTC CGC ATT ATC GAC TTT GCG CTG TCT TAC CAG TAC ATC AAC   192
   49   G   K   F   R   I   I   D   F   A   L   S   Y   Q   Y   I   N    64

193  GGG ATC CGT CGT ATG CAG GGC GTG ATC ACC CAG TCA TTC TTC AAT GAA   240
   65   G   I   R   R   M   Q   G   V   I   T   Q   W   S   F   F   N    80

241  GTG CAG CAC ATT CAG CTG CTG CCA GCA CAG CAG AGA ATG AAA GAA ATG   288
   81    V   Q   H   I   Q   L   L   P   A   Q   Q   R   M   K   E   M    96

289  GAG TTT GTC GAT CTG CTG CCA CTG CCA GAT GCG GTC ACC CAA AAC GAA   336
   97    E   F   V   D   L   L   P   L   P   D   A   V   T   Q   N   E   112

337  TGG TAT CGC GGC ACC GCA GAT GCG GTG ACC CAA AAC CTC GAC ATT ATC   384
  113    W   Y   R   G   T   A   D   A   V   T   Q   N   L   D   I   I   128
```

Fig. 47 continued

| | | | | | | | | | | |
|---|---|---|---|---|---|---|---|---|---|---|
| 385 | CGT | CGT | TAT | AAA | GCG | GAA | TAC | GTG | GTG | ATC | CTG | GCG | GGC | GAC | CAT | ATC | 432 |
| 129 | R | R | Y | K | A | E | Y | V | V | I | L | A | G | D | H | I | 144 |
| 433 | TAC | AAG | CAA | GAC | TAC | TCG | CGT | ATG | CTT | ATC | GAT | CAC | GTC | GAA | AAA | GGT | 480 |
| 145 | Y | K | Q | D | Y | S | R | M | L | I | D | H | V | E | K | G | 160 |
| 481 | GTA | CGT | TGT | ACC | GTT | TGT | GTT | ATG | CCA | GTA | ATT | GAA | GAA | GAA | GCC | TCC | 528 |
| 161 | V | R | C | T | V | C | V | M | P | V | I | E | E | E | A | S | 176 |
| 529 | GCA | TTT | GGC | GTT | ATG | GCG | GTT | GAT | GAG | AAC | GAT | AAA | ACT | ATC | GAA | TTC | 576 |
| 177 | A | F | G | V | M | A | V | D | E | N | D | K | T | I | E | F | 192 |
| 577 | GTG | GAA | AAA | CCT | GCT | ATG | CCG | CCG | TCA | ATG | CCG | AAC | GAT | CCG | AGC | AAA | 624 |
| 193 | V | E | K | P | A | M | P | P | S | M | P | N | D | P | S | K | 208 |
| 625 | TCT | CTG | GCG | AGT | ATG | GGT | ATC | TAC | TTT | GAC | GTC | TTT | GAC | GAC | TAT | CTG | TAT | 672 |
| 209 | S | L | A | S | M | G | I | Y | F | D | V | F | D | A | D | Y | L | Y | 224 |
| 673 | GAA | CTG | CTG | GAA | GAA | GAC | GAT | CCC | AAG | ATC | ACC | GAA | AAC | TCC | AGC | CAC | TTT | 720 |
| 225 | E | L | L | E | E | D | D | P | K | I | T | E | N | S | S | H | D | F | 240 |
| 721 | GGC | AAA | GAT | TTG | ATT | CTC | TCT | TGC | GTA | ACG | CTG | GGT | GCC | TAT | GCC | TAT | GCG | 768 |
| 241 | G | K | D | L | I | L | S | C | V | T | L | G | A | Y | A | Y | A | 256 |
| 769 | CAC | CCG | TTC | CCG | GAT | GTG | GTG | CAA | CTG | TGG | CCG | GAT | GCC | GAG | CCG | 816 |
| 257 | H | P | F | P | D | V | V | Q | L | W | P | D | A | E | P | 272 |
| 817 | TAC | TGG | CGC | TCT | GGT | GTG | ACG | CTG | AAA | GCT | TAC | ATG | TAC | AAA | AGC | AAC | CTC | 864 |
| 273 | Y | W | R | S | G | V | T | L | K | A | Y | M | Y | K | N | L | 288 |
| 865 | GAT | CTG | GCC | TCT | GTG | CCA | CCG | AAA | CCA | GAT | ATG | TAC | GAT | CGC | AAT | TGG | 912 |
| 289 | D | L | A | S | V | P | P | K | P | D | M | Y | D | R | N | W | 304 |
| 913 | CCA | ATT | CGC | ACC | TAC | AAT | GAA | TCA | TTA | CCG | CCA | GCG | AAA | TTC | GTG | CAG | 960 |
| 305 | P | I | R | T | Y | N | E | S | L | P | P | A | K | F | V | Q | 320 |

Fig. 47 continued

| | | | | | | | | | | | | | | | | |
|---|---|---|---|---|---|---|---|---|---|---|---|---|---|---|---|---|
| 961 | GAT | CGC | TCC | GGT | AGC | CAC | GGG | ATG | ACC | CTT | AAC | TCA | CTG | GTT | TCC | GGC | 1008 |
| 321 | D | R | S | G | S | H | G | M | T | L | N | S | L | V | S | G | 336 |
| 1009 | GGT | TGT | GTG | ATC | TCC | GGT | GTG | ATG | GTG | GTG | CAG | TCC | GTT | CTG | TTC | TCG | 1056 |
| 337 | G | C | V | I | S | G | V | M | V | V | Q | S | V | L | F | S | 352 |
| 1057 | CGC | GTT | CGC | GTG | AAT | TCA | TTC | TGC | AAC | ATT | GAT | CGC | GCC | GTA | TTG | TTA | 1104 |
| 353 | R | V | R | V | N | S | F | C | N | I | D | R | A | V | L | L | 368 |
| 1105 | CCG | GAA | GTA | TGG | GTA | GGT | GTT | CGC | TGC | CGT | CTG | CGC | TGC | GTC | ATC | 1152 |
| 369 | P | E | V | W | V | G | V | R | C | R | L | R | C | V | I | 384 |
| 1153 | GAT | CGT | GCT | TGT | GTT | ATT | CCG | GAA | GGC | ATG | GTG | ATT | GGT | GAA | AAC | GCA | 1200 |
| 385 | D | R | A | C | V | I | P | E | G | M | V | I | G | E | N | A | 400 |
| 1201 | GAG | GAA | GAT | GCA | CGT | CGT | TTC | TAT | CGT | TCA | GAA | GGC | ATC | GTG | CTG | 1248 |
| 401 | E | E | D | A | R | R | F | Y | R | S | E | G | I | V | L | 416 |
| 1249 | GTA | ACG | CGC | GAA | ATG | CTA | CGG | AAG | TTA | GGG | CAT | AAA | CAG | GAG | CGA | TAA | 1296 |
| 417 | V | T | R | E | M | L | R | K | L | G | H | K | Q | E | R | * | 432 |
| 1297 | TGC | AGG | TTT | TAC | ATG | TAT | GTT | CAG | AGA | TGT | TT | | | | | | 1328 |
| 433 | C | R | F | Y | M | Y | V | Q | R | C | | | | | | | 442 |

Fig. 48

```
*** INPUT INFORMATION ***

FILE NAME      : ECGLGCWT.SEQ    SEQUENCE : NORMAL    1328 BP

CODON TABLE    : UNIV.TCN

SEQUENCE REGION    :    1 - 1328

TRANSLATION REGION :    1 - 1326

*** DNA TRANSLATION ***

1  ATG GTT AGT TTA GAG AAG AAC GAT CAC TTA ATG TTG GCG CGC CAG CTG    48
   1   M   V   S   L   E   K   N   D   H   L   M   L   A   R   Q   L    16

49  CCA TTG AAA TCT GTT GCC CTG ATA CTG GCG GGA AAA CCG CGT GGT ACC    96
  17   P   L   K   S   V   A   L   I   L   A   G   K   P   R   G   T    32

97  CTG AAG GAT TTA ACC AAT AAG CGA TTT GCG TCT CTG TAC CAC TTC GGC   144
  33   L   K   D   L   T   N   K   R   F   A   S   L   Y   H   F   G    48

145  GGT AAG TTC CGC ATT ATC GAC GTG ATC ACC CAG TAC TTC AAT TGC TCC   192
  49   G   K   F   R   I   I   D   V   I   T   Q   Y   F   N   C   S    64

193  GGG ATC CGT CGT ATG GGC TGG GGC TCA CAG TTC TTT AGA ATG TCC CAC   240
  65   G   I   R   R   M   G   W   G   S   Q   F   F   R   M   S   H    80

241  GTG CAG CAC ATT CAG CGC CTG CTG CCA GCA CAG CAG GCA GAA GAA ACT   288
  81   V   Q   H   I   Q   R   L   L   P   A   Q   Q   A   E   E   T    96

289  GAG TTT GTC GAT CTG CTG CCT CTG GAT CAG AGA ATG AAA GGG GAA AAC   336
  97   E   F   V   D   L   L   P   L   D   Q   R   M   K   G   E   N   112

337  TGG TAT CGC GGC ACC GCA GAT GCG GTC ACC CAA AAC CTC GAC ATT ATC   384
 113   W   Y   R   G   T   A   D   A   V   T   Q   N   L   D   I   I   128
```

Fig. 48 continued

| | | | | | | | | | | | | | | | | |
|---|---|---|---|---|---|---|---|---|---|---|---|---|---|---|---|---|
| 385 | CGT | CGT | TAT | AAA | GCG | GAA | TAC | GTG | GTG | ATC | CTG | GCG | GGC | GAC | CAT | ATC | 432 |
| 129 | R | R | Y | K | A | E | Y | V | V | I | L | A | G | D | H | I | 144 |
| 433 | TAC | AAG | CAA | GAC | TAC | TCG | CGT | ATG | CTT | ATC | GAT | CAC | GTC | GAA | AAA | GGT | 480 |
| 145 | Y | K | Q | D | Y | S | R | M | L | I | D | H | V | E | K | G | 160 |
| 481 | GTA | CGT | TGT | ACC | GTT | GTT | TGT | ATG | CCA | GTA | GAA | GAA | GCC | TCC | 528 |
| 161 | V | R | C | T | V | V | C | M | P | V | E | E | A | S | 176 |
| 529 | GCA | TTT | GGC | GTT | ATG | GCG | GTT | GAT | GAG | AAC | GAT | AAA | ACT | ATC | GAA | TTC | 576 |
| 177 | A | F | G | V | M | A | V | D | E | N | D | K | T | I | E | F | 192 |
| 577 | GTG | GAA | AAA | CCT | GCT | AAC | CCG | TCA | ATG | CCG | ATC | CCG | TAT | CCG | AGC | AAA | 624 |
| 193 | V | E | K | P | A | N | P | S | M | P | I | P | Y | P | S | K | 208 |
| 625 | TCT | CTG | GCG | AGT | ATG | GGT | ATC | TAC | GTC | TTT | GAC | GCC | GAC | TAT | CTG | TAT | 672 |
| 209 | S | L | A | S | M | G | I | Y | V | F | D | A | D | Y | L | Y | 224 |
| 673 | GAA | CTG | CTG | GAA | GAA | ATT | CTC | GAT | CGC | GAA | AAC | GAG | CAC | GAC | TTT | 720 |
| 225 | E | L | L | E | E | I | L | D | R | D | E | N | E | H | D | F | 240 |
| 721 | GGC | AAA | GAT | TTG | CCG | GAT | GTG | ACG | AAG | ATC | CCC | ATC | ACC | GAA | GCC | GGT | CTG | 768 |
| 241 | G | K | D | L | P | D | V | T | K | I | P | I | T | E | A | G | L | 256 |
| 769 | CAC | CCG | TTC | CCG | CTC | GAT | GTG | TGC | GTA | CAA | CTG | GAA | TCC | GAT | CCG | GAT | GCC | 816 |
| 257 | H | P | F | P | L | D | V | C | V | Q | L | E | S | D | P | D | A | 272 |
| 817 | TAC | TGG | CGC | GAT | GTG | TCT | ACG | GGT | GTG | CCG | GAA | CTG | TAC | TGG | ATG | TAC | GAT | 864 |
| 273 | Y | W | R | D | V | S | T | G | V | P | E | L | Y | W | M | Y | D | 288 |
| 865 | GAT | CTG | GCC | TCT | GTG | GTG | CCG | GAA | CTG | GAT | ATG | TAC | GAT | CGC | AAC | TGG | 912 |
| 289 | D | L | A | S | V | V | P | E | L | D | M | Y | D | R | N | W | 304 |
| 913 | CCA | ATT | CGC | ACC | TAC | AAT | GAA | TCA | TTA | CCG | GCG | AAA | TTC | GTG | CAG | 960 |
| 305 | P | I | R | T | Y | N | E | S | L | P | A | K | F | V | Q | 320 |

Fig. 48 continued

```
 961  GAT CGC TCC GGT AGC CAC GGG ATG ACC CTT AAC TCA CTG GTT TCC GGC  1008
 321   D   R   S   G   S   H   G   M   T   L   N   S   L   V   S   G   336

1009  GGT TGT GTG ATC TCC GGT GTG GTG GTG CAG TCC GTT CTG TTC TCG      1056
 337   G   C   V   I   S   G   V   V   V   Q   S   V   L   F   S       352

1057  CGC GTT CGC GTG AAT TCA TTC TGC AAC ATT GAT TCC GCC GTA TTG TTA  1104
 353   R   V   R   V   N   S   F   C   N   I   D   S   A   V   L   L   368

1105  CCG GAA GTA TGG GTA GGT CGC TCG TGC CGT CTG GTG TGC GTC ATC      1152
 369   P   E   V   W   V   G   R   S   C   R   L   V   C   V   I       384

1153  GAT CGT GCT TGT ATT GGT CGC ATG GTG ATT GGT GAA AAC GCA          1200
 385   D   R   A   C   I   G   R   M   V   I   G   E   N   A           400

1201  GAG GAA GAT GCA CGT CCG TTC TAT CGT TCA GAA GGC GTG CTG          1248
 401   E   E   D   A   R   P   F   Y   R   S   E   G   V   L           416

1249  GTA ACG CGC GAA ATG CTA AAG TTA CGG CAT AAA CAG GAG CGA TAA      1296
 417   V   T   R   E   M   L   K   L   R   H   K   Q   E   R   *       432

1297  TGC AGG TTT TAC ATG TAT GTT CAG AGA TGT TT                       1328
 433   C   R   F   Y   M   Y   V   Q   R   C                           442
```

Fig. 49

(Linear) MAP of: Waxy0.Seq   check: 2247 from: 1   to: 1917   With 189 enzymes: *

June 10, 1993   17:59 ..

```
         F              H        F             B       EH          A
         n C            C aM     n  C          s C B C CBca  B SB  S f
         Au v    ME    vHeaM     u Av      B   sMaHsHaHvsoeMNsHcsTMNcTlM
         c4 i    wa    iaIes     4 li      b   HwcgrhchiaRIsaagrmhscrhIl
         iH J    oe    JeIIc     H uJ      v   Io8aFa8aJJIIpeHaFFapiFaIu
         II I    II    IIIII     I II      I   IIIIIIIIIIIIIIIIIIIIIIIII
                  //  /             /              / /  //// // / /// /
       ATGgcggctctggccacgtcgcagctcgtcgcaacgcgcgccggcctgggcgtcccggac
     1 ----------+----------+----------+----------+----------+---------+ 60
       TACcgccgagaccggtgcagcgtcgagcagcgttgcgcgcggccggacccgcagggcctg M   A   A   L   A   T   S   Q   L   V   A   T   R   A   G   L   G   V   P   D   -
```

```
                                         E           E       B
                                         c           c       s
                          FF  F          o   B HN    o       p H        F    F
              M           B   Bnn  nH    ONCAs  as   SONC    BB1Ba      n    nN
       T      Ha    AE   AsADBsuuAuaHHNMllvluDepHBallvAAas2seBMNNAuMAul
       h      ge    cc   cacsaa44c4ehhan0aiw3dIBgsc0aivpna8aIssccc4wc4a
       a      aI    ii   iJianHHHiHIaarl9IJN6eIIaIl9IJaaIJ6HIlpiiiHoiHI
       I      II    II   IIIIIIIIIIIIIIIIIVIIIIIIIIIIVIIIIIIIIIIIIIIIIV
              /          / /  // /// /   /   ///  /      /// / /// /  /
       gcgtccacgttccgccgcggcgccgcgcagggcctgaggggggcccgggcgtcggcggcg
    61 ----------+----------+----------+----------+----------+---------+ 120
       cgcaggtgcaaggcggcgccgcggcgcgtcccggactcccccgggcccgcagccgccgc A   S   T   F   R   R   G   A   A   Q   G   L   R   G   A   R   A   S   A   A   -
```

```
                       B
                       p
              SSS      u         N  S      B B B      F       E        F        B
              aaaSS    1    C    1A a      s sCsCC    n B     BcH     NN  nS  C  sC
              AEuuuccSS1DTT Ma   AavNuS    s sasaaHAuBsHHsoaHBHMMNllMucBTaMAsa
              cc999rrmr0dhh wc   cIas9p    H HcHcchc4aahhaRehahwwaaaw4rshcwsHc
              ii666FFaf2eaa o8   iIIp6h    I I8I88aiHnHaaJIIanaoorIIoHFla8ocI8
              IIIIIIIIIIII  II   IIIIII    I IIIIIIIIIIIIIIIIIIIIVVIIIIIIIIII
              ////// ///          / ///      / /   //  /// ////// / / /
       gcggacacgctcagcatgcggaccagcgcgcgcggcgcccaggcaccagcagcaggcg
   121 ----------+----------+----------+----------+----------+---------+ 180
       cgcctgtgcgagtcgtacgcctggtcgcgcgcgccgcgggtccgtggtcgtcgtccgc A   D   T   L   S   M   R   T   S   A   R   A   A   P   R   H   Q   Q   Q   A   -
```

Fig. 49 continued

```
         F  N                                              N
    B B  n  sS N B                          C    BHC      MM1
   FsABAsDBuHHMpaTlTTsTT                  BH  a  saaHMN   Bbaa
   apcbcasg4hhwBchahhchh                  ch  c  rechsa   boeI
   uMiviJalHaaoIIaIaaGaa                  ga  8  FI8ape   sIII
   IIIIIIIIIIIIIIVIIIII                   II  I  IIIIII   IIII
    /  / //  ///////  //  //                        ///   / /
      cgccgcggggcaggttcccgtcgctcgtcgtgtgcgccagcgccggcatgaacgtcgtc
181   ---------+---------+---------+---------+---------+---------+  240
      gcggcgccccgtccaagggcagcgagcagcacacgcggtcgcggccgtacttgcagcag

R  R  G  R  F  P  S  L  V  V  C  A  S  A  G  M  N  V  V  -

F   H                    F
     BB H  N      B   B H N          B   n  CBa       BM AB      n
    BcsBaHN1    BBBsMHsDaN1         sMM  Au vseM      saMas     Au
    aeacehaa   gcaawhaseaa          rsw  c4 iaIw      aenta     c4
    nfHgIarI   lcnHoaJaIrI          Fpo  iH JJIo      HIlIJ     iH
    IIIIIIIV   IIIIIIIIIIV          III  II IIII      IIIII     II
     // ///      /  ////             /       /          /
      ttcgtcggcgccgagatggcgccgtggagcaagaccggcggcctcggcgacgtcctcggc
241   ---------+---------+---------+---------+---------+---------+  300
      aagcagccgcggctctaccgcggcacctcgttctggccgccggagccgctgcaggagccg

F  V  G  A  E  M  A  P  W  S  K  T  G  G  L  G  D  V  L  G  -

B                                 P
                                s                                 f
     H   F           FHH        Np          N                     1
    CaC   n  BC  CB  G  GC  naa      B   11N         1    BE      1
    veaM AuBsaEvsDdEdvAueeMMBNsBNa21ST   B    a      ss A         1
    iIcn c4srcaiasiaiiic4IIswsacacI8ath  s    I      mp c         0
    JI81 iH1F8eJJaIeIJiHIIpoleGnoI6Iya   l    I      A3 i         8
    IIII IIIIIIIIIIIIIIIIIIIIIIIIIIVII   I    I      II I         I
     / /  / / /   // /  ////// /   // ///                  /
      ggcctgccgccggccatggccgcgaacgggcaccgtgtcatggtcgtctctccccgctac
301   ---------+---------+---------+---------+---------+---------+  360
      ccggacggcggccggtaccggcgcttgcccgtggcacagtaccagcagagagggggcgatg

G  L  P  P  A  M  A  A  N  G  H  R  V  M  V  V  S  P  R  Y  -

E                        S
                      B  cB  S   B                 a      BE      BBE
    F  B    R  B     s  osHc    sH    D            u   D  ss B    sss
    a  s    s  s     a  Ragr    mg    r            3   p  mp c    cmp
    u  r    a  l     H  IJaF    Fa    d            A   n  A3 c    GA3
    I  I    I  I     I  IIII    II    I            I   I  II I    III
                                 /  /                   /         //
      gaccagtacaaggacgcctgggacaccagcgtcgtgtccgagatcaagatgggagacggg
361   ---------+---------+---------+---------+---------+---------+  420
      ctggtcatgttcctgcggaccctgtggtcgcagcacaggctctagttctaccctctgccc

```
                                                    S              H
         M                                          Aa             i
  R      b                         M  AHT      vu  A T             n
  s      o                         w  chh      a9  c h             c
  a      I                         o  iaa      I6  i a             I
  I      I                         I  III      II  I I             I
                                   //          /
     tacgagacggtcaggttcttccactgctacaagcgcggagtggaccgcgtgttcgttgac
421  ----------+----------+----------+----------+----------+----------+ 480
     atgctctgccagtccaagaaggtgacgatgttcgcgcctcacctggcgcacaagcaactg

Y  E  T  V  R  F  F  H  C  Y  K  R  G  V  D  R  V  F  V  D  -

E                                         S        S H
          c S     T                    B       B    BB a  T    BaCaM
          oMc    aB         M         Bs       s    gsDu  a    suveb
          Rnr    qs         n         pa       e    ltp3  q    c9iIo
          I1F    Il         l         mJ       R    IYnA  I    G6JII
          III    II         I         II       I    IIII  I    IIIII
            /                                         / /      / //
     cacccactgttcctggagagggtttggggaaagaccgaggagaagatctacgggcctgtc
481  ----------+----------+----------+----------+----------+----------+ 540
     gtgggtgacaaggacctctcccaaacccctttctggctcctcttctagatgcccggacag

H  P  L  F  L  E  R  V  W  G  K  T  E  E  K  I  Y  G  P  V  -

B
                                                                  s
                                 F  HN             E              p
                              B  Cn gsP    C  C    cBS            1H
       B          S B         s  AvuAipv   v  a  M osc            2g
       s          f b         m  li4cEBu   i  c  w Rar            8i
       1          c v         F  uJHiIII   J  8  o IJF            6A
       I          I I         I  IIIIIII   I  I  I III            II
                                 // ///                           /
     gctggaacggactacagggacaaccagctgcggttcagcctgctatgccagggagcactt
541  ----------+----------+----------+----------+----------+----------+ 600
     cgaccttgcctgatgtccctgttggtcgacgccaagtcggacgatacggtccctcgtgaa

A  G  T  D  Y  R  D  N  Q  L  R  F  S  L  L  C  Q  G  A  L  -

SB                                S
        C  B      BB Nap    C                       BB Aa       B
      M  AvAsS   asDluuD   Av         M            ssMvu   M    s
      w  lilat   mtpa3ld   li         n            apsa9   n    c
      o  uJwJy   HYnIAOe   wJ         l            WEpI6   l    G
      I  IIIII   IIIVIII   II         I            IIIII   I    I
         / /     / // /                             // /
     gaagctccaaggatcctgagcctcaacaacaacccatacttctccggaccatacgggagg
601  ----------+----------+----------+----------+----------+----------+ 660
     cttcgaggttcctaggactcggagttgttgttgggtatgaagaggcctggtatgccctcc

```
                                    S HB
  BBM  A             C            B  aCac
  ssa  a             v          B  sM uvee   B      M
  mae  t             i          s  rs 9iI8   s      n
  FHI  I             R          r  Fp 6JI3   i      l
  III  I             I          I  II IIII   I      I
       /                           /
      gacgtcgtgttcgtctgcaacgactggcacaccggccctctctcgtgctacctcaagagc
661   ----------+----------+----------+----------+----------+----------+ 720
      ctgcagcacaagcagacgttgctgaccgtgtggccgggagagagcacgatggagttctcg

D  V  V  F  V  C  N  D  W  H  T  G  P  L  S  C  Y  L  K  S   -

B  B                S  B  B                 C       S
       M    s  sD       S       f  s  c    F   HAM    ·v       f
       n    m  as       f       a  m  e    o   gcw     i       a
       l    F  Ja       c       N  F  f    k   aio     R       N
       I    I  II       I       I  I  I    I   III     I       I
            /                              /
      aactaccagtcccacggcatctacagggacgcaaagaccgctttctgcatccacaacatc
721   ----------+----------+----------+----------+----------+----------+ 780
      ttgatggtcagggtgccgtagatgtccctgcgtttctggcgaaagacgtaggtgttgtag

N  Y  Q  S  H  G  I  Y  R  D  A  K  T  A  F  C  I  H  N  I   -

E    SH   H
          cBS  agBCa                     S       C             S    H
          osc  uisveM                    MNc     Av            MMNc HiT
          Rar  9ErilS                    scr     li            smcr nnf
          IJF  6IFJIp                    piF     uJ            peiF lfi
          III  IIIIII                    III     II            IIII III
          ///                            //      /             //   /
      tcctaccagggccggttcgccttctccgactacccggagctgaacctcccggagagattc
781   ----------+----------+----------+----------+----------+----------+ 840
      aggatggtcccggccaagcggaagaggctgatgggcctcgacttggagggcctctctaag

S  Y  Q  G  R  F  A  F  S  D  Y  P  E  L  N  L  P  E  R  F   -

P
                          f
                          l                          H     S
                    C     l       C  BBB      Ca     a
            T       T     v  1    v  scsD  B  veM    u  D
            a       a     i  0    i  aecs  s  iIs    3  p
            q       q     J  8    J  JfGa  l  JIp    A  n
            I       I     I  1    I  IIII  I  III    I  I
                                //                //
      aagtcgtccttcgatttcatcgacggctacgagaagcccgtggaaggccggaagatcaac
841   ----------+----------+----------+----------+----------+----------+ 900
      ttcagcaggaagctaaagtagctgccgatgctcttcgggccttccggccttctagttg

```
                                    E
                                 T  c
              H       S    H     t  o S
       M      Ca   BB    Na S Ca  h  AONPa           C              B
       bB     AveMNasDFMAluAcTveXM H1 vllpu          Mv      M      s
       os     liIscmtponva3lraiIhn pl aOau9          ni      n      a
       Ir     wJIpiHYnklaIAwFqJIol hl I9IM6          lJ      l      J
       II     IIIIIIIIIIVIIIIIIII  II IIVII          II      I      I
              /// / // // // //       ////
              tggatgaaggccgggatcctcgaggccgacagggtcctcaccgtcagcccctactacgcc
     901   ----------+---------+---------+---------+---------+---------+ 960
              acctacttccggccctaggagctccggctgtcccaggagtggcagtcggggatgatgcgg

W  M  K  A  G  I  L  E  A  D  R  V  L  T  V  S  P  Y  Y  A   -

B                                         B
                  s                                         s
                  p              E           F              p                N
         B       CB1H            cBS   S   ACn    C        CB1H        H    l     B
         s      Ava2gS   M  B    osc   f   lvu    a       Ava2gST      p    a  H  HsBM
         e      lin8is   s  b    Rar   a   wi4    c       lin8isa      h    I  h  prgs
         R      uJI6At   p  v    IJF   N   NJH    8       uJI6Atq      h    I  a  hFlp
         I      IIIIII   I  I    III   I   III    I       IIIIII       I    I  I  IIII
                / ///    I  I                              / ////              /
              gaggagctcatctccggcatcgccaggggctgcgagctcgacaacatcatgcgcctcacc
     961   ----------+---------+---------+---------+---------+---------+ 1020
              ctcctcgagtagaggccgtagcggtccccgacgctcgagctgttgtagtacgcggagtgg

E  E  L  I  S  G  I  A  R  G  C  E  L  D  N  I  M  R  L  T   -

E
                                                            c
                                 H          N               o   S
                 B     S         i   S      l  BM    A      B          A    B  B
         M   M  sMM    f         n   f      a  sa    a      c         vslllpu  B  c  s
         w   n  rsw    a         c   a      I  ae    t      e         amOaau9  s  e  m
         o   l  Fpo    N         I   N      I  HI    I      f         IF9IIM6  l  f  F
         I   I  III    I         I   I      I  II    I      I         IIIVVII  I  I  I
             /    /                         /              /////
             ggcatcaccggcatcgtcaacggcatggacgtcagcgagtgggacccagcagggacaag
    1021  ----------+---------+---------+---------+---------+---------+ 1080
             ccgtagtggccgtagcagttgccgtacctgcagtcgctcaccctggggtcgtccctgttc

G  I  T  G  I  V  N  G  M  D  V  S  E  W  D  P  S  R  D  K   -

A      H        H       H
                                 B    fM      i     CBB Ga    CB aB    H
         R       M               Rc   la     SAnT  EEvssDdeBMMvsHecSS  HaBM
         s       s               se   Ie     acca  aaiaisiIgnwiaaIeft  hebn
         a       l               af   II     lcIq  egJJEaIIIloJJeIfiy  aIvl
         I       I                II   II    IIII  IIIIIIIIIIIIIIIII   IIII
                                    /         / /  //// // // //
             tacatcgccgtgaagtacgacgtgtcgacggccgtggaggccaaggcgctgaacaaggag
    1081  ----------+---------+---------+---------+---------+---------+ 1140
             atgtagcggcacttcatgctgcacagctgccggcacctccggttccgcgacttgttcctc

```
                        B
                        s
         F              p         S                       N
       nHC C          CNB1     S AaB                      s
       HuavMaMAEPS    vla2FMNc vusM            A  p    B  F
       h4eincwccsf   ian8oscr a9as             c  B    s  a
       aHIR18oiitc   JII6kpiF I6Wp             i  I    l  u
       IIIIIIIIII    IVIIIIII IIII             I  I    I  I
          /  /  //     /  ///  /
        gcgctgcaggcggaggtcgggctcccggtggaccggaacatcccgctggtggcgttcatc
1141    ---------+---------+---------+---------+---------+---------+ 1200
        cgcgacgtccgcctccagcccgagggccacctggccttgtagggcgaccaccgcaagtag

A  L  Q  A  E  V  G  L  P  V  D  R  N  I  P  L  V  A  F  I  -

EE   B
                              cc   s
                              oo H p         SN        FF  H  S  F           N
       C  C                   OOCa B1MBM ANNal     C Bnn  Ga    a  n    C    l
       aEvS         M         llveAa2bsaFalluaAEEvAsuuBdeNAu    u  AvF       a
       caia         w         00iIpn8oaeotaa9Icaaici44ciIoc9    4  lia       I
       8rJp         o         99JIaI6IHIkIII6IiegJiEHHcIIIti6   H  uJu       I
       IIII         I         IIIIIIIIIIIVVIIIIIIIIIIIIIII     I  III       I
          /                     / ///  /  ///    / /// ///  /       /
        ggcaggctggaagagcagaagggccccgacgtcatggcggccgccatcccgcagctcatg
1201    ---------+---------+---------+---------+---------+---------+ 1260
        ccgtccgaccttctcgtcttcccggggctgcagtaccgccggcggtagggcgtcgagtac

G  R  L  E  E  Q  K  G  P  D  V  M  A  A  A  I  P  Q  L  M  -

B
                                                  s
                       S                          p
              M    C   a                         1B              M
       M  BMB a    v   u   D                     B2s       X  T  b  H
       s  bnc e    i   3   p                     s8c       m  a  o  h
       l  vlc I    R   A   n                     g6G       n  q  I  a
       I  III I    I   I I                       III       I  I  I  I
          /                  /                    /
        gagatggtggaggacgtgcagatcgttctgctgggcacgggcaagaagaagttcgagcgc
1261    ---------+---------+---------+---------+---------+---------+ 1320
        ctctaccacctcctgcacgtctagcaagacgacccgtgcccgttcttcttcaagctcgcg

E  M  V  E  D  V  Q  I  V  L  L  G  T  G  K  K  K  F  E  R  -

N       N
       C  l  B   l      BH   B          E           B
       a aMsNS  Ma     Hsa   s         BcBS         s  C  B
       c  Ispsp nI     hae   e         socc    B    Ms aHHsDT
       8  IlHph ll     aJI   R         aRer    s    wH chhash
       I  IIIII II     III   I         JIfF    l    oI 8aaJaa
          // /   /     /                IIII   I    II IIIIII
                                          //          /  //
        atgctcatgagcgccgaggagaagttcccaggcaaggtgcgcgccgtggtcaagttcaac
1321    ---------+---------+---------+---------+---------+---------+ 1380
        tacgagtactcgcggctcctcttcaagggtccgttccacgcgcggcaccagttcaagttg

```
                              B
                              s
         F            H       N  p     M T        F
         n    HC      P GBCC  BBaH M   1 N1CH a s C n
         AuT HaaM H   BfEdsvaBcseaHMaNNaH12ag e p vAu   T
         c4h hecw h   slairicaeaIehseaaIpa8ci I 4 ic4  a
         iHa aI8o a   1MeIFJ8nfHIIapIerIhI68A I 5 JiH  q
         III IIII I   IIIIIIIIIIIIIIIIIIIIVIII I I III I
          /    /       / / /   // // /// / //       /
       gcggcgctggcgcaccacatcatggccggcgccgacgtgctcgccgtcaccagccgcttc
  1381 ---------+---------+---------+---------+---------+---------+ 1440
       cgccgcgaccgcgtggtgtagtaccggccgcggctgcacgagcggcagtggtcggcgaag

A    A  L    A  H  H  I  M  A  G  A  D  V  L  A  V  T  S  R  F  -

B
                  s
             p   F H          F   N
           C B1  nCa        S Cn C s P A                        C
         F v a2 ABuve      fAvuBvMpPvMpS          F    H   H a    HT
         o i n8 cb4iI      ali4sinBsuwaf          o    g   h c    hh
         k J I6 ivHJI      NuJH1R1ItIoBc          k    a   a 8    aa
         I I II IIIII      IIIIIIIIIIII           I    I   I I    II
          / // /           // ///// /                               /
       gagccctgcggcctcatccagctgcaggggatgcgatacggaacgccctgcgcctgcgcg
  1441 ---------+---------+---------+---------+---------+---------+ 1500
       ctcgggacgccggagtaggtcgacgtccctacgctatgccttgcgggacgcggacgcgc

E  P  C  G  L  I  Q  L  Q  G  M  R  Y  G  T  P  C  A  C  A  -

H                                N   FHS
             BB   S H         i                        S  N    1C  naa
             AssMPg i      SAnTM  B   T                MNc 1   HavAueu
             garslr n      accal  c   a                scr a   gIic419
             eWFpeA f      lcIqy  c   q                piF I   aIJiHI6
             IIIIII I      IIIII  I   I                III V   IIIIII
              /////          /                          /       / ///
       tccaccggtggactcgtcgacaccatcatcgaaggcaagaccgggttccacatgggccgc
  1501 ---------+---------+---------+---------+---------+---------+ 1560
       aggtggccacctgagcagctgtggtagtagcttccgttctggcccaaggtgtacccggcg

S  T  G  G  L  V  D  T  I  I  E  G  K  T  G  F  H  M  G  R  -

B     H  M
         p     i  a   M       NBCC     BM A             H
         uDM  SAnMT e Da    lsvaMAEN   sa a          C a    B    C
         1dw   accna I re   aricscca   ae t          E vHeM s    v
         0eo   lcIlq I dI   IFJ8piie   HI I          a iaIs r    i
         III   IIIII I II   VIIIIIII   II I          e JeIc D    R
          //     /    /      / / / /                 I IIII I    I
                                                     ///
       ctcagcgtcgactgtaacgtcgtggagccggcggacgtcaagaaggtggccaccacattg
  1561 ---------+---------+---------+---------+---------+---------+ 1620
       gagtcgcagctgacattgcagcacctcggccgcctgcagttcttccaccggtggtgtaac

```
        F B                                                                    SN
        n s C              B           C B C  S         B                  C   al
        u s aHHTB     BM   s           a sMaMNgSR       s M  B          A  vH  ua
        4 H chhhc     bs   t           c rscnarus      e n  c          1  ip  3I
        H I 8aaac     vl   X           8 Fp8leAna      R l  c          w  Rh  AI
        I I IIIII     II   I           I IIIIIIII      I I  I          I  II  II
             / /                          ///
        cagcgcgccatcaaggtggtcggcacgccggcgtacgaggagatggtgaggaactgcatg
1621    ----------+----------+----------+----------+----------+----------+  1680
        gtcgcgcggtagttccaccagccgtgcggccgcatgctcctctaccactccttgacgtac Q   R   A   I   K   V   V   G   T   P   A   Y   E   E   M   V   R   N   C   M   -

EE   B                                    B
                             cc   s                                    p
            E    S      E    oo H  p SS                                F u
            c S  Ba     c S  OOCa BlNaa      P              M          n l    CB
            Do c suD    oAc  llveAa2luu      BBf    B       a          u 1D   vsA
            pR r t3p    Rlr  OOiIpn8a99      bsl    s       e          4 0d   iav
            nl F YAn    IwF  99JIaI6I66      vlM    r       I          H 2e   JJa
            II I III    III  IIIIIIIVII      III    I       I          I II   III
                /        /      / /////        //                          /
        atccaggatctctcctggaagggccctgccaagaactgggagaacgtgctgctcagcctc
1681    ----------+----------+----------+----------+----------+----------+  1740
        taggtcctagagaggaccttcccgggacggttcttgaccctcttgcacgacgagtcggag I   Q   D   L   S   W   K   G   P   A   K   N   W   E   N   V   L   L   S   L   -

F            E                 S          F
              B C   n S   C   CBcS                           B a        nB  C      B
              sMaMAuNg    a   vsoc         TM                s u  D  T  HAusMa     sS       X
              rncsc4ar    c   iaRr         an                e 3  p  h  hc4rwc     at       c
              Fl8piHeA    8   JJIF         ql                R A  n  a  aiHBo8     Jy       m
              IIIIIIII    I   IIII         II                I I  I  I  IIIIII     II       I
              / / //          //                                       /                /
        ggggtcgccggcggcgagccaggggtcgaaggcgaggagatcgcgccgctcgccaaggag
1741    ----------+----------+----------+----------+----------+----------+  1800
        ccccagcggccgccgctcggtccccagcttccgctcctctagcgcggcgagcggttcctc G   V   A   G   G   E   P   G   V   E   G   E   E   I   A   P   L   A   K   E   -
```

Fig. 49 continued

```
                              EE   B            S
                              cc   s            s
         FH                H  oo E pH    SSS    e
   M    GC   na           CaCMC OOCc Bla NN aaa 8   C
   a   EdvAueTEH          veabvSB11voAa2eMD11PuuuHS3TMT v
   e   aiic4Ihah          iIcoifg00i5pn8Iwpaas993hf8hwh i
   I   eIJiHIara          JI8IRc199J7aI6IonIIt66Aai7aoa R
   I    IIIIIIII          IIIIIIIIIIIIIIIIIVVIIIIIIIII  I
        /  /// /           / / /   / //// //////  /// /
       aacgtggccgcgccctgaagagttcggcctgcagggcccctgatctcgcgcgtggtgcaa
1801   ----------+---------+---------+---------+---------+---------+ 1860
       ttgcaccggcgcgggacttctcaagccggacgtcccggggactagagcgcgcaccacgtt N    V   A   A   P   *   R   V   R   P   A   G   P   L   I   S   R   V   V   Q   -

M   B
                   b   s
                   o   m
                   I   F
                   I   I
       agatgttgggacatcttcttatatatgctgtttcgtttatgtgatatggacaagt..
1861   ----------+---------+---------+---------+---------+------ 1917
       tctacaaccctgtagaagaatatatacgacaaagcaaatacactatacctgttca..

```
*** INPUT INFORMATION ***

FILE   NAME  : MSS3.SEQ           SEQUENCE : NORMAL    2423 BP

CODON TABLE  : UNIV.TCN

SEQUENCE   REGION :     1  -  2423

TRANSLATION REGION :    1  -  2421

*** DNA TRANSLATION ***

1  ATG CCG GGG GCA ATC TCT TCC TCG TCG GCT TTT CTC CTC CCC GTC         48
  1   M   P   G   A   I   S   S   S   S   A   F   L   L   P   V         16

49  GCG TCC TCC TCG CCG CGC AGG CGC AGT GGC GGC CTG GGT GCT GCT GCT     96
 17   A   S   S   S   P   R   R   R   S   G   G   L   G   A   A   L     32

97  CGC TCG TAC GGC TAC AGC GGC TAC CTG CGG TTG CAT TGG GCG CGG        144
 33   R   S   Y   G   Y   S   G   A   E   L   R   L   H   W   A   R     48

145  CGG GGC CCG CCT CAG GAT GGA GCG GCG TCG GTA CGC GCC GCA GCG GCA    192
 49   R   G   P   P   Q   D   G   A   A   S   V   R   A   A   A   A     64

193  CCG GCC GGG GGC GAA AGC GAG GAG GCA GCG AAG AGC TCC TCG TCC        240
 65   P   A   G   G   E   S   E   E   A   A   K   S   S   S   S         80

241  CAG GCG GGC GCT GTT CAG GGC AGC ACG GCC AAG GCT GTG GAT TCT GCT    288
 81   Q   A   G   A   V   Q   G   S   T   A   K   A   V   D   S   A     96

289  TCA CCT CCC AAT CCT TTG ACA TCT GCT CCG AAG CAA AGT CAG AGC GCT    336
 97   S   P   P   N   P   L   T   S   A   P   K   Q   S   Q   S   A    112

337  GCA ATG CAA AAC GGA ACG AGT GGG GGC AGC AGC AGC ACC GCC GCG        384
113   A   M   Q   N   G   T   S   G   G   S   S   S   T   A   A   A    128
```

Fig. 50 continued

| | | | | | | | | | | | | |
|---|---|---|---|---|---|---|---|---|---|---|---|---|
| 385<br>129 | CCG<br>P | GTG<br>V | TCC<br>S | GGA<br>G | CCC<br>P | AAA<br>K | GCT<br>A | GAT<br>D | CAT<br>H | CCA<br>P | TCA<br>S | GCT<br>A | CCT<br>P | GTC<br>V | ACC<br>T | AAG<br>K | 432<br>144 |
| 433<br>145 | AGA<br>R | GAA<br>E | ATC<br>I | GAT<br>D | GCC<br>A | AGT<br>S | GCG<br>A | GTG<br>V | AAG<br>K | CCA<br>P | GAG<br>E | CCC<br>P | GCA<br>A | GGT<br>G | GAT<br>D | GAT<br>D | 480<br>160 |
| 481<br>161 | GCT<br>A | AGA<br>R | CCG<br>P | GTG<br>V | GAA<br>E | AGC<br>S | ATA<br>I | GGC<br>G | GTG<br>V | ATC<br>I | GCT<br>A | GTG<br>V | CCT<br>P | GCT<br>A | GAT<br>D | AAG<br>K | 528<br>176 |
| 529<br>177 | GCT<br>A | GAT<br>D | GCA<br>A | GCT<br>A | CCG<br>P | AGC<br>S | ACA<br>T | GAT<br>D | GCG<br>A | GCG<br>A | AGT<br>S | CCT<br>P | TAT<br>Y | GAC<br>D | | | 576<br>192 |
| 577<br>193 | AGG<br>R | GAG<br>E | GAT<br>D | AAT<br>N | GAA<br>E | CCT<br>P | ACA<br>T | TTG<br>L | CCT<br>P | GGG<br>G | GCG<br>A | AAT<br>N | GTG<br>V | AAC<br>N | | | 624<br>208 |
| 625<br>209 | GTC<br>V | GTG<br>V | GTG<br>V | GCT<br>A | TCT<br>S | GAA<br>E | CCT<br>P | GGC<br>G | TTC<br>F | TGC<br>C | AAG<br>K | ACA<br>T | GGT<br>G | GGC<br>G | | | 672<br>224 |
| 673<br>225 | CTT<br>L | GGA<br>G | GAT<br>D | GTC<br>V | GTC<br>V | GGT<br>G | GCT<br>A | CCT<br>P | TTG<br>L | TGC<br>C | CTG<br>L | GCG<br>A | AGG<br>R | AGA<br>R | GGA<br>G | | 720<br>240 |
| 721<br>241 | CAC<br>H | CGT<br>R | ATG<br>M | GTT<br>V | ATA<br>I | CCA<br>P | AGA<br>R | CGT<br>R | TAC<br>Y | ATT<br>I | GGA<br>G | GAG<br>E | TAT<br>Y | GCC<br>A | GAA<br>E | GCC<br>A | 768<br>256 |
| 769<br>257 | CGG<br>R | GAT<br>D | TTA<br>L | GGT<br>G | GTA<br>V | AGG<br>R | TAC<br>Y | AAG<br>K | GTA<br>V | GCT<br>A | GGA<br>G | CAG<br>Q | TCA<br>S | | | | 816<br>272 |
| 817<br>273 | GAA<br>E | GTT<br>V | ACT<br>T | TAT<br>Y | TTT<br>F | CAC<br>H | TCT<br>S | TAC<br>Y | ATT<br>I | GAT<br>D | GGA<br>G | GTT<br>V | GAT<br>D | TTT<br>F | GTA<br>V | TTC<br>F | 864<br>288 |
| 865<br>289 | GTA<br>V | GAA<br>E | GCC<br>A | CCT<br>P | CCC<br>P | TTC<br>F | CGG<br>R | CAC<br>H | CAC<br>H | AAT<br>N | AAT<br>N | ATT<br>I | TAT<br>Y | GGG<br>G | GGA<br>G | | 912<br>304 |
| 913<br>305 | GAA<br>E | AGA<br>R | TTG<br>L | GAT<br>D | ATT<br>I | TTG<br>L | AAG<br>K | CGC<br>R | ATG<br>M | ATT<br>I | TTG<br>L | TTC<br>F | TGC<br>C | AAG<br>K | GCC<br>A | GCT<br>A | 960<br>320 |

Fig. 50 continued

| | | | | | | | | | | | | | | | | |
|---|---|---|---|---|---|---|---|---|---|---|---|---|---|---|---|---|
| 961 | GTT | GAG | GTT | CCA | TGG | TAT | GCT | CCA | TGT | GGC | GGT | ACT | GTC | TAT | GGT | GAT | 1008 |
| 321 | V | E | V | P | W | Y | A | P | C | G | G | T | V | Y | G | D | 336 |
| 1009 | GGC | AAC | TTA | GTT | AAG | GCC | ATT | GCT | AAT | GAT | TGG | CAT | ACC | GCA | CTT | CCT | 1056 |
| 337 | G | N | L | V | K | A | I | A | N | D | W | H | T | A | L | P | 352 |
| 1057 | GTC | TAT | CTA | AAG | CTT | GTG | ATA | CAC | TAT | CGG | GAC | TAT | GGT | CAG | ATG | GCT | 1104 |
| 353 | V | Y | L | K | L | V | I | H | Y | R | D | Y | G | Q | M | A | 368 |
| 1105 | CGC | TCT | GTG | CTT | GTC | TTC | GTC | ATA | CAC | AAT | GGT | TTG | CAT | CAG | GGT | TAT | 1152 |
| 369 | R | S | V | L | V | F | V | I | H | N | G | L | H | Q | G | Y | 384 |
| 1153 | GTA | GAC | GAC | TTC | GTC | AAT | TTT | GAC | TTG | CCT | GAA | CAC | TAC | CGT | GGC | CCT | 1200 |
| 385 | V | D | D | F | V | N | F | D | L | P | E | H | Y | R | G | P | 400 |
| 1201 | TTC | AAA | CTG | TAT | GAC | ACG | AAG | CTG | GGT | GAT | CAC | AGC | AAC | CAC | GTT | GCT | 1248 |
| 401 | F | K | L | Y | D | T | K | L | G | D | H | S | N | H | V | A | 416 |
| 1249 | GCG | GGG | CTG | AAG | CTG | TGG | GCA | ACT | ATT | GGT | GTG | CGG | GTG | ACC | GTT | TTT | 1296 |
| 417 | A | G | L | K | L | W | A | T | I | G | V | R | V | T | V | F | 432 |
| 1297 | ATG | TGG | GAG | CAG | GAG | TGG | TAC | TCG | GAA | GGG | GGC | CAT | CAC | ATC | AAT | GGC | 1344 |
| 433 | M | W | E | Q | E | W | Y | S | E | G | G | H | H | I | N | G | 448 |
| 1345 | ATA | AAC | CAG | CTG | AAC | GAC | TGG | AAG | CTG | GTG | CAG | GGC | GTG | CTC | TCC | GAC | 1392 |
| 449 | I | N | Q | L | N | D | W | K | L | V | Q | G | V | L | S | D | 464 |
| 1393 | ATG.AGC | GAG | TGG | TAC | CCC | GCT | GTG | GTG | GAC | CTC | GTG | GGC | CGG | CAG | TGC | GAC | 1440 |
| 465 | M | S | E | W | Y | P | A | V | D | L | V | G | R | Q | C | D | 480 |
| 1441 | TAC | ACC | AAC | TAC | ACG | TTC | ACG | GAG | CTG | GGC | ACC | CTC | CAC | AAG | CGC | GAC | 1488 |
| 481 | Y | T | N | Y | T | F | T | E | L | G | T | L | H | K | R | D | 496 |
| 1489 | AAG | GCC | GCC | CTG | CAG | CGG | CAG | CTG | GGC | CTG | CAG | GTC | CGC | GAC | GAC | GTG | 1536 |
| 497 | K | A | A | L | Q | R | Q | L | G | L | Q | V | R | D | D | V | 512 |

Fig. 50 continued

| | | | | | | | | | | |
|---|---|---|---|---|---|---|---|---|---|---|
| 1537<br>513 | CCA<br>P | CTG<br>L | ATC<br>I | GGG<br>G | TTC<br>F | ATC<br>I | GGG<br>G | CGG<br>R | CTG<br>L | GAC<br>D | CAC<br>H | CAG<br>Q | AAG<br>K | GGC<br>G | GTG<br>V | GAC<br>D | 1584<br>528 |
| 1585<br>529 | ATC<br>I | ATC<br>I | GCC<br>A | GAC<br>D | GCG<br>A | ATC<br>I | CAC<br>H | TGG<br>W | ATC<br>I | GCC<br>A | GGG<br>G | CAG<br>Q | GAC<br>D | GTG<br>V | CAG<br>Q | CTC<br>L | 1632<br>544 |
| 1633<br>545 | GTG<br>V | ATG<br>M | CTG<br>L | GGC<br>G | ACC<br>T | GGG<br>G | CGG<br>R | GCC<br>A | GAC<br>D | CTG<br>L | GAG<br>E | GAC<br>D | ATG<br>M | CTG<br>L | CGG<br>R | CGG<br>R | 1680<br>560 |
| 1681<br>561 | TTC<br>F | GAG<br>E | TCG<br>S | GAG<br>E | CAC<br>H | CGG<br>R | AAG<br>K | GTG<br>V | CGC<br>R | CAG<br>Q | GAC<br>D | ATG<br>M | GTG<br>V | GGG<br>G | TTC<br>F | TCG<br>S | 1728<br>576 |
| 1729<br>577 | GTG<br>V | CCC<br>P | CTG<br>L | GCG<br>A | TTC<br>F | GAG<br>E | CGC<br>R | CAC<br>H | ACG<br>T | GCG<br>A | GCG<br>A | GAG<br>E | GAC<br>D | TGG<br>W | GTG<br>V | TCG<br>S | 1776<br>592 |
| 1777<br>593 | CCG<br>P | TCG<br>S | CGG<br>R | GCG<br>A | TTC<br>F | GAG<br>E | CCC<br>P | TGC<br>C | CGC<br>R | CTG<br>L | AAC<br>N | CAG<br>Q | ATC<br>I | TAC<br>Y | CGG<br>R | TCG<br>S | 1824<br>608 |
| 1825<br>609 | TAC<br>Y | GGG<br>G | ACC<br>T | GTG<br>V | GTG<br>V | CCC<br>P | TTC<br>F | GAC<br>D | GGC<br>G | GGC<br>G | GGG<br>G | CTC<br>L | CTC<br>L | GGG<br>G | CTG<br>L | ATG<br>M | 1872<br>624 |
| 1873<br>625 | GTG<br>V | GCG<br>A | CCG<br>P | CCG<br>P | TTC<br>F | GAC<br>D | CGG<br>R | CAC<br>H | GCC<br>A | GAC<br>D | ACC<br>T | GGG<br>G | CTC<br>L | CTC<br>L | TCG<br>S | GCG<br>A | 1920<br>640 |
| 1921<br>641 | GAC<br>D | CGC<br>R | GCG<br>A | GAG<br>E | GCG<br>A | AAC<br>N | CGG<br>R | ATG<br>M | ATC<br>I | GAC<br>D | TGG<br>W | CGC<br>R | CTC<br>L | TCG<br>S | TGC<br>C | CTC<br>L | 1968<br>656 |
| 1969<br>657 | ACC<br>T | ACG<br>T | TAC<br>Y | AAG<br>K | CTC<br>L | AGC<br>S | GAG<br>E | TGG<br>W | AGC<br>S | CAC<br>H | CAC<br>H | TCG<br>S | TGC<br>C | GCC<br>A | GCC<br>A | CGC<br>R | 2016<br>672 |
| 2017<br>673 | GGC<br>G | ATG<br>M | GCC<br>A | GAG<br>E | GAC<br>D | CTC<br>L | AAC<br>N | CGG<br>R | TGG<br>W | GAC<br>D | CAC<br>H | AGG<br>R | GCG<br>A | GCC<br>A | TAT<br>Y | GAG<br>E | 2064<br>688 |
| 2065<br>689 | GAC<br>D | GTG<br>V | CTC<br>L | GTC<br>V | AAG<br>K | GCG<br>A | GCG<br>A | TAC<br>Y | CAG<br>Q | TGG<br>W | TGA<br>* | GCG<br>A | AAT<br>N | TAA<br>* | TTG<br>L | GCG<br>A | 2112<br>704 |

Fig. 50 continued

| | | | | | | | | | | | | | | | | |
|---|---|---|---|---|---|---|---|---|---|---|---|---|---|---|---|---|
| 2113 | ACG | CGA | CGC | TCC | CGC | TGT | CGC | AGG | ACC | TGG | ACG | TTA | TTT | AGA | AGG | CTC | 2160 |
| 705 | T | R | R | S | R | C | R | R | T | W | T | L | F | R | R | L | 720 |
| 2161 | TTC | TCC | CTG | GCT | GCG | TTG | ATG | CGT | GCG | TCG | CAT | TTG | CGC | CGG | GCG | GAC | 2208 |
| 721 | F | S | L | A | A | L | M | R | A | S | H | L | R | R | A | D | 736 |
| 2209 | GGG | CGA | CGG | TGG | TTG | GCC | TAC | CGC | CTA | CGT | CGG | CTG | CGT | CGC | CTG | GGA | 2256 |
| 737 | G | R | R | W | L | A | Y | R | L | R | R | L | R | A | L | G | 752 |
| 2257 | ATT | TGG | GCG | GGC | ACG | ATG | ATG | CCA | CTG | GGC | ACC | GGG | CGC | GGG | GTA | GTA | 2304 |
| 753 | I | W | A | G | T | M | M | P | L | G | T | G | R | G | V | V | 768 |
| 2305 | TGA | TAT | GAA | ACC | GAC | GGC | GGA | GAT | GAG | GCG | CAT | GGC | ATT | TTC | CCA | 2352 |
| 769 | * | Y | E | T | D | G | G | D | E | A | H | G | I | F | P | 784 |
| 2353 | CTG | ATA | AAT | GGG | GAG | TTG | TAT | GCT | ACT | TTA | ATA | TCG | CCA | CTC | CTG | TTA | 2400 |
| 785 | L | I | N | G | E | L | Y | A | T | L | I | S | P | L | L | L | 800 |
| 2401 | GTA | TTT | ATA | TTG | ATG | GCG | GCC | GC | | | | | | | | | 2423 |
| 801 | V | F | I | L | M | A | A | | | | | | | | | | 807 |

Fig. 51

```
*** INPUT INFORMATION ***

FILE NAME   : MSS2C.SEQ              SEQUENCE : NORMAL    2007 BP

CODON TABLE : UNIV.TCN

SEQUENCE    REGION :    1  -  2007

TRANSLATION REGION :    1  -  2007

*** DNA TRANSLATION ***

1  GCT GAG GCT GAG GCC GGG GGC AAG GAC GCG CCG GAG AGG AGC GGC    48
  1   A   E   A   E   A   G   G   K   D   A   P   E   R   S   G    16

49  GAC GCC GCC AGG TTG CCC CGC GCT CGG CCG AAT GCG GTC TCC AAA CGG    96
 17   D   A   A   R   L   P   R   A   R   P   N   A   V   S   K   R    32

97  AGG GAT CCT CTT CAG CAG GTC GGC CGG TAC TGC GCG ACG GGA AAC   144
 33   R   D   P   L   Q   Q   V   G   R   Y   C   A   T   G   N    48

145  ACG GCC AGG ACC GGC GCC GCG TCC TGC CAG AAC GCC GCA TTG GCG GAC   192
 49   T   A   R   T   G   A   A   S   C   Q   N   A   A   L   A   D    64

193  GTT GAG ATC GTT GAG ATC AAG TCC ATC GTC GCC GCG CCG ACG AGC   240
 65   V   E   I   V   E   I   K   S   I   V   A   A   P   T   S    80

241  ATA GTG AAG TTC CCA GGG CGC CTA GGG CTC CCA GAT GAT CCT TCC CTC TGG   288
 81   I   V   K   F   P   G   R   L   G   L   P   D   D   P   S   L   W    96

289  GAC ATA GCA CCG GAG ACT GTC CTC CCA GCC AAG CCG CCA CTG CAT GAA   336
 97   D   I   A   P   E   T   V   L   P   A   K   P   P   L   H   E   112

337  TCG CCT GCG GTT GAC GGA GAT TCA AAT GGA ATT GCA CCT CCT ACA GTT   384
113   S   P   A   V   D   G   D   S   N   G   I   A   P   P   T   V   128
```

Fig. 51 continued

| pos | | | | | | | | | | | | | | | | | pos |
|---|---|---|---|---|---|---|---|---|---|---|---|---|---|---|---|---|---|
| 385 / 129 | GAG E | CCA P | TTA L | GTA V | CAG Q | GAG E | GCC A | ACT T | TGG W | GAT D | TTC F | AAG K | AAA K | TAC Y | ATC I | GGT G | 432 / 144 |
| 433 / 145 | TTT F | GAC D | GAG E | CCT P | TCT S | TTT F | GAA E | GAA E | GCG A | AAG K | GAT D | TCC S | AGG R | GTT V | GCA A | GAT D | 480 / 160 |
| 481 / 161 | GAT D | GCT A | GGT G | TCT S | TTT F | GAA E | CAT H | TAT Y | AAG K | GAT D | ATG M | CTG L | ATT I | GGC G | CTT L | TGT C | 528 / 176 |
| 529 / 177 | GGG G | GAG E | AAT N | GTT V | ATG M | AAC N | GTG V | ATC I | TAT Y | ACA T | GCT A | ATG M | GGA G | GAA E | TGT C | CCA P | 576 / 192 |
| 577 / 193 | TGG W | TGC C | AAA K | ACA T | AGA R | GGA G | CTT L | GGT G | CTT L | GGA G | GCT A | GTG V | GGT G | TGT C | TTA L | CCA P | 624 / 208 |
| 625 / 209 | GCT A | TTA L | GCG A | AGA R | AGA R | GGA G | CAT H | CGT R | GTT V | GAT D | GTG V | GTT V | GTG V | CCA P | AGG R | AAG K | 672 / 224 |
| 673 / 225 | GGG G | GAC D | TAT Y | GTG V | GAA E | GCC A | TTT F | GAT D | ATG M | GGA G | ATC I | CGG R | CAT H | AAA K | TAC Y | TAC Y | 720 / 240 |
| 721 / 241 | GCT A | GCA A | GAC D | CAG Q | TTT F | CTA L | GAA E | GTG V | GTT V | AAC N | TAT Y | GCC A | CAT H | TTT F | ATT I | AAA K | 768 / 256 |
| 769 / 257 | GGA G | GTC V | ATA I | TAT Y | GGG G | CAG Q | TTC F | AGT S | GAC D | GTG V | ATG M | GAA E | TCT S | CGG R | GCA A | GAT D | 816 / 272 |
| 817 / 273 | GAC D | ATA I | TAT Y | GGG G | TTT F | GTT V | GAG E | CAG Q | CCT P | TGG W | ATC I | TTC F | CAC H | CGG R | ATG M | CAA Q | 864 / 288 |
| 865 / 289 | TTT F | TGC C | AAG K | GTT V | GCT A | GAG E | AAT N | CCT P | TGG W | CAC H | ATG M | ATG M | AAG K | TGC C | GGT G | ATT I | 912 / 304 |
| 913 / 305 | GTG V | TGC C | TAC Y | GGA G | GAT D | AAT N | TTG L | GTG V | TTC F | ATT I | GCC A | CGC R | CCA P | ATG M | AAT N | TGG W | 960 / 320 |

Fig. 51 continued

| | | | | | | | | | | | | | | | | |
|---|---|---|---|---|---|---|---|---|---|---|---|---|---|---|---|---|
| 961 | ACT | GCA | CTC | CTG | CCT | GTT | TAT | CTG | AAG | GCA | TAT | TAC | AGA | GAC | CAT | GGG | 1008 |
| 321 | T | A | L | L | P | V | Y | L | K | A | Y | R | D | H | G | | 336 |
| 1009 | TTA | ATG | CAG | TAC | ACT | CGC | GGT | TCC | GTC | CTC | GTC | CAT | AAC | ATC | GGC | CAC | 1056 |
| 337 | L | M | Q | Y | T | R | G | S | V | L | V | H | N | I | G | H | 352 |
| 1057 | CAG | GGC | CGT | GGT | CCT | GTA | CAT | GAA | TTC | CCG | TAC | ATG | GAC | TTG | CTG | AAC | 1104 |
| 353 | Q | G | R | G | P | V | H | E | F | P | Y | M | D | L | L | N | 368 |
| 1105 | ACT | AAC | CTT | CAA | CAT | TTC | GAG | CTG | TAC | GAT | CCC | GTC | GGC | GAG | CAC | 1152 |
| 369 | T | N | L | Q | H | F | E | L | Y | D | P | V | G | E | H | 384 |
| 1153 | GCC | ATC | TTT | GCC | GCG | TGT | GTT | CTG | AAG | ATG | GCA | GAC | CGG | CGT | GTG | GTG | 1200 |
| 385 | A | I | F | A | A | C | V | L | K | M | A | D | R | R | V | V | 400 |
| 1201 | ACT | GTC | AGC | CGC | GGC | TAC | ATC | GAG | CTG | AAG | ACA | GTG | GAA | GGC | GGC | 1248 |
| 401 | T | V | S | R | G | Y | I | E | L | K | T | V | E | G | G | 416 |
| 1249 | TGG | GGC | CTC | CAC | GAC | ATC | AAC | GAC | TGG | TCT | AAC | GAC | TGG | AAG | ATC | AAT | GGC | 1296 |
| 417 | W | G | L | H | D | I | N | D | W | S | N | D | W | K | I | N | G | 432 |
| 1297 | ATT | CGT | GAA | CGG | CGG | ATC | CAC | CAG | GAG | TGG | AAC | TAC | CCC | CTC | CGG | GAC | GTG | 1344 |
| 433 | I | R | E | R | R | I | H | Q | E | W | N | Y | P | L | R | D | V | 448 |
| 1345 | CAC | CTG | CGG | TCG | GAC | GGC | TAC | AAG | GAG | TGG | AAC | TAC | CCC | CTC | CGG | GAC | GTG | 1344 |
| | | | | | | | | | | | | | | | | | |
| 1345 | CAC | CTG | CGG | TCG | GAC | GGC | TAC | AAG | TGG | AAC | TAC | CTG | GGC | TTC | ATC | GGC | GAC | 1392 |
| 449 | H | L | R | S | D | G | Y | K | W | N | Y | L | G | F | I | G | D | 464 |
| 1393 | GCT | GGA | AAG | CGC | GAC | GAC | GTG | CCG | CTG | CTC | CGG | ATC | GGG | CGT | CTG | GAT | 1440 |
| 465 | A | G | K | R | D | D | V | P | L | L | R | I | G | R | L | D | 480 |
| 1441 | GAA | GTG | CGC | GAC | GAC | GTG | CCG | CTG | CTC | GGC | TTC | ATC | GGG | ATG | TGG | CTG | 1488 |
| 481 | E | V | R | D | D | V | P | L | L | G | F | I | G | M | W | L | 496 |
| 1489 | GGA | CAG | AAG | GGC | GTG | GAC | ATC | ATC | GGG | GAC | GCG | ATG | CCG | TGG | ATC | GCG | 1536 |
| 497 | G | Q | K | G | V | D | I | I | G | D | A | M | P | W | I | A | 512 |

Fig. 51 continued

| | | | | | | | | | | | | | | | | |
|---|---|---|---|---|---|---|---|---|---|---|---|---|---|---|---|---|
| 1537 513 | GGG G | CAG Q | GAC D | GTG V | CAG Q | CTG L | GTG V | ATG M | CTG L | GGC G | ACC T | GGC G | CCA P | CCT P | GAC D | CTG L | 1584 528 |
| 1585 529 | GAA E | CGA R | ATG M | CTG L | CAG Q | CAC H | GTG V | TTG L | GAG E | CGG R | CAT H | CCC P | AAC N | AAG K | GTG V | CGC R | 1632 544 |
| 1633 545 | GGG G | TGG W | GTC V | GGG G | CTG L | TTC F | TCG S | GTC V | ATG M | GAG E | CAT H | CGC R | ATC I | ACG T | CCG P | GGC G | 1680 560 |
| 1681 561 | GCC A | AGC S | GTG V | CTG L | GTG V | ATG M | GCA A | TAC Y | CCC P | GCC A | CAT H | CGC R | GGG G | CTG L | AAC N | CAG Q | 1728 576 |
| 1729 577 | CTC L | TAC Y | GCG A | ATG M | GCA A | TAC Y | ACC T | GGC G | ACC T | GTG V | CCT P | GTG V | CAC H | GCC A | GTG V | GGC G | 1776 592 |
| 1777 593 | GGG G | CTC L | AGG R | GAC D | ACC T | TTT F | GAC D | CGC R | GCC A | CCG P | TTC F | TTC F | GGC G | GAC D | GCC A | GGG G | 1824 608 |
| 1825 609 | CTC L | GGG G | TGG W | ACT T | TTT F | CTC L | CTC L | GCC A | GAG E | GCC A | AAG K | AAG K | CTG L | ATC I | GAG E | GTG V | 1872 624 |
| 1873 625 | CTC L | AGC S | CAC H | CAG Q | CAG Q | GCG A | ACG T | ATG M | TCG S | CGA R | AAC N | TAC Y | AGC S | GAG E | TGG W | AAG K | 1920 640 |
| 1921 641 | AGT S | CTC L | CAG Q | GCG A | GGC G | ATG M | CTT L | GTC V | AAC N | AAC N | CTC L | AGC S | TGG W | GAC D | CAC H | GCG A | 1968 656 |
| 1969 657 | GCT A | GAG E | CTC L | TAC Y | GAG E | GAC D | GTC V | CTT L | GTC V | AAG K | TAC Y | CAG Q | TGG W | | | | 2007 669 |

Fig. 52

```
*** INPUT INFORMATION ***

FILE NAME    : MSS1B.SEQ             SEQUENCE : NORMAL    1749 BP
CODON TABLE  : UNIV.TCN

SEQUENCE    REGION :    1 -  1749
TRANSLATION REGION :    1 -  1749

*** DNA TRANSLATION ***

1  TGC GTC GCG GAG CTG AGC AGG GAG GGG CCC GCG CCG CGC CCG CTG CCA    48
  1   C   V   A   E   L   S   R   E   G   P   A   P   R   P   L   P    16

49  CCC GCG CTG CTG GCG CCC CCG CTG GTG CCC GGC TTC CTC GCG CCG CCG    96
 17   P   A   L   L   A   P   P   L   V   P   G   F   L   A   P   P    32

97  GCC GAG CCC ACG GGT GAG GAC CCG GCA TCG ACG CCG CCC GTG CCC GAC   144
 33   A   E   P   T   G   E   D   P   A   S   T   P   P   V   P   D    48

145  GCC GGC CTG GGG GAC CTC GGT CTC GAA CCT GAA GGG ATT GCT GAA GGT   192
 49   A   G   L   G   D   L   G   L   E   P   E   G   I   A   E   G    64

193  TCC ATC GAT AAC ACA GTA GTT GTG GCA AGT GAG CAA GAT CAA TCT GAG   240
 65   S   I   D   N   T   V   V   V   A   S   E   Q   D   Q   S   E    80

241  GTG GTT GGA AAG GAG CAA GCT CGA GCT CGA GTA AAA ACA GCA AGC ATT GTC   288
 81   V   V   G   K   E   Q   A   R   A   K   V   T   Q   S   I   V    96

289  TTT GTA ACC GGC GAA TCT CCT TAT GCA AAG TCT GGG CTA GGA   336
 97   F   V   T   G   E   A   S   P   Y   A   K   S   G   L   G   112

337  GAT GTT TGT GGT TCA TTG CCA GTT GCT CTT GCT CGT GGT CAC CGT   384
113   D   V   C   G   S   L   P   V   A   L   A   A   R   G   H   R   128
```

Fig. 52 continued

| | | | | | | | | | | | | | | | |
|---|---|---|---|---|---|---|---|---|---|---|---|---|---|---|---|
| 385 | GTG | ATG | GTT | GTA | ATG | CCC | AGA | TAT | TTA | AAT | GGT | ACC | TCC | GAT | AAG | AAT | 432 |
| 129 | V | M | V | V | M | P | R | Y | L | N | G | T | S | D | K | N | 144 |
| 433 | TAT | GCA | AAT | GCA | TTT | TAC | AGA | ACA | GAA | AAA | CAC | ATT | CGG | CCA | TGC | TTT | 480 |
| 145 | Y | A | N | A | F | Y | R | T | E | K | H | I | R | P | C | F | 160 |
| 481 | GGT | GAA | CAT | GAA | GTT | GTT | ACC | TTC | TTC | CAT | GAG | ATT | TAT | AGA | GAT | GTT | 528 |
| 161 | G | E | H | E | V | V | T | F | F | H | E | I | Y | R | D | V | 176 |
| 529 | GAC | TGG | GTG | TTT | GTT | GAT | CAT | CCC | TCA | CCC | TAT | CAC | AGA | CCT | GGA | TTA | 576 |
| 177 | D | W | V | F | V | D | H | P | S | P | Y | H | R | P | G | L | 192 |
| 577 | TAT | GGA | GAT | AAG | TTT | GGT | GCT | GCT | TTT | GAT | CCT | AAT | CAG | TTC | AGA | ACA | 624 |
| 193 | Y | G | D | K | F | G | A | A | F | D | P | N | Q | F | R | T | 208 |
| 625 | CTC | CTT | TGC | TAT | GCA | TGT | GCA | GAG | GAG | CCT | CCT | ATC | CTT | GAA | TTG | GGA | 672 |
| 209 | L | L | C | Y | A | C | A | E | E | P | P | I | L | E | L | G | 224 |
| 673 | GGA | TAT | ATT | TAT | GGA | CAG | CAG | AAT | TGC | TTT | GTT | GCA | AAA | GTC | AAT | GAT | CAT | 720 |
| 225 | G | Y | I | Y | G | Q | Q | N | C | F | V | A | K | V | N | D | H | 240 |
| 721 | GCC | AGT | CTA | GTG | CCA | TCC | CGC | CTT | CTT | GCA | AGC | ATT | CTT | GTA | TAT | CCT | GAC | 768 |
| 241 | A | S | L | V | P | S | R | L | L | A | S | I | L | V | Y | P | D | 256 |
| 769 | GTT | TAT | AAA | GAC | TCC | GAG | CTG | GCA | AGC | ACA | TGG | GTA | ATA | CAT | CTT | GAA | 816 |
| 257 | V | Y | K | D | S | E | L | A | S | T | W | V | I | H | L | E | 272 |
| 817 | CAG | GGT | GTA | TAT | GGA | CCT | CTG | GAG | GCA | GCT | TTG | CCA | TTG | GCG | TGG | CCA | 864 |
| 273 | Q | G | V | Y | G | P | L | E | A | A | L | P | L | A | W | P | 288 |
| 865 | GAA | TGG | TAT | AAA | GAC | TTC | CCT | GAA | GCA | GAG | GAG | TTT | AAT | GGG | TGG | AGG | 912 |
| 289 | E | W | Y | K | D | F | P | E | A | E | E | F | N | G | W | R | 304 |
| 913 | CAT | GCC | CTT | GAC | AAG | GGT | GAC | ACT | GTC | AGT | AAG | GGT | GCA | CAT | GCA | GCT | 960 |
| 305 | H | A | L | D | K | G | D | T | V | S | K | G | A | H | A | A | 320 |
| 961 | GTG | ACA | GCA | GAT | CGA | ATC | GTG | ACT | GTC | AGT | AAG | TAT | TCG | TGG | GAG | GTT | 1008 |
| 321 | V | T | A | D | R | I | V | T | V | S | K | Y | S | W | E | V | 336 |

Fig. 52 continued

| | | | | | | | | | | | | | | | |
|---|---|---|---|---|---|---|---|---|---|---|---|---|---|---|---|
| 1009 337 | GTC V | ACA T | ACT T | GCT A | GAA E | GGT G | GGA G | CAG Q | GGC G | CTC L | AAT N | GAG E | CTC L | TTA L | AGC S | TCC S | 1056 352 |
| 1057 353 | AGA R | AAG K | AGT S | GTA V | TTA L | AAC N | GGA G | ATT I | GTA V | AAT N | GGA G | ATT I | GAC D | ATT I | AAT N | GAT D | 1104 368 |
| 1105 369 | TGG W | AAC N | CCT P | GCC A | ACA T | GAC D | AAA K | TGT C | ATC I | CCC P | TGT C | CAT H | TAT Y | TCT S | GTT V | GAT D | 1152 384 |
| 1153 385 | GAC D | CTC L | TCT S | GGA G | AAG K | GCC A | AAA K | TGT C | AAA K | GGT G | GCA A | TTG L | CAG Q | AAG K | GAG E | CTG L | 1200 400 |
| 1201 401 | GGT G | TTA L | CCT P | ATA I | AGG R | CCT P | GAT D | GTT V | GAT D | CTG L | CTC L | ATT I | CAA Q | TTT F | ATT I | AGG R | 1248 416 |
| 1249 417 | TTG L | GAT D | TAT Y | CAG Q | GAA E | GAT D | TGG W | ATG M | AGA R | TCT S | ACA T | GTC V | ATG M | GGC G | ATA I | GAT D | 1296 432 |
| 1297 433 | CTC L | ATG M | CGG R | GAA E | GAT D | GTT V | TGG W | GGA G | TTT F | AGT S | GAG E | TCG S | CTT L | TCT S | GGT G | CCA P | 1344 448 |
| 1345 449 | GAG E | CTT L | GAA E | GAT D | TGG W | ATG M | CCA P | TCC S | ATG M | GAG E | TCC S | ATC I | TTC F | CAC H | AAG K | GAT D | 1392 464 |
| 1393 465 | TTT F | CGT R | GGA G | TGG W | GTT V | ATA I | TTG L | GGA G | TTT F | AGT S | GTT V | CCA P | AGA R | TTC F | GAA E | CGA R | ATA I | ACT T | 1440 480 |
| 1441 481 | GCC A | CTT L | GAA E | GAT D | TAT Y | GCT A | ATG M | CAG Q | CAG Q | TAT Y | CCA P | TCC S | GGC G | TTC F | CCT P | GTT V | AAA K | CCT P | 1488 496 |
| 1489 497 | CTC L | GGG G | TGC C | CTT L | ATA I | TTG L | CAG Q | ACC T | GTG V | GAG E | GAG E | AAC N | TTC F | GTT V | ACA T | GGT G | 1536 512 |
| 1537 513 | GCA A | ACT T | GGG G | GGC G | CTT L | AGA R | GAT D | ACC T | GTG V | TCC S | TGG W | GAG E | AAC N | CCT P | TTC F | CAT H | 1584 528 |
| 1585 529 | GAG E | AAT N | GGA G | GAG E | CAG Q | GGT G | ACA T | GGG G | TGG W | GCA A | TTC F | CCC P | GCA A | CTA L | ACC T | ACA T | 1632 544 |

Fig. 52
continued

| 1633 | GAA | AAC | ATG | TTT | GTG | GAC | ATT | GCG | AAC | TGC | AAT | ATC | TAC | ATA | CAG | GGA | 1680 |
| 545 | E | N | M | F | V | D | I | A | N | C | N | I | Y | I | Q | G | 560 |
| 1681 | ACA | CAA | GTC | CTC | CTG | GGA | AGG | GCT | AAT | GAA | GCG | AGG | CAT | GTC | AAA | AGA | 1728 |
| 561 | T | Q | V | L | L | G | R | A | N | E | A | R | H | V | K | R | 576 |
| 1729 | CTT | CAC | GTG | GGA | CCA | TGC | CGC | | | | | | | | | | 1749 |
| 577 | L | H | V | G | P | C | R | | | | | | | | | | 583 |

Fig. 53

```
TRANSLATE of: mb73be2.seq check: 2027 from: 6 to: 2640
generated symbols 1 to: 878.

LOCUS       MZEGLUCTRN    2640 bp  ss-mRNA            PLN       May 20, 1993
DEFINITION  Maize starch branching enzyme II mRNA, complete cds.
KEYWORDS    1,4-alpha-glucan branching enzyme; amylo-transglycosylase;
            glucanotransferase; starch branching enzyme II.
SOURCE      Zea mays (cultivar B73) 30 days post pollenation endosperm . . . .

Mb73be2.pep  Length: 799  Transit peptide 1-61 May 20, 1993  13:29  Type: P
Check: 2844 ..

1  MAFRVSGAVL  GGAVRAPRLT  GGGEGSLVFR  HTGLFLTRGA  RVGCSGTHGA
  51  MRAAAAARKA  VMVPEGENDG  LASRADSAQF  QSDELEVPDI  SEETTCGAGV
 101  ADAQALNRVR  VVPPPSDGQK  IFQIDPMLQG  YKYHLEYRYS  LYRRIRSDID
 151  EHEGGLEAFS  RSYEKFGFNR  SAEGITYREW  APGAFSAALV  GDFNNWDPNA
 201  DRMSKNEFGV  WEIFLPNNAD  GTSPIPHGSR  VKVRMDTPSG  IKDSIPAWIK
 251  YSVQAPGEIP  YDGIYYDPPE  EVKYVFRHAQ  PKRPKSLRIY  ETHVGMSSPE
 301  PKINTYVNER  DEVLPRIKKL  GYNAVQIMAI  QEHSYYGSFG  YHVTNFFAPS
 351  SRFGTPEELK  SLIDRAHELG  LLVLMDVVHS  HASSNTLDGL  NGFDGTDTHY
 401  FHSGPRGHHW  MWDSRLFNYG  NWEVLRFLLS  NARWWLEEYK  FDGFRFDGVT
 451  SMMYTHHGLQ  VTFTGNFNEY  FGFATDVDAV  VYLMLVNDLI  HGLYPEAVTI
 501  GEDVSGMPTF  ALPVHDGGVG  FDYRMHMAVA  DKWIDLLKQS  DETWKMGDIV
 551  HTLTNRRWLE  KCVTYAESHD  QALVGDKTIA  FWLMDKDMYD  FMALDRPSTP
```

Fig. 53 continued

```
601 TIDRGIALHK MIRLITMGLG GEGYLNFMGN EFGHPEWIDF PRGPQRLPSG
651 KFIPGNNNSY DKCRRRFDLG DADYLRYHGM QEFDQAMQHL EQKYEFMTSD
701 HQYISRKHEE DKVIVFEKGD LVFVFNFHCN NSYFDYRIGC RKPGVYKVVL
751 DSDAGLFGGF SRIHHAAEHF TADCSHDNRP YSFSVYTPSR TCVVYAPVE*
801 *RGTRCCAAC VGLSM*GKTF FQNRQMHACM LQ*GSDTLID AGKPMHLAAL
851 SSLFI*DLQG VN*T*SFRFS LKKKKKKL
```

```
LOCUS       MZEGLUCTRN      2640 bp ss-mRNA              PLN       May 20,1993
DEFINITION  Maize starch branching enzyme II mRNA, complete cds.
KEYWORDS    1,4-alpha-glucan branching enzyme; amylo-transglycosylase;
            glucanotransferase; starch branching enzyme II.
SOURCE      Zea mays (cultivar B73) 30 days post pollenation endosperm
            cDNA to mRNA.
ORGANISM    Zea mays
STANDARD    full automatic
FEATURES             Location/Qualifiers
     sig_peptide     6..188
                     /codon_start=3
     mat_peptide     189..2402
                     /product="starch branching enzyme II"
                     /codon_start=3
     CDS             6..2402
                     /EC_number="2.4.1.18"
                     /product="starch branching enzyme II"
                     /codon_start=3 mb73be2.seq  Length: 2640  May 20, 1993  13:28  Type: N  Check: 2027
..
GCGAGATGGCGTTCCGGTTTCTGGGGGGTGCTCGGTGGGGCCGTAAGGCTCCCGACTCACCGGGGCGGGG
AGGGTAGTCTAGTCTTCCGGCACACCCGGCCTCTTCTTAACTCGGGGTGCTCGAGTTGATGTTCGGGGACGCACG
```

Fig. 53 continued

```
GGGCCATGCCGCGGCCGCGGCCCAGGAAGGCGGTCATGTTCCTGAGGCGAGAATGATGCCTCGCATCAA
GGGCTGACTCGGCTCAATTCCAGTCGGATGAACTCGGAGGTACCAGACATTTCTGAAGAGACAACGTGCGGTGCTG
GTGTGGCTGATGCTCAAGCCTTGAACAGAGTTCGAGTGGTCCCCCACCAAGCGATGACAAAAATATTCCAGA
TTGACCCCATGTTGCAAGCTATAGTACCATCTTGAGTATCGGTACAGCCCTCTATAGAAGAATCCGTTCAGACA
TTGATGAACATGAAGGAGGCTTGGAAGCCTTCCTGGAGCATTTCTGCAGCATGGTGGGTGACTTCAACAACTGGATCCAA
GTATCACATATCGAGAATGGGCTCCTGGAGCATTTTCTGCCTAACAATGCAGATGTACATCAC
ATGCAGATCGTATGAGCAGAAAATGAGTTGGTTTGTGTTTGGGAAATTTTCTGCCTAACAATGCAGATGTACATCAC
CTATTCCTCATGGATCTCGTGTAAAGTGAGAATGCTCCATCAGGGATAAAGATTCAATTCCAGCCTGGA
TCAAGTACTCAGTGCAGGCCCCAACCTAAACGACCAAAATCATTGCGGATATATGAAACACATGTCGGAATGAGTAGCC
ATGTGTTCAGGCATGCCATGCCAACCTAAACGACCAAAATCATTGCGGATATATGAAACACATGTCGGAATGAGTAGCC
CGGAACCGAAGATAAACACATATGTAAACTTAGGGATGAAGTCCTCCCAAGAATAAAAACTTGGATACAATG
CAGTGCAAATAATGCAATCCAAGAGCACTCATATTATGGAAGCTTTGGATACCATGTAACTAATTTTTTGCGC
CAAGTAGTCGTTTGGTACCCCAGAAGAATTCTTTGATTGATAGAGCACACATGAGCTTGGTTGTTGCTAGTTC
TCATGGATGTGGTTCATATGCGTCAAGTAATACTCTGGATGGGTTGAATGGTTTGATGGTACAGATACAC
ATTACTTTCACAGTGGTCCACGTGGCCATCACGTGGAGCTCGAGAGAATAAGTTTGATGGTTTCCGTTTGATGGTG
TTTTAAGATTTCTCTCCAATGCTAGATGGTGGCTCGAGAGAATAAGTTTGATGGTTTCCGTTTGATGGTG
TGACCTCCATGATGTAGACACTCATCACGGATTACTTGATGCTGTTAATTGATCTAATTCATGGATGTTCAATGACTTTATCCTGAGGCTGTAA
CCACCGATGTAGAGATGCAGTGGTTAGTGGACTGAATGCCTACATTTGCCCTCTCAAGCAAAGTGATGAAACTTGGAAGATGGGTTGTACTATC
CCATTGGTGACTCATATGCCTGTGCCTGACAAATAGGAGTTGGTTGATGGACAAGAGCATTACAAACGATGTAACTTATGCTGAAAGTCATGCCCCCTGATAGACCTTCAA
GATGCATATGCCTGTGCCTGACAAATAGGAGTTGGTTGATGGACAAGAGCATTACAAACGATGTAACTTATGCTGAAAGTCATGCCCCCTGATAGACCTTCAA
TGTGTCACACACTGACACAAGACTATTGCGTTTGGGATAGCATTAGAGTTTGGATGAATAACAACAGTTTGATCAGGAGGAGTTAGACTGTATCGTGCTGAAGAGTTCGCGCAAAGAGTCCAAGAGTTTGACCTGGTGATGCAGACT
ATCTTAATTCATGGTTTATTCCAGGGAATAACAACAGTTTGATCAGGAGGAGTTAGACTGTATCGTGCTGAAGAGTTCGCGCAAAGAGTCCAAGAGTTTGACCTGGTGATGCAGACT
GTGGTAAGTTTATTCATGGTTTATTCCAGGGAATAACAACAGTTTGATCAGGAGGAGTTAGACTGTATCGTGCTGAAGAGTTCGCGCAAAGAGTCCAAGAGTTTGACCTGGTGATGCAGACT
ATCTTAGGTATCATGGTATGCAACAACATGTTGATCAAGAGAGGAGTTAGACTGTATCGTGCTGAAAGCCTGGGTGTATAAGGTGG
CTGATCACCAGTAGTTCCACTGCAACAACAGCTATTGGTGGATTTAGACAAGAATCCATCACCAAGCAGAACATGTCGTCTATGCTCCAGTGG
TGTTCAACTTCCACTGCAACAACAGCTATTGGTGGATTTAGACAAGAATCCATCACCAAGCAGAACATGTCGTCTATGCTCCAGTGG
TCTTGACTCCGACGCTGGACTATTGGTGGATTTAGACAAGAATCCATCACCAAGCAGAACATGTCGTCTATGCTCCAGTGG
GTTCGCATGATAATAGCCCATTCGTTGCTGCGCCTACAATAAGGTTCTGATACTTTAATCGATGCTGGAAAAACCTTCTTCAAAACC
AGTGATAGCGGGGTACTCGTTGCTGCGCCATGTGGGGCGTGTGAGGATACTTTAATCGATGCTGGAAAAGCCCATGCATCTCGCTG
GCAGAGATGCATGCATGCTACAATAAGACCCTTCAAGGTGTGTCTGATACTTTAATCGATGCTGGAAAAGCCCATGCATCTCGCTG
CGTTGTCCTCTCTATTTATATAAGACCCTTCAAGGTGTGTCAATTAAACATAAGAGTTTTCGTTTTTTCGCTTAAAAAAA
AAAAAAAAAACTCA
```

Fig. 54

Maize Branching Enzyme I Mature Protein Sequence

```
  1  ATVQEDKTMA TAKGDVDHLP IYDLDPKLEI FKDHFRYRMK RFLEQKGSIE   51
     ENEGSLESFS KGYLKFGINT NEDGTVYREW APAAQEAELI GDFNDWNGAN  101
     HKMEKDKFGV WSIKIDHVKG KPAIPHNSKV KFRFLHGGVW VDRIPALIRY  151
     ATVDASKFGA PYDGVHWDPP ASERYTFKHP RPSKPAAPRI YEAHVGMSGE  201
     KPAVSTYREF ADNVLPRIRA NNYNTVQLMA VMEHSYYASF GYHVTNFFAV  251
     SSRSGTPEDL KYLVDKAHSL GLRVLMDVVH SHASNNVTDG LNGYDVGQST  301
     QESYFHAGDR GYHKLWDSRL FNYANWEVLR FLLSNLRYWL DEFMFDGFRF  351
     DGVTSMLYHH HGINVGFTGN YQEYFSLDTA VDAVVYMMLA NHLMHKLLPE  401
     ATVVAEDVSG MPVLCRPVDE GGVGFDYRLA MAIPDRWIDY LKNKDDSEWS  451
     MGEIAHTLTN RRYTEKCIAY AESHDQSIVG DKTIAFLLMD KEMYTGMSDL  501
     QPASPTIDRG IALQKMIHFI TMALGGDGYL NFMGNEFGHP EWIDFPREGN  551
     NWSYDKCRRQ WSLVDTDHLR YKYMNAFDQA MNALDERFSF LSSSKQIVSD  601
     MNDEEKVIVF ERGDLVFVFN FHPKKTYEGY KVGCDLPGKY RVALDSDALV  651
     FGGHGRVGHD VDHFTSPEGV PGVPETNFNN RPNSFKVLSP PRTCVAYYRV  701
     DEAGAGRRLH AKAETGKTSP AESIDVKASR ASSKEDKEAT AGGKKGWKFA  751
     RQPSDQDTK
```

Fig. 54 continued

```
ID   D11081     unannotated; RNA; UNA; 2763 BP.
XX
AC   D11081;
XX
DT   13-JUL-1992 (Rel. 32, Created)
DT   13-JUL-1992 (Rel. 32, Last updated, Version 1)
XX
DE   Zea mays L. maize branching enzyme-I cDNA to mRNA.
XX
FH   Key             Location/Qualifiers
FH
XX
SQ   Sequence 2763 BP; 719 A; 585 C; 737 G; 722 T; 0 other;

D11081 Length: 2763  February 4, 1993  11:16  Type: N  Check: 6169 ..

1  GCTGTGCCTC GTGTCGCCCT CTTCCTCGCC GACTCCGCTT CCGCCGCCGC
    51  GGCGCTCTCG CTCGCATGCT GATCGGGCGG CACCGCCGGG GATCGCGGGT
   101  GGCGGCAATG TGCGCCCTGAG TGTGTTGTCT GTCCAGTGCA AGGCTCGCCG
   151  GTCAGGGGTG CGGAAGGTCA AGAGCAAATT CGCCACTGCA GCTACTGTGC
   201  AAGAAGATAA AACTATGGCA ACTGCCAAAG GCGATGTCGA CCATCTCCCC
   251  ATATACGACC TGGACCCCAA GCTGGAGATA TTCAAGGACC ATTTCAGGTA
   301  CCGGATGAAA AGATTCCTAG AGCAGAAAGG ATCAATTGAA GAAAATGAGG
   351  GAAGTCTTGA ATCTTTTTCT AAAGGCTATT TGAAATTTGG GATTAATACA
   401  AATGAGGATG GAACTGTATA TCGTGAATGG GCACCTGCTG CGCAGGAGGC
   451  AGAGCTTATT GGTGACTTCA ATGACTGGAA TGGTGCAAAC CATAAGATGG
```

Fig. 54 continued

```
 501  AGAAGGATAA ATTTGGTGTT TGGTCGATCA AAATTGACCA TGTCAAAGGG
 551  AAACCTGCCA TCCCTCACAA TTCCAAGGTT AAATTTCGCT TTCTACATGG
 601  TGGAGTATGG GTTGATCGTA TTCCAGCATT GATTCGTTAT GCGACTGTTG
 651  ATGCCTCTAA ATTTGGAGCT CCCTATGATG GTGTTCATTG GGATCCTCCT
 701  GCTTCTGAAA GGTACACATT TAAGCATCCT CGGCCTTCAA AGCCTGCTGC
 751  TCCACGTATC TATGAAGCCC ATGTAGTAT GAGTGGTGAA AAGCCAGCAG
 801  TAAGCACATA TAGGGAATTT GCAGACAATG TGTTGCCACG CATACGAGCA
 851  AATAACTACA ACACAGTTCA GTTGATGGCA GTTATGGAGC ATTCGTACTA
 901  TGCTTCTTTC GGGTACCATG TGACAAATTT CTTTGCGGTT AGCAGCAGAT
 951  CAGGCACACC AGAGGACCTC AAATATCTTG TTGATAAGGC ACACAGTTTG
1001  GGTTTGCGAG TTCTGATGGA TGTTGTCCAT AGCCATGCAA GTAATAATGT
1051  CACAGATGGT TTAAATGGCT ATGATGTTGG ACAAAGCACC CAAGAGTCCT
1101  ATTTTCATGC GGGAGATAGA GGTTATCATA AACTTTGGGA TAGTCGGCTG
1151  TTCAACTATG CTAACTGGGA GGTATTAAGG TTTCTTCTTT CTAACCTGAG
1201  ATATTGGTTG GATGAATTCA TGTTTGATGG CTTCCGATTT GATGGAGTTA
1251  CATCAATGCT GTATCATCAC CATGGTATCA ATGTGGGGTT TACTGGAAAC
1301  TACCAGGAAT ATTTCAGTTT GGACACAGCT GTGGATGCAG TTGTTTACAT
1351  GATGCTTGCA AACCATTAA TGCACAAACT CTTGCCAGAA GCAACTGTTG
1401  TTGCTGAAGA TGTTTCAGGC ATGCCGGTCC TTTGCCGGCC AGTTGATGAA
```

Fig. 54
continued

```
1451  GGTGGGGGTTG GGTTTGACTA TCGCCTGGCA ATGGCTATCC CTGATAGATG
1501  GATTGACTAC CTGAAGAATA AAGATGACTC TGAGTGGTCG ATGGGTGAAA
1551  TAGCGCATAC TTTGACTAAC AGGAGATATA CTGAAAAATG CATCGCATAT
1601  GCTGAGAGCC ATGATCAGTC TATTGTTGGC GACAAAACTA TTGCATTTCT
1651  CCTGATGGAC AAGGAAATGT ACACTGGCAT GTCAGACTTG CAGCCTGCTT
1701  CACCTACAAT TGATCGAGGG ATTGCACTCC AAAAGATGAT TCACTTCATC
1751  ACAATGGCCC TTGGAGGTGA TGGCTACTTG AATTTTATGG GAAATGAGTT
1801  TGGTCACCCA GAATGGATTG ACTTTCCAAG AGAAGGGAAC AACTGGAGCT
1851  ATGATAAATG CAGACGACAG TGGAGCCTTG TGGACACTGA TCACTTGCGG
1901  TACAAGTACA TGAATGCGTT TGACCAAGCG ATGAATGCGC TCGATGAGAG
1951  ATTTTCCTTC CTTTCGTCGT CAAAGCAGAT CGTCAGCGAC ATGAACGATG
2001  AGGAAAAGT TATTGTCTTT GAACGTGGAG ATTTAGTTTT TGTTTTCAAT
2051  TTCCATCCCA AGAAAACTTA CGAGGGCTAC AAAGTGGGAT GCGATTTGCC
2101  TGGGAAATAC AGAGTAGCCC TGGACTCTGA TGCTCTCGGTC TTCGGTGGAC
2151  ATGGAAGAGT TGGCCACGAC GTGGATCACT TCACGTCGCC TGAAGGGGTG
2201  CCAGGGGTGC CCGAAACGAA CTTCAACAAC CGGCCGAACT CGTTCAAAGT
2251  CCTTTCTCCG CCCCGCACCT GTGTGGCTTA TTACCGTGTA GACGAAGCAG
2301  GGGCTGGACG ACGTCTTCAC GCGAAAGCAG AGACAGGAAA GACGTCTCCA
2351  GCAGAGAGCA TCGACGTCAA AGCTTCCAGA GCTAGTAGCA AAGAAGACAA
2401  GGAGGCAACG GCTGGTGGCA AGAAGGGATG GAAGTTTGCG CGGCAGCCAT
```

Fig. 54 continued

```
2451  CCGATCAAGA TACCAAATGA AGCCACGAGT CCTTGGTGAG GACTGGACTG
2501  GCTGCCGGCG CCCTGTTAGT AGTCCTGCTC TACTGGACTA GCCGCCGCTG
2551  GCGCCCTTGG AACGGTCCTT TCCTGTAGCT TGCAGGCGAC TGGTGTCTCA
2601  TCACCGAGCA GGCAGGCACT GCTTGTATAG CTTTTCTAGA ATAATAATCA
2651  GGGATGGATG GATGGTGTGT ATTGGCTATC TGGCTAGACG TGCATGTGCC
2701  CAGTTTGTAT GTACAGGAGC AGTTCCCGTC CAGAATAAAA AAAAACTTGT
2751  TGGGGGGTTT TTC
```

Fig. 55

```
*** INPUT INFORMATION ***

FILE NAME    : MSTS1TP.SEQ    SEQUENCE : NORMAL    153 BP

CODON TABLE  : UNIV.TCN

SEQUENCE REGION    :    1 -  153

TRANSLATION REGION :    1 -  153

*** DNA TRANSLATION ***

1  ATG GCG ACG CCC TCG GCC GTG GGC GCC GCG TGC CTC CTC GCG CGG    48
  1   M   A   T   P   S   A   V   G   A   A   C   L   L   A   R    16

49  GCC GCC TGG CCG GCC GCC GTC GGC GAC CGG GCG CGG CCG CGG CTC    96
 17   A   A   W   P   A   A   V   G   D   R   A   R   P   R   L    32

97  CAG CGC GTG CTG CGC CGC GTC GCG GAG CTG AGC AGG GAG GGG       144
 33   Q   R   V   L   R   R   V   A   E   L   S   R   E   G        48

145  CCC CAT ATG                                                   153
 49   P   H   M                                                     51
```

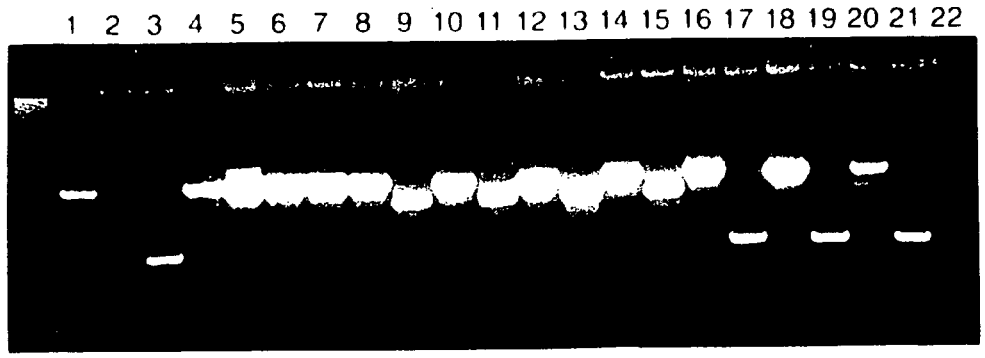

1. Marker;
2. PCR of WT DNA for glgC3;
3. PCR of WT DNA for SSI-2;
4. PCR of WT DNA for SSIIa-2;
5. PCR of C3-6 DNA for glgC3;
6. PCR of C3-9 DNA for glgC3;
7. PCR of C3-29 DNA for glgC3;
8. PCR of C3-35 DNA for glgC3;
9. PCR of C3-Ia-2 DNA for glgC3;
10. PCR of C3-Ia-2 DNA for SSI-2;
11. PCR of C3-Ia-3 DNA for glgC3;
12. PCR of C3-Ia-3 DNA for SSI-2;
13. PCR of C3-Ia-4 DNA for glgC3;
14. PCR of C3-Ia-4 DNA for SSI-2;
15. PCR of C3-Ia-5 DNA for glgC3;
16. PCR of C3-Ia-5 DNA for SSI-2;
17. PCR of C3-IIa-2 DNA for glgC3;
18. PCR of C3-IIa-2 DNA for SSIIa-2;
19. PCR of C3-IIa-5 DNA for glgC3;
20. PCR of C3-IIa-5 DNA for SSIIa-2;
21. PCR of C3-IIa-12 DNA for glgC3;
22. PCR of C3-IIa-12 DNA for SSIIa-2.

Fig. 56

Fig. 57

PLANT LIKE STARCHES AND THE METHOD OF MAKING THEM IN HOSTS

This application is a continuation of U.S. patent application Ser. No. 10/336,753, filed Jan. 6, 2003 now abandoned, which is a continuation of U.S. patent application Ser. No. 09/402,254, filed Oct. 1, 1999 and now abandoned, which is a 371 of PCT/US98/06660, filed Apr. 3, 1998.

BACKGROUND

1. Field of Invention

This invention relates to hosts containing constructs with genes from the starch pathway. More specifically the present invention relates to bacterial hosts that form plant like starches. Additionally the present invention relates to plant hosts that have genes from the starch pathway. The invention further relates to the starches produced by said hosts.

2. Description of Prior Art

The starch using industry includes diverse industries such as candy makers, makers of adhesives and paints, gravy makers, paper producers, etc. Since the demand for starch, (which is formed of amylose and amylopectin), has been dramatically increasing for specialized food and industrial uses, efforts have been undertaken to tailor the quantity and quality of starch for specific food and industrial uses.

This industry has over time looked for a number of different starches having, high viscosity, lower viscosity, higher gelling strength and lower gelling strength, different boiling points etc. Each starch tailored for a number of uses. The industry has utilized mutant starches that have less amylopectin and mutant starches with more amylose for tailored specifications. For example the increased amylose starch has been used in the gelled candy making area. And the industry has used the increased amylopectin starches formed by mutants such as wx and wx su2 containing little amylose and mostly amylopectin for thicken foods like pudding, pies, gravies, frozen foods and batters, stews, canned foods and baby food. Additionally the mutant starches of different types have usefulness as adhesives and as sizing.

The other method used to address the industry needs for tailored starch is the use of chemical modification of the starch. Chemical derivation of the starch are produced by chemically reacting the starch with the monofunctional reagents to introduce the substituents such as phosphate, acetate, succinate groups to stabilize the starch. Unfortunately, these types of starches can be subjected to government regulation and additionally have less acceptance generally due to the added cost of the starch.

Starch is the major form in which carbohydrates are stored in biological systems. Plant starch in chloroplasts is transitory and storage starch accumulates in storage organs of many plant. Starch can be found in all organs of most higher plants including leaves stems and roots and fruits and embryo and endosperm. In addition to higher plants starch similar polysaccharide (glycogen) has been found in bacteria. Many bacteria produce a reserve polysaccharide similar to the glycogen found in animals.

Storage polysaccharide has been classified as being in two groups, group one has storage in the cystol of the cell and the second group within the plastid. *Escherichia coli* produces a polysaccharide within the cytosol. Starch producing plants typically store starch in the plastids. Typical starch bearing plants include cassava, potato, corn, peas, rice, wheat, and barley. The main starch storing tissue of corn, rice wheat and barley and oats, the cereal grains, is the endosperm.

Starches are also classified by the plant source, for example cereal starches are from cereal grains such as maize, rice, wheat, barley, oats and sorghum; tuber and root starch are from potatoes and yams and cassava.

The pathway of starch synthesis is not well understood. Generally, as noted above starch from plants, consists of two major components: amylose and amylopectin. These intertwine in the starch granule of the plants. Amylose is a linear polymer of alpha 1-4 bonded anhydroglucose units while amylopectin is a branched polymer comprised of linear chains alpha 1-4 linked anhydroglucose units with branches resulting from alpha 1-6 linkages between the linear chains. It has been known for sometime that mutant genes in starch bearing plants can be expressed and that the properties of the starch can be altered. The proportion of the two components and their structures in the mutant primarily determine the physical-chemical properties of the starch.

Thus the lack of a clear understanding of the starch synthesis pathway and the difficulty of employing mutants limited the industry to the use of existing and producible mutant starches (cereals containing mutant starch can show a tremendous yield penalty in field environments) or to the chemical modification that could be made to the starch. In the last decade the industry has been studying the effects of certain starch genes in plants and bacteria in an attempt to more clearly understand starch synthesis. Since the late 80's it has been possible to transform plants and bacteria to contain isolated genes. In response to this the industry has transformed potatoes with a bacterial gene GS and with starch soluble synthase III gene in the antisense (forming a mutant). As part of these potato starch experiments bacteria has been transformed with certain potato starch genes. For example the SSSIII gene from potato was transformed into *E. coli* deficient in the glgA gene. The effect of glgC and branching enzyme I and II in combination in a mutant *E. coli* has also been studied and glycogen like product was reported. The starch industry that is commercial does not have a particular interest in the production of glycogen which is the polysaccharide produced by bacteria and animals (the health care industry may have some such interest). The industry has thus not yet been able to generate tailored starches at reasonable prices through plant gene transformation. There remains a need for the industry to find new starches that are useful due to their changed characteristics such as lower viscosity and new starches that are useful because of their higher viscosity and new methods of producing such starches.

Glycogen synthesis in *E. coli* and starch synthesis in higher plants have similar pathways involving ADPGlc pyrophosphorylase, starch synthase (SS), or glycogen synthase (GS), and branching enzyme (BE). It has been suggested that ADPGlc pyrophosphorylase plays a pivotal role in regulating the amount of starch synthesized, while starch synthase and starch branching enzyme primarily determine the starch structure. Multiple forms of SBE and SS have been identified in many plants including maize, rice, pea and potato. In addition to the waxy gene coding for granule bound starch synthase (GBSS), three genes coding for the other forms of SS have been isolated from maize endosperm. Maize is the only cereal crop from which the genes coding for the five forms of SS have been isolated. Clearly a number of these sequences are published and known to those of skill in the art. Genes coding for maize SBE have also been cloned and characterized. Previous reports have demonstrated that maize SBEI has a higher rate of branching amylose than SBEII and preferentially transfers longer chains, while SBEII shows a higher rate of branching amylopectin and preferentially transfers shorter chains. In comparison with SBE, less is known about the specificities and functions of multiple forms of SS. In Waxy maize, which lacks GBSS, only amylopectin is synthesized and amylose is missing. Therefore, it is generally accepted that GBSS, encoded by waxy gene, is primarily responsible for the synthesis of amylose. Study of waxy mutation in *Chlamedomonas reinhardtii* has suggested that GBSS is also involved in amylopectin synthesis. Although it has been reported that *Chlamedomonas reinhardtii* SSII controls the synthesis of intermediate size glucans of amylopectin in *Chlamedomonas*, direct evidence for the functions of SS in higher plants is still missing. Antisense technology has been used to study the functions of SS in potato, however, the results are inconclusive.

In an article written by Hanping Guan et al., entitled "A Maize Branching Enzyme Catalyzes Synthesis of Glycogen-like Polysaccharide in glg B-deficient *Escherichia coli*", published in Proc. Natl. Acad. Sci. USA, Vol. 92, pp. 964-967, February 1995 Plant Biology a specific glycogen like polysaccharide from a transformed *E. coli* was reported. This article taught the transformation of an *E. coli* bacteria with maize BEI and BEII. These enzymes were transformed into two *E. coli* hosts. One of the bacterial hosts was a wild type and the other was a mutant. The mutation to the bacteria was the reduction of the activity of glycogen BE in the AC71(glgB-) so that the mutant was essentially free of BE activity. The paper analyzed the debranched alpha-glucan isolated from the four different transformants. The first host was *E. coli* containing glgB and the second host was the AC71 without any transformed genes then AC71 with maize BEII, and then AC71 with maize BEI, then AC71 with maize BEI and BEII. The resultant polysaccharide products were analyzed by HPLC, by chain length and relative peak area and by mole distribution of chains. The study led to the understanding that BEII could play a role in synthesis of the short chains of amylopectin and BEI could be involved with the longer chains of amylopectin. The paper also noted that the mutant host AC71 produced more chains with chain length of 6 then did the wild type *E. coli*. The paper also noted that the maize BE and the GS of the host did not produce amylopectin like polysaccharides. The article suggested that the concerted action of GS with different BE's could play an important role in determining the final structure of the polysaccharide synthesized. The article by Guan ends by suggesting that his study had established the basis for studying the concerted actions of BE and SS in a bacterial model system.

The expression of *E. coli* GS (glycogen synthases) in potatoes showed a large incidence of highly branched starch. This result was published in an article in Plant Physiol. 104, 1159-1166 by Shewaker et al. This potato does not appear to be of much commercial use at this time.

The industry still needs the option of producing plant like starches in a fermentation process from bacteria and thus without the necessity of breeding and growing environment sensitive plants; and, the option of producing plants that generate the specific tailored starch through a plant host. And the industry needs altered and new starches that are cereal like starches or root and tuber like starches in large quantities and inexpensively thus avoiding having to use chemical modification of starch. The industry needs a host that can be readily transformed to supply different starches tailored to the industry's need. Specifically the industry needs a host that supplies various different starches including those not capable of being made in plants or bacteria presently.

Objects and Advantages

Accordingly, several objects and advantages of the invention are to produce plant like starch through the process of fermentation.

Additional objects and advantages are the production of new starches in plants.

Still further objects and advantages will become apparent from a consideration of the ensuing description and accompanying drawings.

Another object of the present invention is the synthesis of polysaccharides including amylose, amylopectin in *E. coli*, and/or fungal and yeast by plant starch synthesizing enzymes including SS, SBE, bacterial branching enzyme, glycogen synthase and other enzymes in other living organism.

Yet another object of my invention is using each or combination of these enzymes or modified enzymes studied in this patent to produce or to improve polysaccharides in any living organism including starch synthesis in plants.

SUMMARY OF THE INVENTION

The invention provides DNA constructs in a host that include most of the genes in the starch pathway of a plant such that the host produces a plant like polysaccharide. And in one embodiment produces maize starch including slightly different embodiments that make specific maize mutant like starch in a non plant host. This invention encompasses a bacterial host containing a combination of two or more of such genes SSI, SSIIa, SSIIb, SSSIII, GBSS, BEI and BEII when the combination does not form glycogen like material. This invention encompasses a plant host transformed with any of the following maize genes or a plant host having a combination of two or more of the following maize genes SSI, SSIIa, SSIIb, SSSIII, GBSS, BEI and BEII in a hybrid or an inbred rice plant.

Additionally the present invention includes new polysaccharide produced by a transformed host. The host having a wildtype, which does not produce the new polysaccharide, the transformed host expressing at least two exogenous starch synthesis genes, the genes are selected from a group consisting of starch synthesis genes such as SSI, SSIIa, SSIIb, SSSIII, GBSS and optionally including at least one of the BEI and BEII genes wherein the transformed host is capable of producing such new polysaccharide.

The invention also covers a new polysaccharide wherein the host also expresses the exogenous genes selected from the following group consisting of bacterial glycogen inducing genes are selected from the group glgA, glgB, glgC and any mutants thereof. Or wherein the host also expresses the exogenous genes selected from the following group consisting of plant granule bound enzymes. And the new polysaccharide wherein the starch synthesis genes are selected from the group consisting of BEI and BEII.

The present invention broadly encompasses a host containing a transformed Gig C gene and at least one of the starch branching enzymes genes in a host in combination with at least one other transformed starch gene wherein the host produces a polysaccharide product. And a host containing transformed bacterial gene and at least one of the non starch branching enzymes selected from the group consisting of debranching enzymes and soluble starch synthase A method of producing polysaccharides which are non glycogen like in a host comprising transforming a host capable of being used in a fermentation process, with genes selected from the group which produce starch synthesizing enzymes, or glycogen synthesizing enzymes such that the host produces nonglycogen like starch, and employing the host in a fermentation process that produces polysaccharides. The host is bacteria, or a fungal or a yeast. Additionally the method of this invention includes the use of bacterial genes also such as the glycogen synthesizing genes including the glgC, glgA, glgB genes. A method wherein the genes which produce starch synthesizing enzymes include genes encoding for starch soluble synthases I, IIa, IIb, and SS III (du11). A method wherein the genes which produce starch synthesizing enzymes include genes encoding for starch debranching enzyme and branching enzymes. The invention covers the modified starch synthesizing enzymes including the N-terminally truncated SS.

In other words, the invention covers a host transformed to carry a gene active in glycogen production, and at least one nonstarch branching gene active in the production of at least one of the following polysaccharides amylopectin and amylose in its original host. The host can be a monocot or a dicot plant. The host can be a cereal bearing plant, or the host can be a bacteria.

More specifically the invention includes a host wherein at least one nonstarch genes active in the production of at least one of the following polysaccharides, amylopectin and amylose in its original plant, is selected from the group consisting of starch soluble starch synthase I, IIa, IIb, III genes and debranching enzyme gene (su1), GBSS gene, sh2 gene and bt2 gene. A host including at least one of the starch branching enzyme genes such as BEI gene, BEII gene.

The present invention can also be described as a host transformed to carry a gene active in ADPG production, and at least one starch gene active in the production of at least one of the following polysaccharides amylopectin and amylose in its original host wherein the host produces polysaccharides that are plant like starch and not glycogen like.

Additionally the host can be transformed to carry a pyrophosphorylase gene, and glycogen synthase gene.

The scope of the present invention includes a host deficient in alpha 1,4 glucan synthesizing ability and alpha 1,4-1,6 branching enzyme capability transformed to express at least one plant starch soluble synthesis gene. And the host can also include being transformed to express at least one gene encoding for debranching enzyme, and/or a gene encoding for starch soluble synthase enzyme I, starch soluble synthase enzyme IIa, IIb, starch soluble synthase enzyme III. This host can include being transformed to express at least one gene encoding for starch branching enzyme.

This invention also includes the production of a glycogen like material in plants.

Attached hereto are a number of plasmids described by the figures and by Table 1 that are part of the present invention and are claimed herein. One such example is the plasmid wherein the plasmid is in a carrier host and the plasmid contains the SSIIa gene with the N-terminus GENVMNVIVV (seq id no:27) and wherein the gene is approximately 1561 base pairs in length. The invention includes mutant hosts such as mutant plants like waxy rice and potatoes and corn as example and wherein the host is a mutant *E. coli*, or fungus.

BRIEF DESCRIPTION OF THE DRAWINGS

FIG. 43 shows the DNA sequence (SEQ ID NO:36) and the protein sequence (SEQ ID NOs:36 and 37) for glgA having 1488 base pairs.

FIG. 44 shows the DNA sequence (SEQ ID NO:38) and the protein sequence (SEQ ID NOs:38 and 39) for glgB having 2361 base pairs.

FIG. 45a shows the DNA sequence (SEQ ID NO:40) for Zea mays 10-kDa zein gene having 2562 base pairs.

FIG. 45b shows the DNA sequence (SEQ ID NO:42) for Zea mays 10-kDa zein portion of the gene used as the promoter in a number of the plasmids discussed herein.

FIG. 46 shows the DNA sequence (SEQ ID NO:44) and the protein sequence (SEQ ID NOs:44 and 45) for glgC3 (glgC$_3$) having 1328 base pairs containing two mutations P295D, E296K. This is a mutant of the wild type glgC gene.

FIG. 47 shows the DNA sequence (SEQ ID NO:46) and the protein sequence (SEQ ID NOs:46 and 47) for glgC (glgC) having 1328 base pairs.

FIG. 48 shows the DNA sequence (SEQ ID NO:48) and the protein sequence (SEQ ID NOs:48 and 49) for glgCwt (glgCwt) having 1328 base pairs. This is the glgC gene that is found in nature.

FIG. 49 shows the DNA sequence (SEQ ID NO:50) and the protein sequence (SEQ ID NOs:50 and 51) for the maize waxy gene denoted wx herein.

FIG. 50 shows the DNA sequence (SEQ ID NO:52) and the protein sequence (SEQ ID NOs:52 and 53) for the maize starch soluble synthase IIb encoding gene having 2423 base pairs.

FIG. 51 shows the DNA sequence (SEQ ID NO:54) and the protein sequence (SEQ ID NOs:54 and 55) for the maize starch soluble synthase IIa.

FIG. 52 shows the DNA sequence (SEQ ID NO:56) and the protein sequence (SEQ ID NOs:56 and 57) for the maize starch soluble synthase I-2 having 1749 base pairs.

FIG. 53 shows the DNA sequence (SEQ ID NO:58) and the protein sequence (SEQ ID NOs:58 and 59) for the maize branching enzyme II.

FIG. 54 shows the DNA sequence (SEQ ID NO:60) and the protein sequence (SEQ ID NOs:60 and 61) for the maize branching enzyme I.

FIG. 55 shows the DNA sequence (SEQ ID NO:62) and the protein sequence (SEQ ID NOs:62 and 63) (153) for the transit peptide portion of the maize starch soluble synthase I.

FIG. 56, PCR analysis of transgenic rice plants. The genomic DNA isolated from rice plants was PCR amplified using specific primers for the inserted gene. The specific bands were identified on 1% agarose gel compared with non-transgenic rice plant.

FIG. 57. Activity staining of starch synthase on renaturing SDS-PAGE gel with iodine solution. The positive staining of maize SSI-2 indicated the expression of maize SSI-2 in transgenic rice plants.

PREFERRED EMBODIMENT—DESCRIPTION

Figure 1:
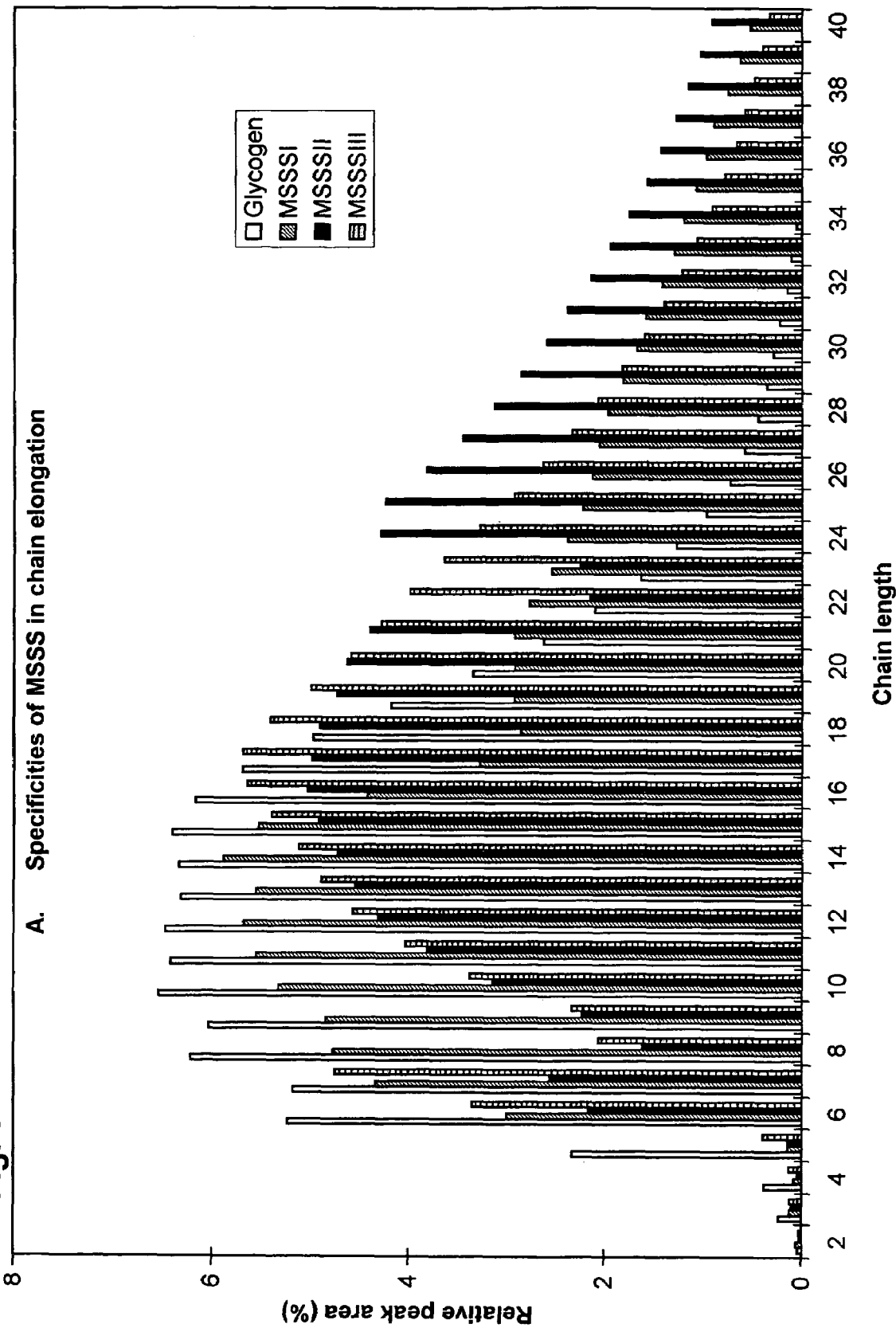
FIG. 1 shows a graph which gives the relative peak area in percent and the chain length of glycogen and starch soluble synthase I (SSI), starch soluble synthase II (SSIIa), starch soluble synthase IIb (SSIIb). Thus this shows the specificities of Maize SS's in chain elongation.
Figure 2:
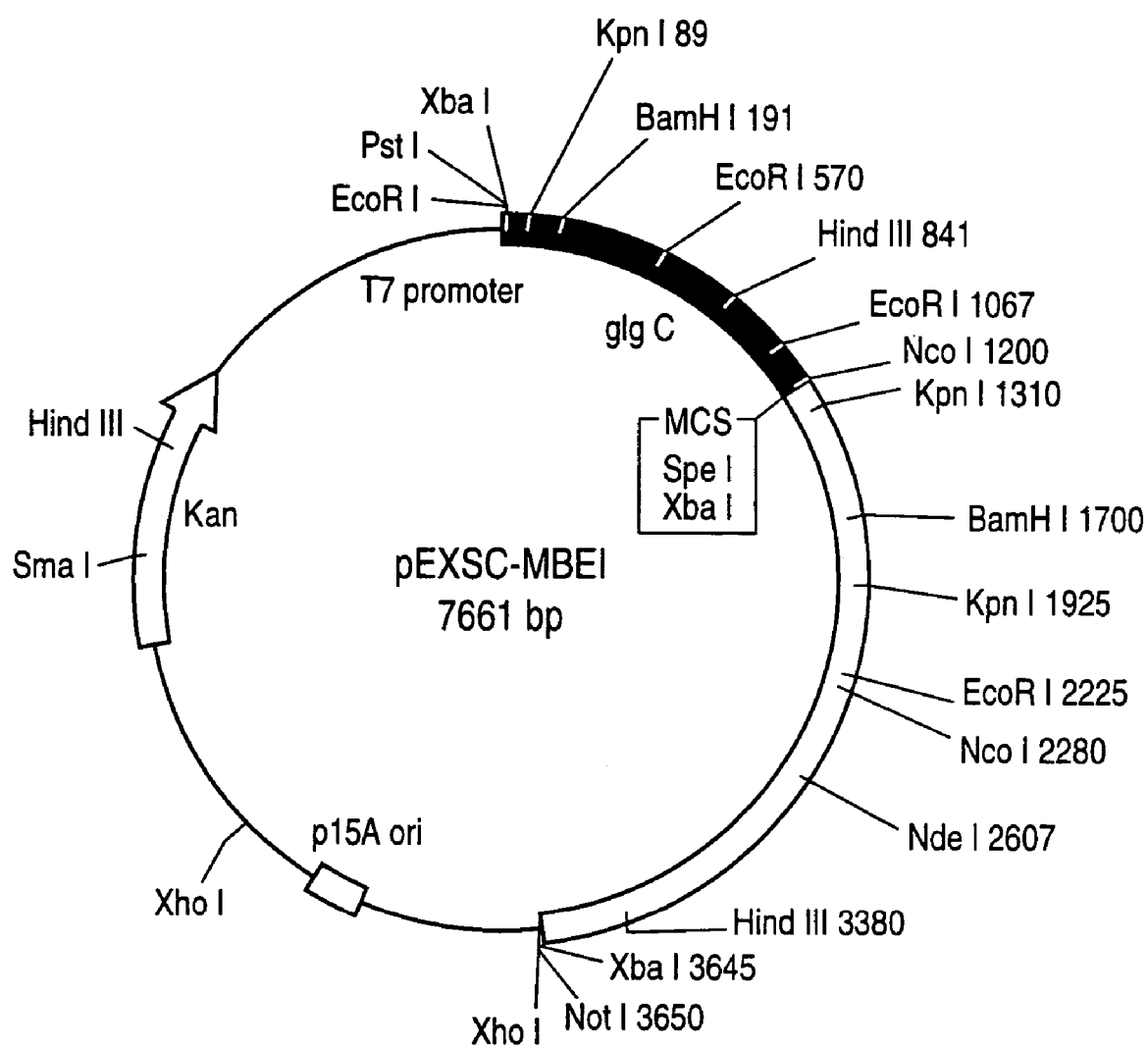
FIG. 2 shows plasmid pEXSC-MBEI with 7661 base pairs and promoter T7 and a Kanamycin gene and glgC and the maize starch branching enzyme I (MBEI).
Figure 3:
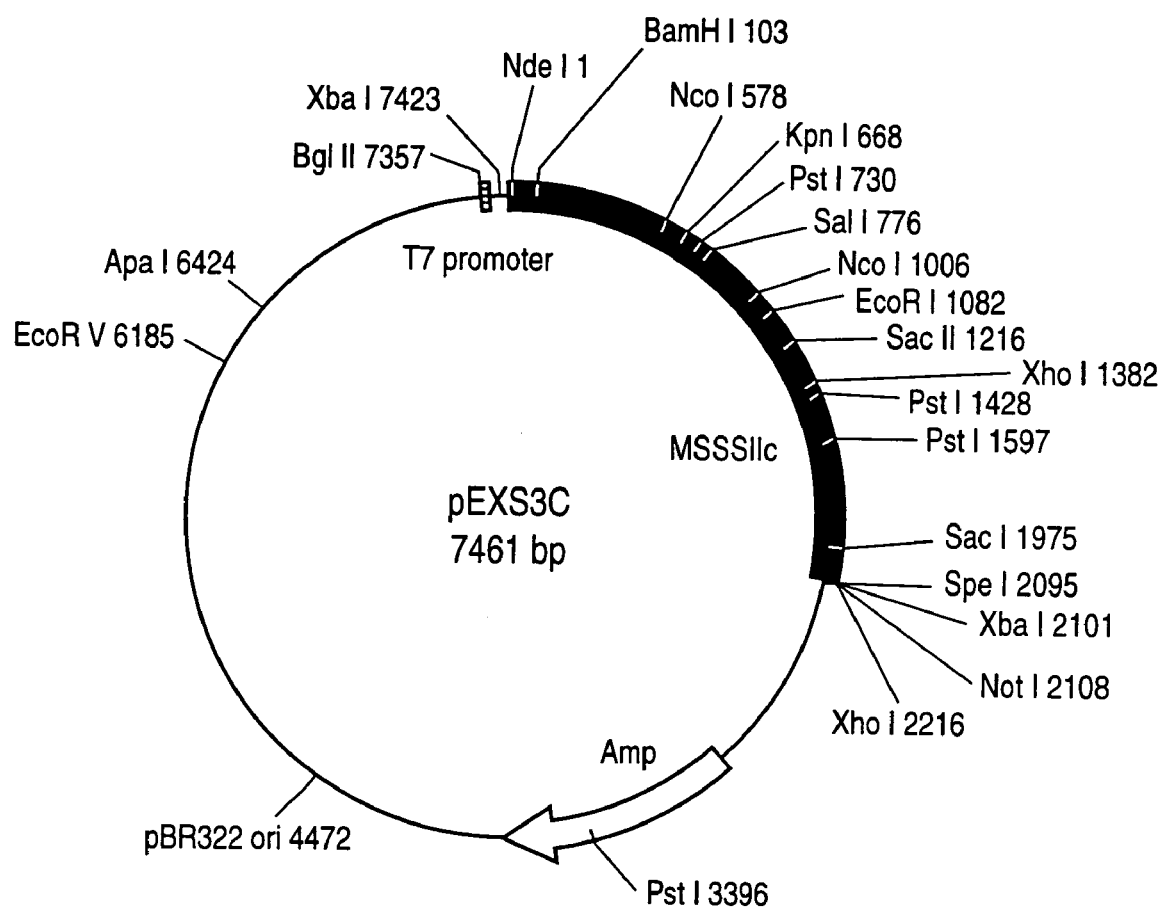
FIG. 3 shows plasmid pEXSC3C with 7461 base pairs and promoter T7 and ampicillin gene and the maize starch soluble synthase gene IIa. pEXS3c is the 1082 bp Nde I-EcoRI fragment containing the N-terminus of MSSSIIa (from MSSIIa in pBSK) subcloned into the Nde I-EcoRI sites of pEXS3a, replacing the N-terminus of IIA-2 with the longer IIa N-terminus. MSSIIa is the mature maize SSIIa and is 2090 bp long. The following sites are not contained in the MSSIIc insert: Apa I, BglII, Eco V, Not, Spe I, and Xba I. The N-terminus of this plasmid is AEAEAGGKD (SEQ ID NO:28).
Figure 4:
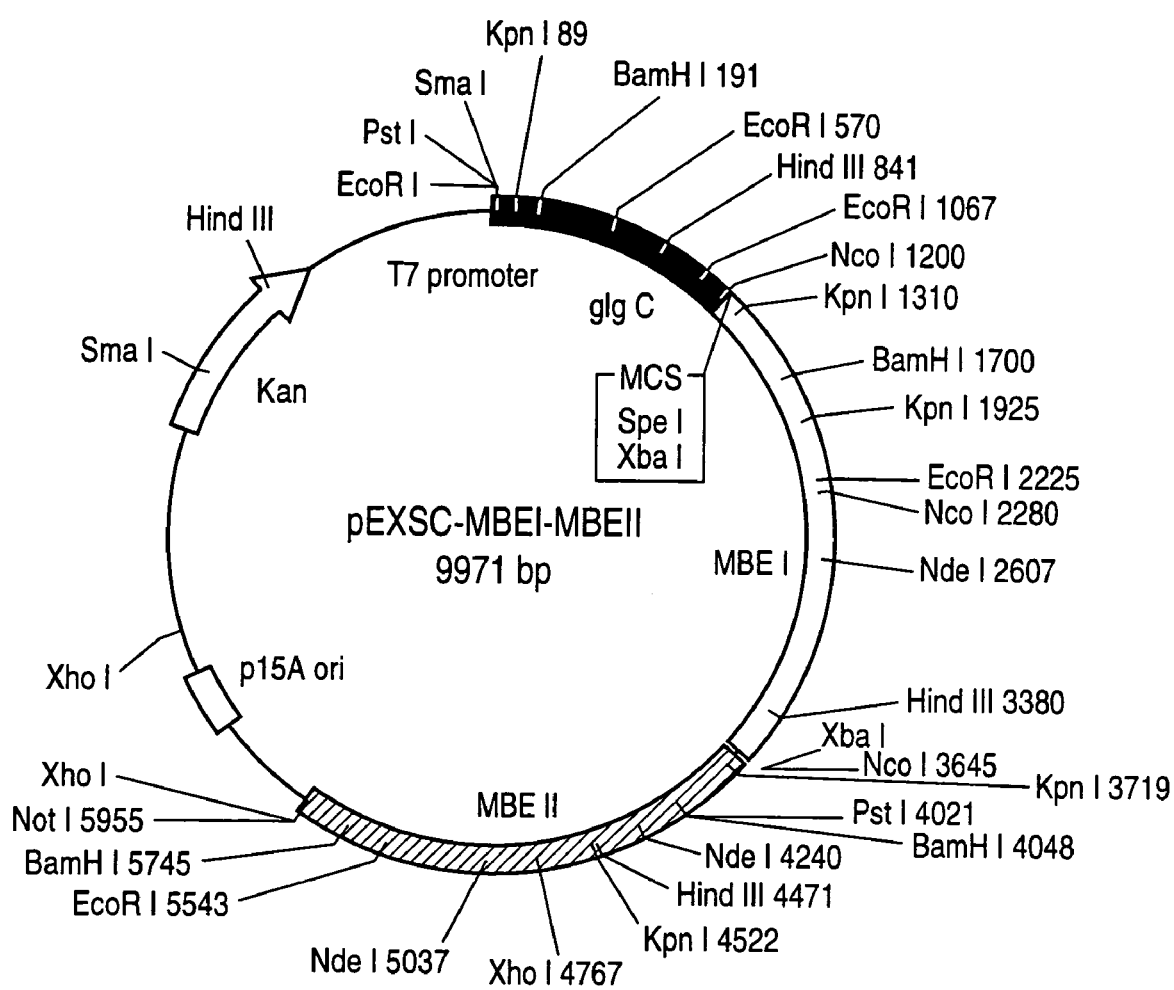
FIG. 4 shows plasmid pEXSC-MBEI-MBEII with 9971 base pairs and promoter T7 and a Kanamycin gene and glgC and the maize starch branching enzyme I (MBEI) and the maize starch branching enzyme II (MBEII).
Figure 5:
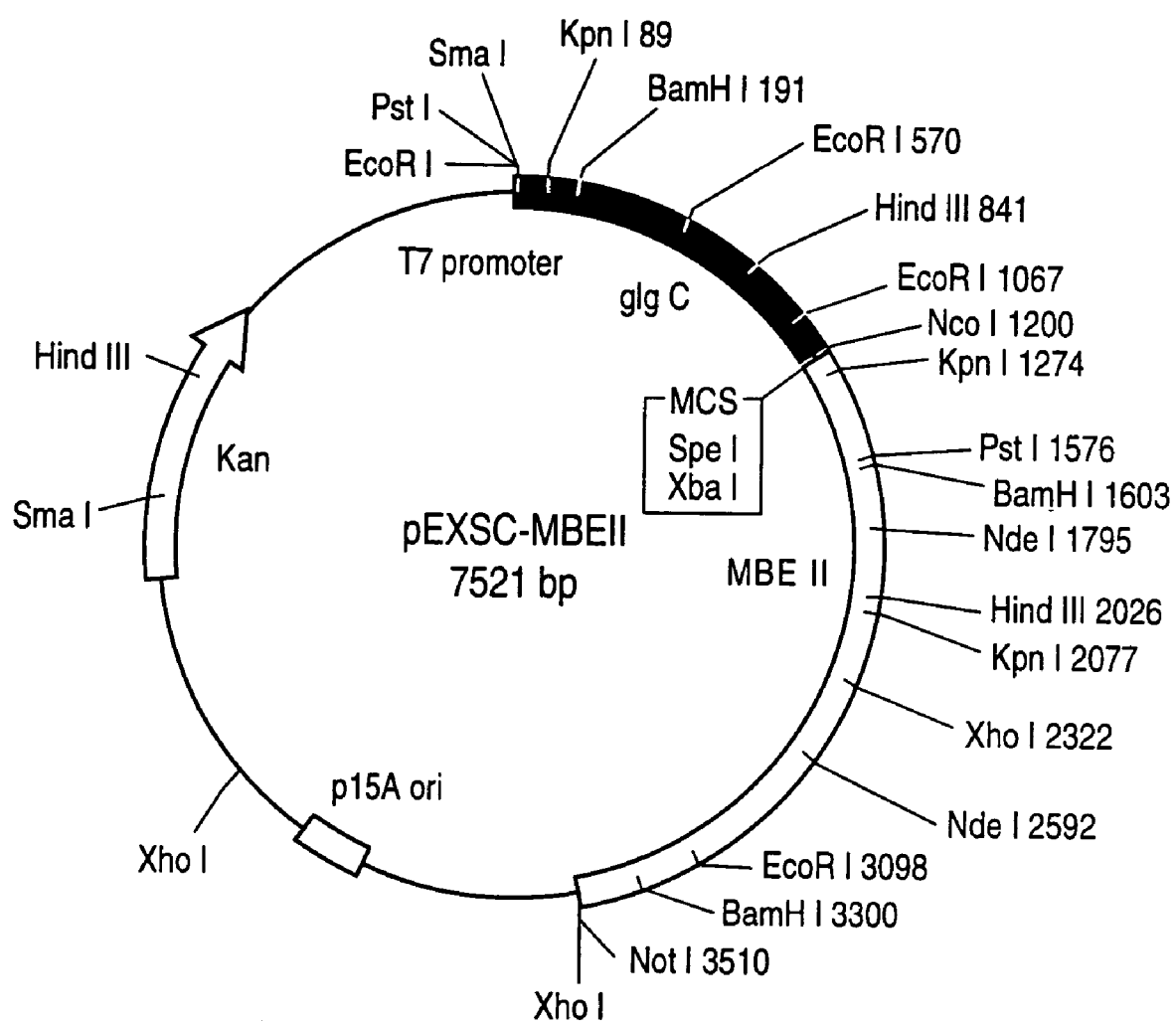
FIG. 5 shows plasmid pEXSC-MBEII with 7521 base pairs and promoter T7 and a Kanamycin gene and glgC and the maize starch branching enzyme II (MBEII).
Figure 6:
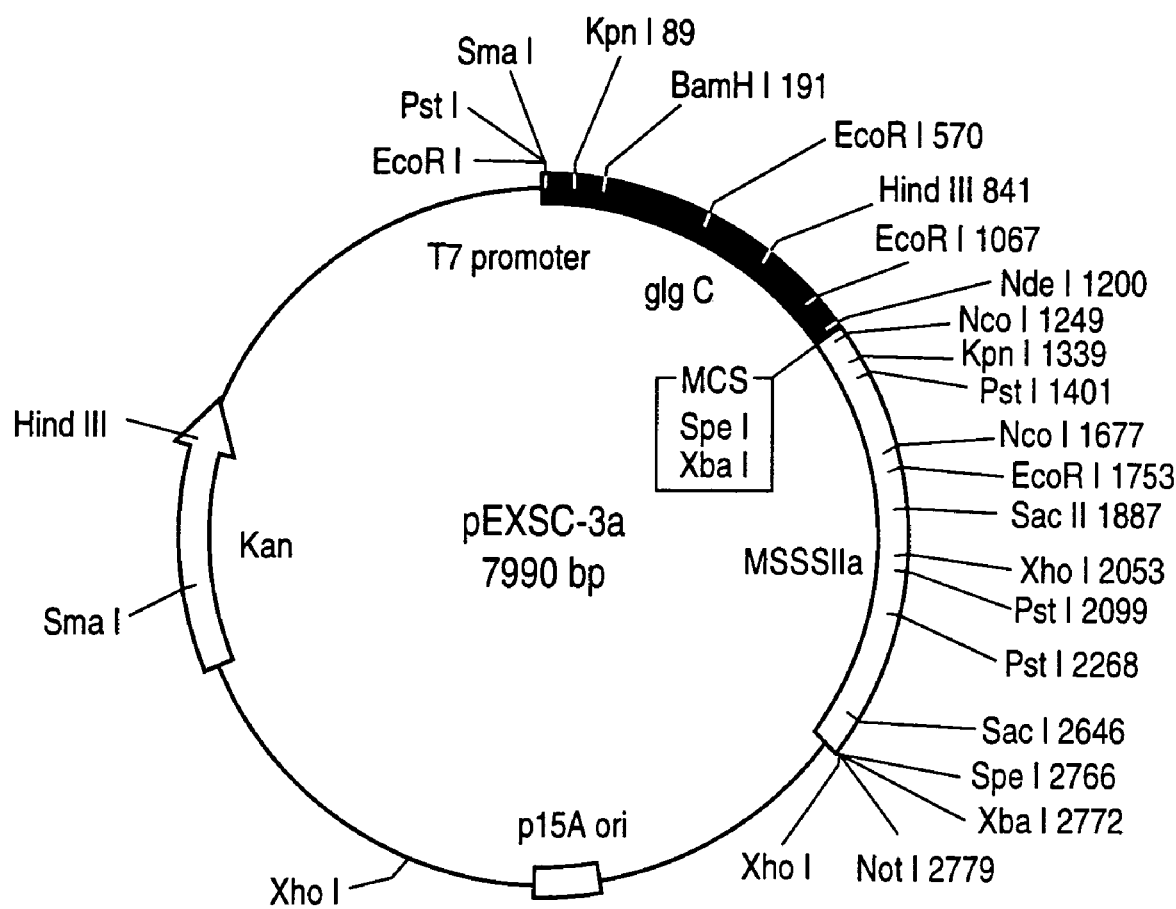
FIG. 6 shows plasmid pEXSC-3a with 7990 base pairs and promoter T7 and a Kanamycin gene and the glgC gene and the maize N-terminally truncated starch synthase gene IIa (MSSIIa-2). The N-terminal sequence is GENVMNVI (SEQ ID NO:1).
Figure 7:
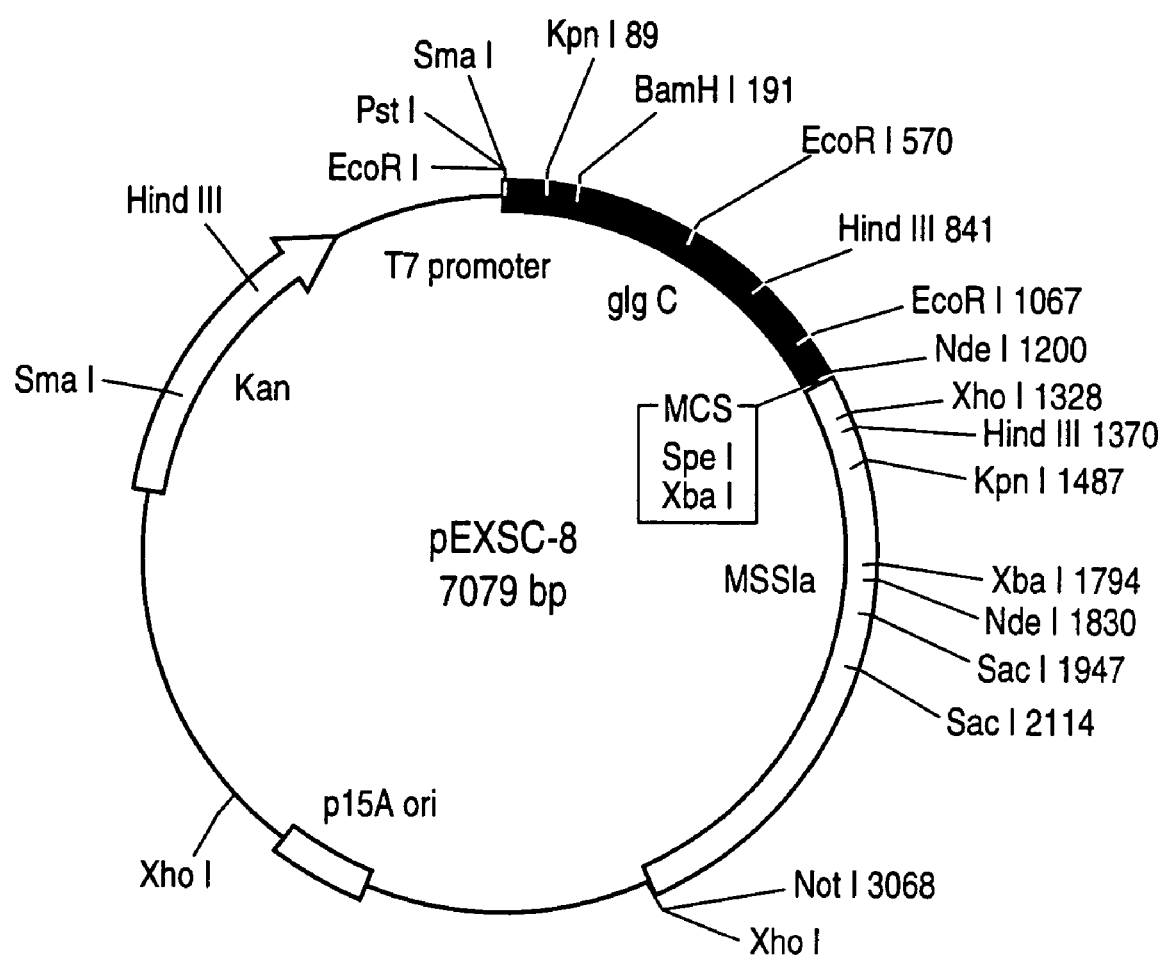
FIG. 7 shows plasmid pEXSC-8 with 7079 base pairs and promoter T7 and a Kanamycin gene and the glgC gene and the maize starch soluble synthase gene I and version I-2 (MSSI-2), an N-terminally truncated SSI.
Figure 8:
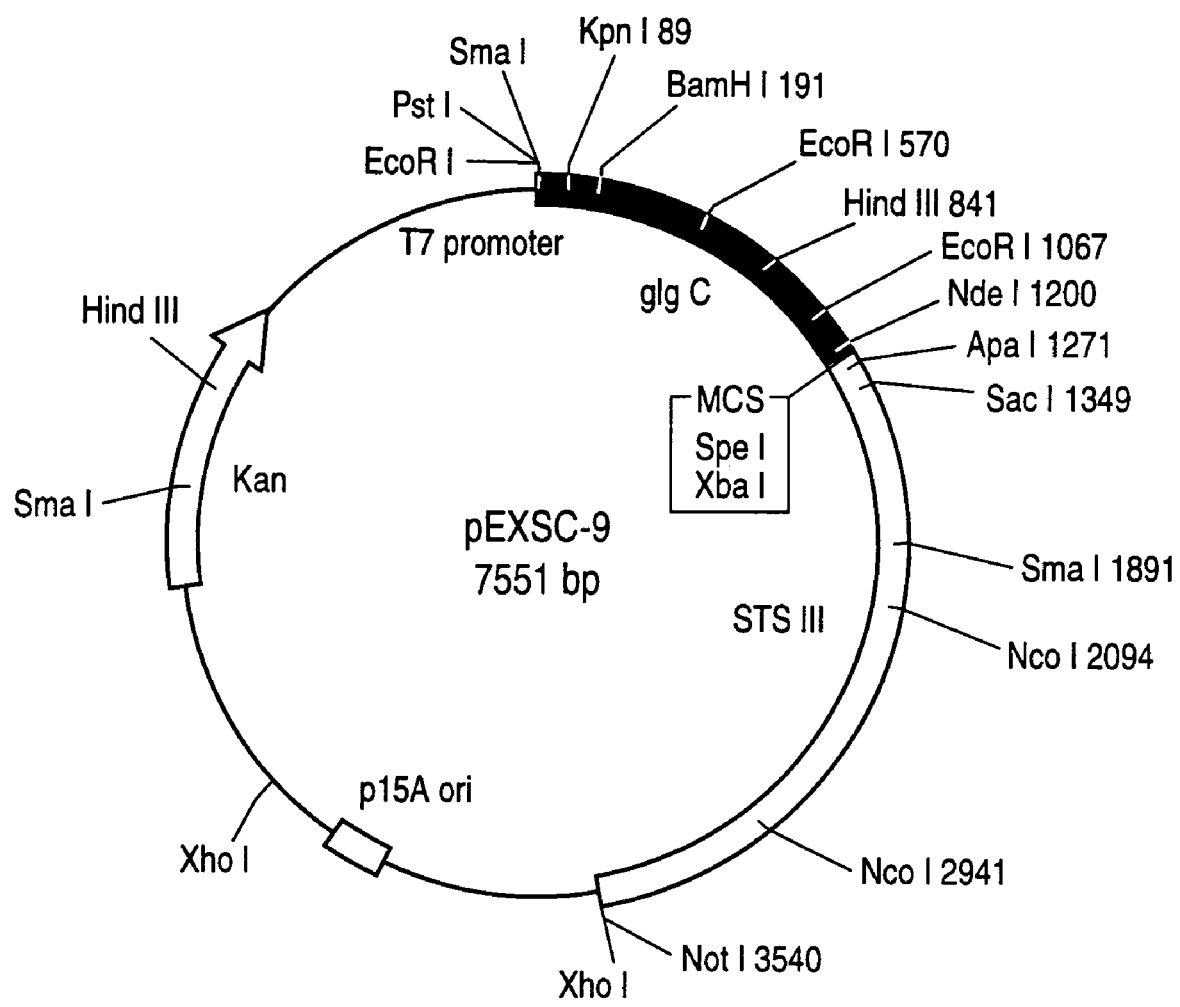
FIG. 8 shows plasmid pEXSC-9 with 7551 base pairs and promoter T7 and a Kanamycin gene and the glgC gene and the maize starch soluble synthase gene IIb (SSIIb). The N-terminal sequence is AAAPAGEE (SEQ ID NO:2).
Figure 9:
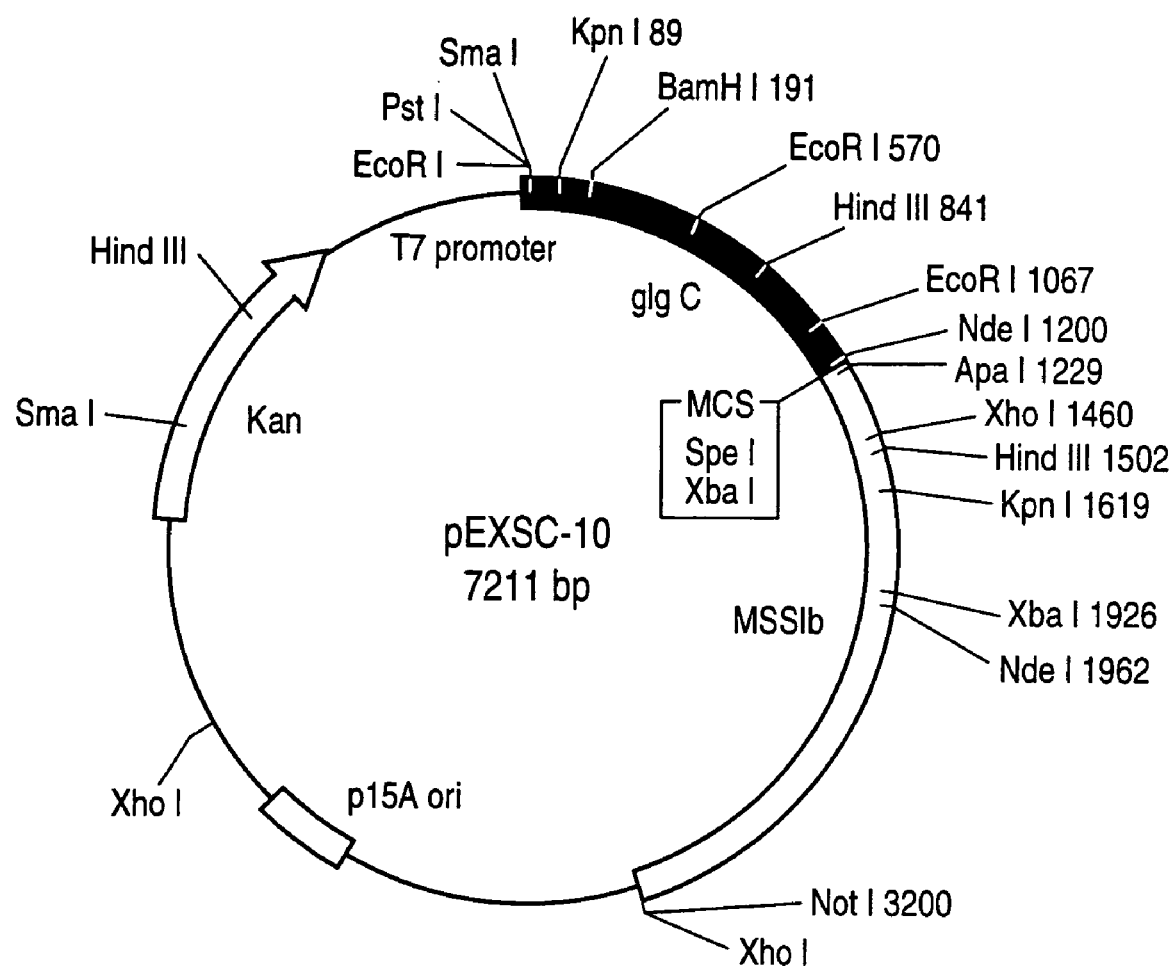
FIG. 9 shows plasmid pEXSC-10 with 7211 base pairs and promoter T7 and a Kanamycin gene and the glgC gene and the maize starch soluble synthase gene I, the full length SSI. The N-terminal sequence is CVAELSREGPA (SEQ ID NO:3).
Figure 10:
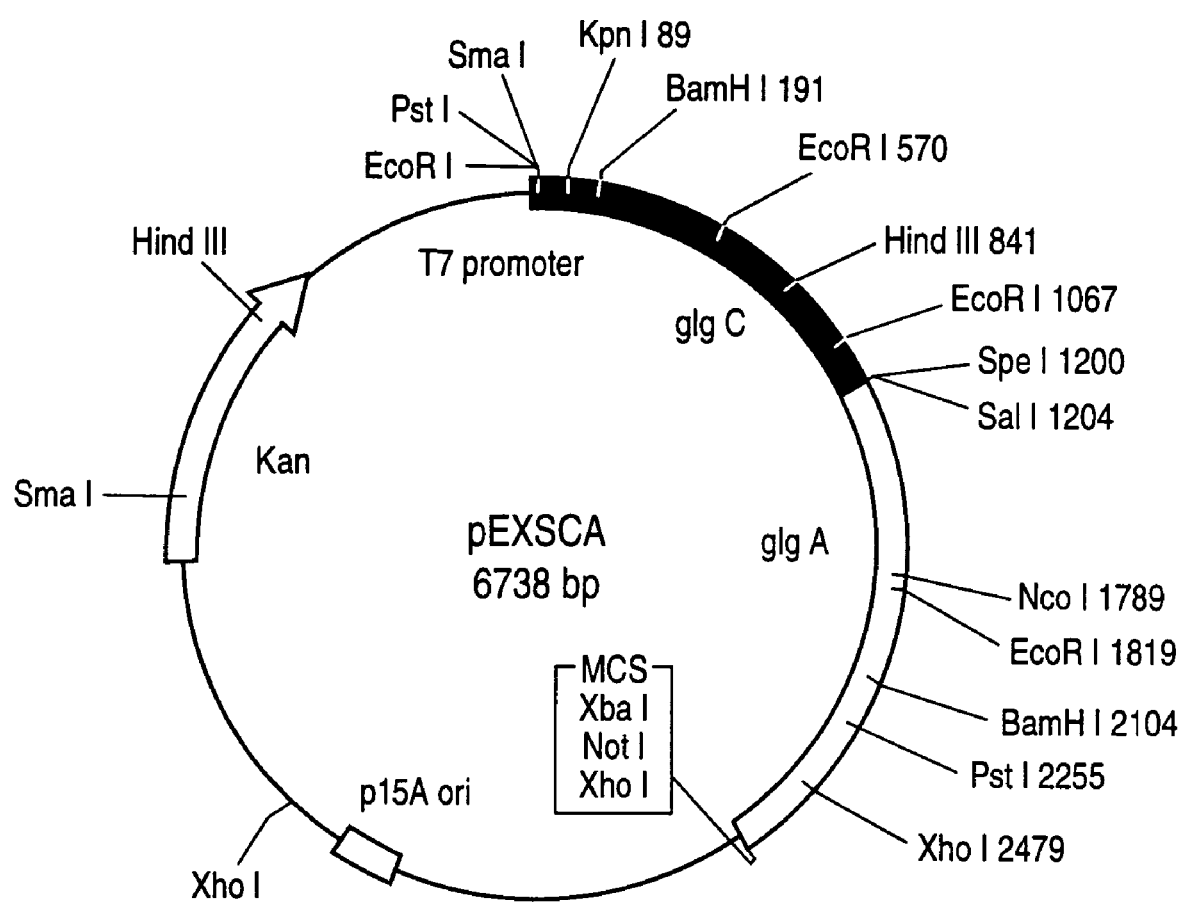
FIG. 10 shows plasmid pEXSCA with 6738 base pairs and promoter T7 and a Kanamycin gene and the glgC gene and the glgA gene.
Figure 11:
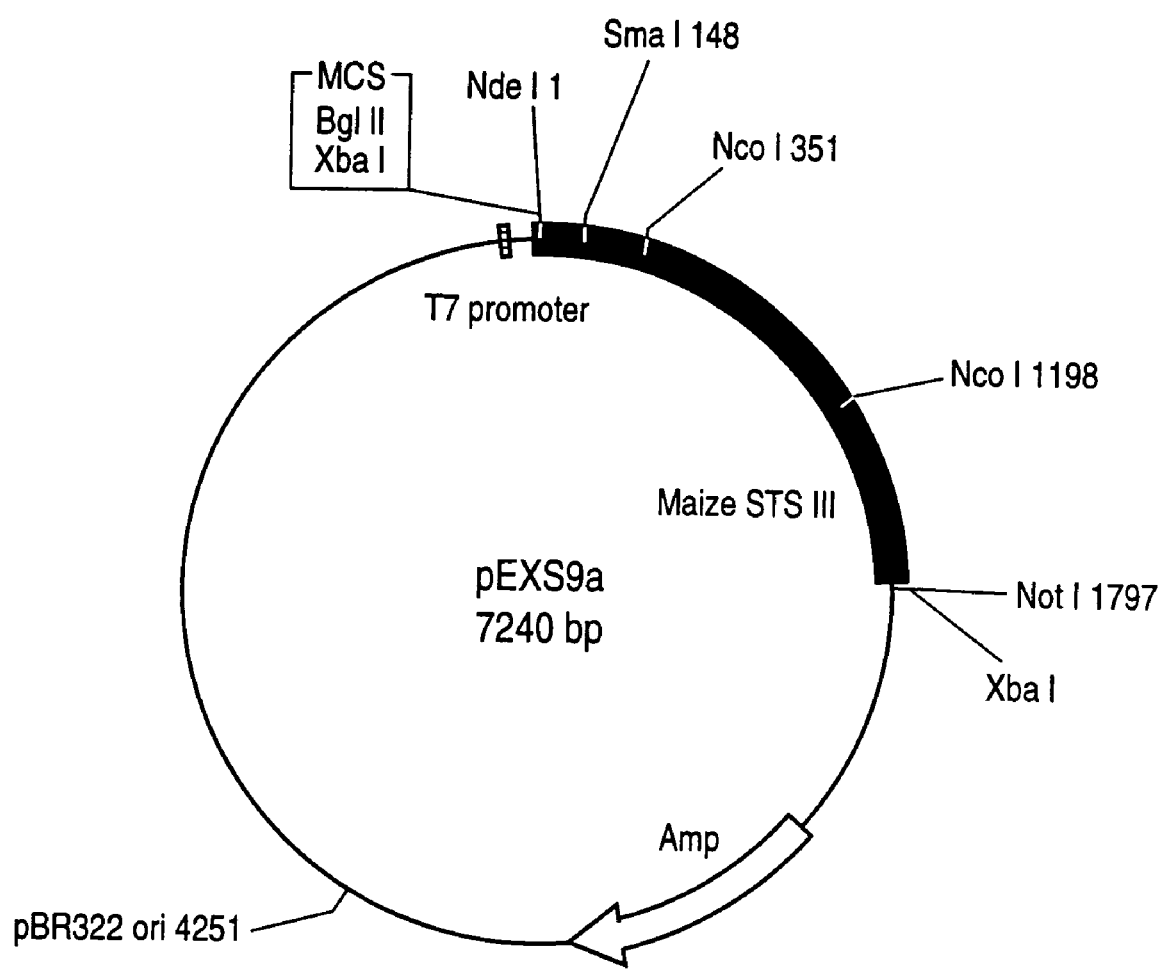
FIG. 11 shows plasmid pEXSC9a with 7240 base pairs and promoter T7 and ampicillin gene and the maize starch soluble synthase gene IIb-2 (Maize SS IIb-2), an N-terminally truncated SSIIb. The N-terminal sequence is MNVVVVASECAP (SEQ ID NO:4).
Figure 12:
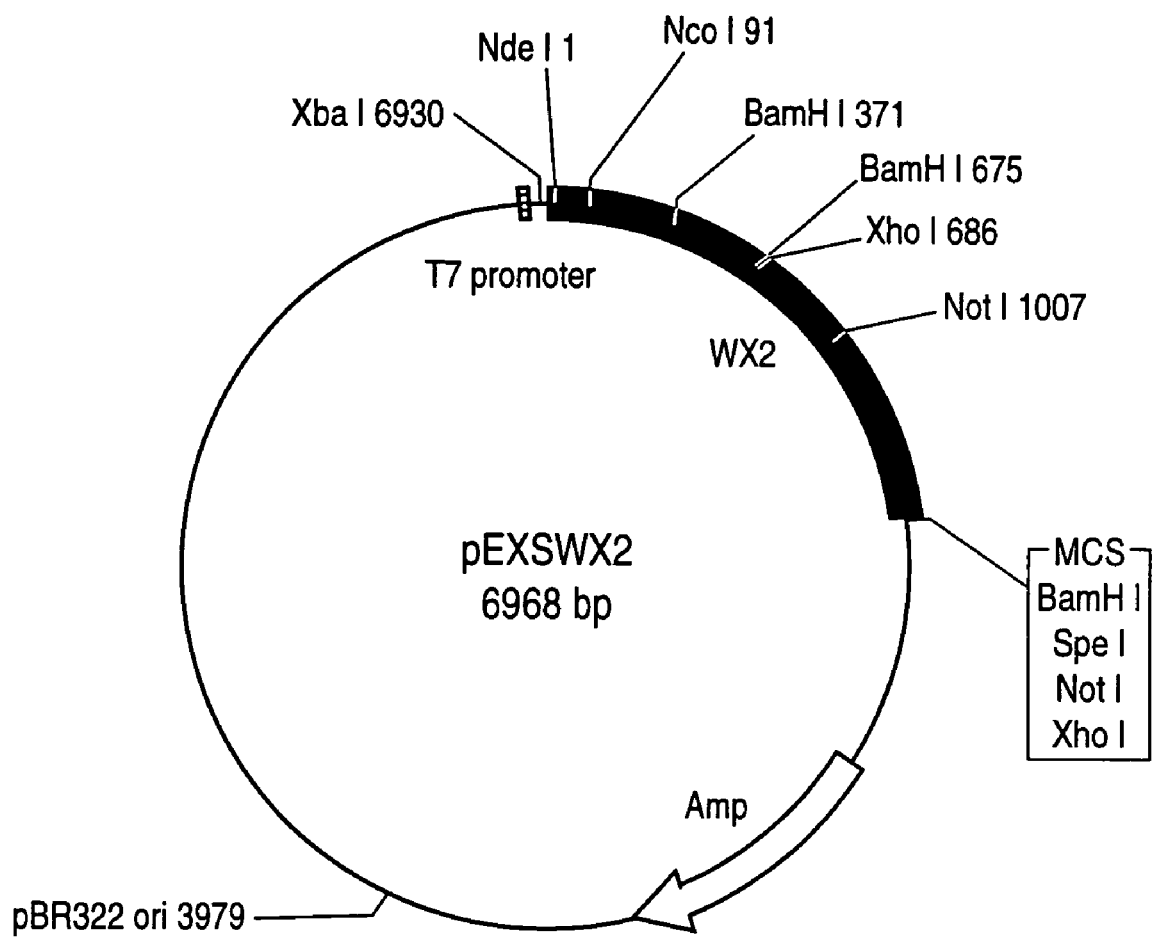
FIG. 12 shows plasmid pEXSWX with 6968 base pairs and promoter T7 and an ampicillin gene and the N-terminally truncated maize WX (maize granular bound starch synthase). The N-terminal sequence for wx is ASAGMNWFVGAEMA (SEQ ID NO:5).
Figure 13:
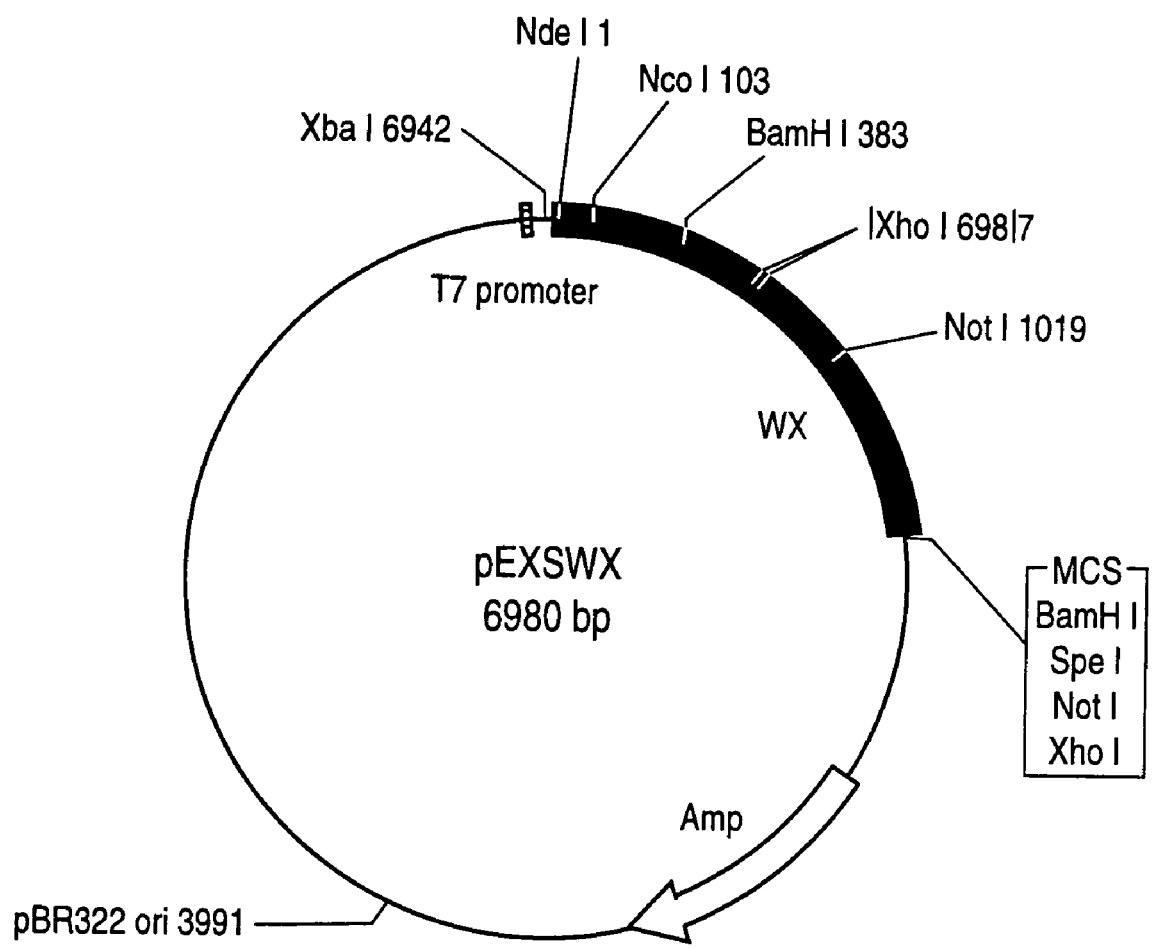
FIG. 13 shows plasmid pEXSWX2 with 6980 base pairs and promoter T7 and an ampicillin gene and the N-terminally-truncated maize WX termed as wx2. The N-terminus of wx2 is MNWFVGAEMA (SEQ ID NO:6).
Figure 14:
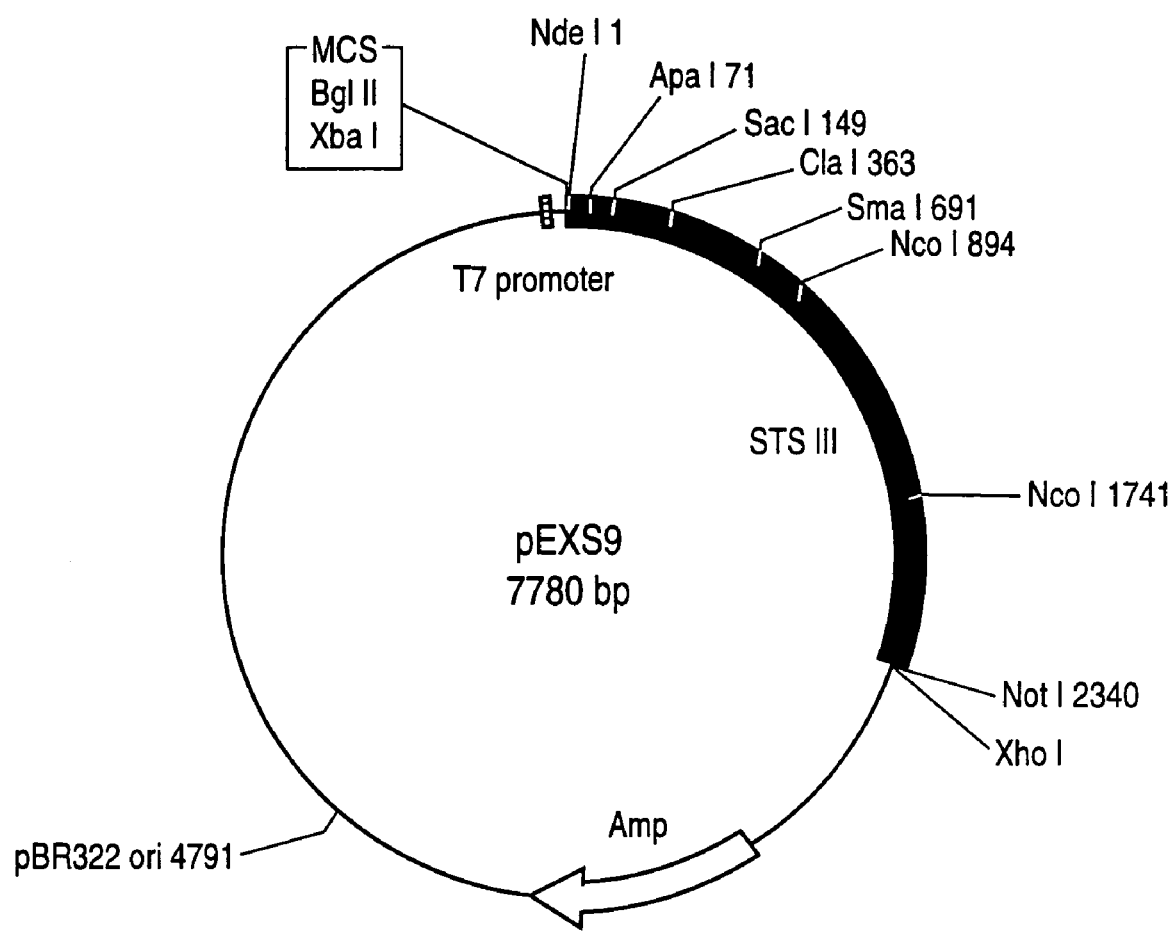
FIG. 14 shows plasmid pEXSC9 with 7780 base pairs and promoter T7 and ampicillin gene and *E. coli* glgc gene and the maize starch soluble synthase gene IIb (Maize SS IIb).
Figure 15:
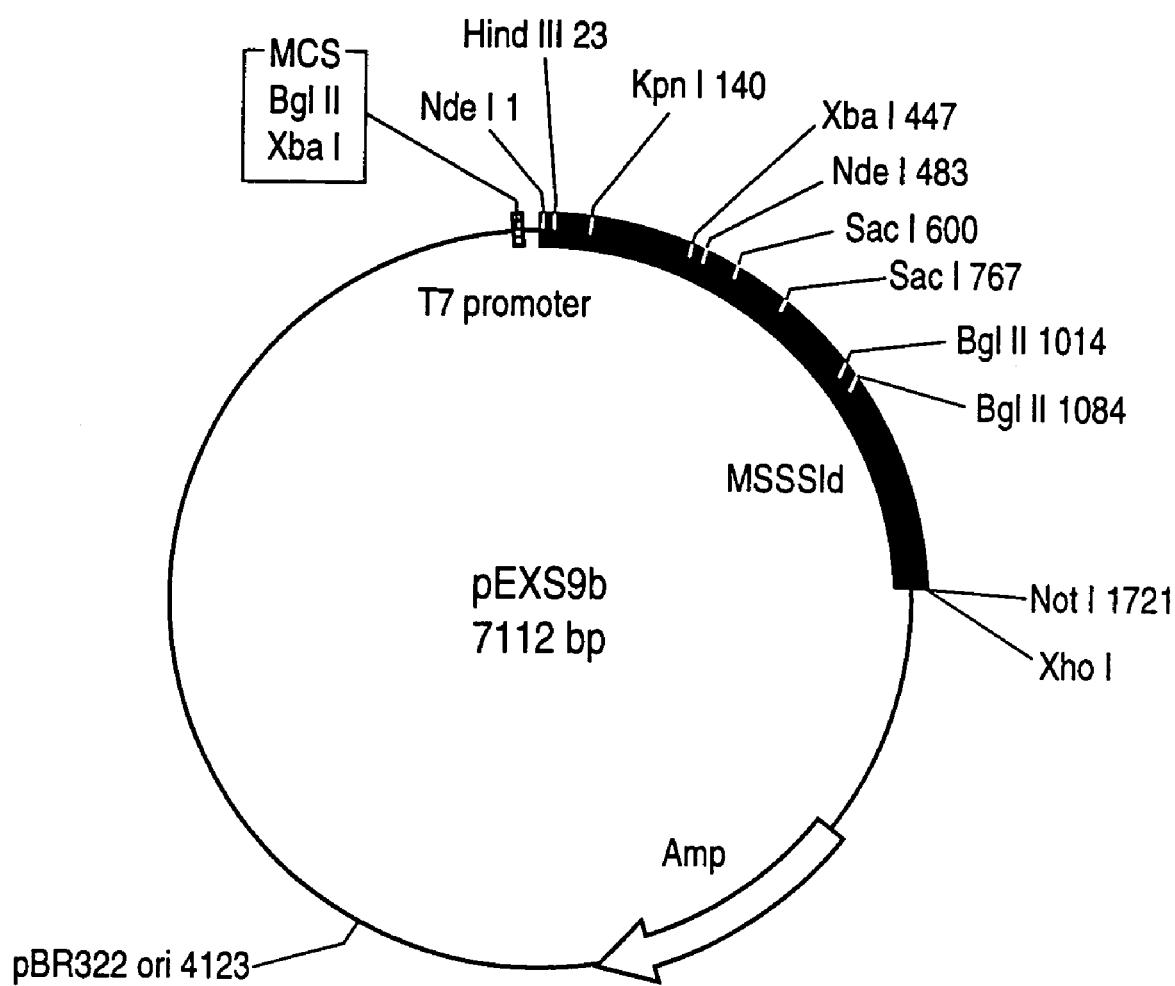
FIG. 15 shows plasmid pEXSC10d with 7112 base pairs and promoter T7 and ampicillin gene, *E. coli* glgC gene and the N-terminally-truncated maize starch soluble synthase gene I termed as Maize SSI-3. The N-terminus of maize SSI-3 is MSIVFTGEASPYA (SEQ ID NO:7).
Figure 16:
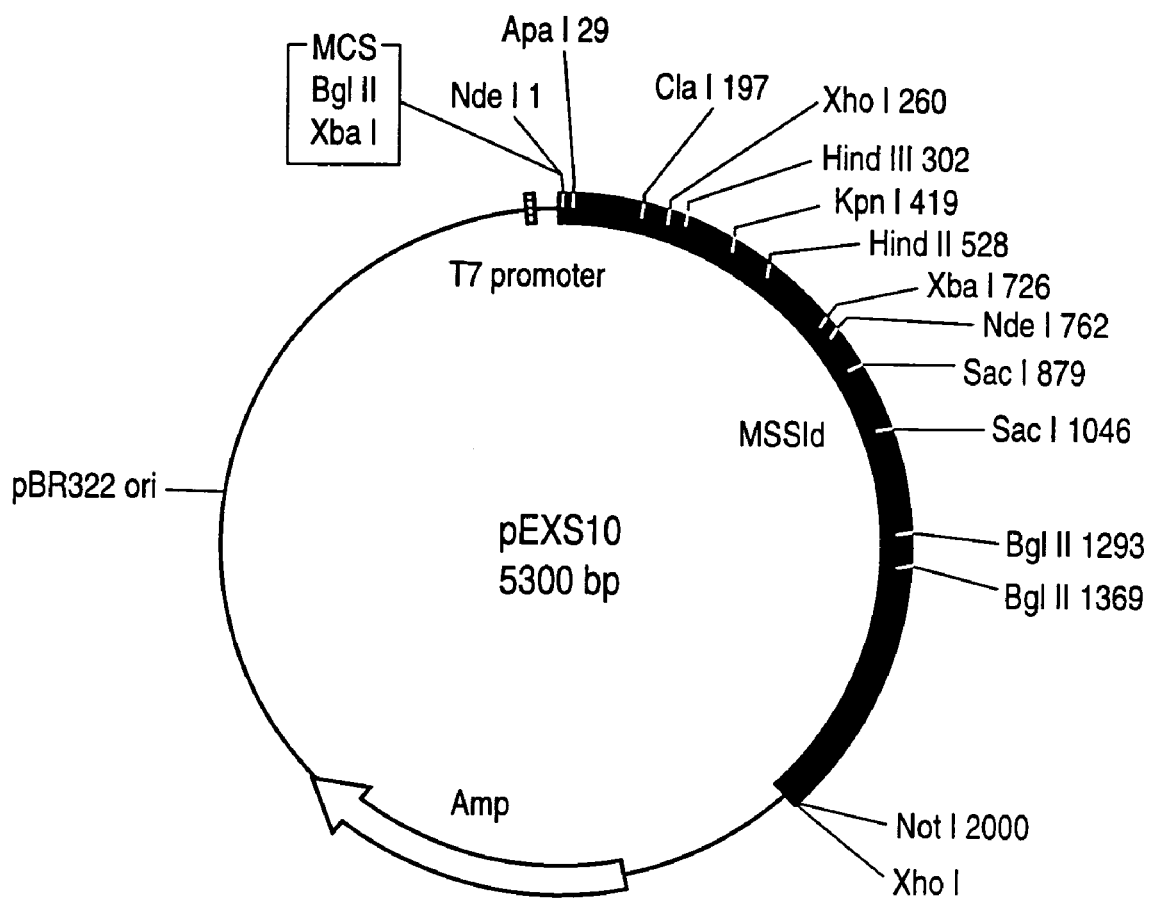
FIG. 16 shows plasmid pEXS10 with 5300 base pairs and promoter T7 and ampicillin gene and the full-length maize starch soluble synthase gene I termed as Maize SS I.
Figure 17:
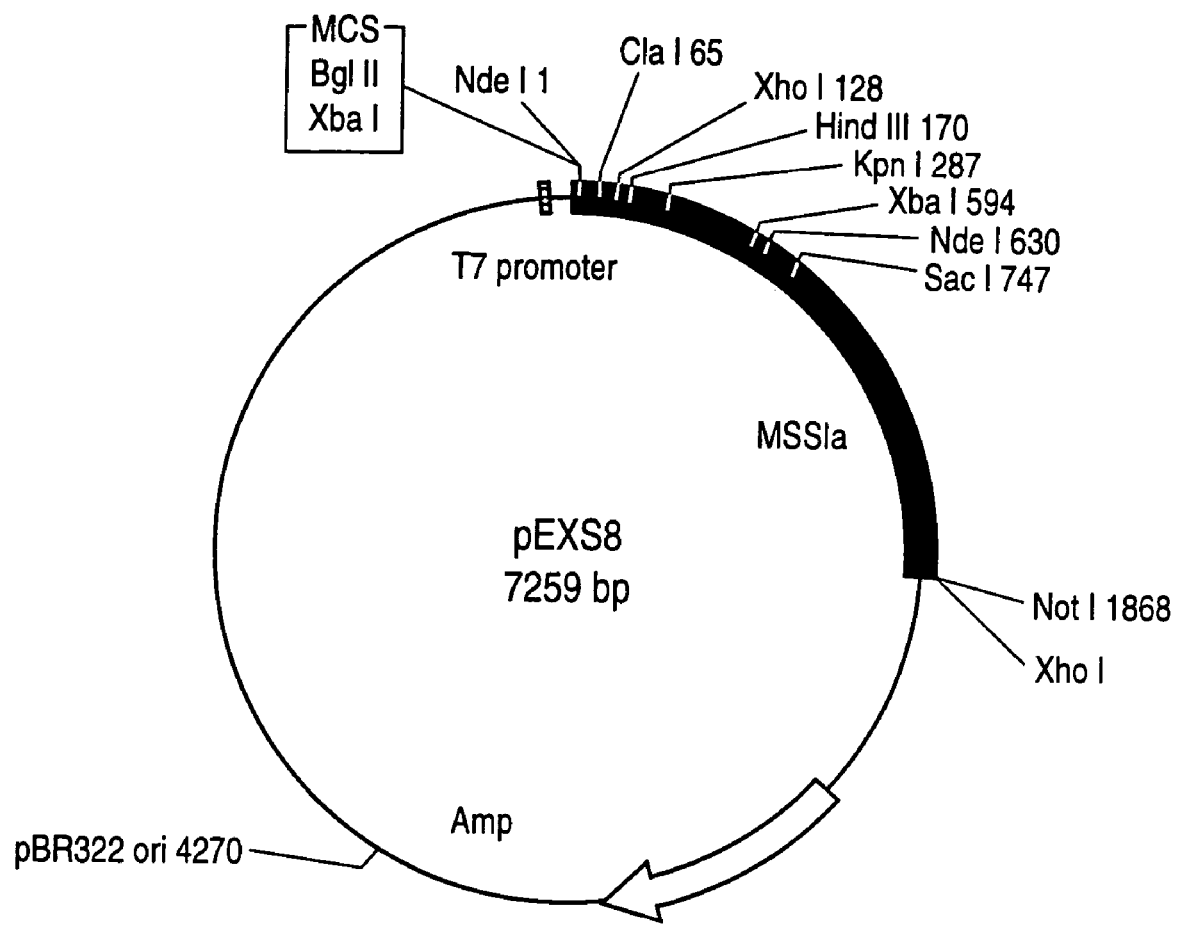
FIG. 17 shows plasmid pEXS8 with 7259 base pairs and promoter T7 and ampicillin gene and the N-terminally-truncated maize starch synthase gene I termed as SSI-2. The N-terminal sequence is CVAELSRDLGLEPEG (SEQ ID NO:8).
Figure 18:
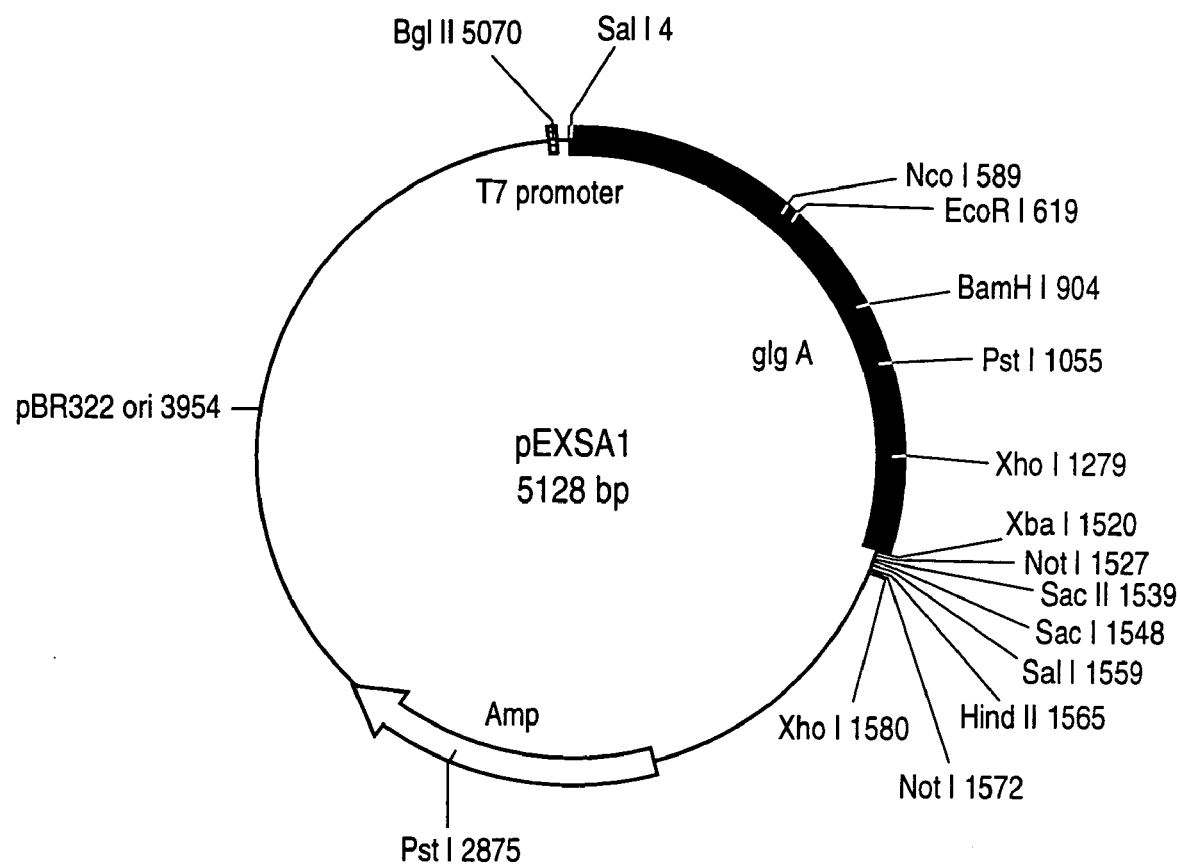
FIG. 18 shows plasmid pEXSCA1 with 5128 base pairs and promoter T7 and ampicillin gene and the glgA. pESCA1 is a 1551 bp SpeI-Sac I fragment containing glgA (from glgA in pBSK) subcloned into the Xba I-Sac I sites of p ET-23d which is commercially available from Novagen in Madison, Wis. under catalog number 69748-1 and called ET-23d(+) DNA.
Figure 19:
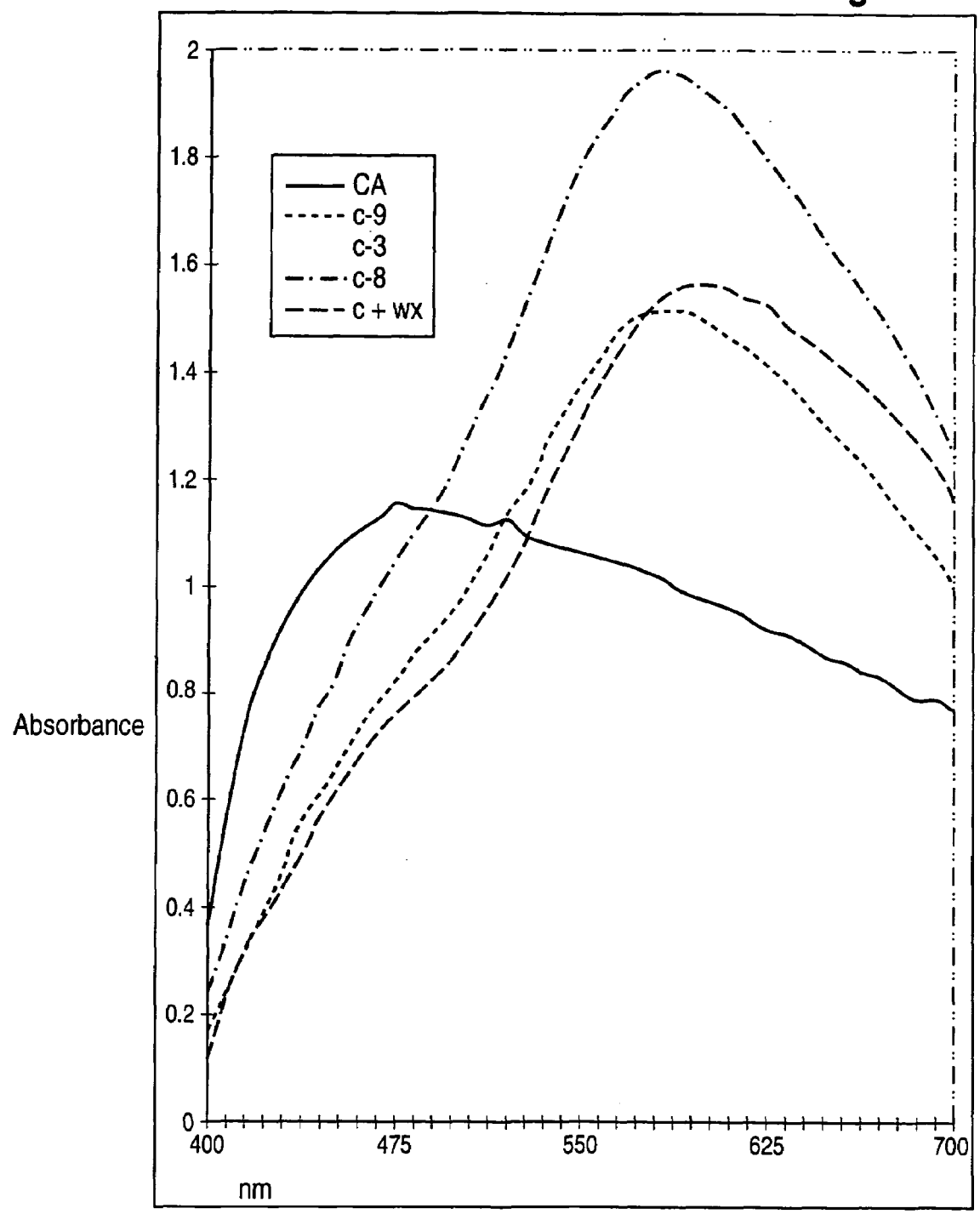
FIG. 19 shows the spectrum of the iodine glucan complex of the product produced by the host containing the glgC and glgA, and the pEXSC9, pEXSC3, pEXSC8, pEXSCwx the X-axis is listing nm and the Y axis is reading absorbance.
Figure 20:
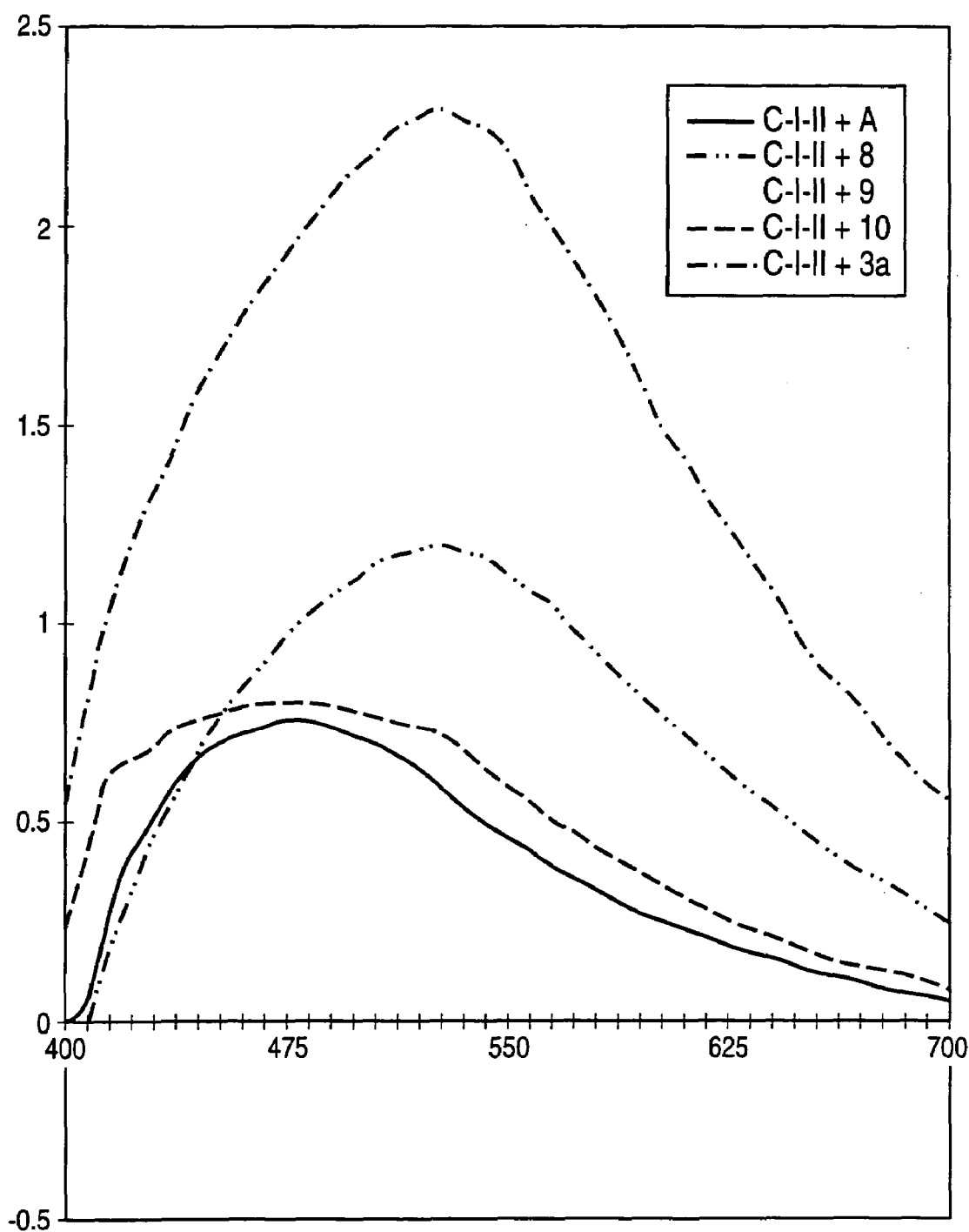
FIG. 20 shows the spectrum of the iodine glucan complex of the product produced by the host containing the glgC, the BEII, the BEII genes and glgA; glgC, the BEI, the BEII genes and maize SSI, SS-2 and glgC, the BEI, the BEII genes and maize SSIIb, and glgC, the BEI, the BEII genes and maize SSIIa-2, and glgC, the BEI, the BEII genes, the X-axis is listing nm and the Y-axis is reading absorbance.

Gene shall mean the entire gene sequence or any mutations or varieties of the codon that produce the desired activity in the host or alternatively the section or sections of the gene sequence necessary to produce the desired activity in the host. For example glgC gene shall mean glgC$_{16}$, glgC$_3$ and other mutants that produce the desired activity in the host. Starch synthase gene shall mean full length SS, N-terminally-truncated SS or mutated SS with starch synthase activity.

Glycogen like—shall mean polysaccharide material such as produced as the main starch product by *E. coli* in its native state and by the hosts as taught in the above described paper by Hanping Guan.

Non Glycogen like—shall mean polysaccharide material which is plant like and is not produced as the main starch product by *E. coli* in it native state and by the hosts as taught in the above described paper by Hanping Guan.

Plant like starch—is non glycogen like.

Transformed gene—shall mean a gene that was somewhere in the lineage of the plant or bacteria introduced into the plant by means other then nature. Thus the progeny of a transformed host would continue to contain a transformed gene.

Transformed host—shall mean any organism containing one or more of the novel plasmids and/or a novel combination of starch genes discussed herein.

Within this application a number of different protocols have been employed to designate the same gene or synthase. MSS#=maize soluble starch synthase, SSS# will likewise mean starch soluble synthase though not necessarily maize. STS# will also designate starch soluble synthase. GBSS=granule bound starch synthase. SBE#=starch branching enzyme, MBE=maize starch branching enzyme, MSBE#=maize starch branching enzyme, and BE#=starch branching enzyme.

The present invention broadly encompasses transforming hosts such as bacteria or plants with plant starch genes that produce a non glycogen like material (a bacteria containing BEI and BEII from maize produces a glycogen like material). Starch bearing plants and organisms hereinafter are referred to as the host. One of the primary aspects of this invention is the generation of plant like starch from a bacterial host and the production of altered starch in a plant host. The present invention has been exemplified in both bacteria and in transformed rice plants. The host can contain though it is not a limitation an unlimited supply of ADPG from the addition of the glgC gene (the bacterial gene) to the plant. Additionally the present invention encompasses plasmids that contain the maize genes and/or the bacterial genes in a construct adapted for use in a bacteria and constructs adapted for use in a plant. The plasmids in the plant construct preferably containing an active promoter recognized by the plant, a transit peptide, and the cleavage site that permits the protein to cleave from the transit peptide when crossing into the amyloplast in the plant. The plasmids used in the rice transformation specifically encompassed the maize 10 kd zein promoter, and the transit peptide from the maize SSI gene in the constructs adapted for plant use. The present invention also encompasses the plant producing the altered starch in the starch storage section of the plant or within the host cell and the altered starch itself. Additionally the present invention encompasses the combination of a number of starch genes in combination being active in a host such that the host produces differing non glycogen polysaccharides. Still further the present invention encompasses a method of making plant like starch in a bacterial host and the method of making altered plant like starch (altered in relationship to the type or amount of starch that the host makes without the constructs containing the genes), in a plant. Yet another object of the present invention is the addition of a gene that encodes for the substrate ADPG used to form starch.

The present invention encompasses a plasmid or combination of plasmids in the same host having a promoter adapted for use in a plant and a gene encoding for ADPGlc pyrophosphorylase, preferably a bacterial gene, and a gene encoding for starch synthase I or its mutant form. The present invention also encompasses the combination of a promoter adapted for use in a plant and optionally a gene encoding for ADPGlc pyrophosphorylase, preferably a bacterial gene, and a gene encoding for starch synthase I or its mutant form, and at least one gene encoding for branching enzyme transformed into a plant host.

The present invention encompasses a plasmid or combination of plasmids in the same host having a promoter adapted for use in a plant and a gene encoding for ADPGlc pyrophosphorylase, preferably a bacterial gene, and a gene encoding for starch synthase IIa or its mutant form. The present invention also encompasses the combination of a promoter adapted for use in a plant and optionally a gene encoding for ADPGlc pyrophosphorylase, and a gene encoding for starch synthase IIa or its mutant form, and at least one gene encoding for branching enzyme transformed into a plant host.

The present invention encompasses a plasmid having a promoter adapted for use in a plant and a gene encoding for ADPGlc pyrophosphorylase, preferably a bacterial gene, and a gene encoding for starch synthase IIb and its mutant form. The present invention also encompasses the combination for a promoter adapted of use in a plant and an optional gene encoding for ADPGlc pyrophosphorylase, and a gene encoding for starch synthase IIb or its mutant form, and at least one gene encoding for branching enzyme transformed into a plant host The present invention encompasses a plasmid having a promoter adapted for use in a plant and a gene encoding for pyrophosphorylase, preferably a bacterial gene, and genes encoding for at least one of the following genes starch synthase I, starch synthase IIa, starch synthase IIb, DU1. The present invention also encompasses the combination of a promoter adapted for use in a plant and a gene encoding for ADPGlc pyrophosphorylase, preferably a bacterial gene, and genes encoding for at least one of the following genes starch synthase I, starch synthase IIa, starch synthase IIb and DU1, and at least one gene encoding for branching enzyme transformed into a plant host.

The present invention encompasses a plasmid or combination of plasmids in the same host having a promoter adapted for use in a plant and a gene encoding for ADPGlc pyrophosphorylase, preferably a bacterial gene, and genes encoding for at least one of the following genes starch synthase I, starch synthase IIa, IIb and starch synthase III (DU1). The present invention also encompasses the combination of a promoter adapted for use in a plant and an optional gene encoding for ADPGlc pyrophosphorylase, preferably a bacterial gene, and genes encoding for at least one of the following genes starch synthase I, starch synthase IIa, IIb, starch synthase III (DU1), and at least one gene encoding for branching enzyme, and at least one gene encoding for the debranching enzyme transformed into a plant host.

The present invention encompasses a plasmid or combination of plasmids in the host having a promoter adapted for use in a bacteria or yeast and a gene encoding for ADPGlc pyrophosphorylase, preferably a bacterial gene, and a gene encoding for starch synthase I. The present invention also encompasses the combination of a promoter adapted for use in a bacteria or yeast and a gene encoding for ADPGlc pyrophosphorylase, preferably a bacterial gene, and a gene encoding for starch synthase I, and at least one gene encoding for branching enzyme transformed into a bacteria or yeast host.

The present invention encompasses a plasmid or combination of plasmids in the host having a promoter adapted for use in a bacteria or yeast and a gene encoding for pyrophosphorylase, preferably a bacterial gene, and a gene encoding for starch synthase IIa. The present invention also encompasses the combination of a promoter adapted for use in a bacteria or yeast and optionally a gene encoding for ADPGlc pyrophosphorylase, preferably a bacterial gene, and a gene encoding for starch synthase IIa, and at least one gene encoding for branching enzyme transformed into a bacteria or yeast host.

The present invention encompasses a plasmid or combination of plasmids in the same host having a promoter adapted for use in a bacteria or yeast and, and a maize gene encoding for starch synthase III (DU1). The present invention also encompasses the combination of a promoter adapted for use in a bacteria or yeast and an optional gene encoding for ADPGlc pyrophosphorylase, preferably a bacterial gene, and a gene encoding for starch synthase II, and at least one gene encoding for branching enzyme transformed into a bacteria or yeast host.

The present invention encompasses a plasmid or combination of plasmids in the same host having a promoter adapted for use in bacteria or in yeast and a gene, and genes encoding for at least one of the following genes starch synthase I, starch synthase IIa, IIb, starch synthase III (DU1). The present invention also encompasses the combination of a promoter adapted for use in bacteria or in yeast and a gene encoding for ADPGlc pyrophosphorylase, preferably a bacterial gene, and genes encoding for at least one of the following genes starch synthase I, starch synthase IIa, IIb, starch synthase III, and at least one gene encoding for branching enzyme transformed into bacteria or into yeast hosts.

The present invention encompasses a plasmid or combination of plasmids in the same host having a promoter adapted for use in bacteria or in yeast and a gene encoding for ADPGlc pyrophosphorylase, preferably a bacterial gene, and genes encoding for at least one of the following genes starch synthase I, starch synthase IIa, IIb, starch synthase III. The present invention also encompasses the combination of a promoter adapted for use in bacteria or in yeast and a gene encoding for pyrophosphorylase, preferably a bacterial gene, and genes encoding for at least one of the following genes starch synthase I, starch synthase IIa, IIb, starch synthase III (DU1), and at least one gene encoding for branching enzyme, and at least one gene encoding for the debranching enzyme transformed in to a bacteria or into a yeast host.

The present invention encompasses the truncated versions of the SSI and the SSII and the SSIII genes that still provide protein that is sufficient to make the polysaccharide.

By transforming different combinations of SS and SBE into $E.\ coli$ HPG204(DE3) or G6MD3 defective in GS and GBE, we obtained the first evidence that maize SSI, SSII and SSIII have different specificities in the size of glucans synthesized (see FIG. 1). Herein, we present the model system to produce differing polysaccharides from hosts with SS and SBE in $E.\ coli$ by metabolic engineering. We also demonstrated that the truncated forms of SS had different Vmax, temperature stability, and kinetic properties (Table, Fig).

We also demonstrated that transformation of starch synthase and/or branching enzyme in $E.\ coli$ resulted in production of polysaccharides differing in size and structure. These polysaccharides can be used in food and nonfood industries to replace and/or complement starch functionalities. A large amount of these polysaccharides can be produced with fermentation technology.

Starch biosynthesis in higher plants and glycogen biosynthesis in $E.\ coli$ have similar reactions which use adenosine diphosphate glucose (ADPGlc) as a substrate. This similarity allows us to use plant starch synthase (SS) and starch branching enzyme (SBE) to complement the functions of glycogen synthase (GS) and glycogen branching enzyme (GBE) in $E.\ coli$ G6MD3, which is deficient in GS and GBE. Transformation of $E.\ coli$ glgC gene and maize starch synthase gene in $E.\ coli$ G6MD3 produced linear a 1,4 glucan similar to amylose. Coexpression of the glgC, maize starch synthase and maize branching enzyme produced branched polysaccharides. However, distinct properties of plant starch branching enzyme and starch synthase make it possible to synthesize different polysaccharides in $E.\ coli$. While maize SSI preferentially synthesis short chains (dp 6-15), SSII and SSIII preferentially transferred long chains (dp>24) and intermediate chains (dp 16-24) respectively. Transformation of different maize starch synthases, $E.\ coli$ glycogen synthase (glgA) and/or maize branching enzymes into $E.\ coli$ HPG96 or $E.\ coli$ G6MD3 resulted in the synthesis of different sizes of polysaccharide with DP 500-4000. These polysaccharides synthesized in $E.\ coli$ by maize SS have different physical-chemical properties than polysaccharides synthesized in natural organisms including starch from plant sources and glycogen from animals. The polysaccharide can be used in food and nonfood industries to replace and/or complement starch functionalities. A large amount of these polysaccharides can be produced by fermentation technology. The following materials were employed in the construction of the present invention some of the starting material are commercially available from Novagen in Madison, Wis. ET-23d(+) DNA under catalog number 69748-1 and BL21(DE3) under catalog number 69387-1; ET-21a(+) DNA under catalog number 697401.

Plant Hosts

The following plasmids have been transformed into rice plants Transgenic 1, MSTSIA (pExs52) and glgC$_3$ (pExs66), MSTSIIa and glgC$_3$ (pExs53 and pExs56). The second group of rice transformants contain MSTSIIc and glgC$_3$ (pExs54 and pExs56). The third group of transformation: transgenic 5 MSTSIII and glgC$_3$ (pExs 61 and pExs 66); transgenic 6 Mwx glgC$_3$ (pExs65 and pExs66). Generally see FIGS. 25-41 for plasmid maps and FIGS. 43-55 for sequences used in the plasmid. Additionally, glgA and glgB and glgC were combined and transformed into rice. This is combining the rice plants starch pathway with the gene encoding for ADPG and the genes encoding for at least one of the following enzymes, SSI, SSII, SSIII, Debranching enzymes, BEI, BEII, GBSS (wx).

These plasmids could have been transformed into other cereals such as corn, wheat, barley, oats, sorghum, milo in substantially the plasmid that is shown in the figures for the plant host. The promoter could be the waxy gene which is published, other additional zein promoters are known and could be used the promoter. The promoter used herein is described in FIGS. 45a and 45b.

Additionally these plasmid with little additional work could be transformed into dicots such as such as potatoes, sweet potato, taro, yam, lotus cassava, peanuts, peas, soybean, beans, chickpeas. The promoter could be selected to target the starch storage area of the particular dicots (some are roots some are tubers). Various method of transforming monocots and dicots are known in the industry and the method of transforming the genes is not critical to the present invention. The plasmid can be introduced into Agrobacterium tumefaciens by the freeze-thaw method of An et al. (1988) Binary vectors. In Plant Molecular Biology Manual A3, S. B. Gelvin and R. A. Schilperoot, eds (Dordrecht, The Netherlands: Kluwer Academic Publishers), pp. 1-19. Preparation of Agrobacterium inoculum carrying the construct and inoculation of plant material, regeneration of shoots, and rooting of shoots are described in Edwards et al. (1995). Biochemical and molecular characterization of a novel starch synthase from potatoes. Plant J. 8, 283-294. Additionally promoters for different dicots are known particularly 35SCaMV and Monsanto has also published a promoter that is useful in potatoes called a patatin promoter.

A number of monocots are also starch bearing plants but until about a decade ago monocots were difficult to develop transformants. The most prominent methods of transformation presently used in monocots is the gunning of micro projectiles into the plants or using Agrobacterium and subsequent regeneration of the plants from the transformed materials. Various tissues and cells can now be transformed with plasmids into monocot hosts. In fact there are teaching from at least five ago on methods of transforming not only callus but also cotyledons. The methods of transforming plants and selecting for the transformants with either selectable or screen able markers are also well known. The use of the marker in the same plasmid and the use of the markers in a separate plasmid that is co transformed into the host are well known in the art by those of ordinary skill in the art. The biotechnology methods of forming plasmids and transforming plants are listed in the book entitled "A Short Protocol In Molecular Biology," 3rd ed., published in 1995 by JOHN WILEY& Sons, Inc. Additionally, methods of transforming with the gun and with protoplasts are taught in a number of issued patents to Dekalb and Agracetus and Ciba.

Preferred Embodiment—Operation

EXAMPLE 1

Construction of the *E. coli* Expression Vector

The expression vector pExs2 was derived from pET-23d (Novagen) and pGP1-2 (15). The expression vectors pExs-trc and pExs-trc3 were derived from pTrc99a (Pharmacia) and pGP1-2. The BglII/PstI fragment (2192 bp) containing the pBR322 origin of replication was deleted from pET-23d and replaced with the BamHI/PstI fragment (3 kb) containing origin p15A and kanamycin resistance gene from pGP1-2. This process generated plasmid pEXS1 containing both ampicillin and kanamycin resistance genes. The ampicillin resistance gene was inactivated by deletion of the ScaI/BglI fragment (360 bp, BglI end was filled in and blunt-end ligated with ScaI end). Inactivation of the ampicillin resistance gene in pEXS1 generated the expression plasmid pEXS2, containing the T7 promoter, T7 terminator, kanamycin resistance gene and p15A origin of replication. Plasmid pTrc99a was digested with Nde1, filled in with klenow fragment and blunt-end ligated to remove NdeI site. A NdeI site was introduced at the NcoI site by mutagenesis to generate plasmid pExs-trc. The BglI and PvuII fragment (2.48 kb) in pExs-trc containing the pBR322 origin of replication was replaced by BglI/BamHI (filled in with Klenow fragment) fragment (3 kb) containing origin p15A and kanamycin resistance gene from pGP1-2 to generate pExs-trc2. The ampicillin resistance gene was inactivated by deletion of the ScaI/BglI fragment (360 bp, BglI end was filled in and blunt-end ligated with ScaI end). Inactivation of the ampicillin resistance gene in pExs-trc2 generated the expression plasmid pExs-trc3.

Construction of expression plasmids for maize SS. For expression of maize SS in *E. coli*, the PCR method was used to modify the N-terminus of maize SS using the following nucleotides:

```
primer (5'-CAAGAATGCTGCGGGAGTC-3'),      (SEQ ID NO:12)
Exs4 primer (5'-AAGTCGACATATGTGCGTCGCGGAG     (SEQ ID NO:13)
Exs23   CTGAGCAG-3'), primer (5'-GGGCCCCATATGAGCATTGTCTTTG     (SEQ ID NO:14)
Exs 57 TAACCGG-3'), primer (5'-CTCGGGCCCATATGGGGAGAATGT      (SEQ ID NO:15)
Exs1    TATGAA-3'), primer (5'-GAGGCATCAATGAACACAAAGTCG-     (SEQ ID NO:16)
Exs2    3'), primer (5'-GAAGGGCCCCATATGGCTGAGGCTG     (SEQ ID NO:17)
Exs33   AGGCCGGGGGCAAG-3'), primer (5'-TTGGATCCATATGGGAGCTGCGGTT     (SEQ ID NO:18)
Exs16   GCATTGGG-3'), primer (5'-CCTGCGGGCTCTGGCTTCACC),       (SEQ ID NO:19)
Exs17 primer (5'-TTGGATCCATATGAACGTCGTCGTG     (SEQ ID NO:20)
Exs 55 GTGGCTTC-3'), primer (5'-GCATACCATGGAACCTCAACAGC-      (SEQ ID NO:21)
56      3'), primer (5'-GGTACCATATGAACGTCGTCTTCGG     (SEQ ID NO:22)
53      CG-3'), primer (5'-GACAGGCCCGTAGATCTTCTCC-       (SEQ ID NO:23)
Exs 54 3'), primer (5'-TTGGTACCATATGGCCAGCGCCGCC     (SEQ ID NO:24)
Exs-wx GGCATGAACG-3').
```

Primer Exs 4 paired respectively with primer Exs23 and Exs 57 was to modify the N-terminus of maize SSSI gene to generate pExs-10 and pExs-1d. Primer Exs2 paired individually with primer Exs33 and Exs1 was to modify the N-terminus of maize SSSII to generate pExs3c and pExs3a. Primer Exs17 paired individually with primer Exs16 and Exs55 was to modify the N-terminus of maize SSSIII to generate pExs-9 and pExs-9a. Primer Exs54 paired individually with primer Exs-wx and Exs53 was used to modify the N-terminus of maize GBSS to generate pExs-wx and pExs-wx2. The modified N-terminus was recombined with the rest of the SS gene in pBluescript SK plasmid. The reconstructed of maize SS was subcloned from pBluescript SK to the NdeI/NotI sites of the expression vector pET-21a (Novagen), pExs-trc, pExs-trc3 (maps are attached, Table I shows the N-terminal sequence of SSS).

EXAMPLE 2

Construction of Expression Plasmids for *E. coli* ADPGlc Pyrophosphorylase, BE and Maize SBE

*E. coli* glgB gene was excised from plasmid pOP12 (16). The BstX1 (filled in)/HindII fragment containing the glgB ribosome binding site and the full length glgB gene was cloned at the SmaI site of pBluescriptSK-(Stratagene). The glgB gene in pBluescriptSK- was subsequently cloned into pEXS2 at the XbaI/SalI sites to generate plasmid pEXSB.

Primer G (5'-GAAGATCTGGCAGGGACCTGCACAC-3') (SEQ ID NO:25) and primer H (5'-GGACTAGTGCAT-TATCGCTCCTGTTTAT-3') (SEQ ID NO:26) were used to PCR the *E. coli* glgC gene coding for ADPGlc pyrophosphorylase from plasmid pOP12. A BglII site and a SpeI site introduced by PCR to the N-terminal and C-terminal site respectively, were used to clone the PCR product into pBluscript SK- at the BamHI and SpeI sites. The glgC gene including its own ribosome binding site was subcloned into expression plasmid pEXS2 at the XbaI (filled in with Klenow fragment) and NotI site to generate plasmid pEXSc. The genes coding for mature maize SBEI and SBEII along with a ribosome binding site were subcloned from plasmids pET-23d-SBEI and pET-23d-SBEII into the plasmid pEXSc at the SpeI site to form the plasmids pEXSc-SBEI and pEXSc-SBEII. The gene coding for mature maize SBEII including a ribosome binding site was cloned into pEXSc-SBEI at the XbaI/NotI sites to form plasmid pEXSc-SBEI-SBEII. *E. coli* glgc gene and genes encoding maize SBEI and SBEII were also cloned in plasmid pExs-trc and pExs-trc3 respectively and together as described for pExs2.

EXAMPLE 3

Isolation of *E. coli* HPG204 Deficient inGBE and GS Activities

Homologous recombination was used for the strain construction. This was done according to the method described by Hamilton et al (Journal of Bacteriology, 1989, 171:4617-4622.) A temperature-sensitive pSC101 replicaon was used to facilitate the selection. The gene coding for spectinomycin adenyltransferase was inserted at PvuII sites in plasmid pOP12 to form plasmid HPG9 which has spectinomycin resistance and has C-terminus of glgB gene and N-terminus of glgA gene deleted. The DNA fragment B=SA= with Spectinomycin resistant gene inserted between partial truncated glgB and glgA was subcloned into plasmid pMAK705 at XbaI site containing temperature sensitive replicon (Hamilton et al. Journal of Bacteriology, 1989, 171:4617-4622) to form plasmid pMak705B=SA=. Plasmid pMak705B=SA= was transformed into TGI cell. After the transformed cell was cultured in 3 mL LB with 100 mg/mL Spectinomycin at room temperature overnight, the cells were plated on LB agar plate containing 100 mg/mL spectinomycin and incubated at 44° C. overnight. Single colonies were inoculated on LB agar plate containing 100 mg/mL spectinomycin and 0.2% glucose and incubated at 44° C. and at 37° C. overnight. The colonies at 37° C. were stained with iodine. The colony with negative staining was selected and grown in 100 mL LB at 37° C. overnight. The cells were harvested and homogenized in an extraction buffer for assaying glycogen synthase and branching enzyme activities. The cell lacking glgA and glgB activities was named as HPG204 [F=traD36 LacI$^q$ D(glgBXCA) D (lacZ)M15proA$^+$B$^+$/SupED (hsdM-mcrB)5($r_k^-$ $m_k^-$ McrB$^-$)thiD(lac-proAB), Spectinomycin$^R$, Chloramphenicol$^R$]. The IDE3 lysogenization kit from Novagen was used for site specific integration of IDE3 prophage into *E. coli* HPG204 to form *E. coli* HPG204(DE3) [was D The lysate was prepared with P1 vir and its transduction into *E. coli* BL21 (DE3) [F=tra36 LacI$^q$ D (glgBXCA)D(LacZ)M15proA$^+$B$^+$/SupED (hsdM-mcrB)5 ($r_k^-$ $m_k^-$ McrB$^-$)thiD(lac-proAB), Spectinomycin$^R$, Chloramphenicol$^R$].

EXAMPLE 4

Expression of Maize SS and SBE in *E. coli*

Plasmid pExs-2 and pExs-trc3 has kanamycin resistance and p15A origin of replication. It is compatible with plasmid pET21a, pExs-trc, pTrc99A containing pBR322 origin. Expression plasmids pExs-2 and pET-21a were used to express SS and SBE in *E. coli* HPG204(DE3). Expression plasmids pExs-trc and pExs-trc3 were used for expression in *E. coli* G6MD3. This made it possible to transform different combinations of maize SS and SBE in *E. coli* HPG204 (DE3), or G6MD3 which is deficient in GS and GBE activity. An overnight culture of cells transformed with maize SS and SBE was diluted 1:20 (v/v) in fresh LB containing 0.2% glucose, 100 mg/mL ampicillin and 50 mg/mL kanamycin. The cells were grown at 37° C. for about 2 h to A600 nm=0.6 before the expression of maize SBE and/or SS was induced by adding isopropyl b-D-thiogalactoside to 0.5 mM. Following growth at 25° C. for 4 h, the cells were harvested in a refrigerated centrifuge.

EXAMPLE 5

Isolation of Highly Branched A-Glucan from *E. coli*

Cell pellet (30 g) was resuspended and lysed by sonication in 150 mL 50 mM tris-acetate buffer (pH 7.5) containing 10 mM EDTA and 5 mM DTT. After a fraction of the homogenate was saved for assaying the STS and SBE activities, the homogenate was centrifuged at 20,000 g for 50 min at 4° C. After collecting the supernatant, the pellet was resuspended in 150 mL water and boiled for 15 min with occasional stirring. The resuspension was centrifuged at 20,000 g for 30 at room temperature. After collecting the supernatant, the pellet was washed again with 100 mL water as above. 0.1 volumes of 50% Trichloric acid (TCA) were added to the pooled fractions. After storing on ice for 30 min, the precipitate was spun down at 15,000 g for 20 min, then washed with 30 mL 5% TCA and centrifuged as above. The supernatant and wash were pooled and one volume of absolute ethanol was added. After storing on ice for 30 min, the polysaccharide was collected by centrifuging at 15,000 g for 15 min. The polysaccharide was redissolved in water and precipitated with ethanol. This step was repeated twice. The pellet was washed with methanol twice, acetone twice and dried over silica gel at room temperature.

EXAMPLE 6

Isolation of Linear a 1,4 Polysaccharide from *E. coli*

Resuspend 50 grams of cell pellet in 250 mL of 50 mM Tris acetate buffer, pH 7.5, containing 10 mM EDTA and 5 mM DTT. Sonicate for 3 minutes (45 seconds/time, output # 8, repeat 4 times with 30 seconds interval). The homogenate is centrifuged at 12,000 rpm (SA1500) for 50 minutes.

The supernatant is checked with iodine staining and discarded. (Same 1 mL homogenate and 1 mL supernatant for enzyme assay. The pellet is resuspended & extracted in 100 mL DMSO. Extract the polysaccharide by heating and stirring in boiling water bath for 15 min. Let it cool down to below 40° C. and centrifuge at 12,000 rpm for 30 min at room temperature. The supernatant is pooled. The pellet is extracted two more times with 100 mL DMSO. Equal volume of absolute ethanol is added into the pooled supernatant, mixed and stored on ice for 30 minutes. Centrifuge at 12,000 rpm for 30 min at 4° C. The pellet is redissolved in 20 mL DMSO by heating in boiling water bath. 80 mL water is added and mixed well. After adding 10 mL butanol to the solution, the solution is mixed and stored at 0° C. for one hr (mix once a while). Centrifuge at 12,000 rpm for 30 min at 4° C. Repeat the step once. The pellet is redissolved in 90 mL hot water by heating in boiling water bath. Insoluble materials are immediately removed by centrifugation at room temperature. Add 10 mL butanol to the supernatant, stay at 0° C. for 1 hr and centrifuge at 12000 rpm for 30 min at 4° C. Repeat the step once. The amylose precipitate is redissolved in 90 mL hot water by heating, and 10 mL butanol are added to the solution. After storing at 40° C. on ice for one hour, it is centrifuged at 4° C. for 30 min. Repeat the step once. The pellet is redissolved in 100 mL 10% butanol by heating. The amylose is stored at 0° C. and precipitated by centrifuging at 12000 rpm for 30 min at 4° C. The pellet is washed with 25 mL methanol 3 times and with acetone once. Dry over silica gel.

EXAMPLE 7

Enzyme Assays 5 mL of supernatant were used to assay STS and SBE activities as previously described (Preiss) with minor modification. The reaction mixture for STS contained 100 mM Bicine buffer, 10 mg/mL glycogen, 0.5 mg/mL BSA, 0.5 M sodium citrate, 25 mM potassium acetate, 10 mM GSH, 3 mM [$^{14}$C]-ADPGlc (500 dpm/nmol) and enzyme in a final volume of 0.1 mL. The reaction was carried out at 25° C. for 15 min and terminated by boiling for 2 min. The unincorporated [$^{14}$C]-ADPGlc was separated with Dowex anion exchange column (200-400 mesh, Sigma Chemical Co.). One unit of activity is defined as 1 nmol Glc incorporated into the a-glucan per min at 25° C. SBE activity was determined by phosphorylase stimulation assay. One unit of activity is defined as 1 mmol Glc incorporated into the a-glucan per min at. 30° C.

EXAMPLE 8

Enzyme Purification

For the recombinant SS purification, the cell pellet was resuspended in sonication buffer (50 mM Tris-acetate, pH 7.5, 10 mM EDTA, and 5 mMDTT; 7 ml buffer per gram of cell mass), and cells were lysed using a Fisher 550 Sonic Dismembrator with 5×1 min. bursts with 30 sec. intervals. The homogenate was centrifuged at 9600 g for 30 minutes. SSI in the supernatant was then precipitated by slowly adding neutralized saturated ammonium sulfate to 40% saturation. After stirring on ice for an additional 50 minutes, proteins were collected by centrifugation at 12500 g for 45 minutes. The protein pellet was then redissolved in buffer A (50 mM Tris, pH 5.5, 1 mM EDTA, and 5 mM DTT) containing 0.1 M KCl and dialyzed against the same buffer, with one change of buffer. After dialysis, the sample was centrifuged at 13000 g for 20 minutes to remove insoluble materials. The resulting supernatant was loaded onto amylase affinity column pre-equilibrated with dialysis buffer, and the flow through was collected. The column was washed with 10 column volumes of buffer a containing 0.1 M KCl, and then with buffer A containing 0.5 M KCl and 0.5 M maltose, collecting fractions during both washes. The active fractions were pooled and dialyzed overnight against buffer A, with one change of buffer. The next day, the amylase column sample was filtered and applied to a mono Q 5/5 FPLC column (Pharmacia). After washing with buffer A, a 20 ml 0-0,4 M KCl gradient was employed. The active fractions were electrophoresed on an 8% SDS-PAGE gel (31) to determine the purity of SSI in those fractions; the fractions which were apparently homogeneous were pooled and concentrated using a Centricon-30 spin column (Amicon).

TABLE 1

Expression of maize starch synthases in *Escherichia coli* BL21 (DE3).

| Plasmids | Maize starch synthase genes | N-terminus | Protein (mg/mL) | Specific Activities* (units/mg Protein) |
|---|---|---|---|---|
| pET21a | Native plasmid | | 1.8 | 0.009 |
| pEXS-3a | SSII(a) | GENVMNVIVV (SEQ ID NO:27) | 2.8 | 0.069 |
| pEXS-3c | SSII(c) | AEAEAGGKD (SEQ ID NO:28) | 2.8 | 0.28 |
| pEXS-1d | SS1(d) | MSIVFVTGEA (SEQ ID NO:29) | 3.0 | 0.23 |
| pEXS-8 | SSI(a) | GDLGLEPEG (SEQ ID NO:30) | 1.9 | 0.097 |
| pExs-10 | SSI(b) | CVAELSREG (SEQ ID NO:31) | 1.2 | 0.043 |

TABLE 1-continued

Expression of maize starch synthases in Escherichia coli BL21 (DE3).

| Plasmids | Maize starch synthase genes | N-terminus | Protein (mg/mL) | Specific Activities* (units/mg Protein) |
|---|---|---|---|---|
| pEXS-9 | SSIII(c) | GSVGAALRSY (SEQ ID NO:32) | 1.8 | 0.515 |
| pEXS-9a | SSIII(a) | MNVVVVASEC (SEQ ID NO:33) | 2.6 | 0.36 |
| pEXS-wx | GBSS (waxy) | ASAGMNVVFV (SEQ ID NO:34) | 2 | 0.033 |
| pEXS-wx2 | GBSS(2) | MNVVFVGAEM (SEQ ID NO:35) | 2.2 | 0.32 |

*One unit activity is defined as one mmol glucose incorporated into a-1,4 glucan per minute at 25° C. using 5 mg/mL glycogen as primer.

TABLE 2

Properties of polysaccharides synthesized in E. coli.

| Plasmid | Protein (Mg/mL) | STS activity (u/mg protein) | BE activity (u/mg protein) | lmax (nm) | DP | CL | Yield (mg dry wt/g wet cell) |
|---|---|---|---|---|---|---|---|
| pExsCA | | | | 580 | 700 | 10.6 | 3.3 |
| pExsC-9 | | | | 585 | 1007 | 35.8 | 4.1 |
| pExsC-3a | 13.3 | .0015 | | 600 | 983 | 53 | 1.0 |
| pExsC-8 | 12.6 | .0032 | | 580 | 435 | 31.8 | 7.4 |
| pExsC-wx | 15.2 | 0.002 | | 600 | 836 | 15.6 | 9.1 |
| pExsC-I-II + pExs9 | 7.84 | 0.08 | 4.71 | 480 | 2333 | 19 | 30 |
| pExsC-I-II + pExs3a | 13.61 | 0.011 | 1.56 | 530 | 3616 | 22 | 36 |
| pExsC-I-II + pExs8 | 11.95 | 0.042 | 3.33 | 525 | 1689 | 17.5 | 131 |
| pExsC-I-II + pExs10 | 8.9 | .0094 | 3.65 | 500 | 3174 | 16.6 | 24.5 |
| pExsC-I-II + pExswx | 11.7 | .007 | 5.4 | 450 | 2970 | 14.8 | 33.8 |
| pExsC-I-II + pExsA1 | 11 | 0.13 | 4.48 | 475 | 3940 | 14 | 28.9 |

TABLE 3

Properties listed by degree of DP of polysaccharides synthesized in E. coli.

| Plasmid | Protein (Mg/mL) | STS activity (u/mg protein) | BE activity (u/mg protein) | lmax (nm) | DP | CL | Yield (mg dry wt/g wet cell) |
|---|---|---|---|---|---|---|---|
| pExsC-I-II + pExsA1 | 11 | 0.13 | 4.48 | 475 | 3940 | 14 | 28.9 |
| pExsC-I-II + pExs3a | 13.61 | 0.011 | 1.56 | 530 | 3616 | 22 | 36 |
| pExsC-I-II + pExs10 | 8.9 | .0094 | 3.65 | 500 | 3174 | 16.6 | 24.5 |
| pExsC-I-II + pExswx | 11.7 | .007 | 5.4 | 450 | 2970 | 14.8 | 33.8 |
| pExsC-I-II + pExs9 | 7.84 | 0.08 | 4.71 | 480 | 2333 | 19 | 30 |
| pExsC-I-II + pExs8 | 11.95 | 0.042 | 3.33 | 525 | 1689 | 17.5 | 131 |
| pExsC-9 | | | | 585 | 1007 | 35.8 | 4.1 |
| pExsC-3a | 13.3 | .0015 | | 600 | 983 | 53 | 1.0 |
| pExsC-wx | 15.2 | 0.002 | | 600 | 836 | 15.6 | 9.1 |
| pExsCA | | | | 580 | 700 | 10.6 | 3.3 |
| pExsC-8 | 12.6 | .0032 | | 580 | 435 | 31.8 | 7.4 |

TABLE 4

Properties listed by degree of λmax of polysaccharides synthesized in E. coli.

| Plasmid | Protein (Mg/mL) | STS activity (u/mg protein) | BE activity (u/mg protein) | lmax (nm) | DP | CL | Yield (mg dry wt/g wet cell) |
|---|---|---|---|---|---|---|---|
| pExsC-3a | 13.3 | .0015 | | 600 | 983 | 53 | 1.0 |
| pExsC-wx | 15.2 | 0.002 | | 600 | 836 | 15.6 | 9.1 |
| pExsC-9 | | | | 585 | 1007 | 35.8 | 4.1 |

TABLE 4-continued

Properties listed by degree of λmax of polysaccharides synthesized in E. coli.

| Plasmid | Protein (Mg/mL) | STS activity (u/mg protein) | BE activity (u/mg protein) | lmax (nm) | DP | CL | Yield (mg dry wt/g wet cell) |
|---|---|---|---|---|---|---|---|
| pExsCA | | | | 580 | 700 | 10.6 | 3.3 |
| pExsC-8 | 12.6 | .0032 | | 580 | 435 | 31.8 | 7.4 |
| pExsC-I-II + pExs3a | 13.61 | 0.011 | 1.56 | 530 | 3616 | 22 | 36 |
| pExsC-I-II + pExs8 | 11.95 | 0.042 | 3.33 | 525 | 1689 | 17.5 | 131 |
| pExsC-I-II + pExs10 | 8.9 | .0094 | 3.65 | 500 | 3174 | 16.6 | 24.5 |
| pExsC-I-II + pExs9 | 7.84 | 0.08 | 4.71 | 480 | 2333 | 19 | 30 |
| pExsC-I-II + pExsA1 | 11 | 0.13 | 4.48 | 475 | 3940 | 14 | 28.9 |
| pExsC-I-II + pExswx | 11.7 | .007 | 5.4 | 450 | 2970 | 14.8 | 33.8 |

TABLE 5

Properties listed by degree of CL of polysaccharides synthesized in E. coli.

| Plasmid | Protein (Mg/mL) | STS activity (u/mg protein) | BE activity (u/mg protein) | lmax (nm) | DP | CL | Yield (mg dry wt/g wet cell) |
|---|---|---|---|---|---|---|---|
| pExsC-3a | 13.3 | .0015 | | 600 | 983 | 53 | 1.0 |
| pExsC-9 | | | | 585 | 1007 | 35.8 | 4.1 |
| pExsC-8 | 12.6 | .0032 | | 580 | 435 | 31.8 | 7.4 |
| pExsC-I-II + pExs3a | 13.61 | 0.011 | 1.56 | 530 | 3616 | 22 | 36 |
| pExsC-I-II + pExs9 | 7.84 | 0.08 | 4.71 | 480 | 2333 | 19 | 30 |
| pExsC-I-II + pExs8 | 11.95 | 0.042 | 3.33 | 525 | 1689 | 17.5 | 131 |
| pExsC-I-II + pExs10 | 8.9 | .0094 | 3.65 | 500 | 3174 | 16.6 | 24.5 |
| pExsC-wx | 15.2 | 0.002 | | 600 | 836 | 15.6 | 9.1 |
| pExsC-I-II + pExswx | 11.7 | .007 | 5.4 | 450 | 2970 | 14.8 | 33.8 |
| pExsC-I-II + pExsA1 | 11 | 0.13 | 4.48 | 475 | 3940 | 14 | 28.9 |
| pExsCA | | | | 580 | 700 | 10.6 | 3.3 |

TABLE 6

Purification Tables for SSI-1, SSI-2, and SSI-3

| | volume (ml) | total mg protein | activity U/mg | total Units | purification (fold) |
|---|---|---|---|---|---|
| SSI-1 | | | | | |
| Homogenate | 630 | 4347 | 0.018 | 76.2 | 1 |
| Supernatant | 570 | 2622 | 0.020 | 53.0 | 1.1 |
| 0-40% (NH$_4$)$_2$SO$_4$ | 48 | 494 | 0.058 | 28.7 | 3.2 |
| amylose column | 17 | 2.6 | 5.03 | 11.3 | 279 |
| monoQ column | 0.27 | 0.26 | 12.2 | 3.2 | 677 |
| SSI-2 | | | | | |
| Homogenate | 380 | 2797 | 0.0356 | 99.6 | 1 |
| Supernatant | 320 | 2118 | 0.0340 | 72 | 1 |
| 0-40% (NH$_4$)$_2$SO$_4$ | 48 | 466 | 0.133 | 61.8 | 3.7 |
| amylose column | 17.5 | 1.2 | 22.6 | 26.5 | 634 |
| monoQ column | 1.0 | 0.325 | 17.2 | 5.6 | 483 |
| SSI-3 | | | | | |
| Homogenate | 1300 | 16770 | 0.23 | 3900 | 1 |
| Supernatant | 1100 | 9790 | 0.31 | 3080 | 1.3 |
| 0-40% (NH$_4$)$_2$SO$_4$ | 237 | 2204 | 1.5 | 3294 | 6.5 |
| amylose column | 63 | 30 | 22.4 | 668 | 97 |
| monoQ column | 3.6 | 3.1 | 30.5 | 93 | 132 |

Notes:
Assays performed during the course of purification contained 10 mg/ml glycogen and 3 mM [U—$^{14}$C]-ADPGlc. Assays were performed at room temperature in the presence of 0.5 M citrate. 1 Unit = 1 μmol [U—$^{14}$C]-glucose transferred per min.

TABLE 7

Primer Kinetics for SSI Enzymes

| | | SSI-3 | SSI-2 | SSI-1 |
|---|---|---|---|---|
| | | Amylopectin | | |
| +citrate | $K_m$ | 240 ± 45 | 230 ± 50 | 150 ± 40 |
| | $V_{max}$ | 26.3 ± 0.5 | 33.4 ± 2.1 | 22.5 ± 0.6 |
| −citrate | $K_m$ | 230 ± 60 | 68 ± 3 | 120 ± 20 |
| | $V_{max}$ | 13.2 ± 0.3 | 9.94 ± 0.18 | 7.62 ± 0.99 |
| | | Glycogen | | |
| +citrate | $^aV_{max}$ | 43.4 ± 2.5 | 45.6 ± 3.3 | 39.0 ± 2.2 |
| −citrate | $^aV_{max}$ | 41.4 ± 2.9 | 45.5 ± 1.5 | 26.1 ± 1.4 |

Notes:
Assays were performed at 37° C. as described in the Materials and Methods.
Data are expressed as the average of three independent determinations along with the standard deviation.
$K_m$ are expressed as μg/ml primer and $V_{max}$ are in μmol/min/mg protein.
ADPGlc = 3 mM in all assays.
$^a$Because saturating glycogen concentrations could not be obtained, a standard 20 mg/ml glycogen was used to compare enzyme rates for that primer.

TABLE 8

ADPGlc Kinetics for STSI enzymes

| | | STSI-3 | 3STSI-2 | STSI-1 |
|---|---|---|---|---|
| +citrate | $K_m$ | 0.33 ± 0.07 | 0.32 ± 0.02 | 0.18 ± 0.02 |
| | $V_m$ | 26.4 ± 1.4 | 32.6 ± 0.8 | 18.0 ± 0.5 |
| −citrate | $K_m$ | 0.62 ± 0.04 | 0.25 ± 0.04 | 0.24 ± 0.02 |
| | $V_m$ | 14.7 ± 1.3 | 11.7 ± 0.7 | 6.38 ± 0.88 |

Assays and data evaluation are as in Table II.
$K_m$ are expressed as mM ADPGlc and $V_m$ are in μmol/min/mg protein.
5 mg/ml amylopectin was used as primer for all assays.

TABLE 9

Purification Tables for SSIIa enzymes
Assays for SSIIa-2 purification contained 10 mg/ml glycogen and 1.5 mM [U—$^{14}$C]-ADPGlc (both are at saturating concentrations). Assays for SSIIa-1 purification contained 5 mg/ml amylopectin and 3 mM [U—$^{14}$C]-ADPGlc. Assays were performed at room temperature in the presence of 0.5 M citrate.
1 U = 1 µmol [U—$^{14}$C]-glucose transferred per min.

|  | volume (ml) | total mg protein | activity U/mg | total Units | purification (fold) |
|---|---|---|---|---|---|
| SSIIa-2 | | | | | |
| Supernatant | 300 | 1620 | 0.0216 | 34.8 | 1 |
| 0-40% (NH$_4$)$_2$SO$_4$ | 53 | 419 | 0.0606 | 25.4 | 2.8 |
| amylose column | 20 | 9.3 | 0.991 | 9.3 | 45.9 |
| monoQ column | 0.9 | 0.94 | 4.81 | 4.5 | 222 |
| SSIIa-1 | | | | | |
| Supernatant | 335 | 2613 | 0.28 | 737 | 1 |
| 0-40% (NH$_4$)$_2$SO$_4$ | 47 | 427 | 0.96 | 409 | 3.4 |
| amylose column | 25 | 11.5 | 8.04 | 92 | 28.7 |
| monoQ column | 1.0 | 4.8 | 9.10 | 44 | 32.5 |

TABLE 10

Primer Kinetics for SSIIa enzymes

|  |  | SSIIa-2 | SSIIa-1 |
|---|---|---|---|
| Amylopectin | | | |
| +citrate | | | |
| 27° C. | $K_m$ | 153 ± 22 | 182 ± 38 |
|  | $V_{max}$ | 7.82 ± 0.63 | 24.1 ± 0.5 |
| 37° C. | $K_m$ | 133 ± 18 | 153 ± 64 |
|  | $V_{max}$ | 15.4 ± 0.6 | 41.1 ± 0.2 |
| −citrate | | | |
| 27° C. | $K_m$ | 234 ± 30 | 404 ± 33 |
|  | $V_{max}$ | 4.31 ± 0.32 | 10.5 ± 0.3 |
| 37° C. | $K_m$ | 1350 ± 220 | NA* |
|  | $V_{max}$ | 7.84 ± 0.25 | NA* |
| Glycogen | | | |
| +citrate | | | |
| 27° C. | $K_m$ | 50.7 ± 3.8 | 162 ± 17 |
|  | $V_{max}$ | 5.53 ± 0.44 | 14.2 ± 0.7 |
| 37° C. | $K_m$ | 76.9 ± 7.8 | 350 ± 11 |
|  | $V_{max}$ | 11.3 ± 0.7 | 31.6 ± 0.8 |

Assays were performed as described in the Materials and Methods.
Data are expressed as the average of three independent determinations along with the standard deviation.
$K_m$ are expressed in µg/ml and $V_{max}$ are in µmol/min/mg protein.
ADPGlc = 3 mM in all assays.
*NA = not applicable; enzyme cannot be saturated by primer under these conditions.

TABLE 11

ADPGlc Kinetics for SSIIa enzymes.

|  |  | SSIIa-2 | SSIIa-1 |
|---|---|---|---|
| with amylopectin as primer | | | |
| +citrate | | | |
| 27° C. | $K_m$ | 0.17 ± 0.04 | 0.48 ± 0.09 |
|  | $V_{max}$ | 4.83 ± 0.42 | 23.0 ± 2.5 |
| 37° C. | $K_m$ | 0.28 ± 0.01 | 0.83 ± 0.08 |
|  | $V_{max}$ | 11.4 ± 0.6 | 49.1 ± 2.6 |
| −citrate | | | |
| 27° C. | $K_m$ | 0.27 ± 0.02 | 0.46 ± 0.06 |
|  | $V_{max}$ | 4.87 ± 0.25 | 12.1 ± 0.8 |
| 37° C. | $K_m$ | 0.28 ± 0.005 | NA* |
|  | $V_{max}$ | 7.86 ± 0.53 | NA* |
| with glycogen as primer | | | |
| with glycogen |  | SSIIa-2 | SSIIa-1 |
| +citrate | | | |
| 27° C. | $K_m$ | 0.16 ± 0.03 | 0.19 ± 0.02 |
|  | $V_{max}$ | 4.41 ± 0.21 | 17.1 ± 0.7 |
| 37° C. | $K_m$ | 0.15 ± 0.03 | 0.37 ± 0.04 |
|  | $V_{max}$ | 7.60 ± 0.94 | 40.1 ± 1.7 |

Assays and data evaluations are as in Table II. Concentration of primer in each case was saturating for each enzyme and was determined by the experiments detailed in Table II.
$K_m$ are expressed as mM ADPGlc and $V_{max}$ are in µmol/min/mg protein.
*NA = not applicable; enzyme cannot be saturated by primer under these conditions.

TABLE 12

Purification Tables for SSIIb-2 and SSIIb-1.
Assays performed during the course of purification contained 10 mg/ml glycogen and 3 mM [U—$^{14}$C]-ADPGlc. Assays were performed at room temperature in the presence of 0.5 M citrate.
1 Unit = 1 µmol [U—$^{14}$C]-glucose transferred per min.

|  | volume (ml) | total mg protein | activity U/mg | total Units | purification (fold) |
|---|---|---|---|---|---|
| SSIIb-2 | | | | | |
| Supernatant | 890 | 9256 | 0.48 | 4450 | 1 |
| 0-40% (NH$_4$)$_2$SO$_4$ | 190 | 2660 | 1.24 | 3306 | 2.6 |
| amylose column | 13 | 31.2 | 50.6 | 1573 | 105 |
| monoQ column | 6.6 | 16.3 | 56.8 | 939 | 118 |
| SSIIb-1 | | | | | |
| Supernatant | 365 | 2336 | 0.64 | 1533 | 1 |
| 0-40% (NH$_4$)$_2$SO$_4$ | 56 | 436 | 2.35 | 1030 | 3.7 |
| amylose column | 80 | 10.4 | 50.2 | 521 | 78 |
| monoQ column | 0.6 | 0.28 | 60.6 | 17.6 | 94 |

TABLE 13

Kinetics for SSIIb enzymes.

|  |  | SSIIb-2 | SSIIb-1 |
|---|---|---|---|
| ADPGlc Kinetics | | | |
| with glycogen | $K_m$ | 0.32 ± 0.04 | 0.71 ± 0.01 |
|  | $V_{max}$ | 130 ± 6 | 76.8 ± 3.2 |
| with amylopectin | $K_m$ | 0.32 ± 0.03 | 0.40 ± 0.02 |
|  | $V_{max}$ | 90.9 ± 4.2 | 72.8 ± 2.8 |
| Primer Kinetics | | | |
| glycogen | $K_m$ | 0.36 ± 0.02 | 0.43 ± 0.02 |
|  | $V_{max}$ | 120 ± 3 | 79.5 ± 3.3 |
| amylopectin | $K_m$ | 0.26 ± 0.04 | 0.074 ± 0.008 |
|  | $V_{max}$ | 84.5 ± 2.4 | 67.9 ± 1.7 |

Assays were performed at 37° C. as described in the Materials and Methods.
Data are expressed as the average of three independent determinations along with the standard deviation.
For ADPGlc kinetics, $K_m$ are expressed in mM ADPGlc.
For primer kinetics, $K_m$ are expressed as mg/ml primer, and 3 mM ADPGlc were used in the assays.
$V_{max}$ are in µmol min$^{-1}$ mg$^{-1}$ protein.

TABLE 14

Comparison of kinetic data for expressed SS's.
Data for SSI and SSIIa are from Imparl-Radosevich et al.. 1998;
Imparl-Radosevich J., Li P., McKean AL, Keeling PL, and Guan HP,
submitted for publication. $K_m$ for amylopectin and glycogen are
expressed in mg/ml; $K_m$ for ADPGlc are in mM and were determined
in the presence of amylopectin and 0.5 M citrate. $V_{max}$ are in
$\mu mol\ min^{-1}\ mg^{-1}$. The $K_m$ for glycogen for SSI could not be
determined as saturating concentrations of glycogen could not be
reached for this enzyme.

| Kinetic Parameter | SSI-3 | SSI-1 | SSIIa-2[a] | SSIIa-1 | SSIIb-2[a] | SSIIb-1 |
|---|---|---|---|---|---|---|
| $K_m$ for amylopectin | 0.24 | 0.15 | 0.13 | 0.15 | 0.26 | 0.07 |
| $K_m$ for glycogen | — | — | 0.077 | 0.35 | 0.36 | 0.43 |
| $K_m$ for ADPGlc | 0.33 | 0.18 | 0.28 | 0.83 | 0.32 | 0.40 |
| $V_{max}$ (with amylopectin) | 26.3 | 22.5 | 15.4 | 41.1 | 84.5 | 67.9 |
| $V_{max}$ (with glycogen) | 43.4 | 39.0 | 11.3 | 31.6 | 120 | 79.5 |

[a]denotes N-terminally truncated form of SS, while any SS with the designation SS-1 is the full length version of the SS.

TABLE 15

The starch synthase activities of the chimerical enzymes.
Generation of chimerical enzymes of maize starch synthase:
the recombination of N-terminal extensions with C-terminal
catalytic domains of starch synthase. The gene coding for
N-terminal extensions of STSI, STSIIa and STSIIb were inserted,
in the same (+) or reverse (−) orientation of original N-terminal
DNA sequence, in front of the C-terminal catalytic somains of
WX2, STSIIa and STSIIb, respectively. The chimerical enzymes were
expressed in E. coli, and the activities were assayed.

|  | WX2 C-catalytic domain | | STSIIa C-catalytic domain | | STSIIb C-catalytic domain | |
|---|---|---|---|---|---|---|
| STSI N-extension | N1-WX2 | | N1-C2 | | N1-C3 | |
|  | (+) | (−) | (+) | (−) | (+) | (−) |
|  | NRA | 9.0 | 6.6 | 39.7 | 89.2 | NRA |
| STSIIa N-extension | N2-WX2 | | N2-C2 | | N2-C3 | |
|  | (+) | (−) | (+) | (−) | (+) | (−) |
|  | 9.2 | 11.2 | 213.8 | 8.7 | 232.5 | NRA |
| STSIIb N-extension | N3-WX2 | | N3-C2 | | N3-C3 | |
|  | (+) | (−) | (+) | (−) | (+) | (−) |
|  | NRA | NRA | 11.2 | NRA | 400.5 | 12.0 |

*N1: STSI N-terminal extension;
N2: STSIIa N-terminal extension;
N3: STSIIb N-terminal extension;
WX2: WX2 C-terminal catalytic domain;
C2: STSIIa C-terminal catalytic domain;
C3: STSIIb C-terminal catalytic domain;
*(+): the N-terminal extensions were inserted in front of the C-terminal catalytic domains in same orientation;
(−): the N-terminal extensions were inserted in front of the C-terminal catalytic domains in reverse orientation;
*Starch synthase enzyme activity: nmol/min mg protein.
*The residue glycogen synthase activity of BL21(DE3) is 2.6 nmol/min mg protein.
*NRA—no recombinant available.

Figure 21:
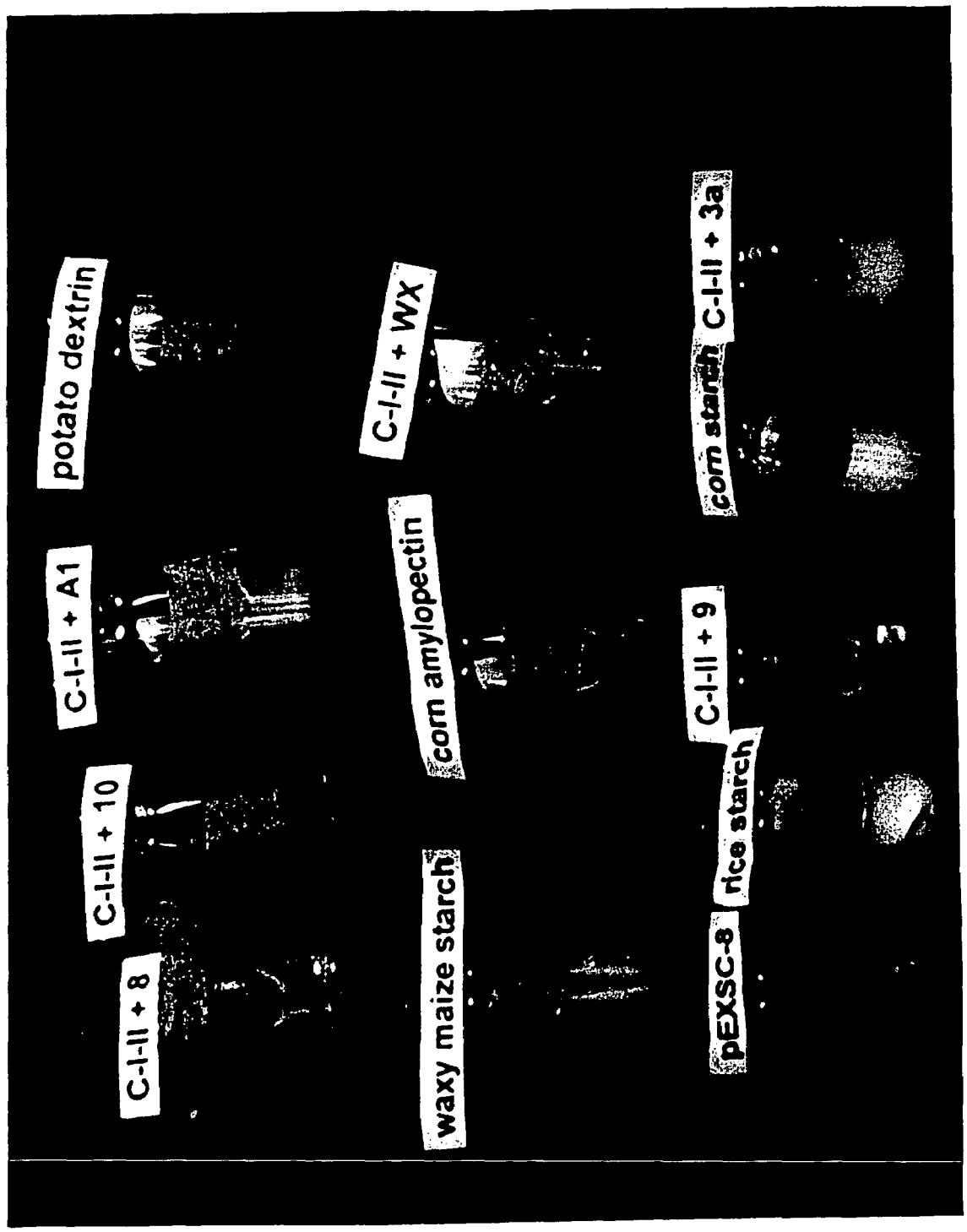
FIG. 21 shows the product produced by the host in small bottles including the product from the host containing glgC, the BEI, the BEII genes and maize SS genes. Encoded as (C-I-II+8), glgC, the BEI, the BEII genes and maize SSI-2 genes and pEXSC10 encoded as (C-I-II+10), glgC, the BEI, the BEII and maize SSI genes and pEXSC9 encoded as (C-I-II+9), glgC, the BEI, the BEII and maize SSIIb genes and pEXSC3a encoded as (C-I-II+3a), glgC, the BEI, the BEII and maize SSIIa-2 genes and pEXSCWX encoded as (C-I-II+WX), glgC, the BEI, the BEII and maizw waxy genes and pEXSCA1 encoded as (C-I-II+A1), containing maize BEI, BEII and *E. coli* glgA genes, potato dextrin, waxy maize starch, corn amylopectin, rice starch, corn starch, pEXSC8.
Figure 22:
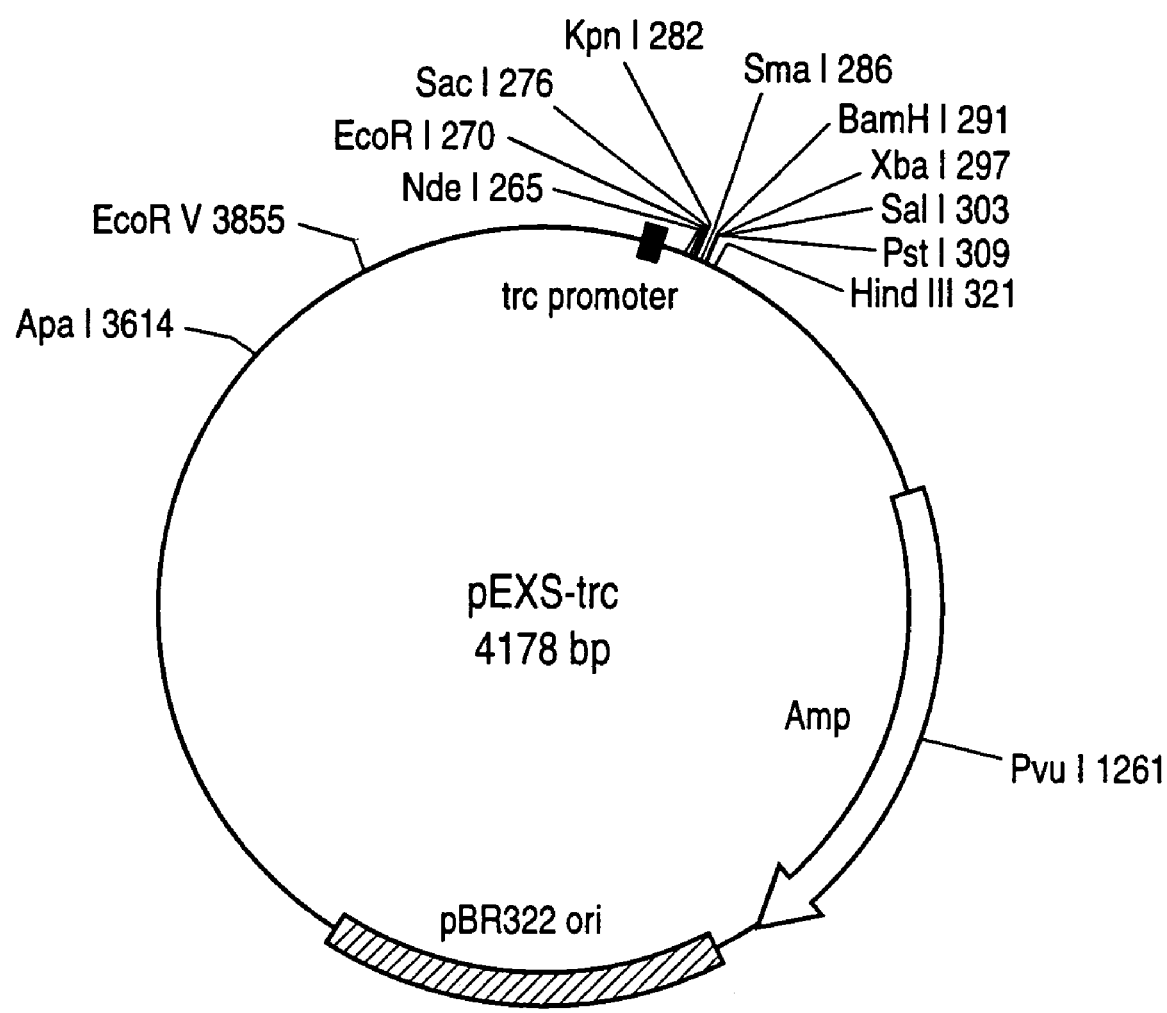
FIG. 22 shows pExs-trc has 4178 base pairs with the trc promoter and the ampicillin gene. PEXS trc is pTrc99A-NdeI which has been mutagenized. (Nco I site in multiple cloning site of p Trc99A-NdeI is mutagenized to Nde I using primers EXS63 AND EXS64.) pEXS-trc contains only one Nde I site and no Nco I sites. The following sites are not contained in pEXS-trc; Bgl II, Cla I, Nco I, Not I, Sac II, SnaB I, Spe I, and Xho I.
Figure 23:
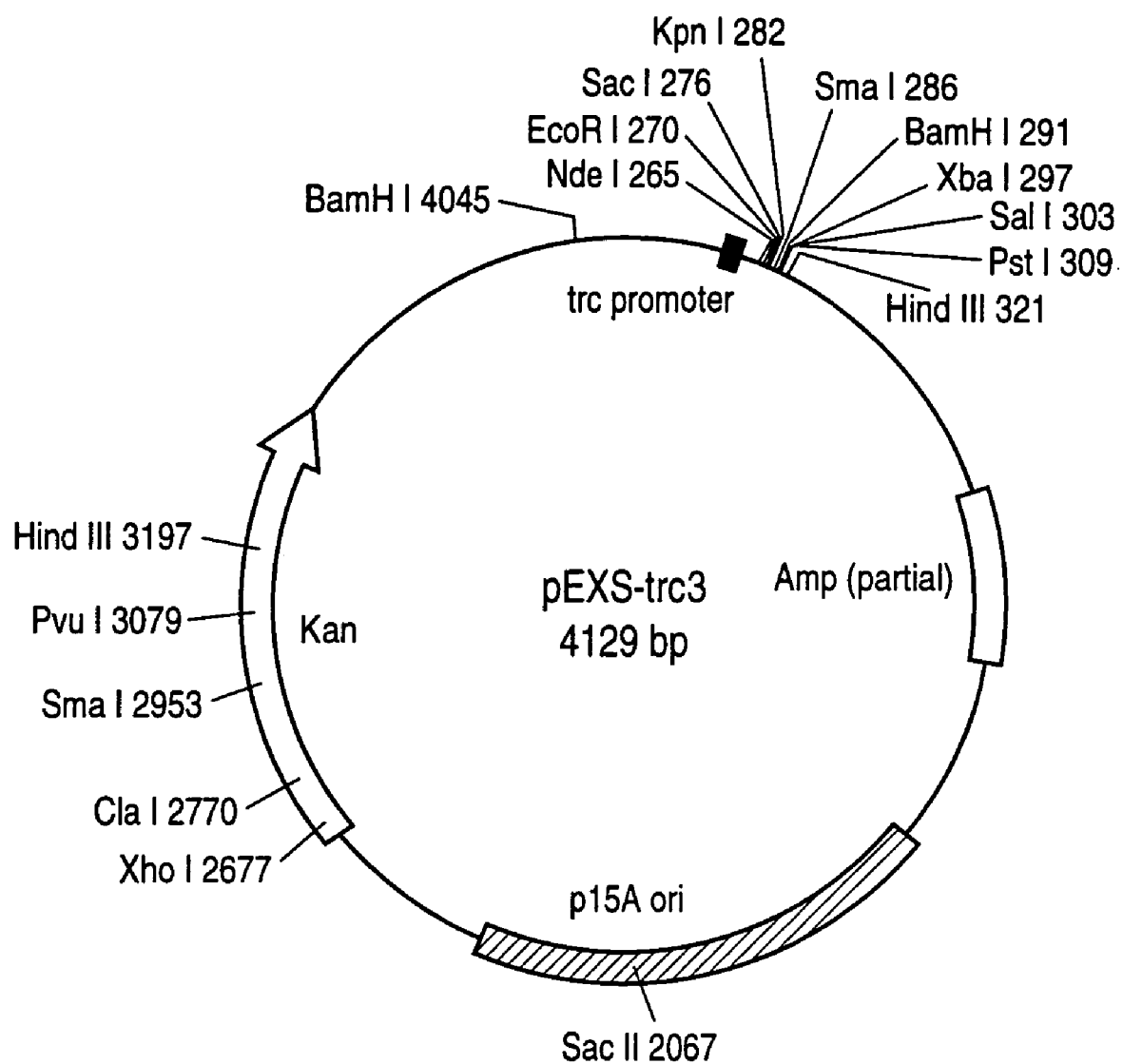
FIG. 23 shows pEXS-trc3 has 4129 base pairs with the trc promoter and the ampicillin gene in partial and the Kanamycin gene. The pEXS-trc3 is pEXS-trc1 cut with BglI (filled in)-Sca I and religated, deleting most of the Amp gene (304 nt from the 5' end remain). The following sites are not contained in p EXS-trc3: Apa I, Bgl II, Eco V, Nco I, Not I, SnaB I, and Spe I.
Figure 24:
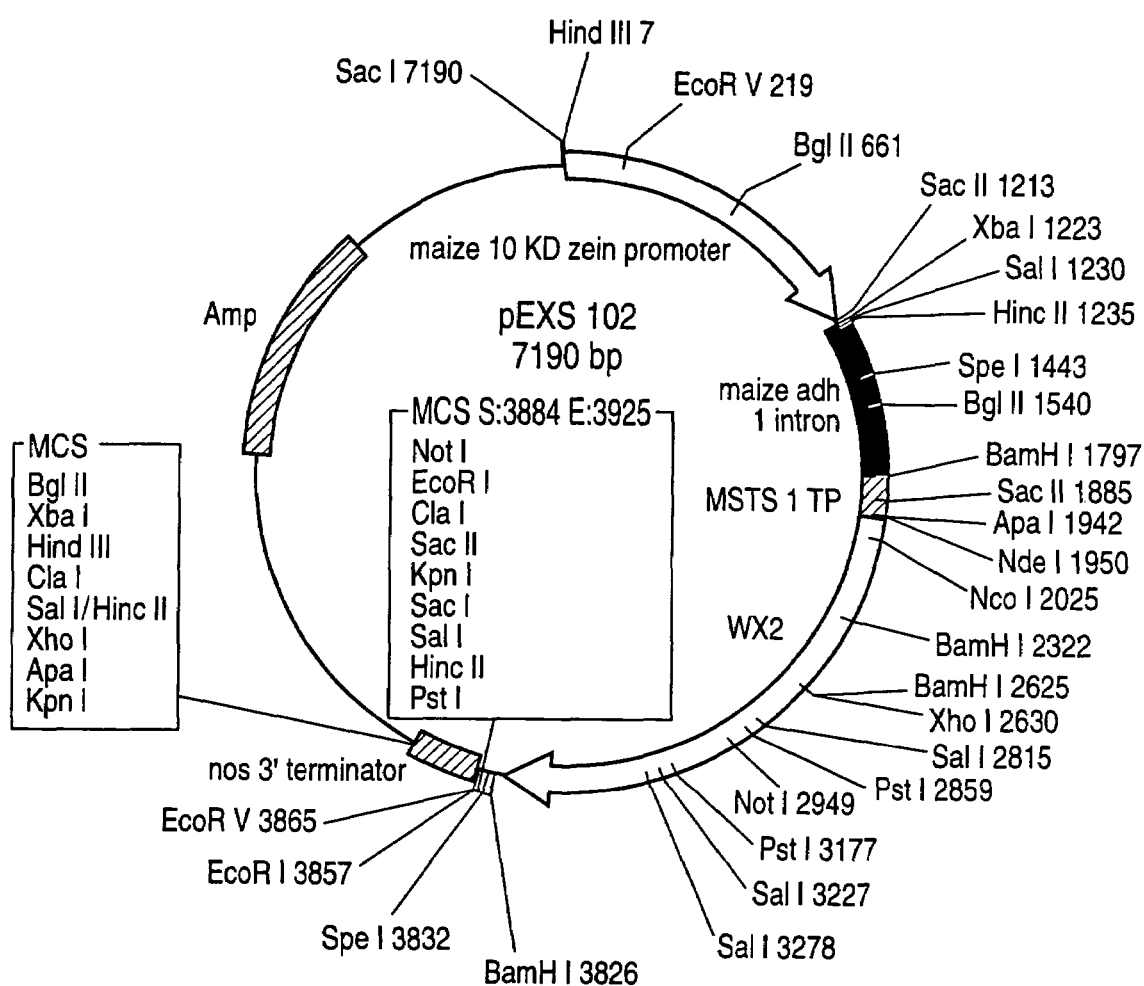
FIG. 24 shows the plasmid PEXS 102 having 7190 base pairs, adapted for plant use containing the maize 10 KD zein promoter, and maize adh I intron, gene coding for the maize starch synthase I transit peptide, and the Waxy 2 gene and the nos terminator and the ampicillin gene.
Figure 25:
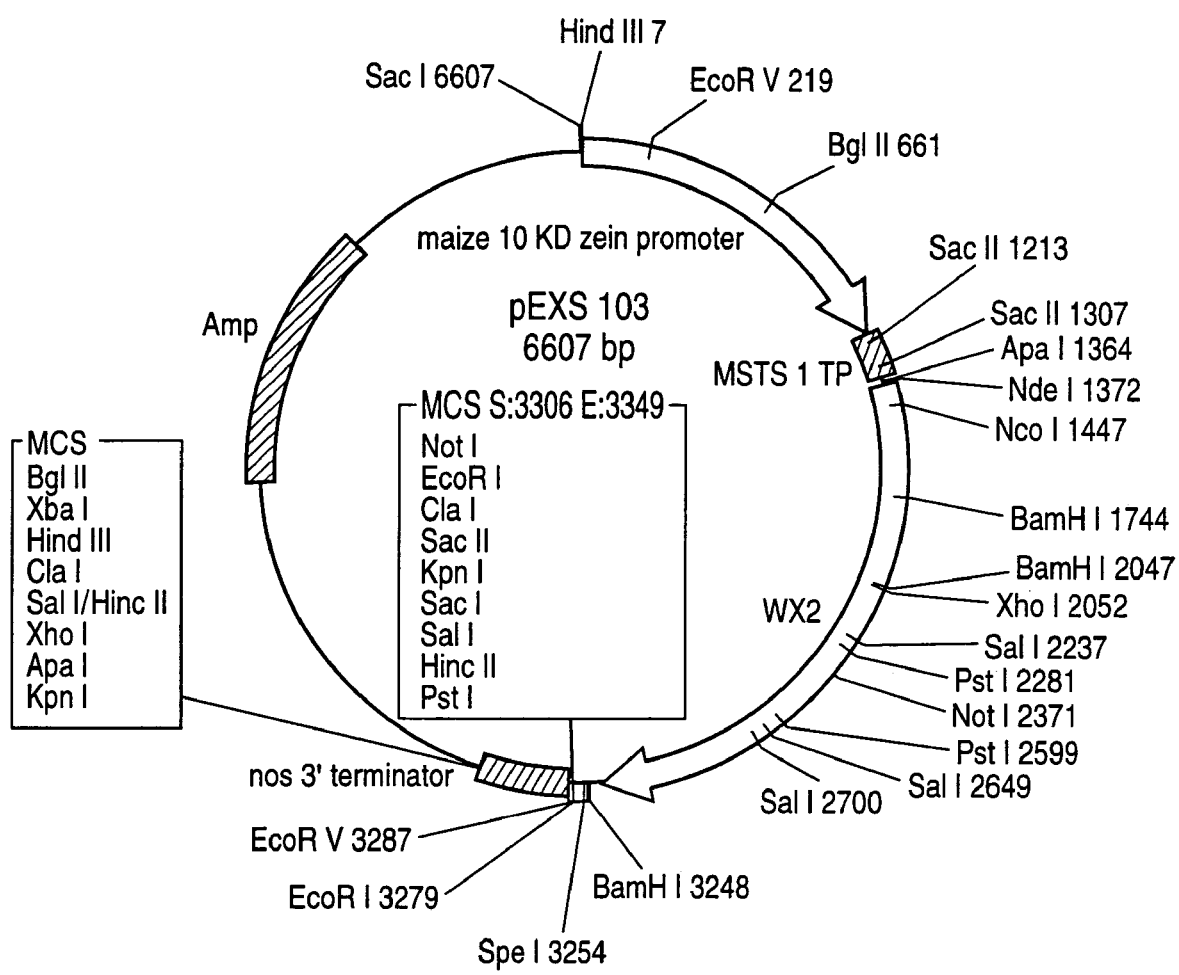
FIG. 25 shows the plasmid pEXS 103 having 6607 base pairs, adapted for plant use containing the maize 10 KD zein promoter, the gene coding for the maize starch synthase I transit peptide, and the Waxy 2 gene and the nos terminator and the ampicillin gene.
Figure 26:
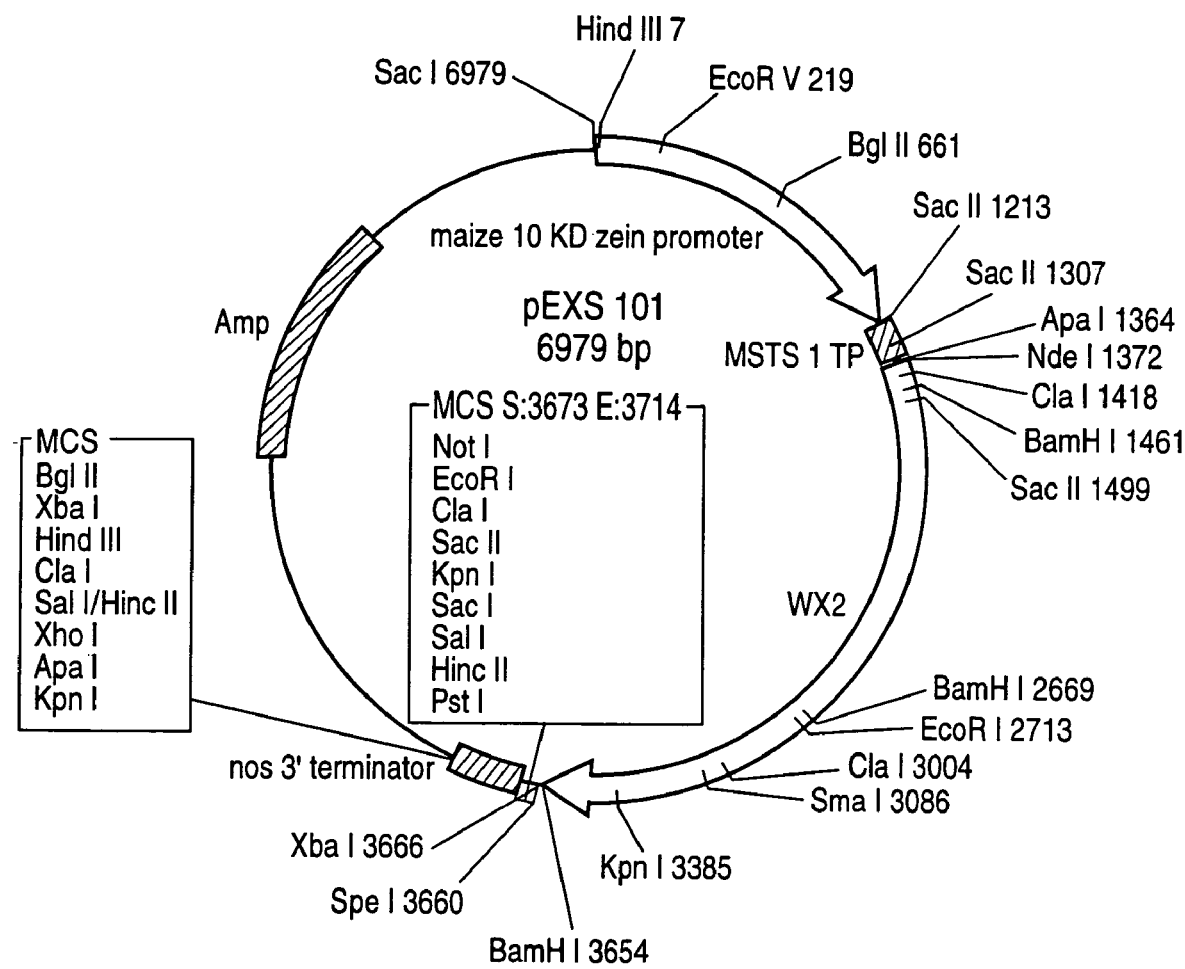
FIG. 26 shows the plasmid pEXS 101 having 6979 base pairs, adapted for plant use containing the maize 10 KD zein promoter, the gene coding for the maize starch synthase I transit peptide, and the glg B gene and the nos terminator and the ampicillin gene.
Figure 27:
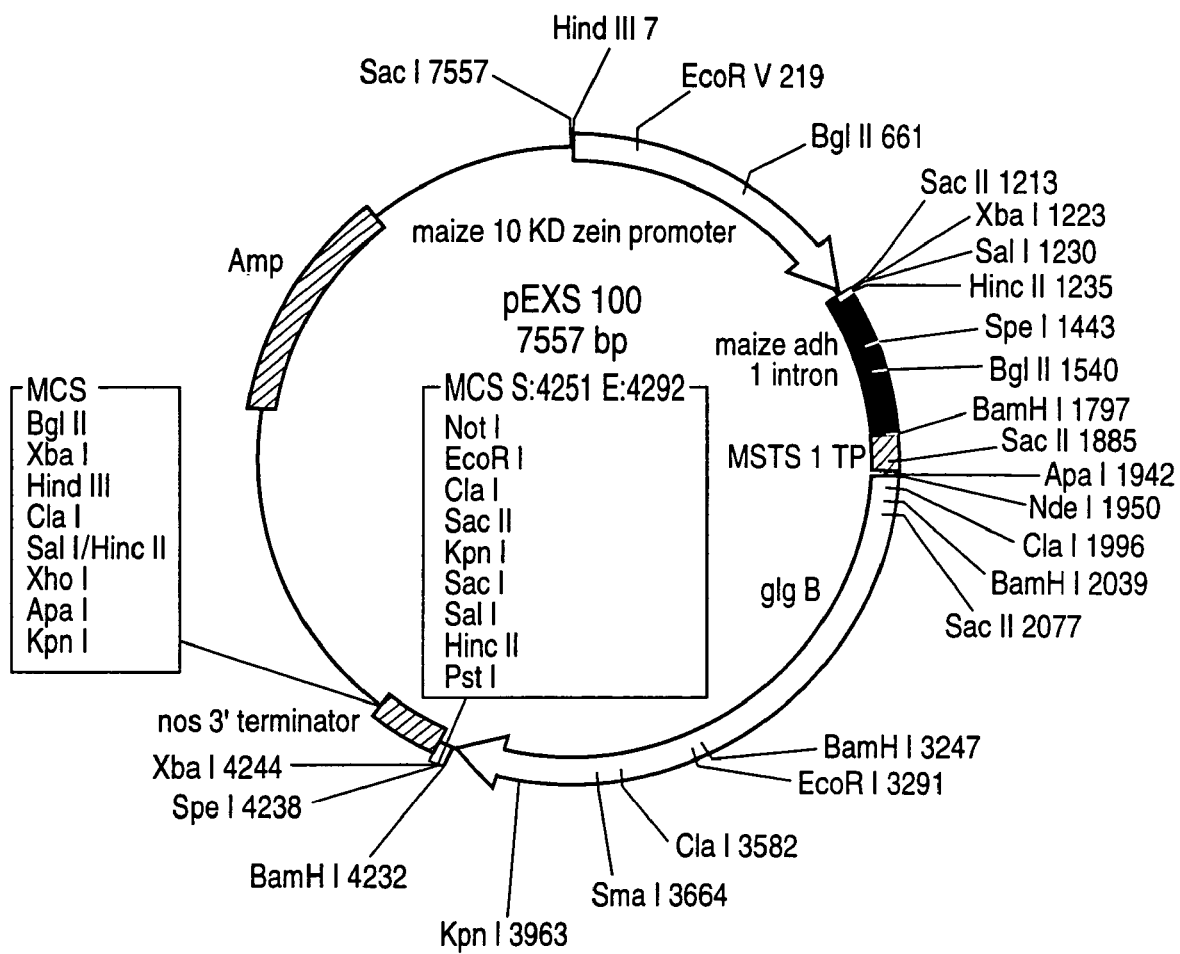
FIG. 27 shows the plasmid pEXS 100 having 7557 base pairs, adapted for plant use containing the maize 10 KD zein promoter, and maize adh I intron, the gene coding for the maize starch synthase I transit peptide, and the glg B gene and the nos terminator and the ampicillin gene.
Figure 28:
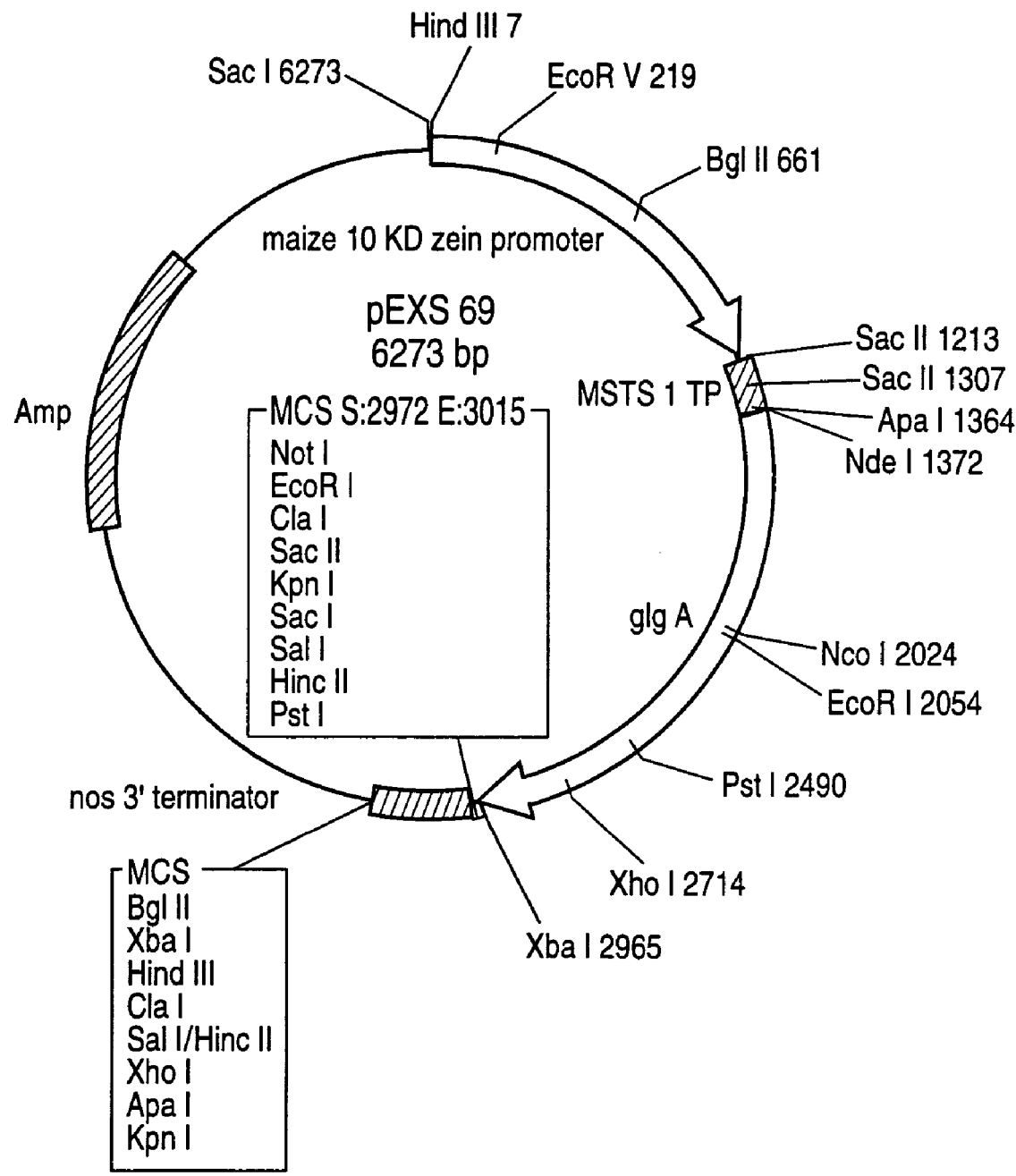
FIG. 28 shows the plasmid pEXS 101 having 6273 base pairs, adapted for plant use containing the maize 10 KD zein promoter, the gene coding for the maize starch synthase I transit peptide, and the glg A gene and the nos terminator and the ampicillin gene.
Figure 29:
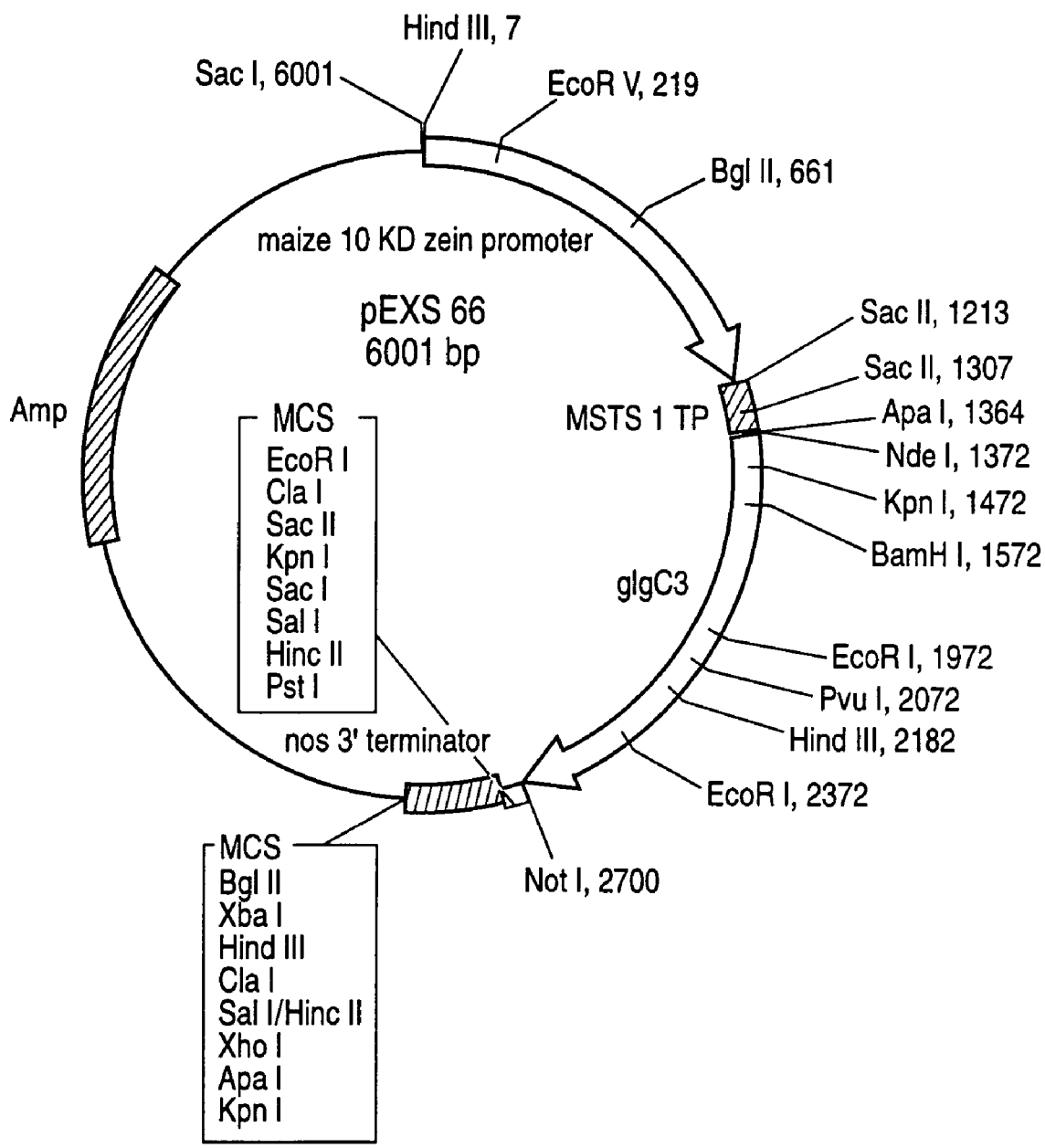
FIG. 29 shows the plasmid PEXS 66 having 6001 base pairs, adapted for plant use containing the maize 10 KD zein promoter, the gene coding for the maize starch synthase I transit peptide, and the glg $C_3$ gene and the nos terminator and the ampicillin gene.
Figure 30:
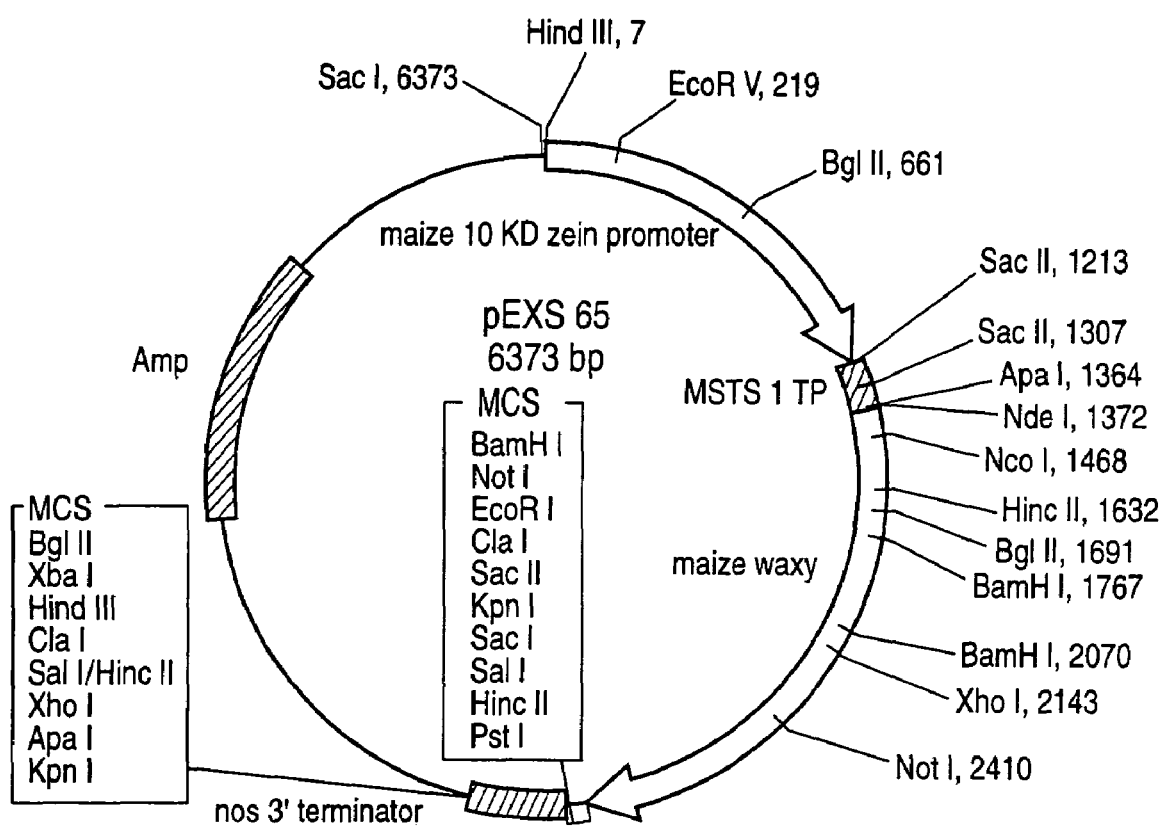
FIG. 30 shows the plasmid pEXS 65 having 6373 base pairs, adapted for plant use containing the maize 10 KD zein promoter, the gene coding for the maize starch synthase I transit peptide, and the maize waxy gene and the nos terminator and the ampicillin gene.
Figure 31:
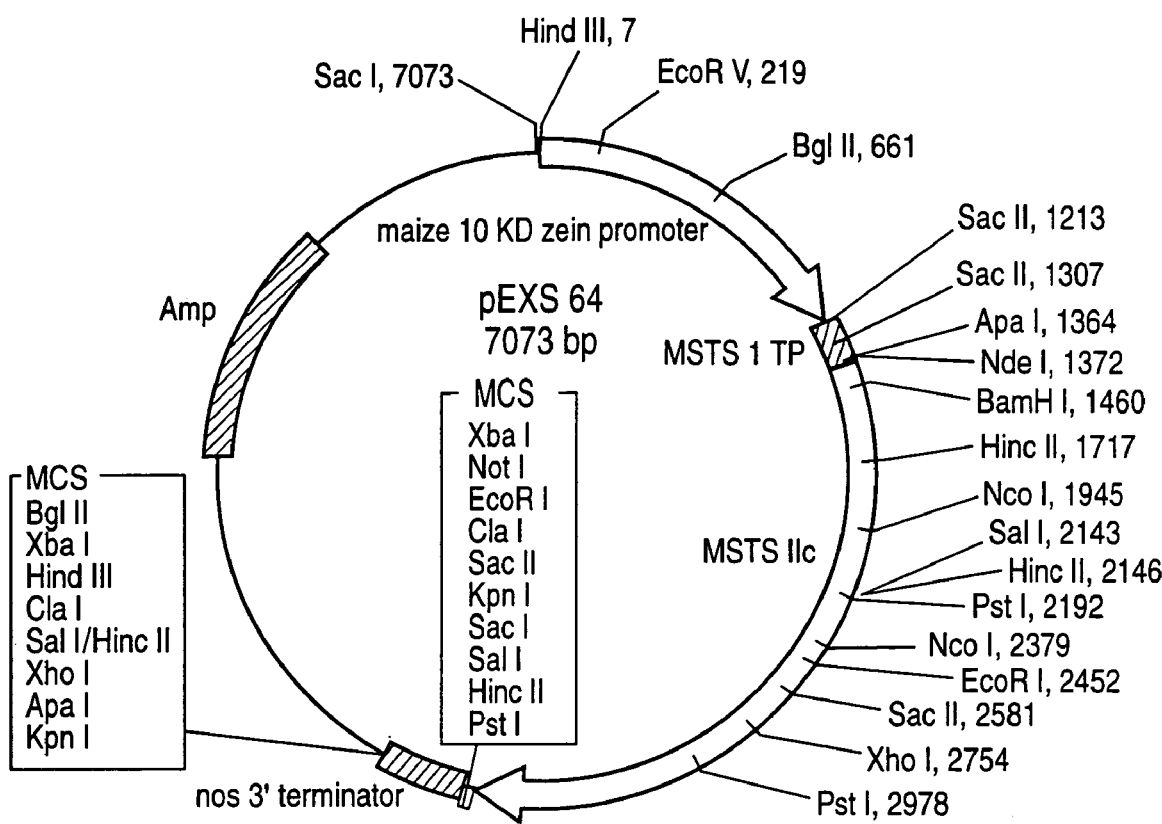
FIG. 31 shows the plasmid pEXS 64 having 7073 base pairs, adapted for plant use containing the maize 10 KD zein promoter, the gene coding for the maize starch synthase I transit peptide, and the maize soluble starch synthase IIa gene and the nos terminator and the ampicillin gene.
Figure 32:
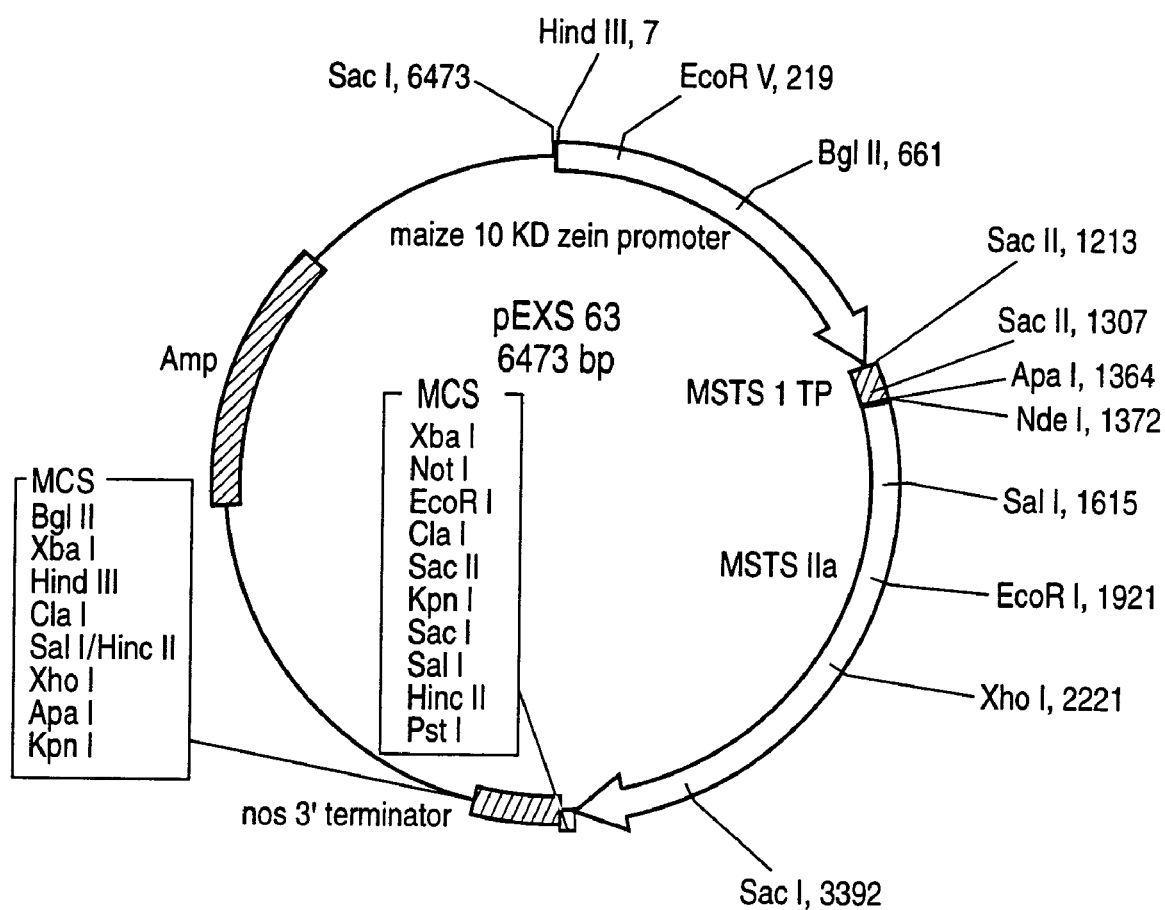
FIG. 32 shows the plasmid pEXS 63 having 6473 base pairs, adapted for plant use containing the maize 10 KD zein promoter, the gene coding for the maize starch synthase I transit peptide, and the maize soluble starch synthase IIa gene and the nos terminator and the ampicillin gene.
Figure 33:
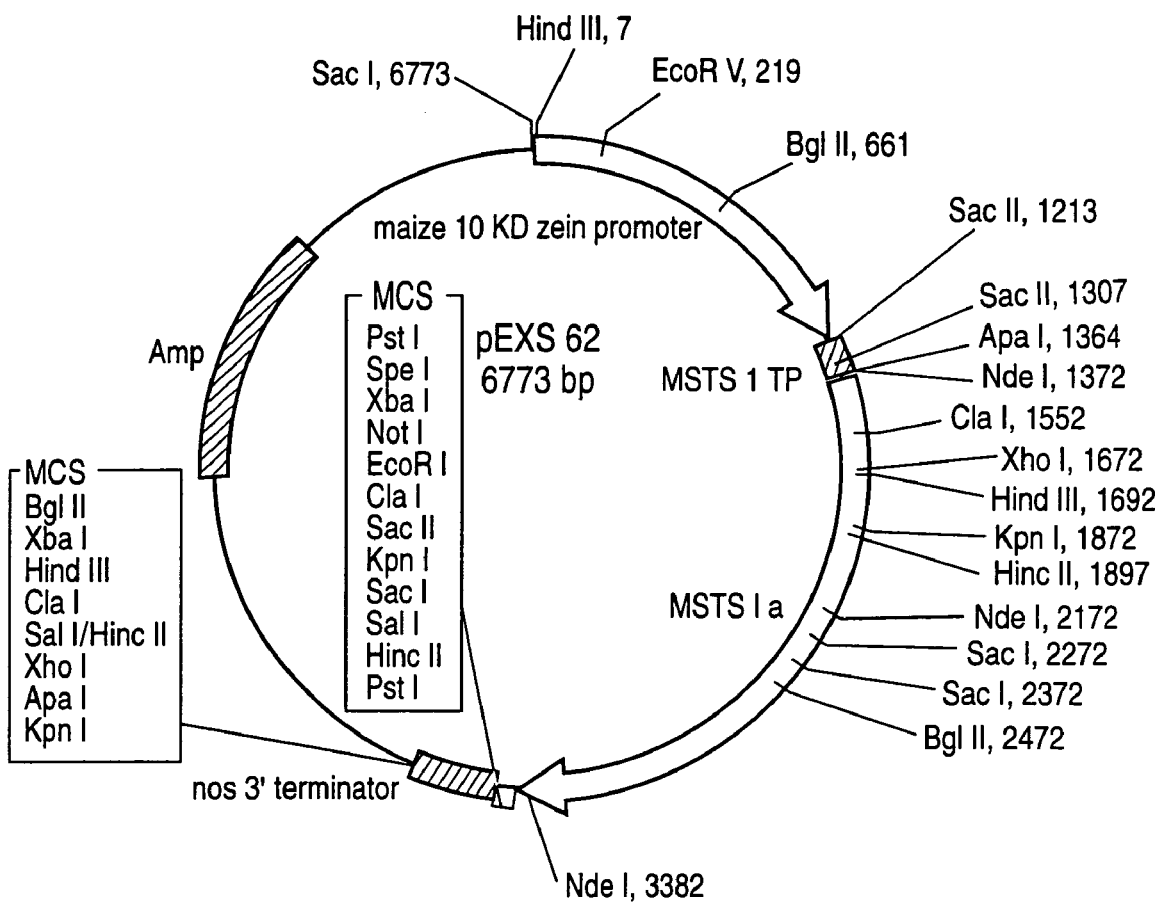
FIG. 33 shows the plasmid pEXS 62 having 6773 base pairs, adapted for plant use containing the maize 10 KD zein promoter, the gene coding for the maize starch synthase I transit peptide, and the maize soluble starch synthase I-2 gene and the nos terminator and the ampicillin gene
Figure 34:
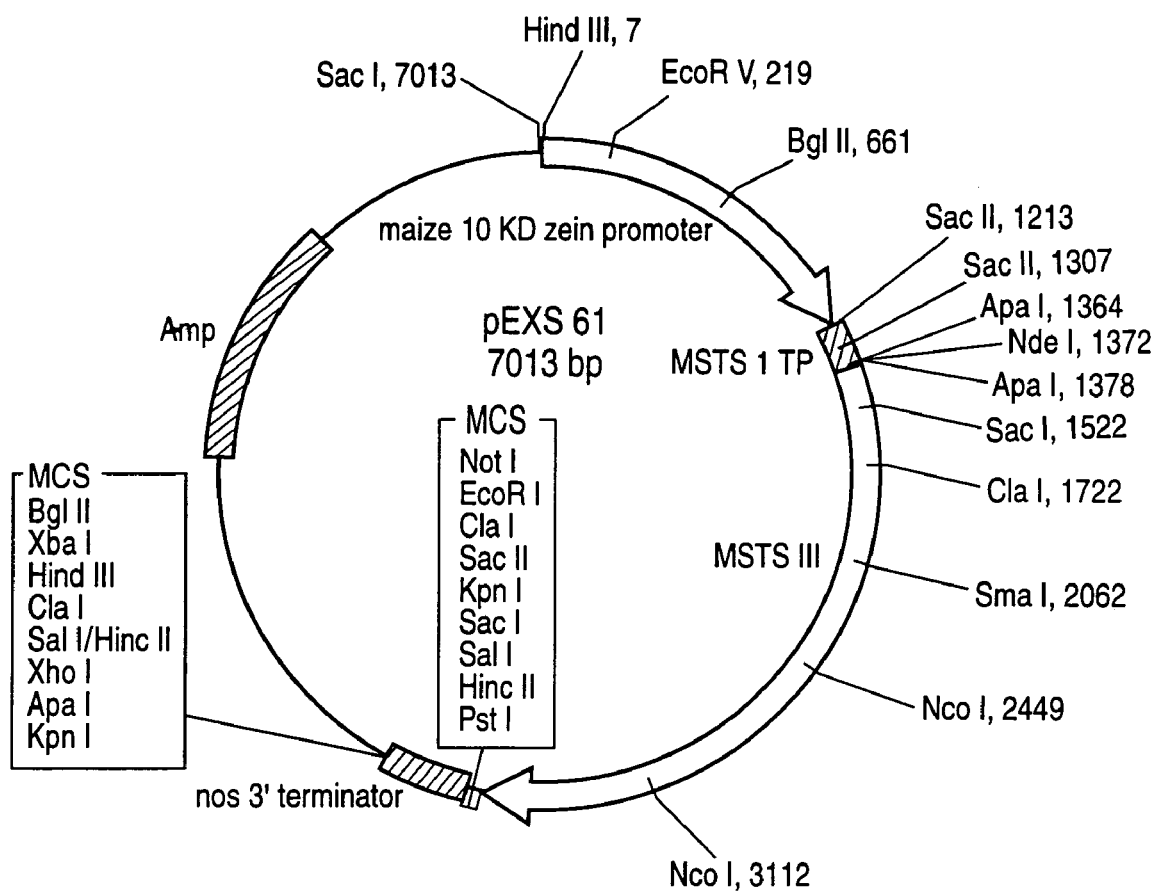
FIG. 34 shows the plasmid PEXS 61 having 7013 base pairs, adapted for plant use containing the maize 10 KD zein promoter, the gene coding for the maize starch synthase I transit peptide, and the maize soluble starch synthase IIb gene and the nos terminator and the ampicillin gene.
Figure 35:
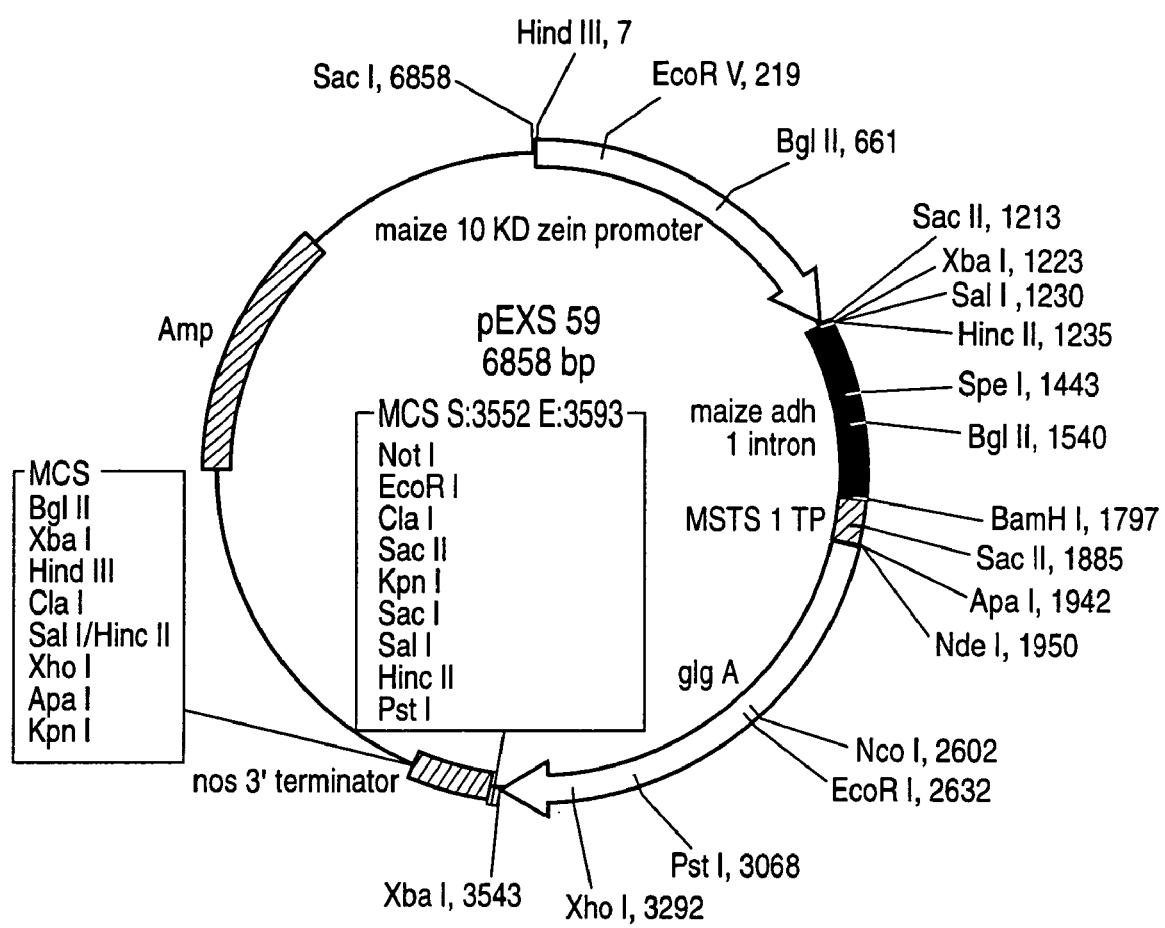
FIG. 35 shows the plasmid pEXS 59 having 6858 base pairs, adapted for plant use containing the maize 10 KD zein promoter, and maize adh I intron, the gene coding for the maize starch synthase I transit peptide, and the *E. coli* glgA gene and the nos terminator and the ampicillin gene
Figure 36:
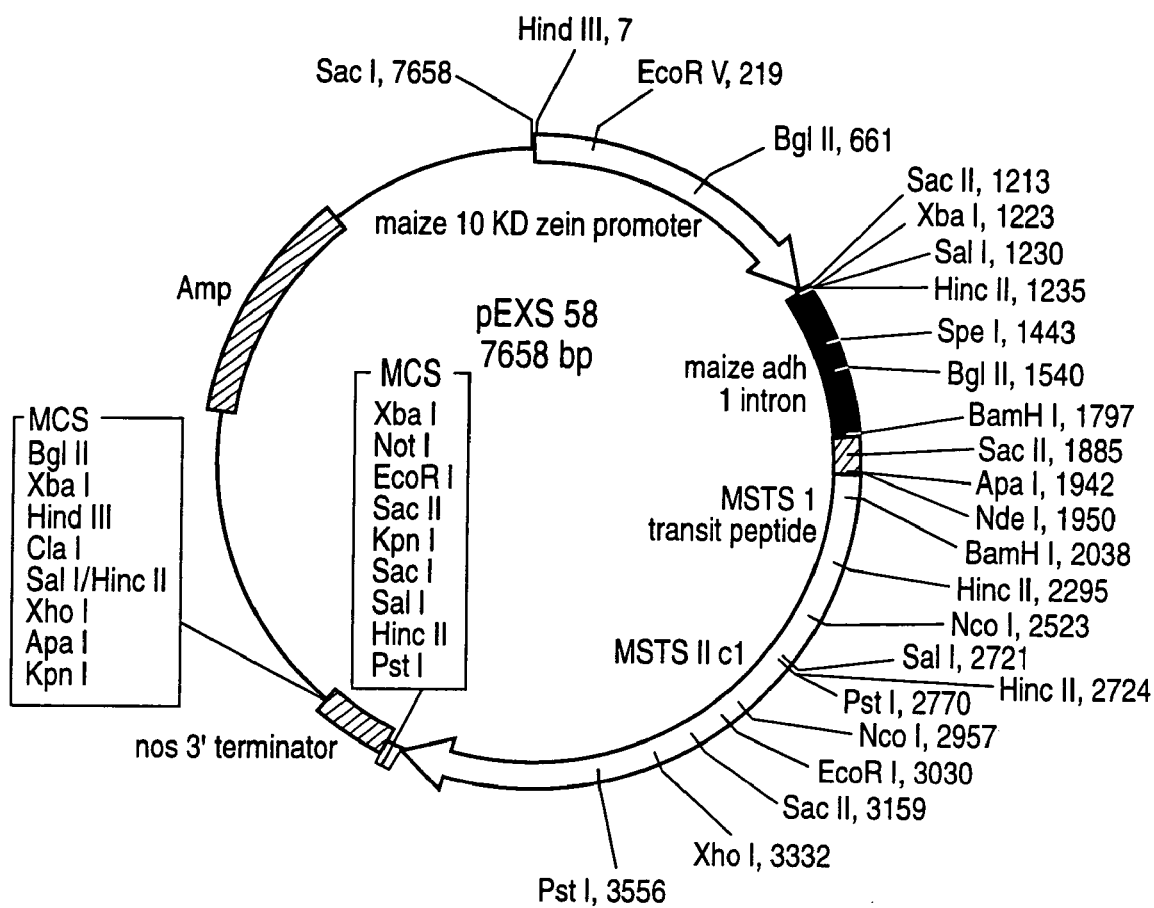
FIG. 36 shows the plasmid pEXS 58 having 7658 base pairs, adapted for plant use containing the maize 10 KD zein promoter, and maize adh I intron, the gene coding for the maize starch synthase I transit peptide, and the maize soluble starch synthase IIa gene and the nos terminator and the ampicillin gene.
Figure 37:
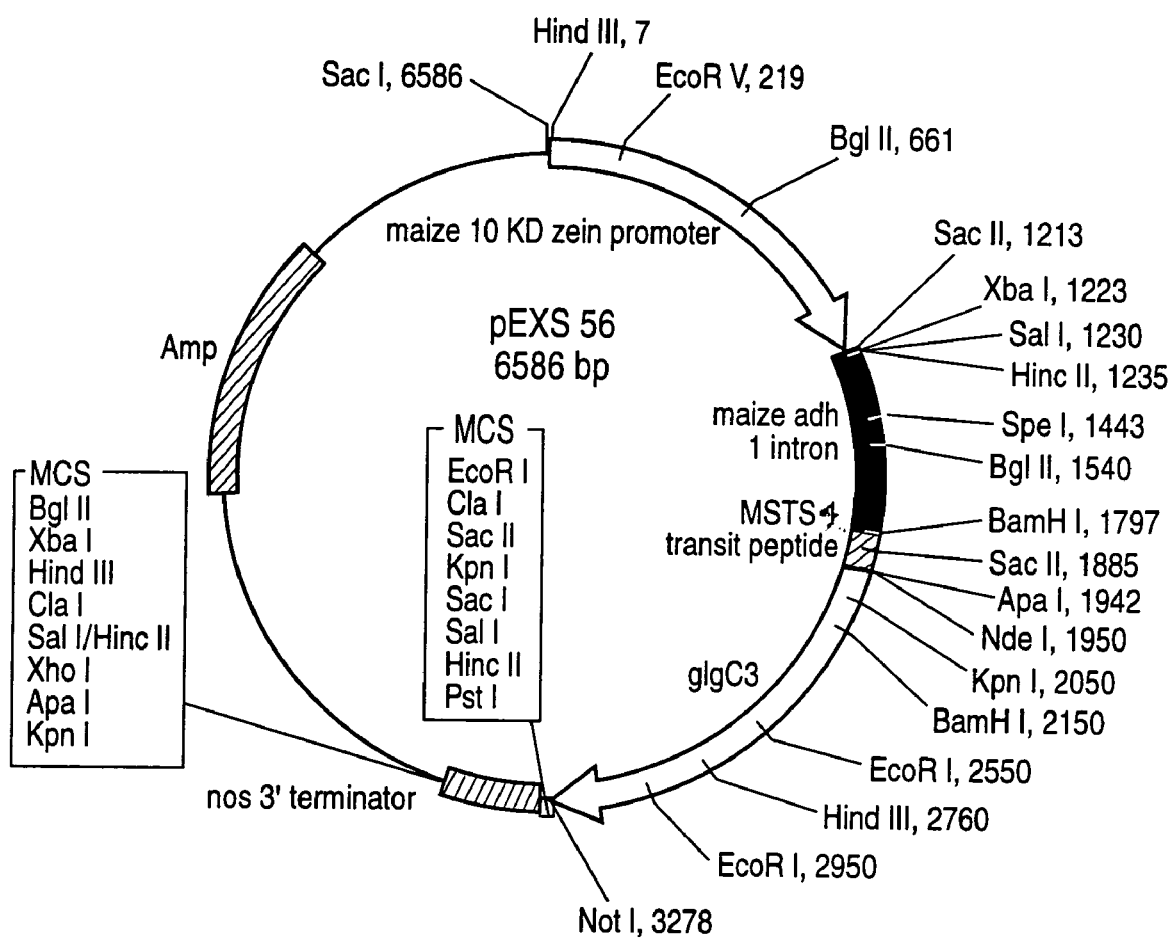
FIG. 37 shows the plasmid pEXS 56 having 6586 base pairs, adapted for plant use containing the maize 10 KD zein promoter, and maize adh I intron, the gene coding for the maize starch synthase I transit peptide, and the glg $C_3$ gene and the nos terminator and the ampicillin gene.
Figure 38:
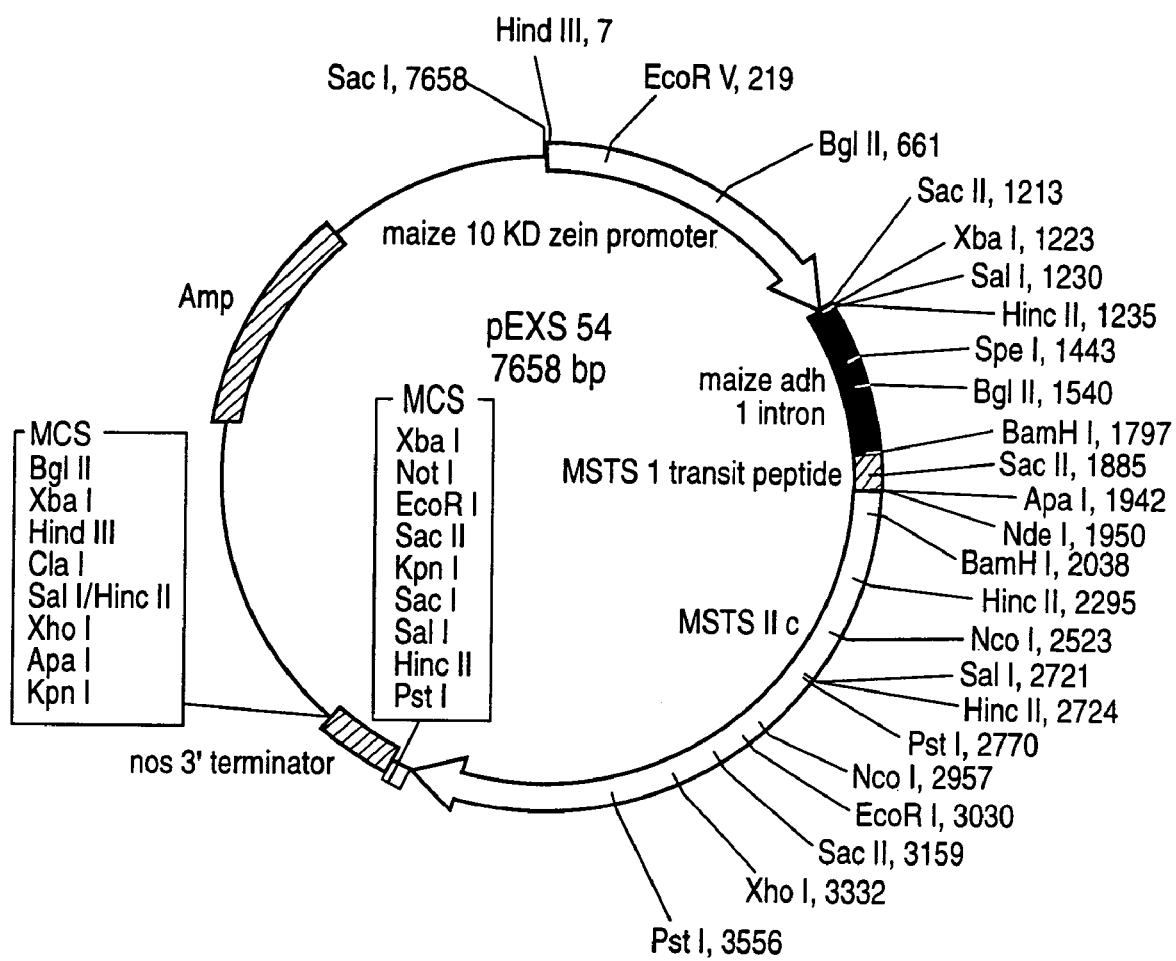
FIG. 38 shows the plasmid pEXS 54 having 7658 base pairs, adapted for plant use containing the maize 10 KD zein promoter, and maize adh I intron, the gene coding for the maize starch synthase I transit peptide, and the Maize SS IIa gene and the nos terminator and the ampicillin gene.
Figure 39:
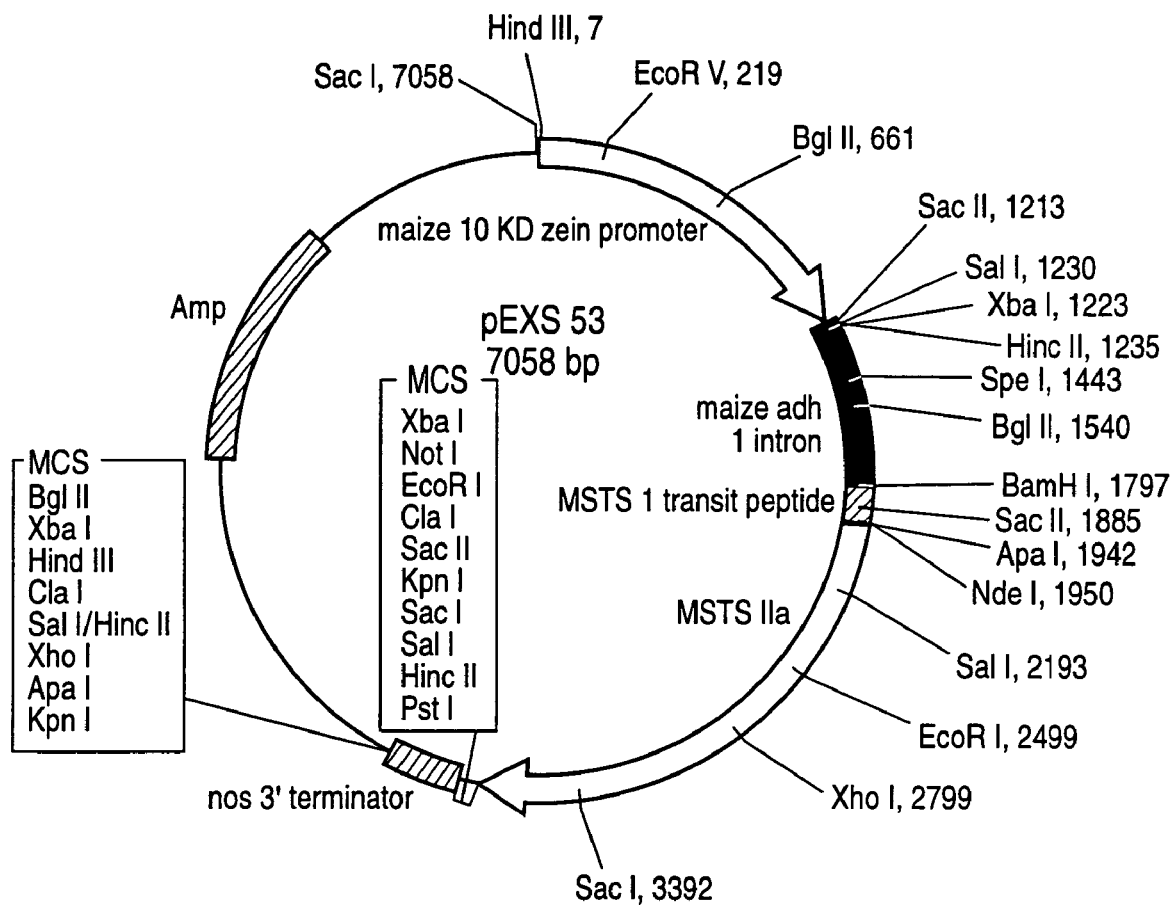
FIG. 39 shows the plasmid pEXS 53 having 7058 base pairs, adapted for plant use containing the maize 10 KD zein promoter, and maize adh I intron, the gene coding for the maize starch synthase I transit peptide, and the maize starch soluble synthase IIa-2 gene and the nos terminator and the ampicillin gene.
Figure 40:
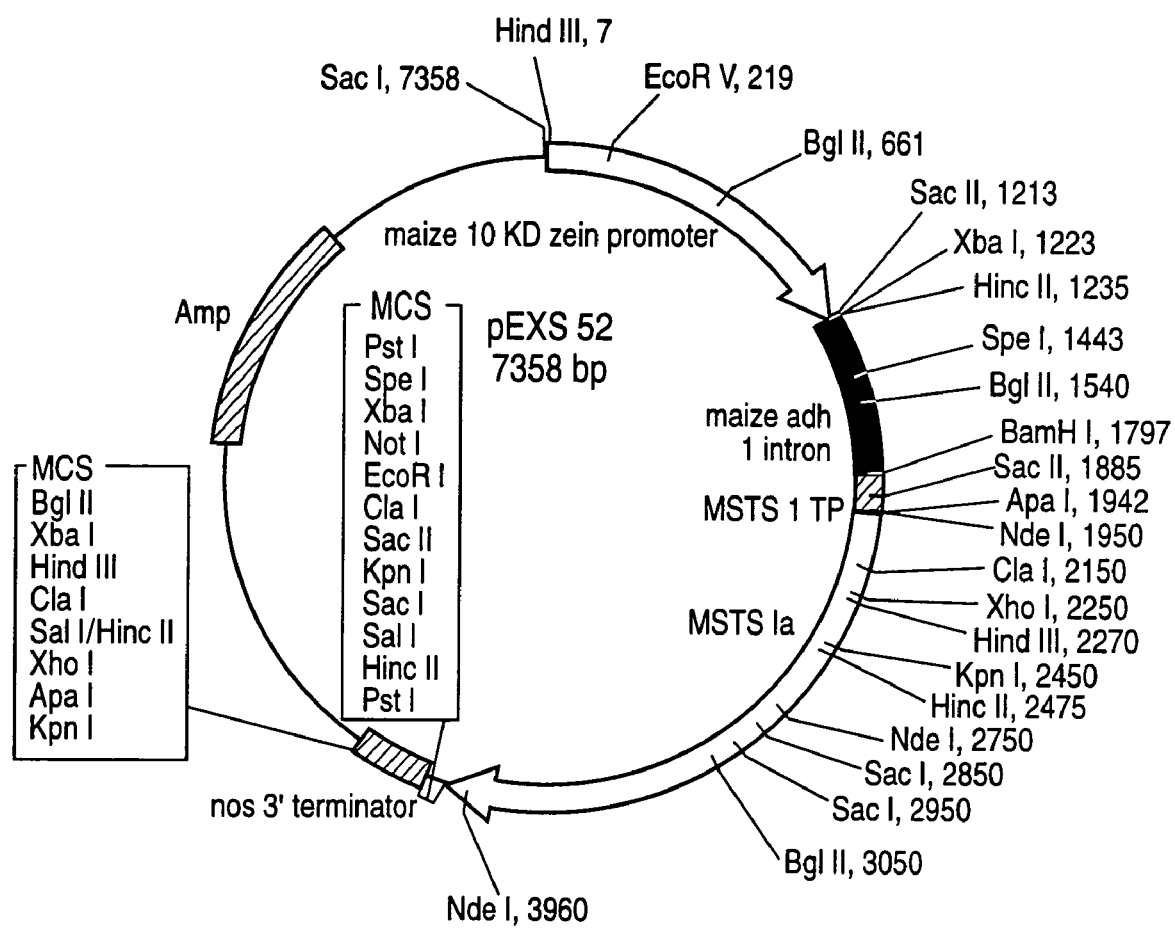
FIG. 40 shows the plasmid pEXS 52 having 7358 base pairs, adapted for plant use containing the maize 10 KD zein promoter, and maize adh I intron, the gene coding for the maize starch synthase I transit peptide, and maize starch soluble synthase I-2 gene and the nos terminator and the ampicillin gene.
Figure 41:
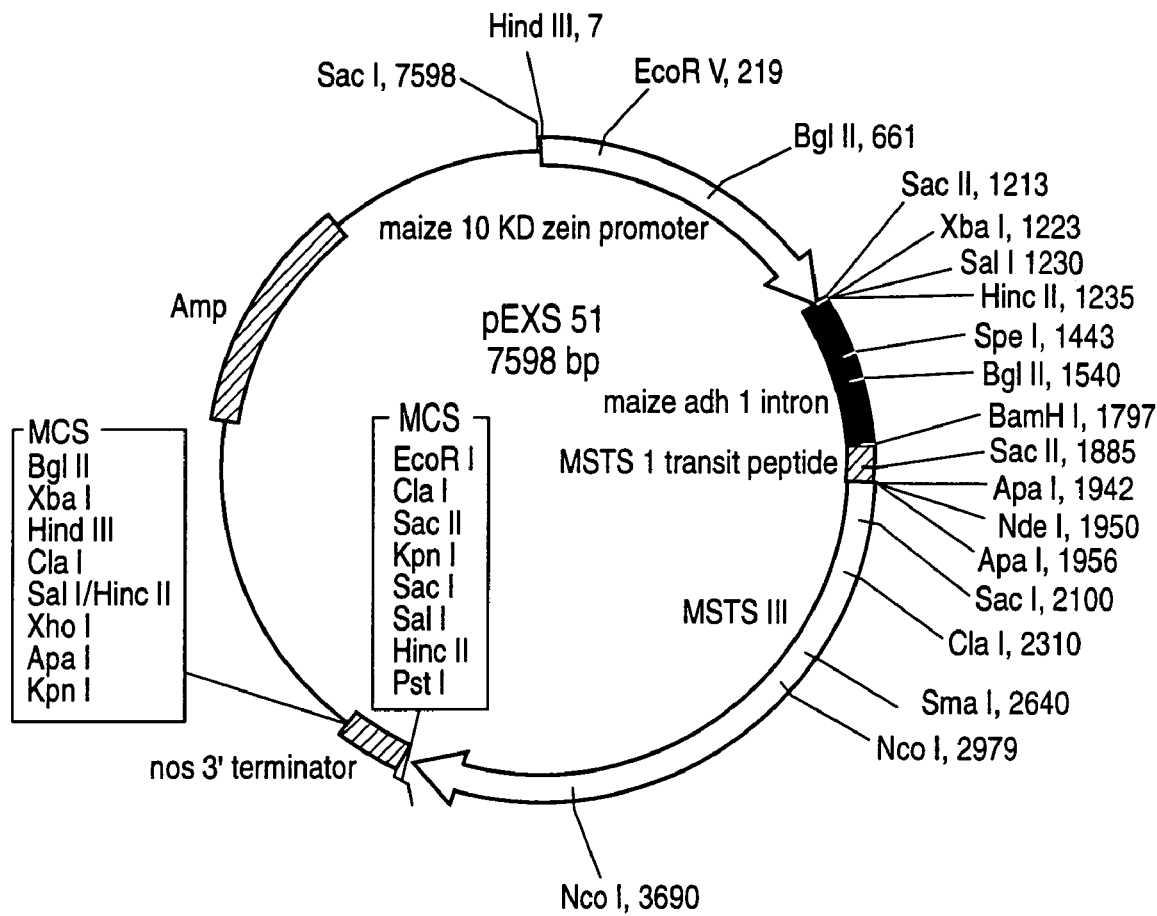
FIG. 41 shows the plasmid pEXS 51 having 7398 base pairs, adapted for plant use containing the maize 10 KD zein promoter, and maize adh I intron, the gene coding for the maize starch synthase I transit peptide, and maize starch soluble synthase Iib gene and the nos terminator and the ampicillin gene.
Figure 42:
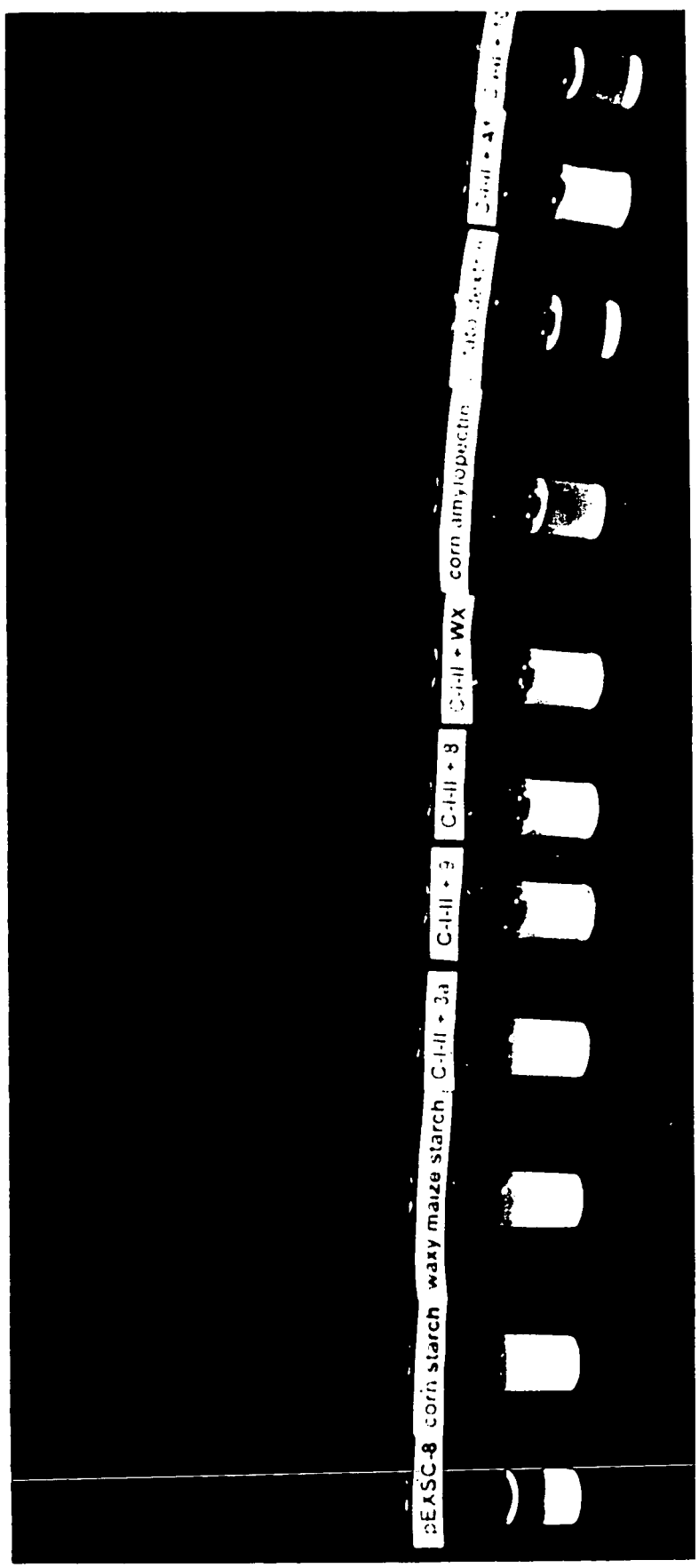
FIG. 42 shows photograph of eleven products of altered starch produced with the present invention. The titled are encoded C-I-II=the glgC gene and the BEI and the BEII genes the following number or alternatively designation means pEXS-and the number. Thus C-I-II=the glgC gene and the BEI and the BEII and EXS-10 plasmid that contains the gene SSI, having the N-terminus shown in Table 1.
Figure 58:
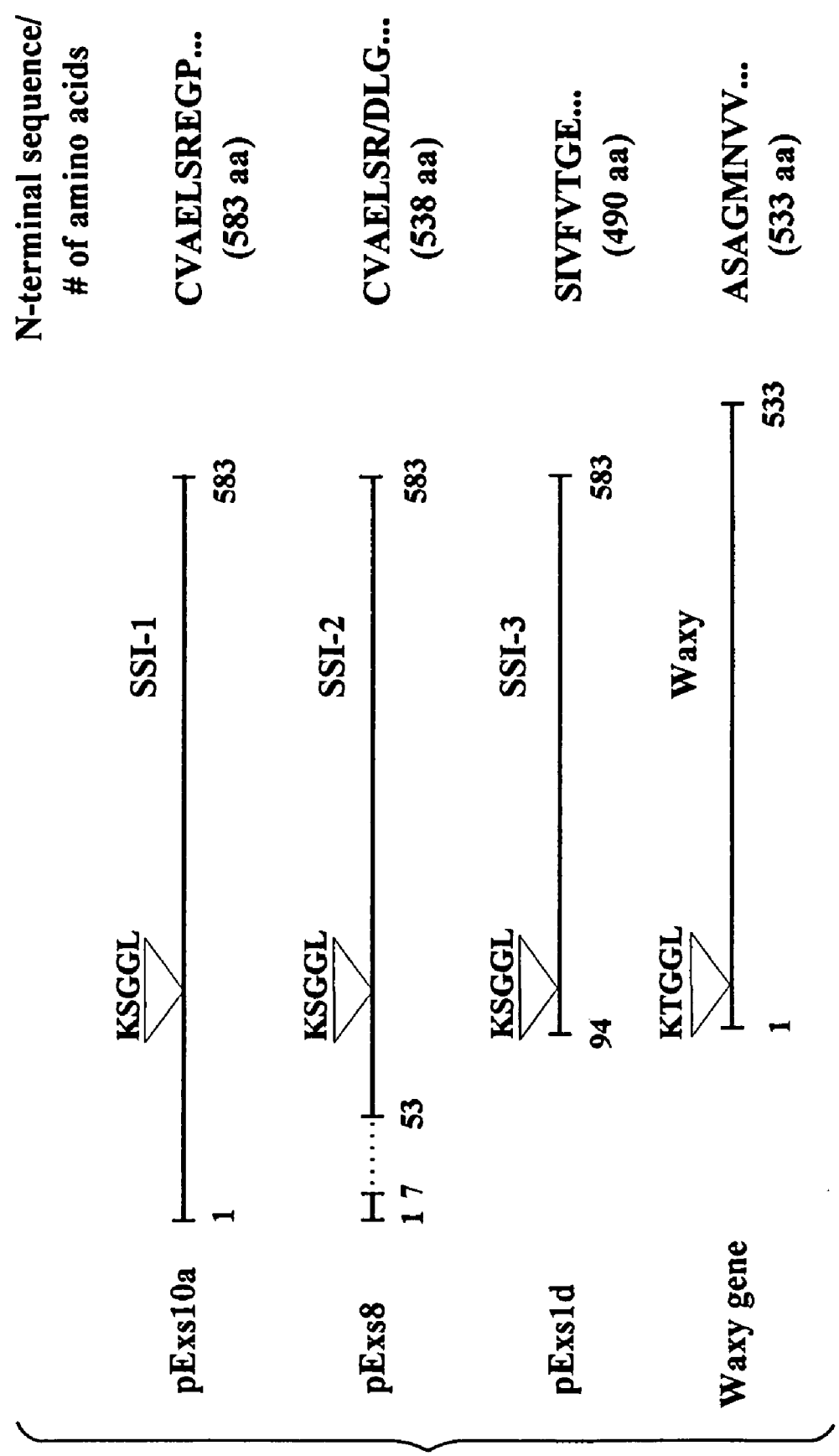
FIG. 58. SSI-1, SSI-2, and SSI-3 construct design. Three forms of SSI were constructed in the pET expression (see Methods). pExs10a encodes SSI-1, the full length maize SSI (583 amino acids) which has the N-terminal sequence CVAELSREGP (SEQ ID NO:64). pExs8 encodes a truncated SSI, SSI-2, with amino acids # 8-52 deleted from the N-terminus of SSI-1 and which has the N-terminal sequence CVAELSR/DLG (SEQ ID NO:65). pExs1d encodes the most truncated form of SSI, SSI-3, with the first 93 amino acids deleted from SSI-1 and which has the N-terminal sequence SIVFVTGE (SEQ ID NO:66). A depiction of the waxygene, encoding GBSS, which has the N-terminal sequence ASAGMNW (SEQ ID NO:67), is also included for comparison. The amino acid motif KS/TGGL (SEQ ID NO:9), the putative binding site for ADGPGlc, in indicated by the triangles. The KS/TGGL (SEQ ID NO:9) motif is located 18 amino acids from the N-terminus in GBSS, while the motif is 106 amino acids from the N-terminus in maize SSI. Drawing not to scale.
Figure 59:
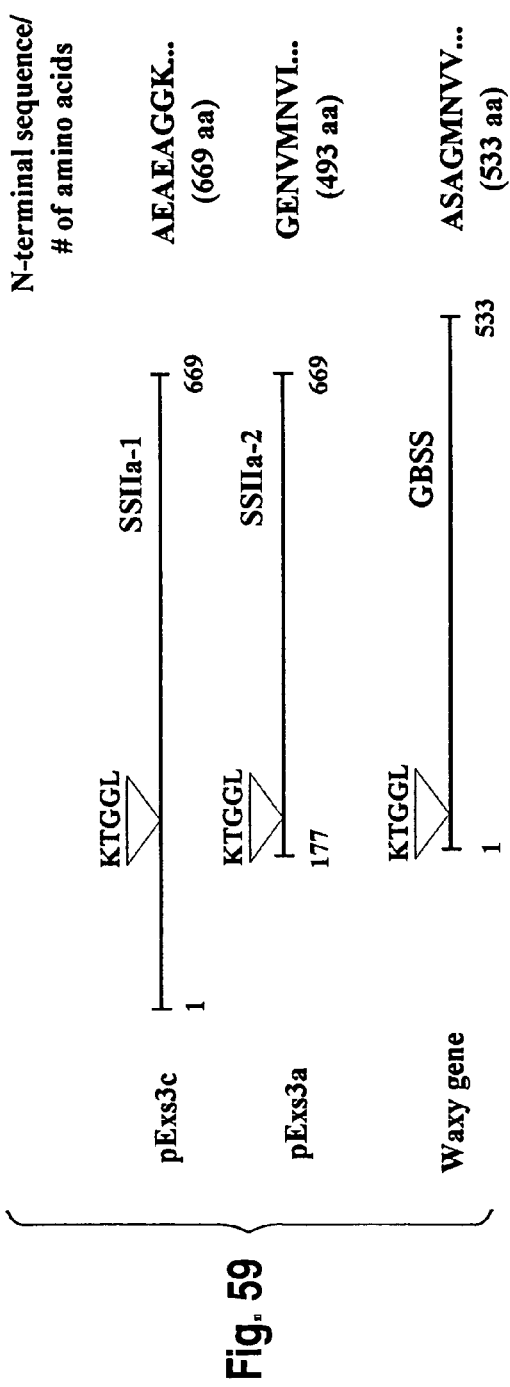
FIG. 59. SSIIa-1 and SSIIa-2 construct diagram. Two forms of SSIIa were constructed in the pET expression system. pExs3c encodes SSIIa-1, the putative full length maize SSIIa which has the N-terminal sequence AEAE-AGGK (SEQ ID NO:68). N-terminal sequencing of SSIIa-1 revealed that the polypeptide chain started at amino acid #1, so the length of SSIIa-1 is 669 amino acids. pExs3a encodes a truncated form of SSIIa, SSIIa-2, with the first 176 N-terminal amino acids deleted from SSIIa (493 amino acids total) and which has the N-terminal sequence GENVMNVI (SEQ ID NO:1). A depiction of the waxy gene, encoding GBSS which has the N-terminal sequence ASAGMNVV (SEQ ID NO:67), is also included for comparison. The amino acid motif KTGGL (SEQ ID NO:10), the putative binding site for ADPGlc, is indicated by the triangles. The KTGGL (SEQ ID NO:10) motif is located 18 amino acids from the N-terminus in GBSS, while the motif is 194 amino acids from the N-terminus in maize SSIIa.
Figure 60:
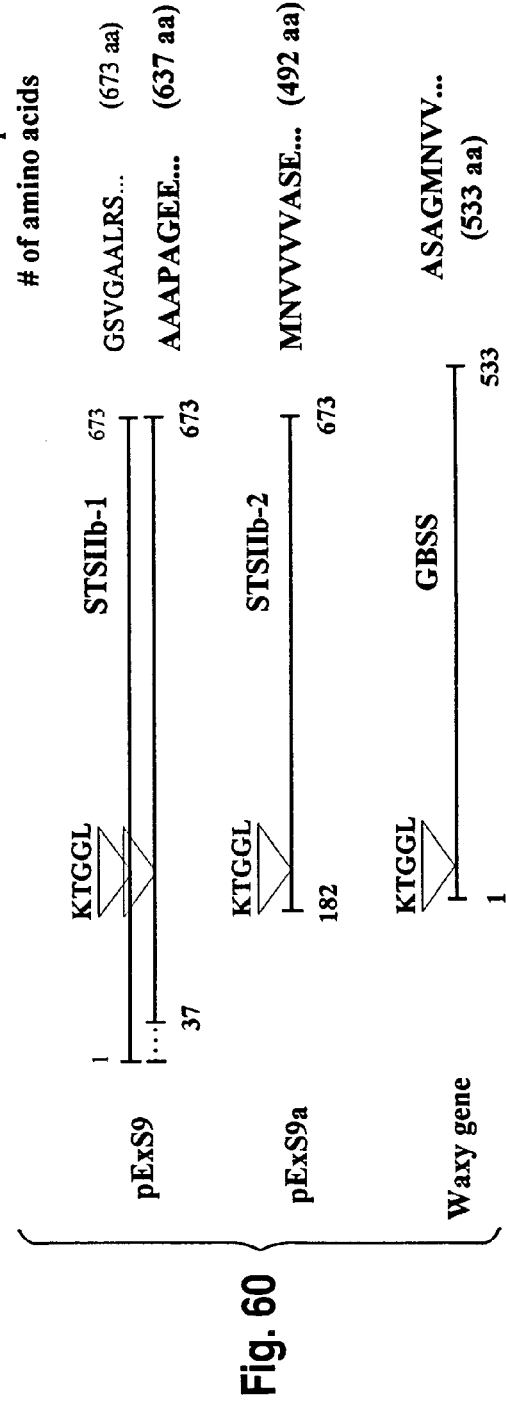
FIG. 60. SSIIb-1 and SSIIb-2 construct diagram. Two forms of SSIIb were constructed in the pET expression system (see Methods). pExs9 encodes SSIIb-1 which has the N-terminal sequence GSVGAALRS (SEQ ID NO:70), the putative full-length maize SSIIb which has the N-terminal sequence AAAPAGEE (SEQ ID NO:2). N-terminal sequencing of SSIIb-1 revealed that the polypeptide chain started at amino acid # 1, so the length of SSIIb-1 is 637 amino acids. pExs9a encodes a truncated form of SSIIb, SSIIb-2, with the first 144 N-terminal amino acids deleted from SSIIb (492 amino acids total) which has the N-terminal sequence MNVVVVASE (SEQ ID NO:71). A depiction of the waxy gene, encoding GBSS which has the N-terminal sequence ASAGMNVV (SEQ ID NO:67), is also included for comparison. The amino acid motif KTGGL (SEQ ID NO:10), the putative binding site for ADPGlc, is indicated by the triangles. The KTGGL (SEQ ID NO:10) motif is located 18 amino acids from the N-terminus in GBSS, while the motif is 158 amino acids from the N-terminus in maize SSIIb.
Figure 61:
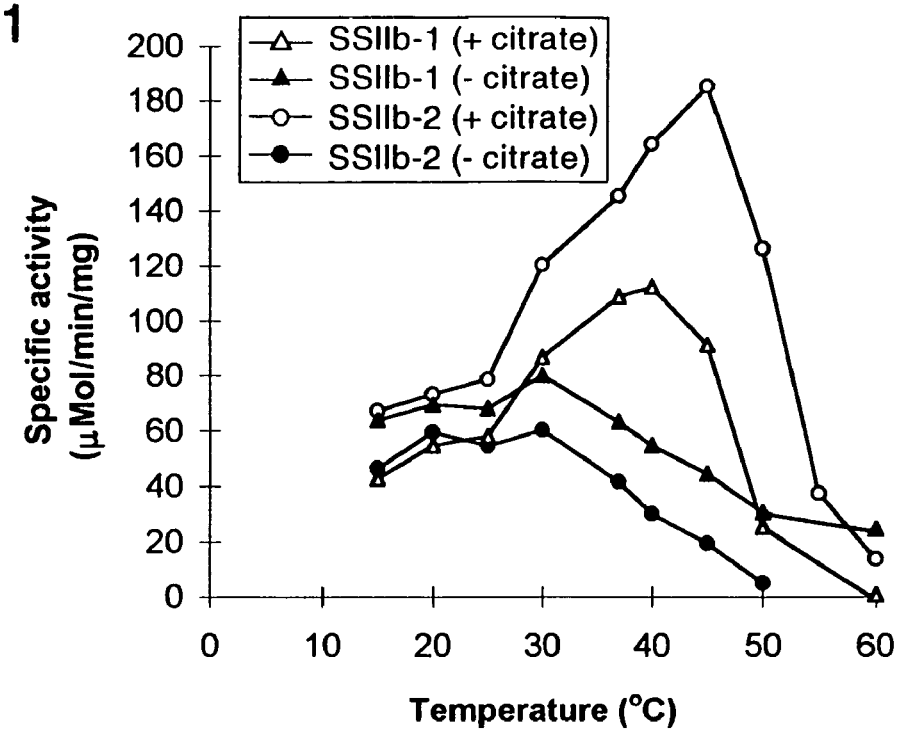
FIG. 61. Temperature curves for SSI enzymes. A; assay components, except enzyme and [U-$^{14}$C]-ADPGlc, were mixed and then preincubated at each temperature for 3 minutes before addition of enzyme and ADPGlc. For all assays, the final concentration of [U-$^{14}$C]-ADPGlc was 3 mM, while amylopectin was 6 mg/ml. Each point is an average of three separate determinations.
Figure 62:
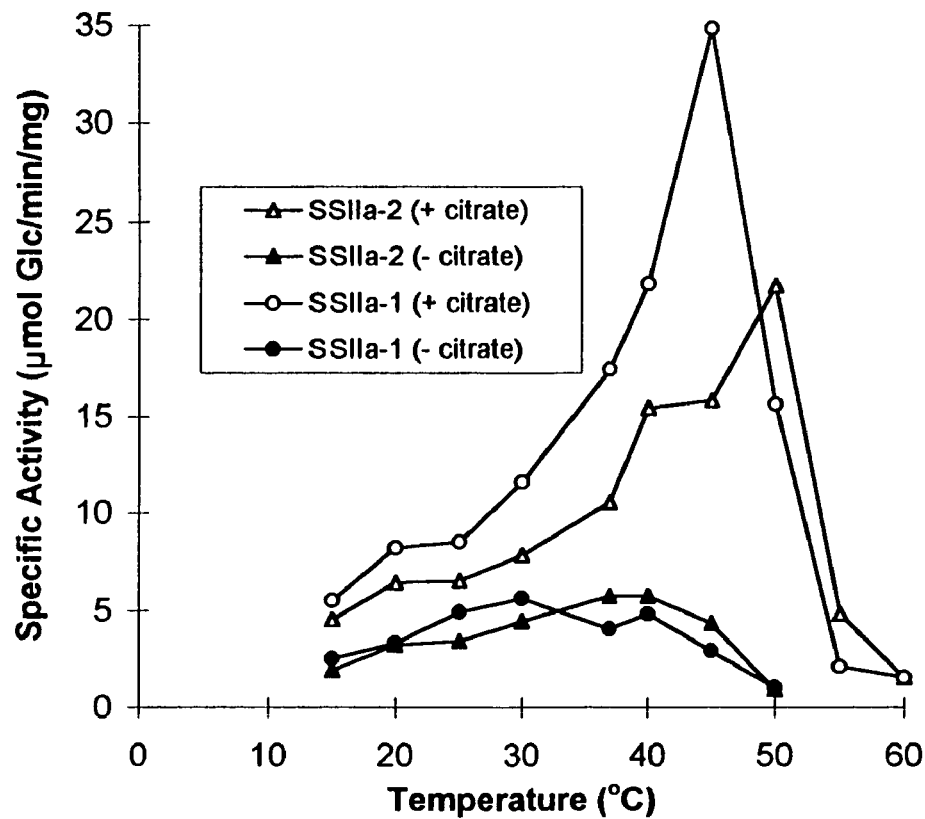
FIG. 62. Temperature optima of SSIIa-1 and SSIIa-2. All assay components, except enzyme and [U-$^{14}$C]-ADPGlc, were mixed and then preincubated at each temperature for 3 minutes before addition of enzyme and ADPGlc. For assays in the presence of 0.5 M citrate, 5 mg/ml amylopectin was used as primer. For assays without citrate, 10 mg/ml amylopectin was used. For all assays, the concentration of [U-$^{14}$C]-ADPGlc was 3 mM. Each point is an average of three separate determinations.
Figure 63:
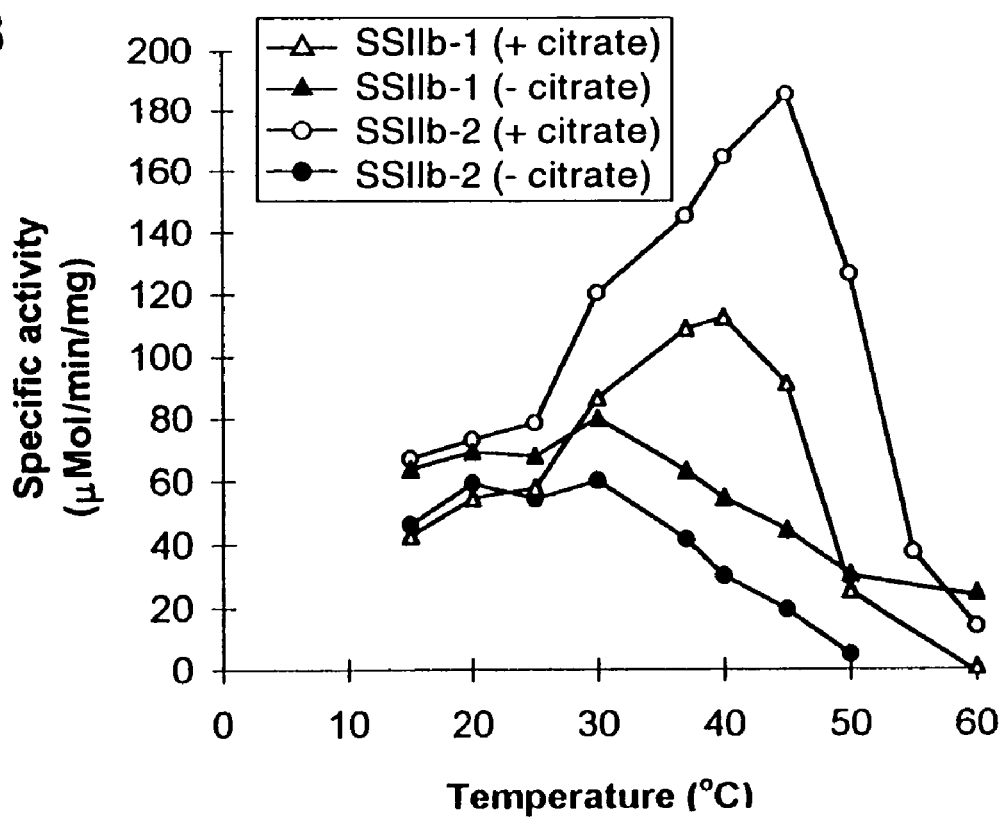
FIG. 63. Temperature optima of SSIIb-1 and SSIIb-2. All assay components, except enzyme and [U-$^{14}$C]-ADPGlc, were mixed and then preincubated at each temperature for 3 minutes before addition of enzyme and ADPGlc. For all assays, the concentration of [U-$^{14}$C]-ADPGlc was 3 mM and the concentration of glycogen was 40 mg/ml. Each point is an average of three separate determinations.

The photographs listed in FIGS. 42 and 21 attempt to show the visual differences that are present into the starches as compared to those known in the art.

Description of the Starch

Corn starch is a milky, slightly thickened gel which is slightly if at all flowable.

Rice starch forms two levels the upper level is a thickened syrup like consistency more flowable than corn starch (less thick than corn starch) opaque milky color (more translucent than corn starch in this level) and a lower level which is a very white glob not transmitting much light through this bottom level of material. This lower level is formed in a very thick mass and does not appear flowable.

Corn amylopectin is slightly less white than the top level of rice starch and is a very slightly opaque milky color (more translucent than corn starch) slightly less flowable than the rice top level.

Potato dextrin is the most transparent almost appearing clear but is still opaque white and it is very flowable appearing only slightly less flowable than water.

Waxy Maize starch will flow very slowly and has the consistency of honey. The color is very opaque transmitting little light and the color is only slightly less light than corn starch.

SSI starch made from plasmid pExs-8 has two distinct levels. The top level appears clear and slightly thicker than the flowability of water. The bottom level appears as a precipitate. This sample resembles the ornaments that contain little figures and plastic flakes resembling snowflakes. Like those ornaments when turned upside down the sample appears to be falling snow. However the flakes in this sample appear to be slightly gummy and appear in the first moments of level mixing to form a opaque white liquid.

SSI starch made from a host containing the following two plasmids pExsC BEI BEII and pExs8 is not as clear as the top level of pExs-8 and appears slightly less thick than pExs-8. It has even more flowability than does Potato Dextrin.

SSIIb starch made from a host containing the following two plasmids pExsC BEI BEII and pExs-9 is not as clear as the top level of pExs-8 and appears slightly less thick than pExs-8. It has even more flowability than does Potato Dextrin.

WAXY starch made from a host containing the following two plasmids pExsC BEI BEII and pExs-wx is not as clear as the top level of pExs-8 but seems to have a few tiny thread like chains that settle to the bottom and when mixed give the material a slightly more white color and appears slightly less thick than pExs-8. It has even more flowability than does Potato Dextrin.

SSII starch made from a host containing the following two plasmids pExsC BEI BEII and pExs-3a is the color of corn starch and maybe slightly whiter but not as white as the bottom level of pExs8 and definitely transmitting more light through and has the flowability characteristic of pExs-8 when mixed.

glgA starch appears to have a very slight precipitate and is comparable in color to corn amylose pectin and ExsC BEI BEII and pExs-wx. And the flowability is between corn amylose and pExsC BEI BEII pExs-wx.

The samples of polysaccharides listed above form groups generally according to color as follows: waxy maize starch and corn starch and pExsC BEI BEII pExs3a and pExsc8 are the whitest group. The flowability characteristics of this group are fairly diverse. With corn starch a lump and Waxy maize starch only slightly flowable and pExsC BEI BEII and pExs-3a and pExsC-8 more like water than syrup. The second group contains corn amylopectin and pExsC BEI BEII pExs-wx and pExsC BEI BEII and pExs-A1 which are less white and clearer. The flowability of corn amylopectin is less than the other two members of this group but it is still similar. The last group is the least white and thus the clearest. This group includes pExsC BEI BEII and pExs-8, potato dextrin, pExsC BEI BEII and pExs-10, pExsC BEI BEII and pExs-9. The flowability of this group is also similar to each other.

Plant Hosts

The following plasmids have been transformed into rice plants. The sequence for the mutant glgC gene is shown in FIG. 46. The plasmids are made substantially in a similar manner as described above for the production of bacterial plasmid. Clearly the plasmid maps shown in FIGS. 25-41 and this application and the listed short protocols allow the ordinarily skilled person in the art to make the present plasmids. The following combinations of plasmids have been transformed into rice plants. Additionally combinations of plasmids including the combination that includes all of the maize genes SSI, SSII, SSII, BEI, BEII, and GBSS in one host or alternatively in two host that are then crossed to form a hybrid having the entire complement of up regulated starch genes are being developed. Clearly the ordinarily skilled person in the art could have placed the sequences in the antisense positions to down regulate these genes to the extent that maize genes will down regulate the partial homologous rice genes. The first group of transgenic are group1, including rice transformants (transformed by microprojectile bombardment) containing MSTSI-2 (pExs52) and glgC$_3$ (pExs66), MSTSIIa-2 and glgC$_3$ (pExs53 and pExs56). The second group of rice transformants contains MSTSIIa and glgC$_3$ (pExs54 and pExs56). The third group of transformation contain: transgenic 5 MSTSIIb and glgC$_3$ (pExs 61 and pExs 66); transgenic 6 Maize wx and glgC$_3$ (pExs65 and pExs66). Additionally, glgA and glgB and glgC are combined and transformed into rice. This last transformant is combining the rice plants starch pathway with the gene encoding for ADPG pyrophosphorylase and the bacterial genes. The combination of the plasmids encoding for at least one of the following enzymes, SSI, SSIIa, SSIIb, SSIII, Debranching enzymes, BEI, BEII, GBSS (wx) and some or all of the bacterial starch genes is also useful. There are presently over 300 transformants in the greenhouse. The T1 transgenic rice plants have been screened and characterized (FIG. 56, 57), 12 plants have successfully expressed maize SSI-2 in rice seeds. 21 plants have successfully expressed maize SSIIb in rice seeds. We are currently screening rice plants down regulated the rice SS expression by cosuppression and have 400 T2 plants in the greenhouse.

Maize Starch Synthase and its Mutant Forms

In order to characterize the multiple forms of maize starch synthase, the genes coding for the full length SS and its N-terminally truncated forms were expressed in *E. coli*. The recombinant enzymes were purified and kinetically characterized. We have demonstrated that different isoforms and its truncated forms all have distinct properties (Table 6-14, FIG. 58-63). The specific activities ($V_{max}$) of the purified maize SSI-1, SSI-2, and SSI-3 were 22.5, 33.4 and 26.3 mol glc/min/mg of protein respectively. Our results have clearly indicated that the catalytic center of SSI is not located in its N-terminal extension. However, N-terminal truncation decreased the enzyme affinity for amylopectin, with the $K_m$ for amylopectin of the truncated SSI-3 being about 60%-90% higher than that of the full length SSI-1. The effects of N-terminal truncation of SSIIa depend upon the assay conditions used. For both SSIIa-1 and SSIIa-2, the $V_{max}$ of each enzyme increased 2-fold upon raising assay temperature from 27° C. to 37° C. (Tables II and III). However, the effect of temperature on ADPGlc affinity was different for SSIIa-1 and SSIIa-2. For the truncated SSIIa-2, the $K_m$ for ADPGlc was not affected by raising temperature. In contrast, the $K_m$ of ADPGlc for the putative full length SSIIa-1 increased 2 fold upon raising the assay temperature from 27° C. to 37° C. (Table III). Interestingly, the truncated SSIIa-2 exhibited a lower $K_m$ for ADPGlc than SSIIa-1 did in all assay conditions used in this study except that they showed similar $K_m$ values for ADPGlc when glycogen was used as a primer at 27° C. Although N-terminal truncation of SSIIa appears to lower the $K_m$ for ADPGlc under most assay conditions, it also must be noted that the maximal velocity of the truncated SSIIa-2 is decreased by about 2-4 fold when compared to SSIIa-1. The truncated SSIIb-2 was found to be more temperature stable than the longer SSIIb-1 in the presence of citrate, while little difference was observed in their pH activity profiles. While the putative full length SSIIb-1 showed similar $V_{max}$ using amylopectin or glycogen as a primer, the N-terminally truncated SSIIb-2 showed a 40% increase in $V_{max}$ using glycogen compared with amylopectin as a primer. N-terminal truncation of SSIIb increased its $V_{max}$ by 25% with amylopectin as a primer. We also demonstrated that chimeric enzymes of maize starch synthase (combining the C-terminal domain of SS with different N-terminal sequences of SS or unrelated sequences would produce a functional enzyme with SS activity and altered properties) (Table 15).

Conclusions, Ramifications, and Scope

Accordingly, it can be seen that, according to the invention, the starch genes can produce new and altered starch in either host, plant or bacteria. Additionally, polysaccharides very similar to corn starch can be produced in a bacterial host.

Although the description above contains many specificities, these should not be construed as limiting the scope of the invention but as merely providing illustrations of some of the presently preferred embodiments of this invention. Various other embodiments and ramifications are possible within its scope. For example, different combinations of the plasmids in either host for the production of useful plant and useful grain and useful polysaccharides.

Thus the scope of the invention should be determined by the appended claims and their legal equivalents, rather than by the examples given. All references cited herein are incorporated herein in their entirety by reference.

SEQUENCE LISTING

<160> NUMBER OF SEQ ID NOS: 86

<210> SEQ ID NO 1
<211> LENGTH: 8
<212> TYPE: PRT
<213> ORGANISM: Zea mays

<400> SEQUENCE: 1

```
Gly Glu Asn Val Met Asn Val Ile
 1               5

<210> SEQ ID NO 2
<211> LENGTH: 8
<212> TYPE: PRT
<213> ORGANISM: Zea mays

<400> SEQUENCE: 2

Ala Ala Ala Pro Ala Gly Glu Glu
 1               5

<210> SEQ ID NO 3
<211> LENGTH: 11
<212> TYPE: PRT
<213> ORGANISM: Zea mays

<400> SEQUENCE: 3

Cys Val Ala Glu Leu Ser Arg Glu Gly Pro Ala
 1               5                  10

<210> SEQ ID NO 4
<211> LENGTH: 12
<212> TYPE: PRT
<213> ORGANISM: Zea mays

<400> SEQUENCE: 4

Met Asn Val Val Val Ala Ser Glu Cys Ala Pro
 1               5                  10

<210> SEQ ID NO 5
<211> LENGTH: 15
<212> TYPE: PRT
<213> ORGANISM: Zea mays

<400> SEQUENCE: 5

Ala Ser Ala Gly Met Asn Val Val Phe Val Gly Ala Glu Met Ala
 1               5                  10                  15

<210> SEQ ID NO 6
<211> LENGTH: 11
<212> TYPE: PRT
<213> ORGANISM: Zea mays

<400> SEQUENCE: 6

Met Asn Val Val Phe Val Gly Ala Glu Met Ala
 1               5                  10

<210> SEQ ID NO 7
<211> LENGTH: 13
<212> TYPE: PRT
<213> ORGANISM: Zea mays

<400> SEQUENCE: 7

Met Ser Ile Val Phe Thr Gly Glu Ala Ser Pro Tyr Ala
 1               5                  10

<210> SEQ ID NO 8
<211> LENGTH: 15
<212> TYPE: PRT
<213> ORGANISM: Zea mays

<400> SEQUENCE: 8

Cys Val Ala Glu Leu Ser Arg Asp Leu Gly Leu Glu Pro Glu Gly
```

```
<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence:
      Illustrative putative binding site
<220> FEATURE:
<221> NAME/KEY: MOD_RES
<222> LOCATION: (2)
<223> OTHER INFORMATION: Ser or Thr

<400> SEQUENCE: 9

Lys Xaa Gly Gly Leu
 1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Thr Gly Gly Leu
 1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Lys Ser Gly Gly Leu
 1               5

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
caagaatgct gcgggagtc                                                  19

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aagtcgacat atgtgcgtcg cggagctgag cag                                  33

<210> SEQ ID NO 14
<211> LENGTH: 32
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 14
gggccccata tgagcattgt ctttgtaacc gg                                  32

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ctcgggccca tatgggggag aatgttatga a                                  31

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gaggcatcaa tgaacacaaa gtcg                                          24

<210> SEQ ID NO 17
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gaagggcccc atatggctga ggctgaggcc gggggcaag                          39

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ttggatccat atgggagctg cggttgcatt ggg                                33

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cctgcgggct ctggcttcac c                                             21

<210> SEQ ID NO 20
<211> LENGTH: 33
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 20
ttggatccat atgaacgtcg tcgtggtggc ttc                                33

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gcataccatg gaacctcaac agc                                           23

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ggtaccatat gaacgtcgtc ttcggcg                                       27

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gacaggcccg tagatcttct cc                                            22

<210> SEQ ID NO 24
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ttggtaccat atggccagcg ccgccggcat gaacg                              35

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gaagatctgg cagggacctg cacac                                         25

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
ggactagtgc attatcgctc ctgtttat                                    28

<210> SEQ ID NO 27
<211> LENGTH: 10
<212> TYPE: PRT
<213> ORGANISM: Escherichia coli

<400> SEQUENCE: 27

Gly Glu Asn Val Met Asn Val Ile Val Val
 1               5                  10

<210> SEQ ID NO 28
<211> LENGTH: 9
<212> TYPE: PRT
<213> ORGANISM: Escherichia coli

<400> SEQUENCE: 28

Ala Glu Ala Glu Ala Gly Gly Lys Asp
 1               5

<210> SEQ ID NO 29
<211> LENGTH: 10
<212> TYPE: PRT
<213> ORGANISM: Escherichia coli

<400> SEQUENCE: 29

Met Ser Ile Val Phe Val Thr Gly Glu Ala
 1               5                  10

<210> SEQ ID NO 30
<211> LENGTH: 9
<212> TYPE: PRT
<213> ORGANISM: Escherichia coli

<400> SEQUENCE: 30

Gly Asp Leu Gly Leu Glu Pro Glu Gly
 1               5

<210> SEQ ID NO 31
<211> LENGTH: 9
<212> TYPE: PRT
<213> ORGANISM: Escherichia coli

<400> SEQUENCE: 31

Cys Val Ala Glu Leu Ser Arg Glu Gly
 1               5

<210> SEQ ID NO 32
<211> LENGTH: 10
<212> TYPE: PRT
<213> ORGANISM: Escherichia coli

<400> SEQUENCE: 32

Gly Ser Val Gly Ala Ala Leu Arg Ser Tyr
 1               5                  10

<210> SEQ ID NO 33
<211> LENGTH: 10
<212> TYPE: PRT
<213> ORGANISM: Escherichia coli

<400> SEQUENCE: 33

```
Met Asn Val Val Val Ala Ser Glu Cys
  1               5                  10

<210> SEQ ID NO 34
<211> LENGTH: 10
<212> TYPE: PRT
<213> ORGANISM: Escherichia coli

<400> SEQUENCE: 34

Ala Ser Ala Gly Met Asn Val Val Phe Val
  1               5                  10

<210> SEQ ID NO 35
<211> LENGTH: 10
<212> TYPE: PRT
<213> ORGANISM: Escherichia coli

<400> SEQUENCE: 35

Met Asn Val Val Phe Val Gly Ala Glu Met
  1               5                  10

<210> SEQ ID NO 36
<211> LENGTH: 1488
<212> TYPE: DNA
<213> ORGANISM: Escherichia coli
<220> FEATURE:
<221> NAME/KEY: CDS
<222> LOCATION: (1)..(1431)
<220> FEATURE:
<221> NAME/KEY: CDS
<222> LOCATION: (1435)..(1488)

<400> SEQUENCE: 36
```

| | | | | | | | | | | | | | | | | |
|---|---|---|---|---|---|---|---|---|---|---|---|---|---|---|---|---|
| atg | cag | gtt | tta | cat | gta | tgt | tca | gag | atg | ttc | ccg | ctg | ctt | aaa | acc | 48 |
| Met | Gln | Val | Leu | His | Val | Cys | Ser | Glu | Met | Phe | Pro | Leu | Leu | Lys | Thr | |
| 1 | | | | 5 | | | | | 10 | | | | | 15 | | |
| ggc | ggt | ctg | gct | gat | gtt | att | ggg | gca | tta | ccc | gca | gca | caa | atc | gca | 96 |
| Gly | Gly | Leu | Ala | Asp | Val | Ile | Gly | Ala | Leu | Pro | Ala | Ala | Gln | Ile | Ala | |
| | | | | 20 | | | | | 25 | | | | | 30 | | |
| gac | ggc | gtt | gac | gct | cgc | gta | ctg | ttg | cct | gca | ttt | ccc | gac | att | cgc | 144 |
| Asp | Gly | Val | Asp | Ala | Arg | Val | Leu | Leu | Pro | Ala | Phe | Pro | Asp | Ile | Arg | |
| | | | 35 | | | | | 40 | | | | | 45 | | | |
| cgt | ggc | gtg | acc | gat | gcg | cag | gta | gta | tcc | cgt | cgt | gat | acc | tcc | gcc | 192 |
| Arg | Gly | Val | Thr | Asp | Ala | Gln | Val | Val | Ser | Arg | Arg | Asp | Thr | Ser | Ala | |
| 50 | | | | | 55 | | | | | 60 | | | | | | |
| gga | cat | atc | acg | ctg | ttg | ttc | ggt | cat | tac | aac | ggg | gtt | ggc | att | tac | 240 |
| Gly | His | Ile | Thr | Leu | Leu | Phe | Gly | His | Tyr | Asn | Gly | Val | Gly | Ile | Tyr | |
| 65 | | | | | 70 | | | | | 75 | | | | | 80 | |
| ctg | att | gac | gcg | ccg | cat | ctc | tat | gat | cgt | ccg | gga | agt | ccg | tat | cac | 288 |
| Leu | Ile | Asp | Ala | Pro | His | Leu | Tyr | Asp | Arg | Pro | Gly | Ser | Pro | Tyr | His | |
| | | | | 85 | | | | | 90 | | | | | 95 | | |
| gat | acc | aac | tta | ttt | gtc | cat | acc | gac | aac | gta | ttg | cgt | ttt | gcg | ctg | 336 |
| Asp | Thr | Asn | Leu | Phe | Val | His | Thr | Asp | Asn | Val | Leu | Arg | Phe | Ala | Leu | |
| | | | | 100 | | | | | 105 | | | | | 110 | | |
| ctg | ggg | tgg | gtt | ggg | gca | gaa | atg | gcc | agc | ggg | ctt | gac | cca | ttc | tgg | 384 |
| Leu | Gly | Trp | Val | Gly | Ala | Glu | Met | Ala | Ser | Gly | Leu | Asp | Pro | Phe | Trp | |
| | | | 115 | | | | | 120 | | | | | 125 | | | |
| cgt | cct | gat | gtg | gtg | cat | gcg | cac | gac | tgg | cat | gca | ggc | ctt | gcg | cct | 432 |
| Arg | Pro | Asp | Val | Val | His | Ala | His | Asp | Trp | His | Ala | Gly | Leu | Ala | Pro | |
| | | 130 | | | | | 135 | | | | | 140 | | | | |
| gcg | tat | ctg | gcg | gcg | cgc | ggg | cgt | ccg | gcg | aag | tcg | gtg | ttt | act | gtg | 480 |
| Ala | Tyr | Leu | Ala | Ala | Arg | Gly | Arg | Pro | Ala | Lys | Ser | Val | Phe | Thr | Val | |
| 145 | | | | | 150 | | | | | 155 | | | | | 160 | |

```
cac aac cta gcc tat caa ggc atg ttt tat gca cat cac atg aat gac    528
His Asn Leu Ala Tyr Gln Gly Met Phe Tyr Ala His His Met Asn Asp
                165                 170                 175 atc caa ttg cca tgg tca ttc ttt aat att cat ggg ctg gaa ttc aac    576
Ile Gln Leu Pro Trp Ser Phe Phe Asn Ile His Gly Leu Glu Phe Asn
            180                 185                 190 gga caa atc tct ttc ctg aag gcc ggt ctg tac tat gcc gat cac att    624
Gly Gln Ile Ser Phe Leu Lys Ala Gly Leu Tyr Tyr Ala Asp His Ile
        195                 200                 205 acg gcg gtc agt cca acc tac gct cgc gag atc acc gaa ccg cag ttt    672
Thr Ala Val Ser Pro Thr Tyr Ala Arg Glu Ile Thr Glu Pro Gln Phe
    210                 215                 220 gcc tac ggt atg gaa ggt ctg ttg caa cag cgt cac cgc gaa ggg cgt    720
Ala Tyr Gly Met Glu Gly Leu Leu Gln Gln Arg His Arg Glu Gly Arg
225                 230                 235                 240 ctt tcc ggc gta ccg aac ggc gtg gac gag aaa atc tgg agt cca gag    768
Leu Ser Gly Val Pro Asn Gly Val Asp Glu Lys Ile Trp Ser Pro Glu
                245                 250                 255 acg gac tta ctg ttg gcc tcg cgt tac acc cgc gat acg ttg gaa gat    816
Thr Asp Leu Leu Leu Ala Ser Arg Tyr Thr Arg Asp Thr Leu Glu Asp
            260                 265                 270 aaa gcg gaa aat aag cgc cag tca caa atc gca atg gga tcc aag gtt    864
Lys Ala Glu Asn Lys Arg Gln Ser Gln Ile Ala Met Gly Ser Lys Val
        275                 280                 285 gac gat aaa gtg ccg ctt ttt gca gtg gtg agc cgt ctg acc agc cag    912
Asp Asp Lys Val Pro Leu Phe Ala Val Val Ser Arg Leu Thr Ser Gln
    290                 295                 300 aaa ggt ctc gat tcg gtg ctg gaa gcc tca ccg ggt tct tcg gag cag    960
Lys Gly Leu Asp Ser Val Leu Glu Ala Ser Pro Gly Ser Ser Glu Gln
305                 310                 315                 320 ggc ggg cag ctg gcg cta ctc ggc gcg ggc gat ccg gtg ctg cag gaa    1008
Gly Gly Gln Leu Ala Leu Leu Gly Ala Gly Asp Pro Val Leu Gln Glu
                325                 330                 335 ggt ttc ctt gcg gcg gca gcg gaa tac ccc ggt cag gtg ggc gtt cag    1056
Gly Phe Leu Ala Ala Ala Ala Glu Tyr Pro Gly Gln Val Gly Val Gln
            340                 345                 350 att ggc tat cac gaa gca ttt tcg cat cgc att atg ggc ggc gcg gac    1104
Ile Gly Tyr His Glu Ala Phe Ser His Arg Ile Met Gly Gly Ala Asp
        355                 360                 365 gtc att ctg gtg ccc agc cgt ttc gaa ccg tgc ggc tta acg caa ctt    1152
Val Ile Leu Val Pro Ser Arg Phe Glu Pro Cys Gly Leu Thr Gln Leu
    370                 375                 380 tat gga tcg aag tac ggt acg ctg ccg tta gtg cga cgc acc ggt ggg    1200
Tyr Gly Ser Lys Tyr Gly Thr Leu Pro Leu Val Arg Arg Thr Gly Gly
385                 390                 395                 400 ctt gct gat acg gtt tct gac tgt tct ctc gag aac ctt gca gat ggc    1248
Leu Ala Asp Thr Val Ser Asp Cys Ser Leu Glu Asn Leu Ala Asp Gly
                405                 410                 415 gtc gcc aat ggg ttt atc ttc gaa gat agt aat gcc tgg tcg ctg tta    1296
Val Ala Asn Gly Phe Ile Phe Glu Asp Ser Asn Ala Trp Ser Leu Leu
            420                 425                 430 cgg act att cga cgt gct ttt gta ctg tgg tcc tgt cct cca ctg tgg    1344
Arg Thr Ile Arg Arg Ala Phe Val Leu Trp Ser Cys Pro Pro Leu Trp
        435                 440                 445 cgg ttt gtg caa cgt cag gct atg gca atg gat ttt ggc tgg cag gtc    1392
Arg Phe Val Gln Arg Gln Ala Met Ala Met Asp Phe Gly Trp Gln Val
    450                 455                 460 gcg gcg aag tcg tac cgt gag ctt tac tat cgc tcg aaa tag ttt tca    1440
Ala Ala Lys Ser Tyr Arg Glu Leu Tyr Tyr Arg Ser Lys     Phe Ser
```

```
                465                 470                 475
gga aac gcc tac atg aat gct ccg ttt aca tat tca tcg ccc acg ctt       1488
Gly Asn Ala Tyr Met Asn Ala Pro Phe Thr Tyr Ser Ser Pro Thr Leu
480                 485                 490                 495

<210> SEQ ID NO 37
<211> LENGTH: 477
<212> TYPE: PRT
<213> ORGANISM: Escherichia coli

<400> SEQUENCE: 37

Met Gln Val Leu His Val Cys Ser Glu Met Phe Pro Leu Leu Lys Thr
 1               5                  10                  15

Gly Gly Leu Ala Asp Val Ile Gly Ala Leu Pro Ala Ala Gln Ile Ala
            20                  25                  30

Asp Gly Val Asp Ala Arg Val Leu Leu Pro Ala Phe Pro Asp Ile Arg
        35                  40                  45

Arg Gly Val Thr Asp Ala Gln Val Val Ser Arg Arg Asp Thr Ser Ala
    50                  55                  60

Gly His Ile Thr Leu Leu Phe Gly His Tyr Asn Gly Val Gly Ile Tyr
65                  70                  75                  80

Leu Ile Asp Ala Pro His Leu Tyr Asp Arg Pro Gly Ser Pro Tyr His
                85                  90                  95

Asp Thr Asn Leu Phe Val His Thr Asp Asn Val Leu Arg Phe Ala Leu
            100                 105                 110

Leu Gly Trp Val Gly Ala Glu Met Ala Ser Gly Leu Asp Pro Phe Trp
        115                 120                 125

Arg Pro Asp Val Val His Ala His Asp Trp His Ala Gly Leu Ala Pro
    130                 135                 140

Ala Tyr Leu Ala Ala Arg Gly Arg Pro Ala Lys Ser Val Phe Thr Val
145                 150                 155                 160

His Asn Leu Ala Tyr Gln Gly Met Phe Tyr Ala His His Met Asn Asp
                165                 170                 175

Ile Gln Leu Pro Trp Ser Phe Phe Asn Ile His Gly Leu Glu Phe Asn
            180                 185                 190

Gly Gln Ile Ser Phe Leu Lys Ala Gly Leu Tyr Tyr Ala Asp His Ile
        195                 200                 205

Thr Ala Val Ser Pro Thr Tyr Ala Arg Glu Ile Thr Glu Pro Gln Phe
    210                 215                 220

Ala Tyr Gly Met Glu Gly Leu Leu Gln Gln Arg His Arg Glu Gly Arg
225                 230                 235                 240

Leu Ser Gly Val Pro Asn Gly Val Asp Glu Lys Ile Trp Ser Pro Glu
                245                 250                 255

Thr Asp Leu Leu Leu Ala Ser Arg Tyr Thr Arg Asp Thr Leu Glu Asp
            260                 265                 270

Lys Ala Glu Asn Lys Arg Gln Ser Gln Ile Ala Met Gly Ser Lys Val
        275                 280                 285

Asp Asp Lys Val Pro Leu Phe Ala Val Val Ser Arg Leu Thr Ser Gln
    290                 295                 300

Lys Gly Leu Asp Ser Val Leu Glu Ala Ser Pro Gly Ser Ser Glu Gln
305                 310                 315                 320

Gly Gly Gln Leu Ala Leu Leu Gly Ala Gly Asp Pro Val Leu Gln Glu
                325                 330                 335

Gly Phe Leu Ala Ala Ala Ala Glu Tyr Pro Gly Gln Val Gly Val Gln
            340                 345                 350
```

```
Ile Gly Tyr His Glu Ala Phe Ser His Arg Ile Met Gly Gly Ala Asp
            355                 360                 365

Val Ile Leu Val Pro Ser Arg Phe Glu Pro Cys Gly Leu Thr Gln Leu
    370                 375                 380

Tyr Gly Ser Lys Tyr Gly Thr Leu Pro Leu Val Arg Arg Thr Gly Gly
385                 390                 395                 400

Leu Ala Asp Thr Val Ser Asp Cys Ser Leu Glu Asn Leu Ala Asp Gly
                405                 410                 415

Val Ala Asn Gly Phe Ile Phe Glu Asp Ser Asn Ala Trp Ser Leu Leu
            420                 425                 430

Arg Thr Ile Arg Arg Ala Phe Val Leu Trp Ser Cys Pro Pro Leu Trp
        435                 440                 445

Arg Phe Val Gln Arg Gln Ala Met Ala Met Asp Phe Gly Trp Gln Val
    450                 455                 460

Ala Ala Lys Ser Tyr Arg Glu Leu Tyr Tyr Arg Ser Lys
465                 470                 475

<210> SEQ ID NO 38
<211> LENGTH: 2361
<212> TYPE: DNA
<213> ORGANISM: Escherichia coli
<220> FEATURE:
<221> NAME/KEY: CDS
<222> LOCATION: (1)..(2184)
<220> FEATURE:
<221> NAME/KEY: CDS
<222> LOCATION: (2188)..(2280)
<220> FEATURE:
<221> NAME/KEY: CDS
<222> LOCATION: (2284)..(2361)

<400> SEQUENCE: 38 atg tcc gat cgt atc gat aga gac gtg att aac gcg cta att gca ggc      48
Met Ser Asp Arg Ile Asp Arg Asp Val Ile Asn Ala Leu Ile Ala Gly
 1               5                  10                  15 cat ttt gcg gat cct ttt tcc gta ctg gga atg cat aaa acc acc gcg      96
His Phe Ala Asp Pro Phe Ser Val Leu Gly Met His Lys Thr Thr Ala
                20                  25                  30 gga ctg gaa gtc cgt gcc ctt tta ccc gac gct acc gat gtg tgg gtg     144
Gly Leu Glu Val Arg Ala Leu Leu Pro Asp Ala Thr Asp Val Trp Val
            35                  40                  45 att gaa ccg aaa acc ggg cgc aaa ctc gca aaa ctg gag tgt ctc gac     192
Ile Glu Pro Lys Thr Gly Arg Lys Leu Ala Lys Leu Glu Cys Leu Asp
        50                  55                  60 tca cgg gga ttc ttt agc ggc gtc att ccg cga cgt aag aat ttt ttc     240
Ser Arg Gly Phe Phe Ser Gly Val Ile Pro Arg Arg Lys Asn Phe Phe
 65                  70                  75                  80 cgc tat cag ttg gct gtt gtc tgg cat ggt cag caa aac ctg att gat     288
Arg Tyr Gln Leu Ala Val Val Trp His Gly Gln Gln Asn Leu Ile Asp
                 85                  90                  95 gat cct tac cgt ttt ggt ccg cta atc cag gaa atg gat gcc tgg cta     336
Asp Pro Tyr Arg Phe Gly Pro Leu Ile Gln Glu Met Asp Ala Trp Leu
            100                 105                 110 tta tct gaa ggt act cac ctg cgc ccg tat gaa acc tta ggc gcg cat     384
Leu Ser Glu Gly Thr His Leu Arg Pro Tyr Glu Thr Leu Gly Ala His
        115                 120                 125 gca gat act atg gat ggc gtc aca ggt acg cgt ttc tct gtc tgg gct     432
Ala Asp Thr Met Asp Gly Val Thr Gly Thr Arg Phe Ser Val Trp Ala
    130                 135                 140 cca aac gcc cgt cgg gtc tcg gtg gtt ggg caa ttc aac tac tgg gac     480
```

```
                                           -continued

Pro Asn Ala Arg Arg Val Ser Val Val Gly Gln Phe Asn Tyr Trp Asp
145                 150                 155                 160 ggt cgc cgt cac ccg atg cgc ctg cgt aaa gag agc ggc atc tgg gaa        528
Gly Arg Arg His Pro Met Arg Leu Arg Lys Glu Ser Gly Ile Trp Glu
                165                 170                 175 ctg ttt atc cct ggg gcg cat aac ggt cag ctc tat aaa tac gag atg        576
Leu Phe Ile Pro Gly Ala His Asn Gly Gln Leu Tyr Lys Tyr Glu Met
            180                 185                 190 att gat gcc aat ggc aac ttg cgt ctg aag tcc gac cct tat gcc ttt        624
Ile Asp Ala Asn Gly Asn Leu Arg Leu Lys Ser Asp Pro Tyr Ala Phe
        195                 200                 205 gaa gcg caa atg cgc ccg gaa acc gcg tct ctt att tgc ggg ctg ccg        672
Glu Ala Gln Met Arg Pro Glu Thr Ala Ser Leu Ile Cys Gly Leu Pro
    210                 215                 220 gaa aag gtt gta cag act gaa gag cgc aaa aaa gcg aat cag ttt gat        720
Glu Lys Val Val Gln Thr Glu Glu Arg Lys Lys Ala Asn Gln Phe Asp
225                 230                 235                 240 gcg cca atc tct att tat gaa gtt cac ctg ggt tcc tgg cgt cgc cac        768
Ala Pro Ile Ser Ile Tyr Glu Val His Leu Gly Ser Trp Arg Arg His
                245                 250                 255 acc gac aac aat ttc tgg ttg agc tac cgc gag ctg gcc gat caa ctg        816
Thr Asp Asn Asn Phe Trp Leu Ser Tyr Arg Glu Leu Ala Asp Gln Leu
            260                 265                 270 gtg cct tat gct aaa tgg atg ggc ttt acc cac ctc gaa cta ctg ccc        864
Val Pro Tyr Ala Lys Trp Met Gly Phe Thr His Leu Glu Leu Leu Pro
        275                 280                 285 att aac gag cat ccc ttc gat ggc agt tgg ggt tat cag cca acc ggc        912
Ile Asn Glu His Pro Phe Asp Gly Ser Trp Gly Tyr Gln Pro Thr Gly
    290                 295                 300 ctg tat gcg cca acc cgc cgt ttt ggt act cgc gac gac ttc cgt tat        960
Leu Tyr Ala Pro Thr Arg Arg Phe Gly Thr Arg Asp Asp Phe Arg Tyr
305                 310                 315                 320 ttc att gat gcc gca cac gca gct ggt ctg aac gtg att ctc gac tgg       1008
Phe Ile Asp Ala Ala His Ala Ala Gly Leu Asn Val Ile Leu Asp Trp
                325                 330                 335 gtg cca ggc cac ttc ccg act gat gac ttt gcg ctt gcc gaa ttt gat       1056
Val Pro Gly His Phe Pro Thr Asp Asp Phe Ala Leu Ala Glu Phe Asp
            340                 345                 350 ggc acg aac ttg tat gaa cac agc gat ccg cgt gaa ggc tat cat cag       1104
Gly Thr Asn Leu Tyr Glu His Ser Asp Pro Arg Glu Gly Tyr His Gln
        355                 360                 365 gac tgg aac acg ctg atc tac aac tat ggt cgc cgt gaa gtc agt aac       1152
Asp Trp Asn Thr Leu Ile Tyr Asn Tyr Gly Arg Arg Glu Val Ser Asn
    370                 375                 380 ttc ctc gtc ggt aac gcg ctt tac tgg att gaa cgt ttt ggt att gat       1200
Phe Leu Val Gly Asn Ala Leu Tyr Trp Ile Glu Arg Phe Gly Ile Asp
385                 390                 395                 400 gcg ctg cgc gtc gat gcg gtg gcg tca atg att tat cgc gac tac agc       1248
Ala Leu Arg Val Asp Ala Val Ala Ser Met Ile Tyr Arg Asp Tyr Ser
                405                 410                 415 cgt aaa gag ggg gag tgg atc ccg aac gaa ttt ggc ggg cgc gag aat       1296
Arg Lys Glu Gly Glu Trp Ile Pro Asn Glu Phe Gly Gly Arg Glu Asn
            420                 425                 430 ctt gaa gcg att gaa ttc ttg cgt aat acc aac cgt att ctt ggt gag       1344
Leu Glu Ala Ile Glu Phe Leu Arg Asn Thr Asn Arg Ile Leu Gly Glu
        435                 440                 445 cag gtt tcc ggt gcg gtg aca atg gct gag gag tct acc gat ttc cct       1392
Gln Val Ser Gly Ala Val Thr Met Ala Glu Glu Ser Thr Asp Phe Pro
    450                 455                 460
```

-continued

```
ggc gtt tct cgt ccg cag gat atg ggc ggt ctg ggc ttc tgg tac aag    1440
Gly Val Ser Arg Pro Gln Asp Met Gly Gly Leu Gly Phe Trp Tyr Lys
465                 470                 475                 480 tgg aac ctc ggc tgg atg cat gac acc ttg gac tac atg aag ctc gac    1488
Trp Asn Leu Gly Trp Met His Asp Thr Leu Asp Tyr Met Lys Leu Asp
                485                 490                 495 ccg gtt tat cgt cag tat cat cac gat aaa ctg acc ttc ggg att ctc    1536
Pro Val Tyr Arg Gln Tyr His His Asp Lys Leu Thr Phe Gly Ile Leu
            500                 505                 510 tac aac tac act gaa aac ttc gtc ctg ccg ttg tcg cat gat gaa gtg    1584
Tyr Asn Tyr Thr Glu Asn Phe Val Leu Pro Leu Ser His Asp Glu Val
        515                 520                 525 gtc cac ggt aaa aaa tcg att ctc gac cgc atg ccg ggc gac gca tgg    1632
Val His Gly Lys Lys Ser Ile Leu Asp Arg Met Pro Gly Asp Ala Trp
    530                 535                 540 cag aaa ttc gcg aac ctg cgc gcc tac tat ggc tgg atg tgg gca ttc    1680
Gln Lys Phe Ala Asn Leu Arg Ala Tyr Tyr Gly Trp Met Trp Ala Phe
545                 550                 555                 560 ccg ggc aag aaa cta ctg ttc atg ggt aac gaa ttt gcc cag ggc cgc    1728
Pro Gly Lys Lys Leu Leu Phe Met Gly Asn Glu Phe Ala Gln Gly Arg
                565                 570                 575 gag tgg aac cat gac gcc agc ctc gac tgg cat ctg ttg gaa ggc ggc    1776
Glu Trp Asn His Asp Ala Ser Leu Asp Trp His Leu Leu Glu Gly Gly
            580                 585                 590 gat aac tgg cac cac ggt gtc cag cgt ctg gtg cgc gat ctg aac ctc    1824
Asp Asn Trp His His Gly Val Gln Arg Leu Val Arg Asp Leu Asn Leu
        595                 600                 605 acc tac cgc cac cat aaa gca atg cat gaa ctg gat ttt gac ccg tac    1872
Thr Tyr Arg His His Lys Ala Met His Glu Leu Asp Phe Asp Pro Tyr
    610                 615                 620 ggc ttt gaa tgg ctg gtg gtg gat gac aaa gaa cgc tcg gtg ctg atc    1920
Gly Phe Glu Trp Leu Val Val Asp Asp Lys Glu Arg Ser Val Leu Ile
625                 630                 635                 640 ttt gtg cgt cgc gat aaa gag ggt aac gaa atc atc gtt gcc agt aac    1968
Phe Val Arg Arg Asp Lys Glu Gly Asn Glu Ile Ile Val Ala Ser Asn
                645                 650                 655 ttt acg ccg gta ccg cgt cat gat tat cgc ttc ggc ata aac cag ccg    2016
Phe Thr Pro Val Pro Arg His Asp Tyr Arg Phe Gly Ile Asn Gln Pro
            660                 665                 670 ggc aaa tgg cgt gaa atc ctc aat acc gat tcc atg cac tat cac ggc    2064
Gly Lys Trp Arg Glu Ile Leu Asn Thr Asp Ser Met His Tyr His Gly
        675                 680                 685 agt aat gca ggc aat ggc ggc acg gta cac agc gat gag att gcc agc    2112
Ser Asn Ala Gly Asn Gly Gly Thr Val His Ser Asp Glu Ile Ala Ser
    690                 695                 700 cac ggt cgt cag cat tca cta agc ctg acg cta cca ccg ctg gcc act    2160
His Gly Arg Gln His Ser Leu Ser Leu Thr Leu Pro Pro Leu Ala Thr
705                 710                 715                 720 atc tgg ctg gtt cgg gag gca gaa tga cac aac tcg cca ttg gca aac    2208
Ile Trp Leu Val Arg Glu Ala Glu     His Asn Ser Pro Leu Ala Asn
                725                     730                 735 ccg ctc ccc tcg gcg cgc att acg acg gtc agg gcg tca act tca cac    2256
Pro Leu Pro Ser Ala Arg Ile Thr Thr Val Arg Ala Ser Thr Ser His
            740                 745                 750 ttt tct ccg ctc atg ccg agc ggg tag aac tgt gtg tct ttg acg cca    2304
Phe Ser Pro Leu Met Pro Ser Gly     Asn Cys Val Ser Leu Thr Pro
        755                         760                 765 atg gcc agg aac atc gct atg act tgc cag ggc aca gtg gca aca ttt    2352
Met Ala Arg Asn Ile Ala Met Thr Cys Gln Gly Thr Val Ala Thr Phe
    770                 775                 780
```

```
ggc acg gtt                                                    2361
Gly Thr Val
        785

<210> SEQ ID NO 39
<211> LENGTH: 728
<212> TYPE: PRT
<213> ORGANISM: Escherichia coli

<400> SEQUENCE: 39

Met Ser Asp Arg Ile Asp Arg Asp Val Ile Asn Ala Leu Ile Ala Gly
 1               5                  10                  15

His Phe Ala Asp Pro Phe Ser Val Leu Gly Met His Lys Thr Thr Ala
             20                  25                  30

Gly Leu Glu Val Arg Ala Leu Leu Pro Asp Ala Thr Asp Val Trp Val
         35                  40                  45

Ile Glu Pro Lys Thr Gly Arg Lys Leu Ala Lys Leu Glu Cys Leu Asp
 50                  55                  60

Ser Arg Gly Phe Phe Ser Gly Val Ile Pro Arg Arg Lys Asn Phe Phe
 65                  70                  75                  80

Arg Tyr Gln Leu Ala Val Val Trp His Gly Gln Gln Asn Leu Ile Asp
             85                  90                  95

Asp Pro Tyr Arg Phe Gly Pro Leu Ile Gln Glu Met Asp Ala Trp Leu
            100                 105                 110

Leu Ser Glu Gly Thr His Leu Arg Pro Tyr Glu Thr Leu Gly Ala His
        115                 120                 125

Ala Asp Thr Met Asp Gly Val Thr Gly Thr Arg Phe Ser Val Trp Ala
130                 135                 140

Pro Asn Ala Arg Arg Val Ser Val Val Gly Gln Phe Asn Tyr Trp Asp
145                 150                 155                 160

Gly Arg Arg His Pro Met Arg Leu Arg Lys Glu Ser Gly Ile Trp Glu
            165                 170                 175

Leu Phe Ile Pro Gly Ala His Asn Gly Gln Leu Tyr Lys Tyr Glu Met
        180                 185                 190

Ile Asp Ala Asn Gly Asn Leu Arg Leu Lys Ser Asp Pro Tyr Ala Phe
    195                 200                 205

Glu Ala Gln Met Arg Pro Glu Thr Ala Ser Leu Ile Cys Gly Leu Pro
210                 215                 220

Glu Lys Val Val Gln Thr Glu Glu Arg Lys Lys Ala Asn Gln Phe Asp
225                 230                 235                 240

Ala Pro Ile Ser Ile Tyr Glu Val His Leu Gly Ser Trp Arg Arg His
            245                 250                 255

Thr Asp Asn Asn Phe Trp Leu Ser Tyr Arg Glu Leu Ala Asp Gln Leu
        260                 265                 270

Val Pro Tyr Ala Lys Trp Met Gly Phe Thr His Leu Glu Leu Leu Pro
    275                 280                 285

Ile Asn Glu His Pro Phe Asp Gly Ser Trp Gly Tyr Gln Pro Thr Gly
290                 295                 300

Leu Tyr Ala Pro Thr Arg Arg Phe Gly Thr Arg Asp Asp Phe Arg Tyr
305                 310                 315                 320

Phe Ile Asp Ala Ala His Ala Ala Gly Leu Asn Val Ile Leu Asp Trp
            325                 330                 335

Val Pro Gly His Phe Pro Thr Asp Asp Phe Ala Leu Ala Glu Phe Asp
        340                 345                 350
```

```
Gly Thr Asn Leu Tyr Glu His Ser Asp Pro Arg Glu Gly Tyr His Gln
            355                 360                 365

Asp Trp Asn Thr Leu Ile Tyr Asn Tyr Gly Arg Arg Glu Val Ser Asn
        370                 375                 380

Phe Leu Val Gly Asn Ala Leu Tyr Trp Ile Glu Arg Phe Gly Ile Asp
385                 390                 395                 400

Ala Leu Arg Val Asp Ala Val Ala Ser Met Ile Tyr Arg Asp Tyr Ser
                405                 410                 415

Arg Lys Glu Gly Glu Trp Ile Pro Asn Glu Phe Gly Arg Glu Asn
                420                 425                 430

Leu Glu Ala Ile Glu Phe Leu Arg Asn Thr Asn Arg Ile Leu Gly Glu
            435                 440                 445

Gln Val Ser Gly Ala Val Thr Met Ala Glu Ser Thr Asp Phe Pro
    450                 455                 460

Gly Val Ser Arg Pro Gln Asp Met Gly Leu Gly Phe Trp Tyr Lys
465                 470                 475                 480

Trp Asn Leu Gly Trp Met His Asp Thr Leu Asp Tyr Met Lys Leu Asp
                485                 490                 495

Pro Val Tyr Arg Gln Tyr His His Asp Lys Leu Thr Phe Gly Ile Leu
                500                 505                 510

Tyr Asn Tyr Thr Glu Asn Phe Val Leu Pro Leu Ser His Asp Glu Val
            515                 520                 525

Val His Gly Lys Lys Ser Ile Leu Asp Arg Met Pro Gly Asp Ala Trp
    530                 535                 540

Gln Lys Phe Ala Asn Leu Arg Ala Tyr Tyr Gly Trp Met Trp Ala Phe
545                 550                 555                 560

Pro Gly Lys Lys Leu Leu Phe Met Gly Asn Glu Phe Ala Gln Gly Arg
                565                 570                 575

Glu Trp Asn His Asp Ala Ser Leu Asp Trp His Leu Leu Glu Gly Gly
            580                 585                 590

Asp Asn Trp His His Gly Val Gln Arg Leu Val Arg Asp Leu Asn Leu
        595                 600                 605

Thr Tyr Arg His His Lys Ala Met His Glu Leu Asp Phe Asp Pro Tyr
610                 615                 620

Gly Phe Glu Trp Leu Val Val Asp Asp Lys Glu Arg Ser Val Leu Ile
625                 630                 635                 640

Phe Val Arg Arg Asp Lys Glu Gly Asn Glu Ile Val Ala Ser Asn
                645                 650                 655

Phe Thr Pro Val Pro Arg His Asp Tyr Arg Phe Gly Ile Asn Gln Pro
            660                 665                 670

Gly Lys Trp Arg Glu Ile Leu Asn Thr Asp Ser Met His Tyr His Gly
        675                 680                 685

Ser Asn Ala Gly Asn Gly Gly Thr Val His Ser Asp Glu Ile Ala Ser
    690                 695                 700

His Gly Arg Gln His Ser Leu Ser Leu Thr Leu Pro Pro Leu Ala Thr
705                 710                 715                 720

Ile Trp Leu Val Arg Glu Ala Glu
                725

<210> SEQ ID NO 40
<211> LENGTH: 2562
<212> TYPE: DNA
<213> ORGANISM: Zea mays

<400> SEQUENCE: 40
```

-continued

```
aagcttgcta ctttctttcc ttaatgttga tttcccctttt gttagatgtt ctttgtgtta      60
tatacactct gtatacaagg atgcgataca cacatcagct agtcctaatg atgccaccga     120
ctttacttga ggaaaaggaa acaaatatga tgtggccatc acattctcaa taacaatgac     180
catgtgcgca atgacatacc atcatatttg atatcataaa aataaattta ttatcaaagt     240
aaacatatag ttcatatatc agatattaaa gtgataagaa caaatattac attttatctt     300
atataaaatg acgaaaaagg tacgagttga aaaggagtcc aaccccttttt ttatagcttg     360
ttcggttgct tgttctcttc ggctagcgag gtggtagaat gtgagagtgt tgcgcgtgga     420
ttcccgtcgt agtgttctta ggtgatttct cacggcccat ctgtgatata gcgactcata     480
tgtggtgtaa tagcccattg ggagaagggg agagatatag atctacgtga tttgcacgtg     540
atgcacgacg aacgaaactg gtggtttaaa gtagtagagg tttgtcatta gaggtgtaaa     600
tggtacatat attatccgtt catattcgaa tttgatccgt ataagagggc taagatctaa     660
tccgtataca agtccaagta ttaagtatcc gatccatatc ggatctttat ccgtatccgt     720
atactcaaaa tttgatgttt aagatttaa tatatattta aactttatag gaactcgata     780
atatttgtat ctgatttgaa ttatgaaaac aaatatggaa cgattaattt cagtctatat     840
ccgttccgat atttgtcatg ctttgctaaa aatacctttta caaggcatct tgtgcagatt     900
atatattaat ctgaaatcag ttagagaagc ctacaaattt gaccaaatgc cgagtcatcc     960
ggcttatccc ctttccaact ttcagttctg caagcgccag aaatcgtttt tcatctacat    1020
tgtctttgtt gcctgcatac atctataaat aggacctgct agatcaatcg cagtccatcg    1080
gcctcagtcg cacatatcta ctatactata ctctaggaag caaggacacc accgccatgg    1140
cagccaagat gcttgcattg ttcgctctcc tagctctttg tgcaagcgcc actagtgcga    1200
cccatattcc agggcacttg ccaccagtca tgccattggg taccatgaac ccatgcatgc    1260
agtactgcat gatgcaacag gggcttgcca gcttgatggc gtgtccgtcc ctgatgctgc    1320
agcaactgtt ggccttaccg cttcagacga tgccagtgat gatgccacag atgatgacgc    1380
ctaacatgat gtcaccattg atgatgccga gcatgatgtc accaatggtc ttgccgagca    1440
tgatgtcgca aataatgatg ccacaatgtc actgcgacgc cgtctcgcag attatgctgc    1500
aacagcagtt accattcatg ttcaacccaa tggccatgac gattccaccc atgttcttac    1560
agcaacccttt tgttggtgct gcattctaga tagaaatatt tgtgttgtat cgaataatga    1620
gttgacatgc catcgcgtgt gactcattat taacaataaa acaagtttcc tcttattatc    1680
ttttttatatc tctccctatc cattttttgca aagcccatta tcctttactc cctaagtccc    1740
aatatatttt agaccttaaa ttgtatgtct atattcaaaa gaatgacaat aaatctagac    1800
atatatataa aacacataca ttaagtattg tatgaatcta ttaaaatgct aaaacgacta    1860
atattatggg acgagggag tactttatta gtagattaca ttgttatttt ctctattcca    1920
aatataagtc tggttttttca atcaatcaat atatattacc atgtccaaac attttgaatt    1980
atatatctag gtgcagcatc cgtgcacgat cgtaaaagaa gcagtcacgg tgttggtccc    2040
aaaaactaat cgtccgttgt cggtcaccta taaagattca tgaagagaac caaaataagg    2100
caatataatt aatgtaatat gactcctcct tttgaattac ttaggaataa cataagcaaa    2160
caaaaaaagg agaagatcaa ggtaaataaa ggcatttttgt gagaaaacat ggaagcataa    2220
gaatgcataa gtaatgattt tgtgtctcttt atattttttt tattcacgtg aatttacata    2280
gataccatcg gatgttcgat ggtaatacaa tgatgccttta gctccgagag cttcgaatga    2340
```

```
tgagcgattt aaaaatactc ctatcaattg ttcgaaagtt ctttgtctca tgcatgggca    2400
atgtacctct atttataggg acggtgcgac gtacaaattt gtataaaatt atatttttat    2460
tcccaaatcc tatgcatatg tgtcggggac cataattagg ggtaccctca aggctcctaa    2520
ttctcagctg gtaaccccat cagcataaag ctgcaaaggc ct                      2562

<210> SEQ ID NO 41
<211> LENGTH: 150
<212> TYPE: PRT
<213> ORGANISM: Zea mays

<400> SEQUENCE: 41

Met Ala Ala Lys Met Leu Ala Leu Phe Ala Leu Leu Ala Leu Cys Ala
1               5                   10                  15

Ser Ala Thr Ser Ala Thr His Ile Pro Gly His Leu Pro Pro Val Met
            20                  25                  30

Pro Leu Gly Thr Met Asn Pro Cys Met Gln Tyr Cys Met Met Gln Gln
        35                  40                  45

Gly Leu Ala Ser Leu Met Ala Cys Pro Ser Leu Met Leu Gln Gln Leu
    50                  55                  60

Leu Ala Leu Pro Leu Gln Thr Met Pro Val Met Met Pro Gln Met Met
65                  70                  75                  80

Thr Pro Asn Met Met Ser Pro Leu Met Met Pro Ser Met Met Ser Pro
                85                  90                  95

Met Val Leu Pro Ser Met Met Ser Gln Ile Met Met Pro Gln Cys His
            100                 105                 110

Cys Asp Ala Val Ser Gln Ile Met Leu Gln Gln Gln Leu Pro Phe Met
        115                 120                 125

Phe Asn Pro Met Ala Met Thr Ile Pro Pro Met Phe Leu Gln Gln Pro
    130                 135                 140

Phe Val Gly Ala Ala Phe
145                 150

<210> SEQ ID NO 42
<211> LENGTH: 1141
<212> TYPE: DNA
<213> ORGANISM: Zea mays

<400> SEQUENCE: 42
aagcttgcta ctttctttcc ttaatgttga tttcccctttt gttagatgtt ctttgtgtta     60
tatacactct gtatacaagg atgcgataca cacatcagct agtcctaatg atgccaccga    120
ctttacttga ggaaaaggaa acaaatatga tgtggccatc acattctcaa taacaatgac    180
catgtgcgca atgacatacc atcatatttg atatcataaa ataaattta ttatcaaagt     240 aaacatatag ttcatatatc agatatttaaa gtgataagaa caaatattac attttatctt    300
atataaaatg acgaaaaagg tacgagttga aaggagtcc aaccccttttt ttatagcttg    360 ttcggttgct tgttctcttc ggctagcgag gtggtagaat gtgagagtgt tgcgcgtgga    420
ttcccgtcgt agtgttctta ggtgatttct cacggcccat ctgtgatata gcgactcata    480
tatgtggtgt aatagcccat tgggagaagg ggagagatat agatctacgt gatttgcacg    540
tgatgcacga cgaacgaaac tggtggttta agtagtaga ggtttgtcat tagaggtgta     600
aatggtacat atattatccg ttcatattcg aatttgatcc gtataagagg gctaagatct    660
aatccgtata caagtccaag tattaagtat ccgatccata tcggatcttt atccgtatcc    720
gtatactcaa aatttgatgt ttaagatttt aatatatatt taaactttat aggaactcga    780
```

```
taatatttgt atctgatttg aattatgaaa acaaatatgg aacgattaat ttcagtctat      840
atccgttccg atatttgtca tgctttgcta aaaataccct tacaaggcat cttgtgcaga      900
ttatatatta atctgaaatc agttagagaa gcctacaaat ttgaccaaat gccgagtcat      960
ccggcttatc cccttccaa ctttcagttc tgcaagcgcc agaaatcgtt tttcatctac      1020
attgtctttg ttgcctgcat acatctataa ataggacctg ctagatcaat cgcagtccat      1080
cggcctcagt cgcacatatc tactatacta tactctagga agcaaggaca ccaccgccat      1140
g                                                                     1141
```

<210> SEQ ID NO 43
<211> LENGTH: 150
<212> TYPE: PRT
<213> ORGANISM: Zea mays

<400> SEQUENCE: 43

```
Met Ala Ala Lys Met Leu Ala Leu Phe Ala Leu Leu Ala Leu Cys Ala
 1               5                  10                  15

Ser Ala Thr Ser Ala Thr His Ile Pro Gly His Leu Pro Pro Val Met
            20                  25                  30

Pro Leu Gly Thr Met Asn Pro Cys Met Gln Tyr Cys Met Met Gln Gln
        35                  40                  45

Gly Leu Ala Ser Leu Met Ala Cys Pro Ser Leu Met Leu Gln Gln Leu
    50                  55                  60

Leu Ala Leu Pro Leu Gln Thr Met Pro Val Met Met Pro Gln Met Met
65                  70                  75                  80

Thr Pro Asn Met Met Ser Pro Leu Met Met Pro Ser Met Met Ser Pro
                85                  90                  95

Met Val Leu Pro Ser Met Met Ser Gln Ile Met Met Pro Gln Cys His
                100                 105                 110

Cys Asp Ala Val Ser Gln Ile Met Leu Gln Gln Gln Leu Pro Phe Met
            115                 120                 125

Phe Asn Pro Met Ala Met Thr Ile Pro Pro Met Phe Leu Gln Gln Pro
        130                 135                 140

Phe Val Gly Ala Ala Phe
145                 150
```

<210> SEQ ID NO 44
<211> LENGTH: 1328
<212> TYPE: DNA
<213> ORGANISM: Escherichia coli
<220> FEATURE:
<221> NAME/KEY: CDS
<222> LOCATION: (1)..(1293)
<220> FEATURE:
<221> NAME/KEY: CDS
<222> LOCATION: (1297)..(1326)

<400> SEQUENCE: 44

```
atg gtt agt tta gag aag aac gat cac tta atg ttg gcg cgc cag ctg     48
Met Val Ser Leu Glu Lys Asn Asp His Leu Met Leu Ala Arg Gln Leu
 1               5                  10                  15 cca ttg aaa tct gtt gcc ctg ata ctg gcg gga gga cgt ggt acc cgc     96
Pro Leu Lys Ser Val Ala Leu Ile Leu Ala Gly Gly Arg Gly Thr Arg
            20                  25                  30 ctg aag gat tta acc aat aag cga gca aaa ccg gcc gta cac ttc ggc    144
Leu Lys Asp Leu Thr Asn Lys Arg Ala Lys Pro Ala Val His Phe Gly
        35                  40                  45
```

-continued

| | | |
|---|---|---|
| ggt aag ttc cgc att atc gac ttt gcg ctg tct aac tgc atc aac tcc<br>Gly Lys Phe Arg Ile Ile Asp Phe Ala Leu Ser Asn Cys Ile Asn Ser<br>50                       55                     60 | 192 |
| ggg atc cgt cgt atg ggc gtg atc acc cag tac cag tcc cac act ctg<br>Gly Ile Arg Arg Met Gly Val Ile Thr Gln Tyr Gln Ser His Thr Leu<br>65                       70                     75                     80 | 240 |
| gtg cag cac att cag cgc ggc tgg tca ttc ttc aat gaa gaa atg aac<br>Val Gln His Ile Gln Arg Gly Trp Ser Phe Phe Asn Glu Glu Met Asn<br>85                       90                     95 | 288 |
| gag ttt gtc gat ctg ctg cca gca cag cag aga atg aaa ggg gaa aac<br>Glu Phe Val Asp Leu Leu Pro Ala Gln Gln Arg Met Lys Gly Glu Asn<br>                  100                105                110 | 336 |
| tgg tat cgc ggc acc gca gat gcg gtc acc caa aac ctc gac att atc<br>Trp Tyr Arg Gly Thr Ala Asp Ala Val Thr Gln Asn Leu Asp Ile Ile<br>        115                120                125 | 384 |
| cgt cgt tat aaa gcg gaa tac gtg gtg atc ctg gcg ggc gac cat atc<br>Arg Arg Tyr Lys Ala Glu Tyr Val Val Ile Leu Ala Gly Asp His Ile<br>130                     135                140 | 432 |
| tac aag caa gac tac tcg cgt atg ctt atc gat cac gtc gaa aaa ggt<br>Tyr Lys Gln Asp Tyr Ser Arg Met Leu Ile Asp His Val Glu Lys Gly<br>145                     150                155                160 | 480 |
| gta cgt tgt acc gtt gtt tgt atg cca gta ccg att gaa gaa gcc tcc<br>Val Arg Cys Thr Val Val Cys Met Pro Val Pro Ile Glu Glu Ala Ser<br>                    165                170                175 | 528 |
| gca ttt ggc gtt atg gcg gtt gat gag aac gat aaa act atc gaa ttc<br>Ala Phe Gly Val Met Ala Val Asp Glu Asn Asp Lys Thr Ile Glu Phe<br>                  180                185                190 | 576 |
| gtg gaa aaa cct gct aac ccg ccg tca atg ccg aac gat ccg agc aaa<br>Val Glu Lys Pro Ala Asn Pro Pro Ser Met Pro Asn Asp Pro Ser Lys<br>        195                200                205 | 624 |
| tct ctg gcg agt atg ggt atc tac gtc ttt gac gcc gac tat ctg tat<br>Ser Leu Ala Ser Met Gly Ile Tyr Val Phe Asp Ala Asp Tyr Leu Tyr<br>210                     215                220 | 672 |
| gaa ctg ctg gaa gaa gac gat cgc gat gag aac tcc agc cac gac ttt<br>Glu Leu Leu Glu Glu Asp Asp Arg Asp Glu Asn Ser Ser His Asp Phe<br>225                     230                235                240 | 720 |
| ggc aaa gat ttg att ccc aag atc acc gaa gcc ggt ctg gcc tat gcg<br>Gly Lys Asp Leu Ile Pro Lys Ile Thr Glu Ala Gly Leu Ala Tyr Ala<br>                  245                250                255 | 768 |
| cac ccg ttc ccg ctc tct tgc gta caa tcc gac ccg gat gcc gag ccg<br>His Pro Phe Pro Leu Ser Cys Val Gln Ser Asp Pro Asp Ala Glu Pro<br>                  260                265                270 | 816 |
| tac tgg cgc gat gtg ggt acg ctg gaa gct tac tgg aaa gcg aac ctc<br>Tyr Trp Arg Asp Val Gly Thr Leu Glu Ala Tyr Trp Lys Ala Asn Leu<br>        275                280                285 | 864 |
| gat ctg gcc tct gtg gtg gac aaa ctg gat atg tac gat cgc aat tgg<br>Asp Leu Ala Ser Val Val Asp Lys Leu Asp Met Tyr Asp Arg Asn Trp<br>290                     295                300 | 912 |
| cca att cgc acc tac aat gaa tca tta ccg cca gcg aaa ttc gtg cag<br>Pro Ile Arg Thr Tyr Asn Glu Ser Leu Pro Pro Ala Lys Phe Val Gln<br>305                     310                315                320 | 960 |
| gat cgc tcc ggt agc cac ggg atg acc ctt aac tca ctg gtt tcc ggc<br>Asp Arg Ser Gly Ser His Gly Met Thr Leu Asn Ser Leu Val Ser Gly<br>                  325                330                335 | 1008 |
| ggt tgt gtg atc tcc ggt tcg gtg gtg gtg cag tcc gtt ctg ttc tcg<br>Gly Cys Val Ile Ser Gly Ser Val Val Val Gln Ser Val Leu Phe Ser<br>                  340                345                350 | 1056 |
| cgc gtt cgc gtg aat tca ttc tgc aac att gat tcc gcc gta ttg tta<br>Arg Val Arg Val Asn Ser Phe Cys Asn Ile Asp Ser Ala Val Leu Leu<br>        355                360                365 | 1104 |

-continued

```
ccg gaa gta tgg gta ggt cgc tcg tgc cgt ctg cgc cgc tgc gtc atc    1152
Pro Glu Val Trp Val Gly Arg Ser Cys Arg Leu Arg Arg Cys Val Ile
370                 375                 380 gat cgt gct tgt gtt att ccg gaa ggc atg gtg att ggt gaa aac gca    1200
Asp Arg Ala Cys Val Ile Pro Glu Gly Met Val Ile Gly Glu Asn Ala
385                 390                 395                 400 gag gaa gat gca cgt cgt ttc tat cgt tca gaa gaa ggc atc gtg ctg    1248
Glu Glu Asp Ala Arg Arg Phe Tyr Arg Ser Glu Glu Gly Ile Val Leu
            405                 410                 415 gta acg cgc gaa atg cta cgg aag tta ggg cat aaa cag gag cga taa    1296
Val Thr Arg Glu Met Leu Arg Lys Leu Gly His Lys Gln Glu Arg
420                 425                 430 tgc agg ttt tac atg tat gtt cag aga tgt tt                         1328
Cys Arg Phe Tyr Met Tyr Val Gln Arg Cys
        435                 440
```

<210> SEQ ID NO 45
<211> LENGTH: 431
<212> TYPE: PRT
<213> ORGANISM: Escherichia coli

<400> SEQUENCE: 45

```
Met Val Ser Leu Glu Lys Asn Asp His Leu Met Leu Ala Arg Gln Leu
1               5                   10                  15

Pro Leu Lys Ser Val Ala Leu Ile Leu Ala Gly Gly Arg Gly Thr Arg
                20                  25                  30

Leu Lys Asp Leu Thr Asn Lys Arg Ala Lys Pro Ala Val His Phe Gly
            35                  40                  45

Gly Lys Phe Arg Ile Ile Asp Phe Ala Leu Ser Asn Cys Ile Asn Ser
        50                  55                  60

Gly Ile Arg Arg Met Gly Val Ile Thr Gln Tyr Gln Ser His Thr Leu
65                  70                  75                  80

Val Gln His Ile Gln Arg Gly Trp Ser Phe Phe Asn Glu Glu Met Asn
                85                  90                  95

Glu Phe Val Asp Leu Leu Pro Ala Gln Gln Arg Met Lys Gly Glu Asn
            100                 105                 110

Trp Tyr Arg Gly Thr Ala Asp Ala Val Thr Gln Asn Leu Asp Ile Ile
        115                 120                 125

Arg Arg Tyr Lys Ala Glu Tyr Val Val Ile Leu Ala Gly Asp His Ile
130                 135                 140

Tyr Lys Gln Asp Tyr Ser Arg Met Leu Ile Asp His Val Glu Lys Gly
145                 150                 155                 160

Val Arg Cys Thr Val Val Cys Met Pro Val Pro Ile Glu Glu Ala Ser
                165                 170                 175

Ala Phe Gly Val Met Ala Val Asp Glu Asn Asp Lys Thr Ile Glu Phe
            180                 185                 190

Val Glu Lys Pro Ala Asn Pro Pro Ser Met Pro Asn Asp Pro Ser Lys
        195                 200                 205

Ser Leu Ala Ser Met Gly Ile Tyr Val Phe Asp Ala Asp Tyr Leu Tyr
210                 215                 220

Glu Leu Leu Glu Glu Asp Asp Arg Asp Glu Asn Ser Ser His Asp Phe
225                 230                 235                 240

Gly Lys Asp Leu Ile Pro Lys Ile Thr Glu Ala Gly Leu Ala Tyr Ala
                245                 250                 255

His Pro Phe Pro Leu Ser Cys Val Gln Ser Asp Pro Asp Ala Glu Pro
            260                 265                 270
```

```
Tyr Trp Arg Asp Val Gly Thr Leu Glu Ala Tyr Trp Lys Ala Asn Leu
            275                 280                 285

Asp Leu Ala Ser Val Val Asp Lys Leu Asp Met Tyr Asp Arg Asn Trp
        290                 295                 300

Pro Ile Arg Thr Tyr Asn Glu Ser Leu Pro Ala Lys Phe Val Gln
305                 310                 315                 320

Asp Arg Ser Gly Ser His Gly Met Thr Leu Asn Ser Leu Val Ser Gly
                325                 330                 335

Gly Cys Val Ile Ser Gly Ser Val Val Gln Ser Val Leu Phe Ser
                340                 345                 350

Arg Val Arg Val Asn Ser Phe Cys Asn Ile Asp Ser Ala Val Leu Leu
            355                 360                 365

Pro Glu Val Trp Val Gly Arg Ser Cys Arg Leu Arg Arg Cys Val Ile
        370                 375                 380

Asp Arg Ala Cys Val Ile Pro Glu Gly Met Val Ile Gly Glu Asn Ala
385                 390                 395                 400

Glu Glu Asp Ala Arg Arg Phe Tyr Arg Ser Glu Glu Gly Ile Val Leu
                405                 410                 415

Val Thr Arg Glu Met Leu Arg Lys Leu Gly His Lys Gln Glu Arg
            420                 425                 430

<210> SEQ ID NO 46
<211> LENGTH: 1328
<212> TYPE: DNA
<213> ORGANISM: Escherichia coli
<220> FEATURE:
<221> NAME/KEY: CDS
<222> LOCATION: (1)..(1293)
<220> FEATURE:
<221> NAME/KEY: CDS
<222> LOCATION: (1297)..(1326)

<400> SEQUENCE: 46 atg gtt agt tta gag aag aac gat cac tta atg ttg gcg cgc cag ctg    48
Met Val Ser Leu Glu Lys Asn Asp His Leu Met Leu Ala Arg Gln Leu
1               5                  10                  15 cca ttg aaa tct gtt gcc ctg ata ctg gcg gga gga cgt ggt acc cgc    96
Pro Leu Lys Ser Val Ala Leu Ile Leu Ala Gly Gly Arg Gly Thr Arg
            20                  25                  30 ctg aag gat tta acc aat aag cga gca aaa ccg gcc gta cac ttc ggc   144
Leu Lys Asp Leu Thr Asn Lys Arg Ala Lys Pro Ala Val His Phe Gly
        35                  40                  45 ggt aag ttc cgc att atc gac ttt gcg ctg tct aac tgc atc aac tcc   192
Gly Lys Phe Arg Ile Ile Asp Phe Ala Leu Ser Asn Cys Ile Asn Ser
    50                  55                  60 ggg atc cgt cgt atg ggc gtg atc acc cag tac cag tcc cac act ctg   240
Gly Ile Arg Arg Met Gly Val Ile Thr Gln Tyr Gln Ser His Thr Leu
65                  70                  75                  80 gtg cag cac att cag cgc ggc tgg tca ttc ttc aat gaa gaa atg aac   288
Val Gln His Ile Gln Arg Gly Trp Ser Phe Phe Asn Glu Glu Met Asn
                85                  90                  95 gag ttt gtc gat ctg ctg cca gca cag cag aga atg aaa ggg gaa aac   336
Glu Phe Val Asp Leu Leu Pro Ala Gln Gln Arg Met Lys Gly Glu Asn
            100                 105                 110 tgg tat cgc ggc acc gca gat gcg gtc acc caa aac ctc gac att atc   384
Trp Tyr Arg Gly Thr Ala Asp Ala Val Thr Gln Asn Leu Asp Ile Ile
        115                 120                 125 cgc cgt tat aaa gcg gaa tac gtg gtg atc ctg gcg ggc gac cat atc   432
Arg Arg Tyr Lys Ala Glu Tyr Val Val Ile Leu Ala Gly Asp His Ile
```

```
            130                 135                 140
tac aag caa gac tac tcg cgt atg ctt atc gat cac gtc gaa aaa ggc      480
Tyr Lys Gln Asp Tyr Ser Arg Met Leu Ile Asp His Val Glu Lys Gly
145                 150                 155                 160 gca cgt tgc acc gtt gct tgt atg cca gta ccg att gaa gaa gcc tcc      528
Ala Arg Cys Thr Val Ala Cys Met Pro Val Pro Ile Glu Glu Ala Ser
                165                 170                 175 gca ttt ggc gtt atg gcg gtt gat gag aac gat aaa att atc gaa ttc      576
Ala Phe Gly Val Met Ala Val Asp Glu Asn Asp Lys Ile Ile Glu Phe
            180                 185                 190 gtt gaa aaa cct gct aac ccg ccg tca atg ccg aac gat ccg agc aaa      624
Val Glu Lys Pro Ala Asn Pro Pro Ser Met Pro Asn Asp Pro Ser Lys
        195                 200                 205 tct ctg gcg agt atg ggt atc tac gtc ttt gac gcc gac tat ctg tat      672
Ser Leu Ala Ser Met Gly Ile Tyr Val Phe Asp Ala Asp Tyr Leu Tyr
    210                 215                 220 gaa ctg ctg gaa gaa gac gat cgc gat gag aac tcc agc cac gac ttt      720
Glu Leu Leu Glu Glu Asp Asp Arg Asp Glu Asn Ser Ser His Asp Phe
225                 230                 235                 240 ggc aaa gat ttg att ccc aag atc acc gaa gcc ggt ctg gcc tat gcg      768
Gly Lys Asp Leu Ile Pro Lys Ile Thr Glu Ala Gly Leu Ala Tyr Ala
                245                 250                 255 cac ccg ttc ccg ctc tct tgc gta caa tcc gac ccg gat gcc gag ccg      816
His Pro Phe Pro Leu Ser Cys Val Gln Ser Asp Pro Asp Ala Glu Pro
            260                 265                 270 tac tgg cgc gat gtg ggt acg ctg gaa gct tac tgg aaa gcg aac ctc      864
Tyr Trp Arg Asp Val Gly Thr Leu Glu Ala Tyr Trp Lys Ala Asn Leu
        275                 280                 285 gat ctg gcc tct gtg gtg ccg gaa ctg gat atg tac gat cgc aat tgg      912
Asp Leu Ala Ser Val Val Pro Glu Leu Asp Met Tyr Asp Arg Asn Trp
    290                 295                 300 cca att cgc acc tac aat gaa tca tta ccg cca gcg aaa ttc gtg cag      960
Pro Ile Arg Thr Tyr Asn Glu Ser Leu Pro Pro Ala Lys Phe Val Gln
305                 310                 315                 320 gat cgc tcc ggt agc cac ggg atg acc ctt aac tca ctg gtt tcc ggc     1008
Asp Arg Ser Gly Ser His Gly Met Thr Leu Asn Ser Leu Val Ser Gly
                325                 330                 335 ggt tgt gtg atc tcc ggt tcg gtg gtg gtg cag tcc gtt ctg ttc tcg     1056
Gly Cys Val Ile Ser Gly Ser Val Val Val Gln Ser Val Leu Phe Ser
            340                 345                 350 cgc gtt cgc gtg aat tca ttc tgc aac att gat tcc gcc gta ttg tta     1104
Arg Val Arg Val Asn Ser Phe Cys Asn Ile Asp Ser Ala Val Leu Leu
        355                 360                 365 ccg gaa gta tgg gta ggt cgc tcg tgc cgt ctg cgc cgc tgc gtc atc     1152
Pro Glu Val Trp Val Gly Arg Ser Cys Arg Leu Arg Arg Cys Val Ile
    370                 375                 380 gat cgt gct tgt gtt att ccg gaa ggc atg gtg att ggt gaa aac gca     1200
Asp Arg Ala Cys Val Ile Pro Glu Gly Met Val Ile Gly Glu Asn Ala
385                 390                 395                 400 gag gaa gat gca cgt cgt ttc tat cgt tca gaa gaa ggc atc gtg ctg     1248
Glu Glu Asp Ala Arg Arg Phe Tyr Arg Ser Glu Glu Gly Ile Val Leu
                405                 410                 415 gta acg cgc gaa atg cta cgg aag tta ggg cat aaa cag gag cga taa     1296
Val Thr Arg Glu Met Leu Arg Lys Leu Gly His Lys Gln Glu Arg
            420                 425                 430 tgc agg ttt tac atg tat gtt cag aga tgt tt                          1328
Cys Arg Phe Tyr Met Tyr Val Gln Arg Cys
        435                 440
```

```
<210> SEQ ID NO 47
<211> LENGTH: 431
<212> TYPE: PRT
<213> ORGANISM: Escherichia coli

<400> SEQUENCE: 47
```

| | | | | | | | | | | | | | | |
|---|---|---|---|---|---|---|---|---|---|---|---|---|---|---|
| Met | Val | Ser | Leu | Glu | Lys | Asn | Asp | His | Leu | Met | Leu | Ala | Arg | Gln | Leu |
| 1 | | | | 5 | | | | | 10 | | | | | 15 | |
| Pro | Leu | Lys | Ser | Val | Ala | Leu | Ile | Leu | Ala | Gly | Gly | Arg | Gly | Thr | Arg |
| | | | 20 | | | | | 25 | | | | | 30 | | |
| Leu | Lys | Asp | Leu | Thr | Asn | Lys | Arg | Ala | Lys | Pro | Ala | Val | His | Phe | Gly |
| | | | 35 | | | | | 40 | | | | | 45 | | |
| Gly | Lys | Phe | Arg | Ile | Ile | Asp | Phe | Ala | Leu | Ser | Asn | Cys | Ile | Asn | Ser |
| | | 50 | | | | | 55 | | | | | 60 | | | |
| Gly | Ile | Arg | Arg | Met | Gly | Val | Ile | Thr | Gln | Tyr | Gln | Ser | His | Thr | Leu |
| 65 | | | | | 70 | | | | | 75 | | | | | 80 |
| Val | Gln | His | Ile | Gln | Arg | Gly | Trp | Ser | Phe | Phe | Asn | Glu | Glu | Met | Asn |
| | | | | 85 | | | | | 90 | | | | | 95 | |
| Glu | Phe | Val | Asp | Leu | Leu | Pro | Ala | Gln | Gln | Arg | Met | Lys | Gly | Glu | Asn |
| | | | | 100 | | | | | 105 | | | | | 110 | |
| Trp | Tyr | Arg | Gly | Thr | Ala | Asp | Ala | Val | Thr | Gln | Asn | Leu | Asp | Ile | Ile |
| | | | 115 | | | | | 120 | | | | | 125 | | |
| Arg | Arg | Tyr | Lys | Ala | Glu | Tyr | Val | Val | Ile | Leu | Ala | Gly | Asp | His | Ile |
| | | 130 | | | | | 135 | | | | | 140 | | | |
| Tyr | Lys | Gln | Asp | Tyr | Ser | Arg | Met | Leu | Ile | Asp | His | Val | Glu | Lys | Gly |
| 145 | | | | | 150 | | | | | 155 | | | | | 160 |
| Ala | Arg | Cys | Thr | Val | Ala | Cys | Met | Pro | Val | Pro | Ile | Glu | Glu | Ala | Ser |
| | | | | 165 | | | | | 170 | | | | | 175 | |
| Ala | Phe | Gly | Val | Met | Ala | Val | Asp | Glu | Asn | Asp | Lys | Ile | Ile | Glu | Phe |
| | | | | 180 | | | | | 185 | | | | | 190 | |
| Val | Glu | Lys | Pro | Ala | Asn | Pro | Pro | Ser | Met | Pro | Asn | Asp | Pro | Ser | Lys |
| | | | 195 | | | | | 200 | | | | | 205 | | |
| Ser | Leu | Ala | Ser | Met | Gly | Ile | Tyr | Val | Phe | Asp | Ala | Asp | Tyr | Leu | Tyr |
| | | 210 | | | | | 215 | | | | | 220 | | | |
| Glu | Leu | Leu | Glu | Glu | Asp | Asp | Arg | Asp | Glu | Asn | Ser | Ser | His | Asp | Phe |
| 225 | | | | | 230 | | | | | 235 | | | | | 240 |
| Gly | Lys | Asp | Leu | Ile | Pro | Lys | Ile | Thr | Glu | Ala | Gly | Leu | Ala | Tyr | Ala |
| | | | | 245 | | | | | 250 | | | | | 255 | |
| His | Pro | Phe | Pro | Leu | Ser | Cys | Val | Gln | Ser | Asp | Pro | Asp | Ala | Glu | Pro |
| | | | | 260 | | | | | 265 | | | | | 270 | |
| Tyr | Trp | Arg | Asp | Val | Gly | Thr | Leu | Glu | Ala | Tyr | Trp | Lys | Ala | Asn | Leu |
| | | | 275 | | | | | 280 | | | | | 285 | | |
| Asp | Leu | Ala | Ser | Val | Val | Pro | Glu | Leu | Asp | Met | Tyr | Asp | Arg | Asn | Trp |
| | | 290 | | | | | 295 | | | | | 300 | | | |
| Pro | Ile | Arg | Thr | Tyr | Asn | Glu | Ser | Leu | Pro | Pro | Ala | Lys | Phe | Val | Gln |
| 305 | | | | | 310 | | | | | 315 | | | | | 320 |
| Asp | Arg | Ser | Gly | Ser | His | Gly | Met | Thr | Leu | Asn | Ser | Leu | Val | Ser | Gly |
| | | | | 325 | | | | | 330 | | | | | 335 | |
| Gly | Cys | Val | Ile | Ser | Gly | Ser | Val | Val | Gln | Ser | Val | Leu | Phe | Ser | |
| | | | | 340 | | | | | 345 | | | | | 350 | |
| Arg | Val | Arg | Val | Asn | Ser | Phe | Cys | Asn | Ile | Asp | Ser | Ala | Val | Leu | Leu |
| | | | 355 | | | | | 360 | | | | | 365 | | |
| Pro | Glu | Val | Trp | Val | Gly | Arg | Ser | Cys | Arg | Leu | Arg | Arg | Cys | Val | Ile |
| | | 370 | | | | | 375 | | | | | 380 | | | |

-continued

```
Asp Arg Ala Cys Val Ile Pro Glu Gly Met Val Ile Gly Glu Asn Ala
385                 390                 395                 400

Glu Glu Asp Ala Arg Arg Phe Tyr Arg Ser Glu Gly Ile Val Leu
            405                 410                 415

Val Thr Arg Glu Met Leu Arg Lys Leu Gly His Lys Gln Glu Arg
        420                 425                 430

<210> SEQ ID NO 48
<211> LENGTH: 1328
<212> TYPE: DNA
<213> ORGANISM: Escherichia coli
<220> FEATURE:
<221> NAME/KEY: CDS
<222> LOCATION: (1)..(1293)
<220> FEATURE:
<221> NAME/KEY: CDS
<222> LOCATION: (1297)..(1326)

<400> SEQUENCE: 48 atg gtt agt tta gag aag aac gat cac tta atg ttg gcg cgc cag ctg      48
Met Val Ser Leu Glu Lys Asn Asp His Leu Met Leu Ala Arg Gln Leu
 1               5                  10                  15 cca ttg aaa tct gtt gcc ctg ata ctg gcg gga gga cgt ggt acc cgc      96
Pro Leu Lys Ser Val Ala Leu Ile Leu Ala Gly Gly Arg Gly Thr Arg
             20                  25                  30 ctg aag gat tta acc aat aag cga gca aaa ccg gcc gta cac ttc ggc     144
Leu Lys Asp Leu Thr Asn Lys Arg Ala Lys Pro Ala Val His Phe Gly
         35                  40                  45 ggt aag ttc cgc att atc gac ttt gcg ctg tct aac tgc atc aac tcc     192
Gly Lys Phe Arg Ile Ile Asp Phe Ala Leu Ser Asn Cys Ile Asn Ser
     50                  55                  60 ggg atc cgt cgt atg ggc gtg atc acc cag tac cag tcc cac act ctg     240
Gly Ile Arg Arg Met Gly Val Ile Thr Gln Tyr Gln Ser His Thr Leu
 65                  70                  75                  80 gtg cag cac att cag cgc ggc tgg tca ttc ttc aat gaa gaa atg aac     288
Val Gln His Ile Gln Arg Gly Trp Ser Phe Phe Asn Glu Glu Met Asn
                 85                  90                  95 gag ttt gtc gat ctg ctg cca gca cag cag aga atg aaa ggg gaa aac     336
Glu Phe Val Asp Leu Leu Pro Ala Gln Gln Arg Met Lys Gly Glu Asn
            100                 105                 110 tgg tat cgc ggc acc gca gat gcg gtc acc caa aac ctc gac att atc     384
Trp Tyr Arg Gly Thr Ala Asp Ala Val Thr Gln Asn Leu Asp Ile Ile
        115                 120                 125 cgc cgt tat aaa gcg gaa tac gtg gtg atc ctg gcg ggc gac cat atc     432
Arg Arg Tyr Lys Ala Glu Tyr Val Val Ile Leu Ala Gly Asp His Ile
    130                 135                 140 tac aag caa gac tac tcg cgt atg ctt atc gat cac gtc gaa aaa ggc     480
Tyr Lys Gln Asp Tyr Ser Arg Met Leu Ile Asp His Val Glu Lys Gly
145                 150                 155                 160 gca cgt tgc acc gtt gct tgt atg cca gta ccg att gaa gaa gcc tcc     528
Ala Arg Cys Thr Val Ala Cys Met Pro Val Pro Ile Glu Glu Ala Ser
                165                 170                 175 gca ttt ggc gtt atg gcg gtt gat gag aac gat aaa att atc gaa ttc     576
Ala Phe Gly Val Met Ala Val Asp Glu Asn Asp Lys Ile Ile Glu Phe
            180                 185                 190 gtt gaa aaa cct gct aac ccg ccg tca atg ccg aac gat ccg agc aaa     624
Val Glu Lys Pro Ala Asn Pro Pro Ser Met Pro Asn Asp Pro Ser Lys
        195                 200                 205 tct ctg gcg agt atg ggt atc tac gtc ttt gac gcc gac tat ctg tat     672
Ser Leu Ala Ser Met Gly Ile Tyr Val Phe Asp Ala Asp Tyr Leu Tyr
    210                 215                 220
```

```
gaa ctg ctg gaa gaa gac gat cgc gat gag aac tcc agc cac gac ttt       720
Glu Leu Leu Glu Glu Asp Asp Arg Asp Glu Asn Ser Ser His Asp Phe
225                 230                 235                 240 ggc aaa gat ttg att ccc aag atc acc gaa gcc ggt ctg gcc tat gcg       768
Gly Lys Asp Leu Ile Pro Lys Ile Thr Glu Ala Gly Leu Ala Tyr Ala
            245                 250                 255 cac ccg ttc ccg ctc tct tgc gta caa tcc gac ccg gat gcc gag ccg       816
His Pro Phe Pro Leu Ser Cys Val Gln Ser Asp Pro Asp Ala Glu Pro
        260                 265                 270 tac tgg cgc gat gtg ggt acg ctg gaa gct tac tgg aaa gcg aac ctc       864
Tyr Trp Arg Asp Val Gly Thr Leu Glu Ala Tyr Trp Lys Ala Asn Leu
    275                 280                 285 gat ctg gcc tct gtg gtg ccg aaa ctg gat atg tac gat cgc aat tgg       912
Asp Leu Ala Ser Val Val Pro Lys Leu Asp Met Tyr Asp Arg Asn Trp
290                 295                 300 cca att cgc acc tac aat gaa tca tta ccg cca gcg aaa ttc gtg cag       960
Pro Ile Arg Thr Tyr Asn Glu Ser Leu Pro Pro Ala Lys Phe Val Gln
305                 310                 315                 320 gat cgc tcc ggt agc cac ggg atg acc ctt aac tca ctg gtt tcc ggc      1008
Asp Arg Ser Gly Ser His Gly Met Thr Leu Asn Ser Leu Val Ser Gly
            325                 330                 335 ggt tgt gtg atc tcc ggt tcg gtg gtg gtg cag tcc gtt ctg ttc tcg      1056
Gly Cys Val Ile Ser Gly Ser Val Val Val Gln Ser Val Leu Phe Ser
        340                 345                 350 cgc gtt cgc gtg aat tca ttc tgc aac att gat tcc gcc gta ttg tta      1104
Arg Val Arg Val Asn Ser Phe Cys Asn Ile Asp Ser Ala Val Leu Leu
    355                 360                 365 ccg gaa gta tgg gta ggt cgc tcg tgc cgt ctg cgc cgc tgc gtc atc      1152
Pro Glu Val Trp Val Gly Arg Ser Cys Arg Leu Arg Arg Cys Val Ile
370                 375                 380 gat cgt gct tgt gtt att ccg gaa ggc atg gtg att ggt gaa aac gca      1200
Asp Arg Ala Cys Val Ile Pro Glu Gly Met Val Ile Gly Glu Asn Ala
385                 390                 395                 400 gag gaa gat gca cgt cgt ttc tat cgt tca gaa gaa ggc atc gtg ctg      1248
Glu Glu Asp Ala Arg Arg Phe Tyr Arg Ser Glu Glu Gly Ile Val Leu
            405                 410                 415 gta acg cgc gaa atg cta cgg aag tta ggg cat aaa cag gag cga taa      1296
Val Thr Arg Glu Met Leu Arg Lys Leu Gly His Lys Gln Glu Arg
        420                 425                 430 tgc agg ttt tac atg tat gtt cag aga tgt tt                           1328
Cys Arg Phe Tyr Met Tyr Val Gln Arg Cys
    435                 440
```

<210> SEQ ID NO 49
<211> LENGTH: 431
<212> TYPE: PRT
<213> ORGANISM: Escherichia coli

<400> SEQUENCE: 49

```
Met Val Ser Leu Glu Lys Asn Asp His Leu Met Leu Ala Arg Gln Leu
 1               5                  10                  15

Pro Leu Lys Ser Val Ala Leu Ile Leu Ala Gly Gly Arg Gly Thr Arg
            20                  25                  30

Leu Lys Asp Leu Thr Asn Lys Arg Ala Lys Pro Ala Val His Phe Gly
        35                  40                  45

Gly Lys Phe Arg Ile Ile Asp Phe Ala Leu Ser Asn Cys Ile Asn Ser
    50                  55                  60

Gly Ile Arg Arg Met Gly Val Ile Thr Gln Tyr Gln Ser His Thr Leu
65                  70                  75                  80
```

-continued

```
Val Gln His Ile Gln Arg Gly Trp Ser Phe Phe Asn Glu Glu Met Asn
                 85                  90                  95

Glu Phe Val Asp Leu Leu Pro Ala Gln Gln Arg Met Lys Gly Glu Asn
            100                 105                 110

Trp Tyr Arg Gly Thr Ala Asp Ala Val Thr Gln Asn Leu Asp Ile Ile
        115                 120                 125

Arg Arg Tyr Lys Ala Glu Tyr Val Ile Leu Ala Gly Asp His Ile
    130                 135                 140

Tyr Lys Gln Asp Tyr Ser Arg Met Leu Ile Asp His Val Glu Lys Gly
145                 150                 155                 160

Ala Arg Cys Thr Val Ala Cys Met Pro Val Pro Ile Glu Glu Ala Ser
                165                 170                 175

Ala Phe Gly Val Met Ala Val Asp Glu Asn Asp Lys Ile Ile Glu Phe
            180                 185                 190

Val Glu Lys Pro Ala Asn Pro Pro Ser Met Pro Asn Asp Pro Ser Lys
        195                 200                 205

Ser Leu Ala Ser Met Gly Ile Tyr Val Phe Asp Ala Asp Tyr Leu Tyr
    210                 215                 220

Glu Leu Leu Glu Glu Asp Asp Arg Asp Glu Asn Ser Ser His Asp Phe
225                 230                 235                 240

Gly Lys Asp Leu Ile Pro Lys Ile Thr Glu Ala Gly Leu Ala Tyr Ala
                245                 250                 255

His Pro Phe Pro Leu Ser Cys Val Gln Ser Asp Pro Asp Ala Glu Pro
            260                 265                 270

Tyr Trp Arg Asp Val Gly Thr Leu Glu Ala Tyr Trp Lys Ala Asn Leu
        275                 280                 285

Asp Leu Ala Ser Val Val Pro Lys Leu Asp Met Tyr Asp Arg Asn Trp
    290                 295                 300

Pro Ile Arg Thr Tyr Asn Glu Ser Leu Pro Pro Ala Lys Phe Val Gln
305                 310                 315                 320

Asp Arg Ser Gly Ser His Gly Met Thr Leu Asn Ser Leu Val Ser Gly
                325                 330                 335

Gly Cys Val Ile Ser Gly Ser Val Val Gln Ser Val Leu Phe Ser
            340                 345                 350

Arg Val Arg Val Asn Ser Phe Cys Asn Ile Asp Ser Ala Val Leu Leu
        355                 360                 365

Pro Glu Val Trp Val Gly Arg Ser Cys Arg Leu Arg Arg Cys Val Ile
    370                 375                 380

Asp Arg Ala Cys Val Ile Pro Glu Gly Met Val Ile Gly Glu Asn Ala
385                 390                 395                 400

Glu Glu Asp Ala Arg Arg Phe Tyr Arg Ser Glu Glu Gly Ile Val Leu
                405                 410                 415

Val Thr Arg Glu Met Leu Arg Lys Leu Gly His Lys Gln Glu Arg
            420                 425                 430
```

<210> SEQ ID NO 50
<211> LENGTH: 1915
<212> TYPE: DNA
<213> ORGANISM: Zea mays
<220> FEATURE:
<221> NAME/KEY: CDS
<222> LOCATION: (1)..(1815)
<220> FEATURE:
<221> NAME/KEY: CDS
<222> LOCATION: (1819)..(1914)

<400> SEQUENCE: 50

```
atg gcg gct ctg gcc acg tcg cag ctc gtc gca acg cgc gcc ggc ctg        48
Met Ala Ala Leu Ala Thr Ser Gln Leu Val Ala Thr Arg Ala Gly Leu
 1               5                  10                  15 ggc gtc ccg gac gcg tcc acg ttc cgc cgc ggc gcc gcg cag ggc ctg        96
Gly Val Pro Asp Ala Ser Thr Phe Arg Arg Gly Ala Ala Gln Gly Leu
                20                  25                  30 agg ggg gcc cgg gcg tcg gcg gcg gcg gac acg ctc agc atg cgg acc       144
Arg Gly Ala Arg Ala Ser Ala Ala Ala Asp Thr Leu Ser Met Arg Thr
         35                  40                  45 agc gcg cgc gcg gcg ccc agg cac cag cag cag gcg cgc cgc ggg ggc       192
Ser Ala Arg Ala Ala Pro Arg His Gln Gln Gln Ala Arg Arg Gly Gly
 50                  55                  60 agg ttc ccg tcg ctc gtc gtg tgg gcc agc gcc ggc atg aac gtc gtc       240
Arg Phe Pro Ser Leu Val Val Trp Ala Ser Ala Gly Met Asn Val Val
 65                  70                  75                  80 ttc gtc ggc gcc gag atg gcg ccg tgg agc aag acc ggc ggc ctc ggc       288
Phe Val Gly Ala Glu Met Ala Pro Trp Ser Lys Thr Gly Gly Leu Gly
                 85                  90                  95 gac gtc ctc ggc ggc ctg ccg ccg gcc atg gcc gcg aac ggg cac cgt       336
Asp Val Leu Gly Gly Leu Pro Pro Ala Met Ala Ala Asn Gly His Arg
             100                 105                 110 gtc atg gtc gtc tct ccc cgc tac gac cag tac aag gac gcc tgg gac       384
Val Met Val Val Ser Pro Arg Tyr Asp Gln Tyr Lys Asp Ala Trp Asp
             115                 120                 125 acc agc gtc gtg tcc gag atc aag atg gga gac ggg tac gag acg gtc       432
Thr Ser Val Val Ser Glu Ile Lys Met Gly Asp Gly Tyr Glu Thr Val
130                 135                 140 agg ttc ttc cac tgc tac aag cgc gga gtg gac cgc gtg ttc gtt gac       480
Arg Phe Phe His Cys Tyr Lys Arg Gly Val Asp Arg Val Phe Val Asp
145                 150                 155                 160 cac cca ctg ttc ctg gag agg gtt tgg gga aag acc gag gag aag atc       528
His Pro Leu Phe Leu Glu Arg Val Trp Gly Lys Thr Glu Glu Lys Ile
                165                 170                 175 tac ggg cct gtc gct gga acg gac tac agg gac aac cag ctg cgg ttc       576
Tyr Gly Pro Val Ala Gly Thr Asp Tyr Arg Asp Asn Gln Leu Arg Phe
            180                 185                 190 agc ctg cta tgc cag gca gca ctt gaa gct cca agg atc ctg agc ctc       624
Ser Leu Leu Cys Gln Ala Ala Leu Glu Ala Pro Arg Ile Leu Ser Leu
            195                 200                 205 aac aac aac cca tac ttc tcc gga cca tac ggg gag gac gtc gtg ttc       672
Asn Asn Asn Pro Tyr Phe Ser Gly Pro Tyr Gly Glu Asp Val Val Phe
        210                 215                 220 gtc tgc aac gac tgg cac acc ggc cct ctc tcg tgc tac ctc aag agc       720
Val Cys Asn Asp Trp His Thr Gly Pro Leu Ser Cys Tyr Leu Lys Ser
225                 230                 235                 240 aac tac cag tcc cac ggc atc tac agg gac gca aag acc gct ttc tgc       768
Asn Tyr Gln Ser His Gly Ile Tyr Arg Asp Ala Lys Thr Ala Phe Cys
                245                 250                 255 atc cac aac atc tcc tac cag ggc cgg ttc gcc ttc tcc gac tac ccg       816
Ile His Asn Ile Ser Tyr Gln Gly Arg Phe Ala Phe Ser Asp Tyr Pro
            260                 265                 270 gag ctg aac ctc ccg gag aga ttc aag tcg tcc ttc gat ttc atc gac       864
Glu Leu Asn Leu Pro Glu Arg Phe Lys Ser Ser Phe Asp Phe Ile Asp
        275                 280                 285 ggc tac gag aag ccc gtg gaa ggc cgg aag atc aac tgg atg aag gcc       912
Gly Tyr Glu Lys Pro Val Glu Gly Arg Lys Ile Asn Trp Met Lys Ala
    290                 295                 300 ggg atc ctc gag gcc gac agg gtc ctc acc gtc agc ccc tac tac gcc       960
Gly Ile Leu Glu Ala Asp Arg Val Leu Thr Val Ser Pro Tyr Tyr Ala
```

-continued

```
                  305                 310                 315                 320
gag gag ctc atc tcc ggc atc gcc agg ggc tgc gag ctc gac aac atc           1008
Glu Glu Leu Ile Ser Gly Ile Ala Arg Gly Cys Glu Leu Asp Asn Ile
                    325                 330                 335 atg cgc ctc acc ggc atc acc ggc atc gtc aac ggc atg gac gtc agc           1056
Met Arg Leu Thr Gly Ile Thr Gly Ile Val Asn Gly Met Asp Val Ser
                    340                 345                 350 gag tgg gac ccc agc agg gac aag tac atc gcc gtg aag tac gac gtg           1104
Glu Trp Asp Pro Ser Arg Asp Lys Tyr Ile Ala Val Lys Tyr Asp Val
                    355                 360                 365 tcg acg gcc gtg gag gcc aag gcg ctg aac aag gag gcg ctg cag gcg           1152
Ser Thr Ala Val Glu Ala Lys Ala Leu Asn Lys Glu Ala Leu Gln Ala
        370                 375                 380 gag gtc ggg ctc ccg gtg gac cgg aac atc ccg ctg gtg gcg ttc atc           1200
Glu Val Gly Leu Pro Val Asp Arg Asn Ile Pro Leu Val Ala Phe Ile
385                 390                 395                 400 ggc agg ctg gaa gag cag aag ggc ccc gac gtc atg gcg gcc gcc atc           1248
Gly Arg Leu Glu Glu Gln Lys Gly Pro Asp Val Met Ala Ala Ala Ile
                    405                 410                 415 ccg cag ctc atg gag atg gtg gag gac gtg cag atc gtt ctg ctg ggc           1296
Pro Gln Leu Met Glu Met Val Glu Asp Val Gln Ile Val Leu Leu Gly
            420                 425                 430 acg ggc aag aag aag ttc gag cgc atg ctc atg agc gcc gag gag aag           1344
Thr Gly Lys Lys Lys Phe Glu Arg Met Leu Met Ser Ala Glu Glu Lys
                435                 440                 445 ttc cca ggc aag gtg cgc gcc gtg gtc aag ttc aac gcg gcg ctg gcg           1392
Phe Pro Gly Lys Val Arg Ala Val Val Lys Phe Asn Ala Ala Leu Ala
    450                 455                 460 cac cac atc atg gcc ggc gcc gac gtg ctc gcc gtc acc agc cgc ttc           1440
His His Ile Met Ala Gly Ala Asp Val Leu Ala Val Thr Ser Arg Phe
465                 470                 475                 480 gag ccc tgc ggc ctc atc cag ctg cag ggg atg cga tac gga acg ccc           1488
Glu Pro Cys Gly Leu Ile Gln Leu Gln Gly Met Arg Tyr Gly Thr Pro
                    485                 490                 495 tgc gcc tgc gcg tcc acc ggt gga ctc gtc gac acc atc atc gaa ggc           1536
Cys Ala Cys Ala Ser Thr Gly Gly Leu Val Asp Thr Ile Ile Glu Gly
                    500                 505                 510 aag acc ggg ttc cac atg ggc cgc ctc agc gtc gac tgt aac gtc gtg           1584
Lys Thr Gly Phe His Met Gly Arg Leu Ser Val Asp Cys Asn Val Val
                515                 520                 525 gag ccg gcg gac gtc aag aag gtg gcc acc aca ttg cag cgc gcc atc           1632
Glu Pro Ala Asp Val Lys Lys Val Ala Thr Thr Leu Gln Arg Ala Ile
530                 535                 540 aag gtg gtc ggc acg ccg gcg tac gag gag atg gtg agg aac tgc atg           1680
Lys Val Val Gly Thr Pro Ala Tyr Glu Glu Met Val Arg Asn Cys Met
545                 550                 555                 560 atc cag gat ctc tcc tgg aag ggc cct gcc aag aac tgg gag aac gtg           1728
Ile Gln Asp Leu Ser Trp Lys Gly Pro Ala Lys Asn Trp Glu Asn Val
                    565                 570                 575 ctg ctc agc ctc ggg gtc gcc ggc ggc gag cca ggg gtc gaa ggc gag           1776
Leu Leu Ser Leu Gly Val Ala Gly Gly Glu Pro Gly Val Glu Gly Glu
                580                 585                 590 gag atc gcg ccg ctc gcc aag gag aac gtg gcc gcg ccc tga aga gtt           1824
Glu Ile Ala Pro Leu Ala Lys Glu Asn Val Ala Ala Pro     Arg Val
            595                 600                 605 cgg cct gca ggg ccc ctg atc tcg cgc gtg gtg caa aga tgt tgg gac           1872
Arg Pro Ala Gly Pro Leu Ile Ser Arg Val Val Gln Arg Cys Trp Asp
        610                 615                 620 atc ttc tta tat atg ctg ttt cgt tta tgt gat atg gac aag t                 1915
```

```
Ile Phe Leu Tyr Met Leu Phe Arg Leu Cys Asp Met Asp Lys
625                 630                 635

<210> SEQ ID NO 51
<211> LENGTH: 605
<212> TYPE: PRT
<213> ORGANISM: Zea mays

<400> SEQUENCE: 51

Met Ala Ala Leu Ala Thr Ser Gln Leu Val Ala Thr Arg Ala Gly Leu
 1               5                  10                  15

Gly Val Pro Asp Ala Ser Thr Phe Arg Arg Gly Ala Ala Gln Gly Leu
            20                  25                  30

Arg Gly Ala Arg Ala Ser Ala Ala Ala Asp Thr Leu Ser Met Arg Thr
        35                  40                  45

Ser Ala Arg Ala Ala Pro Arg His Gln Gln Gln Ala Arg Arg Gly Gly
    50                  55                  60

Arg Phe Pro Ser Leu Val Val Trp Ala Ser Gly Met Asn Val Val
65                  70                  75                  80

Phe Val Gly Ala Glu Met Ala Pro Trp Ser Lys Thr Gly Gly Leu Gly
                85                  90                  95

Asp Val Leu Gly Gly Leu Pro Pro Ala Met Ala Ala Asn Gly His Arg
            100                 105                 110

Val Met Val Val Ser Pro Arg Tyr Asp Gln Tyr Lys Asp Ala Trp Asp
        115                 120                 125

Thr Ser Val Val Ser Glu Ile Lys Met Gly Asp Gly Tyr Glu Thr Val
    130                 135                 140

Arg Phe Phe His Cys Tyr Lys Arg Gly Val Asp Arg Val Phe Val Asp
145                 150                 155                 160

His Pro Leu Phe Leu Glu Arg Val Trp Gly Lys Thr Glu Lys Ile
                165                 170                 175

Tyr Gly Pro Val Ala Gly Thr Asp Tyr Arg Asp Asn Gln Leu Arg Phe
            180                 185                 190

Ser Leu Leu Cys Gln Ala Ala Leu Glu Ala Pro Arg Ile Leu Ser Leu
        195                 200                 205

Asn Asn Asn Pro Tyr Phe Ser Gly Pro Tyr Gly Glu Asp Val Val Phe
    210                 215                 220

Val Cys Asn Asp Trp His Thr Gly Pro Leu Ser Cys Tyr Leu Lys Ser
225                 230                 235                 240

Asn Tyr Gln Ser His Gly Ile Tyr Arg Asp Ala Lys Thr Ala Phe Cys
                245                 250                 255

Ile His Asn Ile Ser Tyr Gln Gly Arg Phe Ala Phe Ser Asp Tyr Pro
            260                 265                 270

Glu Leu Asn Leu Pro Glu Arg Phe Lys Ser Ser Phe Asp Phe Ile Asp
        275                 280                 285

Gly Tyr Glu Lys Pro Val Glu Gly Arg Lys Ile Asn Trp Met Lys Ala
    290                 295                 300

Gly Ile Leu Glu Ala Asp Arg Val Leu Thr Val Ser Pro Tyr Tyr Ala
305                 310                 315                 320

Glu Glu Leu Ile Ser Gly Ile Ala Arg Gly Cys Glu Leu Asp Asn Ile
                325                 330                 335

Met Arg Leu Thr Gly Ile Thr Gly Ile Val Asn Gly Met Asp Val Ser
            340                 345                 350

Glu Trp Asp Pro Ser Arg Asp Lys Tyr Ile Ala Val Lys Tyr Asp Val
        355                 360                 365
```

```
Ser Thr Ala Val Glu Ala Lys Ala Leu Asn Lys Glu Ala Leu Gln Ala
    370                 375                 380

Glu Val Gly Leu Pro Val Asp Arg Asn Ile Pro Leu Val Ala Phe Ile
385                 390                 395                 400

Gly Arg Leu Glu Glu Gln Lys Gly Pro Asp Val Met Ala Ala Ile
                405                 410                 415

Pro Gln Leu Met Glu Met Val Glu Asp Val Gln Ile Val Leu Leu Gly
            420                 425                 430

Thr Gly Lys Lys Lys Phe Glu Arg Met Leu Met Ser Ala Glu Glu Lys
        435                 440                 445

Phe Pro Gly Lys Val Arg Ala Val Lys Phe Asn Ala Ala Leu Ala
    450                 455                 460

His His Ile Met Ala Gly Ala Asp Val Leu Ala Val Thr Ser Arg Phe
465                 470                 475                 480

Glu Pro Cys Gly Leu Ile Gln Leu Gln Gly Met Arg Tyr Gly Thr Pro
                485                 490                 495

Cys Ala Cys Ala Ser Thr Gly Gly Leu Val Asp Thr Ile Ile Glu Gly
            500                 505                 510

Lys Thr Gly Phe His Met Gly Arg Leu Ser Val Asp Cys Asn Val Val
        515                 520                 525

Glu Pro Ala Asp Val Lys Lys Val Ala Thr Thr Leu Gln Arg Ala Ile
    530                 535                 540

Lys Val Val Gly Thr Pro Ala Tyr Glu Glu Met Val Arg Asn Cys Met
545                 550                 555                 560

Ile Gln Asp Leu Ser Trp Lys Gly Pro Ala Lys Asn Trp Glu Asn Val
                565                 570                 575

Leu Leu Ser Leu Gly Val Ala Gly Gly Pro Gly Val Glu Gly Glu
            580                 585                 590

Glu Ile Ala Pro Leu Ala Lys Glu Asn Val Ala Ala Pro
        595                 600                 605

<210> SEQ ID NO 52
<211> LENGTH: 2423
<212> TYPE: DNA
<213> ORGANISM: Zea mays
<220> FEATURE:
<221> NAME/KEY: CDS
<222> LOCATION: (1)..(2094)
<220> FEATURE:
<221> NAME/KEY: CDS
<222> LOCATION: (2107)..(2304)
<220> FEATURE:
<221> NAME/KEY: CDS
<222> LOCATION: (2308)..(2421)

<400> SEQUENCE: 52 atg ccg ggg gca atc tct tcc tcg tcg tcg gct ttt ctc ctc ccc gtc      48
Met Pro Gly Ala Ile Ser Ser Ser Ser Ser Ala Phe Leu Leu Pro Val
1               5                   10                  15 gcg tcc tcc tcg ccg cgg cgc agg cgg ggc agt gtg ggt gct gct ctg      96
Ala Ser Ser Ser Pro Arg Arg Arg Arg Gly Ser Val Gly Ala Ala Leu
            20                  25                  30 cgc tcg tac ggc tac agc ggc gcg gag ctg cgg ttg cat tgg gcg cgg     144
Arg Ser Tyr Gly Tyr Ser Gly Ala Glu Leu Arg Leu His Trp Ala Arg
        35                  40                  45 cgg ggc ccg cct cag gat gga gcg gcg tcg gta cgc gcc gca gcg gca     192
Arg Gly Pro Pro Gln Asp Gly Ala Ala Ser Val Arg Ala Ala Ala Ala
    50                  55                  60
```

-continued

| | | |
|---|---|---|
| ccg gcc ggg ggc gaa agc gag gag gca gcg aag agc tcc tcc tcg tcc<br>Pro Ala Gly Gly Glu Ser Glu Glu Ala Ala Lys Ser Ser Ser Ser Ser<br>65                               70                        75                        80 | 240 | |
| cag gcg ggc gct gtt cag ggc agc acg gcc aag gct gtg gat tct gct<br>Gln Ala Gly Ala Val Gln Gly Ser Thr Ala Lys Ala Val Asp Ser Ala<br>                        85                        90                        95 | 288 | |
| tca cct ccc aat cct ttg aca tct gct ccg aag caa agt cag agc gct<br>Ser Pro Pro Asn Pro Leu Thr Ser Ala Pro Lys Gln Ser Gln Ser Ala<br>                100                      105                      110 | 336 | |
| gca atg caa aac gga acg agt ggg ggc agc agc gcg agc acc gcc gcg<br>Ala Met Gln Asn Gly Thr Ser Gly Gly Ser Ser Ala Ser Thr Ala Ala<br>                115                      120                      125 | 384 | |
| ccg gtg tcc gga ccc aaa gct gat cat cca tca gct cct gtc acc aag<br>Pro Val Ser Gly Pro Lys Ala Asp His Pro Ser Ala Pro Val Thr Lys<br>130                               135                      140 | 432 | |
| aga gaa atc gat gcc agt gcg gtg aag cca gag ccc gca ggt gat gat<br>Arg Glu Ile Asp Ala Ser Ala Val Lys Pro Glu Pro Ala Gly Asp Asp<br>145                               150                      155                      160 | 480 | |
| gct aga ccg gtg gaa agc ata ggc atc gct gaa ccg gtg gat gct aag<br>Ala Arg Pro Val Glu Ser Ile Gly Ile Ala Glu Pro Val Asp Ala Lys<br>                        165                      170                      175 | 528 | |
| gct gat gca gct ccg gct aca gat gcg gcg gcg agt gct cct tat gac<br>Ala Asp Ala Ala Pro Ala Thr Asp Ala Ala Ala Ser Ala Pro Tyr Asp<br>                180                      185                      190 | 576 | |
| agg gag gat aat gaa cct ggc cct ttg gct ggg cct aat gtg atg aac<br>Arg Glu Asp Asn Glu Pro Gly Pro Leu Ala Gly Pro Asn Val Met Asn<br>                        195                      200                      205 | 624 | |
| gtc gtc gtg gtg gct tct gaa tgt gct cct ttc tgc aag aca ggt ggc<br>Val Val Val Val Ala Ser Glu Cys Ala Pro Phe Cys Lys Thr Gly Gly<br>210                               215                      220 | 672 | |
| ctt gga gat gtc gtg ggt gct ttg cct aag gct ctg gcg agg aga gga<br>Leu Gly Asp Val Val Gly Ala Leu Pro Lys Ala Leu Ala Arg Arg Gly<br>225                               230                      235                      240 | 720 | |
| cac cgt gtt atg gtc gtg ata cca aga tat gga gag tat gcc gaa gcc<br>His Arg Val Met Val Val Ile Pro Arg Tyr Gly Glu Tyr Ala Glu Ala<br>                        245                      250                      255 | 768 | |
| cgg gat tta ggt gta agg aga cgt tac aag gta gct gga cag gat tca<br>Arg Asp Leu Gly Val Arg Arg Arg Tyr Lys Val Ala Gly Gln Asp Ser<br>                260                      265                      270 | 816 | |
| gaa gtt act tat ttt cac tct tac att gat gga gtt gat ttt gta ttc<br>Glu Val Thr Tyr Phe His Ser Tyr Ile Asp Gly Val Asp Phe Val Phe<br>                        275                      280                      285 | 864 | |
| gta gaa gcc cct ccc ttc cgg cac cgg cac aat aat att tat ggg gga<br>Val Glu Ala Pro Pro Phe Arg His Arg His Asn Asn Ile Tyr Gly Gly<br>290                               295                      300 | 912 | |
| gaa aga ttg gat att ttg aag cgc atg att ttg ttc tgc aag gcc gct<br>Glu Arg Leu Asp Ile Leu Lys Arg Met Ile Leu Phe Cys Lys Ala Ala<br>305                               310                      315                      320 | 960 | |
| gtt gag gtt cca tgg tat gct cca tgt ggc ggt act gtc tat ggt gat<br>Val Glu Val Pro Trp Tyr Ala Pro Cys Gly Gly Thr Val Tyr Gly Asp<br>                        325                      330                      335 | 1008 | |
| ggc aac tta gtt ttc att gct aat gat tgg cat acc gca ctt ctg cct<br>Gly Asn Leu Val Phe Ile Ala Asn Asp Trp His Thr Ala Leu Leu Pro<br>                        340                      345                      350 | 1056 | |
| gtc tat cta aag gcc tat tac cgg gac aat ggt ttg atg cag tat gct<br>Val Tyr Leu Lys Ala Tyr Tyr Arg Asp Asn Gly Leu Met Gln Tyr Ala<br>                        355                      360                      365 | 1104 | |
| cgc tct gtg ctt gtg ata cac aac att gct cat cag ggt cgt ggc cct<br>Arg Ser Val Leu Val Ile His Asn Ile Ala His Gln Gly Arg Gly Pro<br>                        370                      375                      380 | 1152 | |

```
gta gac gac ttc gtc aat ttt gac ttg cct gaa cac tac atc gac cac     1200
Val Asp Asp Phe Val Asn Phe Asp Leu Pro Glu His Tyr Ile Asp His
385                 390                 395                 400 ttc aaa ctg tat gac aac att ggt ggg gat cac agc aac gtt ttt gct     1248
Phe Lys Leu Tyr Asp Asn Ile Gly Gly Asp His Ser Asn Val Phe Ala
                405                 410                 415 gcg ggg ctg aag acg gca gac cgg gtg gtg acc gtt agc aat ggc tac     1296
Ala Gly Leu Lys Thr Ala Asp Arg Val Val Thr Val Ser Asn Gly Tyr
            420                 425                 430 atg tgg gag ctg aag act tcg gaa ggc ggg tgg ggc ctc cac gac atc     1344
Met Trp Glu Leu Lys Thr Ser Glu Gly Gly Trp Gly Leu His Asp Ile
        435                 440                 445 ata aac cag aac gac tgg aag ctg cag ggc atc gtg aac ggc atc gac     1392
Ile Asn Gln Asn Asp Trp Lys Leu Gln Gly Ile Val Asn Gly Ile Asp
    450                 455                 460 atg agc gag tgg aac ccc gct gtg gac gtg cac ctc cac tcc gac gac     1440
Met Ser Glu Trp Asn Pro Ala Val Asp Val His Leu His Ser Asp Asp
465                 470                 475                 480 tac acc aac tac acg ttc gag acg ctg gac acc ggc aag cgg cag tgc     1488
Tyr Thr Asn Tyr Thr Phe Glu Thr Leu Asp Thr Gly Lys Arg Gln Cys
                485                 490                 495 aag gcc gcc ctg cag cgg cag ctg ggc ctg cag gtc cgc gac gac gtg     1536
Lys Ala Ala Leu Gln Arg Gln Leu Gly Leu Gln Val Arg Asp Asp Val
            500                 505                 510 cca ctg atc ggg ttc atc ggg cgg ctg gac cac cag aag ggc gtg gac     1584
Pro Leu Ile Gly Phe Ile Gly Arg Leu Asp His Gln Lys Gly Val Asp
        515                 520                 525 atc atc gcc gac gcg atc cac tgg atc gcg ggg cag gac gtg cag ctc     1632
Ile Ile Ala Asp Ala Ile His Trp Ile Ala Gly Gln Asp Val Gln Leu
    530                 535                 540 gtg atg ctg ggc acc ggg cgg gcc gac ctg gag gac atg ctg cgg cgg     1680
Val Met Leu Gly Thr Gly Arg Ala Asp Leu Glu Asp Met Leu Arg Arg
545                 550                 555                 560 ttc gag tcg gag cac agc gac aag gtg cgc gcg tgg gtg ggg ttc tcg     1728
Phe Glu Ser Glu His Ser Asp Lys Val Arg Ala Trp Val Gly Phe Ser
                565                 570                 575 gtg ccc ctg gcg cac cgc atc acg gcg ggc gcg gac atc ctg ctg atg     1776
Val Pro Leu Ala His Arg Ile Thr Ala Gly Ala Asp Ile Leu Leu Met
            580                 585                 590 ccg tcg cgg ttc gag ccg tgc ggg ctg aac cag ctc tac gcc atg gcg     1824
Pro Ser Arg Phe Glu Pro Cys Gly Leu Asn Gln Leu Tyr Ala Met Ala
        595                 600                 605 tac ggg acc gtg ccc gtg gtg cac gcc gtg ggg ggg ctc cgg gac acg     1872
Tyr Gly Thr Val Pro Val Val His Ala Val Gly Gly Leu Arg Asp Thr
    610                 615                 620 gtg gcg ccg ttc gac ccg ttc aac gac acc ggg ctc ggg tgg acg ttc     1920
Val Ala Pro Phe Asp Pro Phe Asn Asp Thr Gly Leu Gly Trp Thr Phe
625                 630                 635                 640 gac cgc gcg gag gcg aac cgg atg atc gac gcg ctc tcg cac tgc ctc     1968
Asp Arg Ala Glu Ala Asn Arg Met Ile Asp Ala Leu Ser His Cys Leu
                645                 650                 655 acc acg tac cgg aac tac aag gag agc tgg cgc gcc tgc agg gcg cgc     2016
Thr Thr Tyr Arg Asn Tyr Lys Glu Ser Trp Arg Ala Cys Arg Ala Arg
            660                 665                 670 ggc atg gcc gag gac ctc agc tgg gac cac gcc gcc gtg ctg tat gag     2064
Gly Met Ala Glu Asp Leu Ser Trp Asp His Ala Ala Val Leu Tyr Glu
        675                 680                 685 gac gtg ctc gtc aag gcg aag tac cag tgg tgagcgaatt aa ttg gcg acg    2115
Asp Val Leu Val Lys Ala Lys Tyr Gln Trp                Leu Ala Thr
```

```
                690              695                   700
cga cgc cgc tcc tgt cgc agg acc tgg acg tta ttt aga agg ctc ttc    2163
Arg Arg Arg Ser Cys Arg Arg Thr Trp Thr Leu Phe Arg Arg Leu Phe
            705                 710                 715 tcc ctg gcg gct ttg atg cgt gcg tcg cat ttg cgc cgg gcg gac ggg    2211
Ser Leu Ala Ala Leu Met Arg Ala Ser His Leu Arg Arg Ala Asp Gly
            720                 725                 730 cga cgg tgg ttg gcc tac cgc cta cgt cgg ctg cgt gcc ctg gga att    2259
Arg Arg Trp Leu Ala Tyr Arg Leu Arg Arg Leu Arg Ala Leu Gly Ile
            735                 740                 745 tgg gcg ggc acg atg atg cca ctg ggc acc ggg cgc ggg gta gta tga    2307
Trp Ala Gly Thr Met Met Pro Leu Gly Thr Gly Arg Gly Val Val
750                 755                 760 tat gaa acc gac ggc gat gga gat gag gcg cat ggc att ttc cca ctg    2355
Tyr Glu Thr Asp Gly Asp Gly Asp Glu Ala His Gly Ile Phe Pro Leu
765                 770                 775                 780 ata aat ggg gag ttg tat gct act tta ata tcg cca ctc ctg tta gta    2403
Ile Asn Gly Glu Leu Tyr Ala Thr Leu Ile Ser Pro Leu Leu Leu Val
            785                 790                 795 ttt ata ttg atg gcg gcc gc                                         2423
Phe Ile Leu Met Ala Ala
800

<210> SEQ ID NO 53
<211> LENGTH: 698
<212> TYPE: PRT
<213> ORGANISM: Zea mays

<400> SEQUENCE: 53

Met Pro Gly Ala Ile Ser Ser Ser Ser Ala Phe Leu Leu Pro Val
1               5                   10                  15

Ala Ser Ser Ser Pro Arg Arg Arg Gly Ser Val Gly Ala Ala Leu
                20                  25                  30

Arg Ser Tyr Gly Tyr Ser Gly Ala Glu Leu Arg Leu His Trp Ala Arg
            35                  40                  45

Arg Gly Pro Pro Gln Asp Gly Ala Ala Ser Val Arg Ala Ala Ala Ala
        50                  55                  60

Pro Ala Gly Gly Glu Ser Glu Glu Ala Lys Ser Ser Ser Ser
65                  70                  75                  80

Gln Ala Gly Ala Val Gln Gly Ser Thr Ala Lys Ala Val Asp Ser Ala
                85                  90                  95

Ser Pro Pro Asn Pro Leu Thr Ser Ala Pro Lys Gln Ser Gln Ser Ala
            100                 105                 110

Ala Met Gln Asn Gly Thr Ser Gly Ser Ser Ala Ser Thr Ala Ala
        115                 120                 125

Pro Val Ser Gly Pro Lys Ala Asp His Pro Ser Ala Pro Val Thr Lys
130                 135                 140

Arg Glu Ile Asp Ala Ser Ala Val Lys Pro Glu Pro Ala Gly Asp Asp
145                 150                 155                 160

Ala Arg Pro Val Glu Ser Ile Gly Ile Ala Glu Pro Val Asp Ala Lys
                165                 170                 175

Ala Asp Ala Ala Pro Ala Thr Asp Ala Ala Ser Ala Pro Tyr Asp
            180                 185                 190

Arg Glu Asp Asn Glu Pro Gly Pro Leu Ala Gly Pro Asn Val Met Asn
        195                 200                 205

Val Val Val Val Ala Ser Glu Cys Ala Pro Phe Cys Lys Thr Gly Gly
210                 215                 220
```

-continued

```
Leu Gly Asp Val Val Gly Ala Leu Pro Lys Ala Leu Ala Arg Arg Gly
225                 230                 235                 240

His Arg Val Met Val Val Ile Pro Arg Tyr Gly Glu Tyr Ala Glu Ala
            245                 250                 255

Arg Asp Leu Gly Val Arg Arg Tyr Lys Val Ala Gly Gln Asp Ser
        260                 265                 270

Glu Val Thr Tyr Phe His Ser Tyr Ile Asp Gly Val Asp Phe Val Phe
        275                 280                 285

Val Glu Ala Pro Pro Phe Arg His Arg Asn Asn Ile Tyr Gly Gly
290                 295                 300

Glu Arg Leu Asp Ile Leu Lys Arg Met Ile Leu Phe Cys Lys Ala Ala
305                 310                 315                 320

Val Glu Val Pro Trp Tyr Ala Pro Cys Gly Thr Val Tyr Gly Asp
                325                 330                 335

Gly Asn Leu Val Phe Ile Ala Asn Asp Trp His Thr Ala Leu Leu Pro
            340                 345                 350

Val Tyr Leu Lys Ala Tyr Tyr Arg Asp Asn Gly Leu Met Gln Tyr Ala
        355                 360                 365

Arg Ser Val Leu Val Ile His Asn Ile Ala His Gln Gly Arg Gly Pro
        370                 375                 380

Val Asp Asp Phe Val Asn Phe Asp Leu Pro Glu His Tyr Ile Asp His
385                 390                 395                 400

Phe Lys Leu Tyr Asp Asn Ile Gly Gly Asp His Ser Asn Val Phe Ala
                405                 410                 415

Ala Gly Leu Lys Thr Ala Asp Arg Val Val Thr Val Ser Asn Gly Tyr
            420                 425                 430

Met Trp Glu Leu Lys Thr Ser Glu Gly Gly Trp Gly Leu His Asp Ile
        435                 440                 445

Ile Asn Gln Asn Asp Trp Lys Leu Gln Gly Ile Val Asn Gly Ile Asp
450                 455                 460

Met Ser Glu Trp Asn Pro Ala Val Asp Val His Leu His Ser Asp Asp
465                 470                 475                 480

Tyr Thr Asn Tyr Thr Phe Glu Thr Leu Asp Thr Gly Lys Arg Gln Cys
                485                 490                 495

Lys Ala Ala Leu Gln Arg Gln Leu Gly Leu Gln Val Arg Asp Asp Val
            500                 505                 510

Pro Leu Ile Gly Phe Ile Gly Arg Leu Asp His Gln Lys Gly Val Asp
        515                 520                 525

Ile Ile Ala Asp Ala Ile His Trp Ile Ala Gly Gln Asp Val Gln Leu
530                 535                 540

Val Met Leu Gly Thr Gly Arg Ala Asp Leu Glu Asp Met Leu Arg Arg
545                 550                 555                 560

Phe Glu Ser Glu His Ser Asp Lys Val Arg Ala Trp Val Gly Phe Ser
                565                 570                 575

Val Pro Leu Ala His Arg Ile Thr Ala Gly Ala Asp Ile Leu Leu Met
            580                 585                 590

Pro Ser Arg Phe Glu Pro Cys Gly Leu Asn Gln Leu Tyr Ala Met Ala
        595                 600                 605

Tyr Gly Thr Val Pro Val Val His Ala Val Gly Gly Leu Arg Asp Thr
        610                 615                 620

Val Ala Pro Phe Asp Pro Phe Asn Asp Thr Gly Leu Gly Trp Thr Phe
625                 630                 635                 640
```

```
Asp Arg Ala Glu Ala Asn Arg Met Ile Asp Ala Leu Ser His Cys Leu
            645                 650                 655

Thr Thr Tyr Arg Asn Tyr Lys Glu Ser Trp Arg Ala Cys Arg Ala Arg
        660                 665                 670

Gly Met Ala Glu Asp Leu Ser Trp Asp His Ala Ala Val Leu Tyr Glu
            675                 680                 685

Asp Val Leu Val Lys Ala Lys Tyr Gln Trp
    690                 695

<210> SEQ ID NO 54
<211> LENGTH: 2007
<212> TYPE: DNA
<213> ORGANISM: Zea mays
<220> FEATURE:
<221> NAME/KEY: CDS
<222> LOCATION: (1)..(2007)

<400> SEQUENCE: 54 gct gag gct gag gcc ggg ggc aag gac gcg ccg ccg gag agg agc ggc      48
Ala Glu Ala Glu Ala Gly Gly Lys Asp Ala Pro Pro Glu Arg Ser Gly
 1               5                  10                  15 gac gcc gcc agg ttg ccc cgc gct cgg cgc aat gcg gtc tcc aaa cgg      96
Asp Ala Ala Arg Leu Pro Arg Ala Arg Arg Asn Ala Val Ser Lys Arg
             20                  25                  30 agg gat cct ctt cag ccg gtc ggc cgg tac ggc tcc gcg acg gga aac     144
Arg Asp Pro Leu Gln Pro Val Gly Arg Tyr Gly Ser Ala Thr Gly Asn
         35                  40                  45 acg gcc agg acc ggc gcc gcg tcc tgc cag aac gcc gca ttg gcg gac     192
Thr Ala Arg Thr Gly Ala Ala Ser Cys Gln Asn Ala Ala Leu Ala Asp
     50                  55                  60 gtt gag atc gtt gag atc aag tcc atc gtc gcc gcg ccg ccg acg agc     240
Val Glu Ile Val Glu Ile Lys Ser Ile Val Ala Ala Pro Pro Thr Ser
 65                  70                  75                  80 ata gtg aag ttc cca ggg cgc ggg cta cag gat gat cct tcc ctc tgg     288
Ile Val Lys Phe Pro Gly Arg Gly Leu Gln Asp Asp Pro Ser Leu Trp
                 85                  90                  95 gac ata gca ccg gag act gtc ctc cca gcc ccg aag cca ctg cat gaa     336
Asp Ile Ala Pro Glu Thr Val Leu Pro Ala Pro Lys Pro Leu His Glu
            100                 105                 110 tcg cct gcg gtt gac gga gat tca aat gga att gca cct cct aca gtt     384
Ser Pro Ala Val Asp Gly Asp Ser Asn Gly Ile Ala Pro Pro Thr Val
        115                 120                 125 gag cca tta gta cag gag gcc act tgg gat ttc aag aaa tac atc ggt     432
Glu Pro Leu Val Gln Glu Ala Thr Trp Asp Phe Lys Lys Tyr Ile Gly
    130                 135                 140 ttt gac gag cct gac gaa gcg aag gat gat tcc agg gtt ggt gca gat     480
Phe Asp Glu Pro Asp Glu Ala Lys Asp Asp Ser Arg Val Gly Ala Asp
145                 150                 155                 160 gat gct ggt tct ttt gaa cat tat ggg aca atg att ctg ggc ctt tgt     528
Asp Ala Gly Ser Phe Glu His Tyr Gly Thr Met Ile Leu Gly Leu Cys
                165                 170                 175 ggg gag aat gtt atg aac gtg atc gtg gtg gct gct gaa tgt tct cca     576
Gly Glu Asn Val Met Asn Val Ile Val Val Ala Ala Glu Cys Ser Pro
            180                 185                 190 tgg tgc aaa aca ggt ggt ctt gga gat gtt gtg gga gct tta ccc aag     624
Trp Cys Lys Thr Gly Gly Leu Gly Asp Val Val Gly Ala Leu Pro Lys
        195                 200                 205 gct tta gcg aga aga gga cat cgt gtt atg gtt gtg gta cca agg tat     672
Ala Leu Ala Arg Arg Gly His Arg Val Met Val Val Pro Arg Tyr
    210                 215                 220
```

-continued

| | | |
|---|---|---|
| ggg gac tat gtg gaa gcc ttt gat atg gga atc cgg aaa tac tac aaa<br>Gly Asp Tyr Val Glu Ala Phe Asp Met Gly Ile Arg Lys Tyr Tyr Lys<br>225                      230                            235                      240 | 720 |
| gct gca gga cag gac cta gaa gtg aac tat ttc cat gca ttt att gat<br>Ala Ala Gly Gln Asp Leu Glu Val Asn Tyr Phe His Ala Phe Ile Asp<br>                        245                            250                        255 | 768 |
| gga gtc gac ttt gtg ttc att gat gcc tct ttc cgg cac cgt caa gat<br>Gly Val Asp Phe Val Phe Ile Asp Ala Ser Phe Arg His Arg Gln Asp<br>              260                          265                          270 | 816 |
| gac ata tat ggg gga agt agg cag gaa atc atg aag cgc atg att ttg<br>Asp Ile Tyr Gly Gly Ser Arg Gln Glu Ile Met Lys Arg Met Ile Leu<br>                  275                          280                        285 | 864 |
| ttt tgc aag gtt gct gtt gag gtt cct tgg cac gtt cca tgc ggt ggt<br>Phe Cys Lys Val Ala Val Glu Val Pro Trp His Val Pro Cys Gly Gly<br>290                      295                            300 | 912 |
| gtg tgc tac gga gat gga aat ttg gtg ttc att gcc atg aat tgg cac<br>Val Cys Tyr Gly Asp Gly Asn Leu Val Phe Ile Ala Met Asn Trp His<br>305                      310                            315                      320 | 960 |
| act gca ctc ctg cct gtt tat ctg aag gca tat tac aga gac cat ggg<br>Thr Ala Leu Leu Pro Val Tyr Leu Lys Ala Tyr Tyr Arg Asp His Gly<br>                            325                            330                        335 | 1008 |
| tta atg cag tac act cgc tcc gtc ctc gtc ata cat aac atc ggc cac<br>Leu Met Gln Tyr Thr Arg Ser Val Leu Val Ile His Asn Ile Gly His<br>                        340                            345                        350 | 1056 |
| cag ggc cgt ggt cct gta cat gaa ttc ccg tac atg gac ttg ctg aac<br>Gln Gly Arg Gly Pro Val His Glu Phe Pro Tyr Met Asp Leu Leu Asn<br>              355                          360                          365 | 1104 |
| act aac ctt caa cat ttc gag ctg tac gat ccc gtc ggt ggc gag cac<br>Thr Asn Leu Gln His Phe Glu Leu Tyr Asp Pro Val Gly Gly Glu His<br>370                      375                            380 | 1152 |
| gcc aac atc ttt gcc gcg tgt gtt ctg aag atg gca gac cgg gtg gtg<br>Ala Asn Ile Phe Ala Ala Cys Val Leu Lys Met Ala Asp Arg Val Val<br>385                      390                            395                      400 | 1200 |
| act gtc agc cgc ggc tac ctg tgg gag ctg aag aca gtg gaa ggc ggc<br>Thr Val Ser Arg Gly Tyr Leu Trp Glu Leu Lys Thr Val Glu Gly Gly<br>                        405                            410                        415 | 1248 |
| tgg ggc ctc cac gac atc atc cgt tct aac gac tgg aag atc aat ggc<br>Trp Gly Leu His Asp Ile Ile Arg Ser Asn Asp Trp Lys Ile Asn Gly<br>                  420                          425                        430 | 1296 |
| att cgt gaa cgc atc gac cac cag gag tgg aac ccc aag gtg gac gtg<br>Ile Arg Glu Arg Ile Asp His Gln Glu Trp Asn Pro Lys Val Asp Val<br>              435                          440                          445 | 1344 |
| cac ctg cgg tcg gac ggc tac acc aac tac tcc ctc gag aca ctc gac<br>His Leu Arg Ser Asp Gly Tyr Thr Asn Tyr Ser Leu Glu Thr Leu Asp<br>450                      455                            460 | 1392 |
| gct gga aag cgg cag tgc aag gcg gcc ctg cag cgg gac gtg ggc ctg<br>Ala Gly Lys Arg Gln Cys Lys Ala Ala Leu Gln Arg Asp Val Gly Leu<br>465                      470                            475                      480 | 1440 |
| gaa gtg cgc gac gac gtg ccg ctg ctc ggc ttc atc ggg cgt ctg gat<br>Glu Val Arg Asp Asp Val Pro Leu Leu Gly Phe Ile Gly Arg Leu Asp<br>                        485                            490                        495 | 1488 |
| gga cag aag ggc gtg gac atc atc ggg gac gcg atg ccg tgg atc gcg<br>Gly Gln Lys Gly Val Asp Ile Ile Gly Asp Ala Met Pro Trp Ile Ala<br>                        500                            505                        510 | 1536 |
| ggg cag gac gtg cag ctg gtg atg ctg ggc acc ggc cca cct gac ctg<br>Gly Gln Asp Val Gln Leu Val Met Leu Gly Thr Gly Pro Pro Asp Leu<br>                  515                          520                        525 | 1584 |
| gaa cga atg ctg cag cac ttg gag cgg gag cat ccc aac aag gtg cgc<br>Glu Arg Met Leu Gln His Leu Glu Arg Glu His Pro Asn Lys Val Arg<br>530                      535                            540 | 1632 |

```
ggg tgg gtc ggg ttc tcg gtc cta atg gtg cat cgc atc acg ccg ggc      1680
Gly Trp Val Gly Phe Ser Val Leu Met Val His Arg Ile Thr Pro Gly
545                 550                 555                 560 gcc agc gtg ctg gtg atg ccc tcc cgc ttc gcc ggc ggg ctg aac cag      1728
Ala Ser Val Leu Val Met Pro Ser Arg Phe Ala Gly Gly Leu Asn Gln
                565                 570                 575 ctc tac gcg atg gca tac ggc acc gtc cct gtg gtg cac gcc gtg ggc      1776
Leu Tyr Ala Met Ala Tyr Gly Thr Val Pro Val Val His Ala Val Gly
            580                 585                 590 ggg ctc agg gac acc gtg gcg ccg ttc gac ccg ttc ggc gac gcc ggg      1824
Gly Leu Arg Asp Thr Val Ala Pro Phe Asp Pro Phe Gly Asp Ala Gly
        595                 600                 605 ctc ggg tgg act ttt gac cgc gcc gag gcc aac aag ctg atc gag gtg      1872
Leu Gly Trp Thr Phe Asp Arg Ala Glu Ala Asn Lys Leu Ile Glu Val
    610                 615                 620 ctc agc cac tgc ctc gac acg tac cga aac tac gag gag agc tgg aag      1920
Leu Ser His Cys Leu Asp Thr Tyr Arg Asn Tyr Glu Glu Ser Trp Lys
625                 630                 635                 640 agt ctc cag gcg cgc ggc atg tcg cag aac ctc agc tgg gac cac gcg      1968
Ser Leu Gln Ala Arg Gly Met Ser Gln Asn Leu Ser Trp Asp His Ala
                645                 650                 655 gct gag ctc tac gag gac gtc ctt gtc aag tac cag tgg                  2007
Ala Glu Leu Tyr Glu Asp Val Leu Val Lys Tyr Gln Trp
            660                 665

<210> SEQ ID NO 55
<211> LENGTH: 669
<212> TYPE: PRT
<213> ORGANISM: Zea mays

<400> SEQUENCE: 55

Ala Glu Ala Glu Ala Gly Gly Lys Asp Ala Pro Pro Glu Arg Ser Gly
1               5                   10                  15

Asp Ala Ala Arg Leu Pro Arg Ala Arg Asn Ala Val Ser Lys Arg
            20                  25                  30

Arg Asp Pro Leu Gln Pro Val Gly Arg Tyr Gly Ser Ala Thr Gly Asn
        35                  40                  45

Thr Ala Arg Thr Gly Ala Ala Ser Cys Gln Asn Ala Ala Leu Ala Asp
    50                  55                  60

Val Glu Ile Val Glu Ile Lys Ser Ile Val Ala Ala Pro Thr Ser
65              70                  75                  80

Ile Val Lys Phe Pro Gly Arg Gly Leu Gln Asp Asp Pro Ser Leu Trp
                85                  90                  95

Asp Ile Ala Pro Glu Thr Val Leu Pro Ala Pro Lys Pro Leu His Glu
            100                 105                 110

Ser Pro Ala Val Asp Gly Asp Ser Asn Gly Ile Ala Pro Thr Val
        115                 120                 125

Glu Pro Leu Val Gln Glu Ala Thr Trp Asp Phe Lys Lys Tyr Ile Gly
    130                 135                 140

Phe Asp Glu Pro Asp Glu Ala Lys Asp Ser Arg Val Gly Ala Asp
145                 150                 155                 160

Asp Ala Gly Ser Phe Glu His Tyr Gly Thr Met Ile Leu Gly Leu Cys
                165                 170                 175

Gly Glu Asn Val Met Asn Val Ile Val Ala Ala Glu Cys Ser Pro
            180                 185                 190

Trp Cys Lys Thr Gly Gly Leu Gly Asp Val Val Gly Ala Leu Pro Lys
        195                 200                 205
```

```
Ala Leu Ala Arg Arg Gly His Arg Val Met Val Val Pro Arg Tyr
    210                 215                 220

Gly Asp Tyr Val Glu Ala Phe Asp Met Gly Ile Arg Lys Tyr Lys
225                 230                 235                 240

Ala Ala Gly Gln Asp Leu Glu Val Asn Tyr Phe His Ala Phe Ile Asp
                245                 250                 255

Gly Val Asp Phe Val Phe Ile Asp Ala Ser Phe Arg His Arg Gln Asp
            260                 265                 270

Asp Ile Tyr Gly Gly Ser Arg Gln Glu Ile Met Lys Arg Met Ile Leu
        275                 280                 285

Phe Cys Lys Val Ala Val Glu Val Pro Trp His Val Pro Cys Gly Gly
    290                 295                 300

Val Cys Tyr Gly Asp Gly Asn Leu Val Phe Ile Ala Met Asn Trp His
305                 310                 315                 320

Thr Ala Leu Leu Pro Val Tyr Leu Lys Ala Tyr Tyr Arg Asp His Gly
                325                 330                 335

Leu Met Gln Tyr Thr Arg Ser Val Leu Val Ile His Asn Ile Gly His
            340                 345                 350

Gln Gly Arg Gly Pro Val His Glu Phe Pro Tyr Met Asp Leu Leu Asn
        355                 360                 365

Thr Asn Leu Gln His Phe Glu Leu Tyr Asp Pro Val Gly Gly Glu His
    370                 375                 380

Ala Asn Ile Phe Ala Ala Cys Val Leu Lys Met Ala Asp Arg Val Val
385                 390                 395                 400

Thr Val Ser Arg Gly Tyr Leu Trp Glu Leu Lys Thr Val Glu Gly Gly
                405                 410                 415

Trp Gly Leu His Asp Ile Ile Arg Ser Asn Asp Trp Lys Ile Asn Gly
            420                 425                 430

Ile Arg Glu Arg Ile Asp His Gln Glu Trp Asn Pro Lys Val Asp Val
        435                 440                 445

His Leu Arg Ser Asp Gly Tyr Thr Asn Tyr Ser Leu Glu Thr Leu Asp
    450                 455                 460

Ala Gly Lys Arg Gln Cys Lys Ala Ala Leu Gln Arg Asp Val Gly Leu
465                 470                 475                 480

Glu Val Arg Asp Asp Val Pro Leu Leu Gly Phe Ile Gly Arg Leu Asp
                485                 490                 495

Gly Gln Lys Gly Val Asp Ile Ile Gly Asp Ala Met Pro Trp Ile Ala
            500                 505                 510

Gly Gln Asp Val Gln Leu Val Met Leu Gly Thr Gly Pro Pro Asp Leu
        515                 520                 525

Glu Arg Met Leu Gln His Leu Glu Arg Glu His Pro Asn Lys Val Arg
    530                 535                 540

Gly Trp Val Gly Phe Ser Val Leu Met Val His Arg Ile Thr Pro Gly
545                 550                 555                 560

Ala Ser Val Leu Val Met Pro Ser Arg Phe Ala Gly Gly Leu Asn Gln
                565                 570                 575

Leu Tyr Ala Met Ala Tyr Gly Thr Val Pro Val Val His Ala Val Gly
            580                 585                 590

Gly Leu Arg Asp Thr Val Ala Pro Phe Asp Pro Phe Gly Asp Ala Gly
        595                 600                 605

Leu Gly Trp Thr Phe Asp Arg Ala Glu Ala Asn Lys Leu Ile Glu Val
    610                 615                 620
```

```
Leu Ser His Cys Leu Asp Thr Tyr Arg Asn Tyr Glu Glu Ser Trp Lys
625                 630                 635                 640

Ser Leu Gln Ala Arg Gly Met Ser Gln Asn Leu Ser Trp Asp His Ala
                645                 650                 655

Ala Glu Leu Tyr Glu Asp Val Leu Val Lys Tyr Gln Trp
            660                 665

<210> SEQ ID NO 56
<211> LENGTH: 1749
<212> TYPE: DNA
<213> ORGANISM: Zea mays
<220> FEATURE:
<221> NAME/KEY: CDS
<222> LOCATION: (1)..(1749)

<400> SEQUENCE: 56 tgc gtc gcg gag ctg agc agg gag ggg ccc gcg ccg cgc ccg ctg cca      48
Cys Val Ala Glu Leu Ser Arg Glu Gly Pro Ala Pro Arg Pro Leu Pro
 1               5                  10                  15 ccc gcg ctg ctg gcg ccc ccg ctc gtg ccc ggc ttc ctc gcg ccg ccg      96
Pro Ala Leu Leu Ala Pro Pro Leu Val Pro Gly Phe Leu Ala Pro Pro
            20                  25                  30 cc gag ccc acg ggt gag ccg gca tcg acg ccg ccg ccc gtg ccc gac      144
Ala Glu Pro Thr Gly Glu Pro Ala Ser Thr Pro Pro Pro Val Pro Asp
        35                  40                  45 cc ggc ctg ggg gac ctc ggt ctc gaa cct gaa ggg att gct gaa ggt      192
Ala Gly Leu Gly Asp Leu Gly Leu Glu Pro Glu Gly Ile Ala Glu Gly
    50                  55                  60 cc atc gat aac aca gta gtt gtg gca agt gag caa gat tct gag att      240
Ser Ile Asp Asn Thr Val Val Val Ala Ser Glu Gln Asp Ser Glu Ile
65                  70                  75                  80 tg gtt gga aag gag caa gct cga gct aaa gta aca caa agc att gtc      288
Val Val Gly Lys Glu Gln Ala Arg Ala Lys Val Thr Gln Ser Ile Val
                85                  90                  95 tt gta acc ggc gaa gct tct cct tat gca aag tct ggg ggt cta gga      336
Phe Val Thr Gly Glu Ala Ser Pro Tyr Ala Lys Ser Gly Gly Leu Gly
            100                 105                 110 at gtt tgt ggt tca ttg cca gtt gct ctt gct gct cgt ggt cac cgt      384
Asp Val Cys Gly Ser Leu Pro Val Ala Leu Ala Ala Arg Gly His Arg
        115                 120                 125 tg atg gtt gta atg ccc aga tat tta aat ggt acc tcc gat aag aat      432
Val Met Val Val Met Pro Arg Tyr Leu Asn Gly Thr Ser Asp Lys Asn
    130                 135                 140 at gca aat gca ttt tac aca gaa aaa cac att cgg att cca tgc ttt      480
Tyr Ala Asn Ala Phe Tyr Thr Glu Lys His Ile Arg Ile Pro Cys Phe
145                 150                 155                 160 gc ggt gaa cat gaa gtt acc ttc ttc cat gag tat aga gat tca gtt      528
Gly Gly Glu His Glu Val Thr Phe Phe His Glu Tyr Arg Asp Ser Val
                165                 170                 175 ac tgg gtg ttt gtt gat cat ccc tca tat cac aga cct gga aat tta      576
Asp Trp Val Phe Val Asp His Pro Ser Tyr His Arg Pro Gly Asn Leu
            180                 185                 190 at gga gat aag ttt ggt gct ttt ggt gat aat cag ttc aga tac aca      624
Tyr Gly Asp Lys Phe Gly Ala Phe Gly Asp Asn Gln Phe Arg Tyr Thr
        195                 200                 205 tc ctt tgc tat gct gca tgt gag gct cct ttg atc ctt gaa ttg gga      672
Leu Leu Cys Tyr Ala Ala Cys Glu Ala Pro Leu Ile Leu Glu Leu Gly
    210                 215                 220 ga tat att tat gga cag aat tgc atg ttt gtt gtc aat gat tgg cat      720
Gly Tyr Ile Tyr Gly Gln Asn Cys Met Phe Val Val Asn Asp Trp His
225                 230                 235                 240
```

```
cc agt cta gtg cca gtc ctt ctt gct gca aaa tat aga cca tat ggt    768
Ala Ser Leu Val Pro Val Leu Leu Ala Ala Lys Tyr Arg Pro Tyr Gly
            245                 250                 255 tt tat aaa gac tcc cgc agc att ctt gta ata cat aat tta gca cat    816
Val Tyr Lys Asp Ser Arg Ser Ile Leu Val Ile His Asn Leu Ala His
        260                 265                 270 ag ggt gta gag cct gca agc aca tat cct gac ctt ggg ttg cca cct    864
Gln Gly Val Glu Pro Ala Ser Thr Tyr Pro Asp Leu Gly Leu Pro Pro
            275                 280                 285 aa tgg tat gga gct ctg gag tgg gta ttc cct gaa tgg gcg agg agg    912
Glu Trp Tyr Gly Ala Leu Glu Trp Val Phe Pro Glu Trp Ala Arg Arg
        290                 295                 300 at gcc ctt gac aag ggt gag gca gtt aat ttt ttg aaa ggt gca gtt    960
His Ala Leu Asp Lys Gly Glu Ala Val Asn Phe Leu Lys Gly Ala Val
305                 310                 315                 320 gtg aca gca gat cga atc gtg act gtc agt aag ggt tat tcg tgg gag  1008
Val Thr Ala Asp Arg Ile Val Thr Val Ser Lys Gly Tyr Ser Trp Glu
            325                 330                 335 gtc aca act gct gaa ggt gga cag ggc ctc aat gag ctc tta agc tcc  1056
Val Thr Thr Ala Glu Gly Gly Gln Gly Leu Asn Glu Leu Leu Ser Ser
        340                 345                 350 aga aag agt gta tta aac gga att gta aat gga att gac att aat gat  1104
Arg Lys Ser Val Leu Asn Gly Ile Val Asn Gly Ile Asp Ile Asn Asp
            355                 360                 365 tgg aac cct gcc aca gac aaa tgt atc ccc tgt cat tat tct gtt gat  1152
Trp Asn Pro Ala Thr Asp Lys Cys Ile Pro Cys His Tyr Ser Val Asp
        370                 375                 380 gac ctc tct gga aag gcc aaa tgt aaa ggt gca ttg cag aag gag ctg  1200
Asp Leu Ser Gly Lys Ala Lys Cys Lys Gly Ala Leu Gln Lys Glu Leu
385                 390                 395                 400 ggt tta cct ata agg cct gat gtt cct ctg att ggc ttt att gga agg  1248
Gly Leu Pro Ile Arg Pro Asp Val Pro Leu Ile Gly Phe Ile Gly Arg
            405                 410                 415 ttg gat tat cag aaa ggc att gat ctc att caa ctt atc ata cca gat  1296
Leu Asp Tyr Gln Lys Gly Ile Asp Leu Ile Gln Leu Ile Ile Pro Asp
        420                 425                 430 ctc atg cgg gaa gat gtt caa ttt gtc atg ctt gga tct ggt gac cca  1344
Leu Met Arg Glu Asp Val Gln Phe Val Met Leu Gly Ser Gly Asp Pro
            435                 440                 445 gag ctt gaa gat tgg atg aga tct aca gag tcg atc ttc aag gat aaa  1392
Glu Leu Glu Asp Trp Met Arg Ser Thr Glu Ser Ile Phe Lys Asp Lys
450                 455                 460 ttt cgt gga tgg gtt gga ttt agt gtt cca gtt tcc cac cga ata act  1440
Phe Arg Gly Trp Val Gly Phe Ser Val Pro Val Ser His Arg Ile Thr
465                 470                 475                 480 gcc ggc tgc gat ata ttg tta atg cca tcc aga ttc gaa cct tgt ggt  1488
Ala Gly Cys Asp Ile Leu Leu Met Pro Ser Arg Phe Glu Pro Cys Gly
            485                 490                 495 ctc aat cag cta tat gct atg cag tat ggc aca gtt cct gtt gtc cat  1536
Leu Asn Gln Leu Tyr Ala Met Gln Tyr Gly Thr Val Pro Val Val His
        500                 505                 510 gca act ggg ggc ctt aga gat acc gtg gag aac ttc aac cct ttc ggt  1584
Ala Thr Gly Gly Leu Arg Asp Thr Val Glu Asn Phe Asn Pro Phe Gly
            515                 520                 525 gag aat gga gag cag ggt aca ggg tgg gca ttc gca ccc cta acc aca  1632
Glu Asn Gly Glu Gln Gly Thr Gly Trp Ala Phe Ala Pro Leu Thr Thr
530                 535                 540 gaa aac atg ttt gtg gac att gcg aac tgc aat atc tac ata cag gga  1680
Glu Asn Met Phe Val Asp Ile Ala Asn Cys Asn Ile Tyr Ile Gln Gly
```

```
                545                 550                 555                 560
aca caa gtc ctc ctg gga agg gct aat gaa gcg agg cat gtc aaa aga                1728
Thr Gln Val Leu Leu Gly Arg Ala Asn Glu Ala Arg His Val Lys Arg
                565                 570                 575 ctt cac gtg gga cca tgc cgc                                                    1749
Leu His Val Gly Pro Cys Arg
                580
```

<210> SEQ ID NO 57
<211> LENGTH: 583
<212> TYPE: PRT
<213> ORGANISM: Zea mays

<400> SEQUENCE: 57

```
Cys Val Ala Glu Leu Ser Arg Glu Gly Pro Ala Pro Arg Pro Leu Pro
 1               5                  10                  15

Pro Ala Leu Leu Ala Pro Pro Leu Val Pro Gly Phe Leu Ala Pro Pro
            20                  25                  30

Ala Glu Pro Thr Gly Glu Pro Ala Ser Thr Pro Pro Val Pro Asp
        35                  40                  45

Ala Gly Leu Gly Asp Leu Gly Leu Glu Pro Glu Gly Ile Ala Glu Gly
    50                  55                  60

Ser Ile Asp Asn Thr Val Val Ala Ser Glu Gln Asp Ser Glu Ile
65                  70                  75                  80

Val Val Gly Lys Glu Gln Ala Arg Ala Lys Val Thr Gln Ser Ile Val
                85                  90                  95

Phe Val Thr Gly Glu Ala Ser Pro Tyr Ala Lys Ser Gly Gly Leu Gly
            100                 105                 110

Asp Val Cys Gly Ser Leu Pro Val Ala Leu Ala Ala Arg Gly His Arg
        115                 120                 125

Val Met Val Val Met Pro Arg Tyr Leu Asn Gly Thr Ser Asp Lys Asn
    130                 135                 140

Tyr Ala Asn Ala Phe Tyr Thr Glu Lys His Ile Arg Ile Pro Cys Phe
145                 150                 155                 160

Gly Gly Glu His Glu Val Thr Phe Phe His Glu Tyr Arg Asp Ser Val
                165                 170                 175

Asp Trp Val Phe Val Asp His Pro Ser Tyr His Arg Pro Gly Asn Leu
            180                 185                 190

Tyr Gly Asp Lys Phe Gly Ala Phe Gly Asp Asn Gln Phe Arg Tyr Thr
        195                 200                 205

Leu Leu Cys Tyr Ala Ala Cys Glu Ala Pro Leu Ile Leu Glu Leu Gly
    210                 215                 220

Gly Tyr Ile Tyr Gly Gln Asn Cys Met Phe Val Val Asn Asp Trp His
225                 230                 235                 240

Ala Ser Leu Val Pro Val Leu Leu Ala Lys Tyr Arg Pro Tyr Gly
                245                 250                 255

Val Tyr Lys Asp Ser Arg Ser Ile Leu Val Ile His Asn Leu Ala His
            260                 265                 270

Gln Gly Val Glu Pro Ala Ser Thr Tyr Pro Asp Leu Gly Leu Pro Pro
        275                 280                 285

Glu Trp Tyr Gly Ala Leu Glu Trp Val Phe Pro Glu Trp Ala Arg Arg
    290                 295                 300

His Ala Leu Asp Lys Gly Glu Ala Val Asn Phe Leu Lys Gly Ala Val
305                 310                 315                 320

Val Thr Ala Asp Arg Ile Val Thr Val Ser Lys Gly Tyr Ser Trp Glu
```

```
                325                 330                 335
Val Thr Thr Ala Glu Gly Gly Gln Gly Leu Asn Glu Leu Leu Ser Ser
            340                 345                 350

Arg Lys Ser Val Leu Asn Gly Ile Val Asn Gly Ile Asp Ile Asn Asp
            355                 360                 365

Trp Asn Pro Ala Thr Asp Lys Cys Ile Pro Cys His Tyr Ser Val Asp
            370                 375             380

Asp Leu Ser Gly Lys Ala Lys Cys Lys Gly Ala Leu Gln Lys Glu Leu
385                 390                 395                 400

Gly Leu Pro Ile Arg Pro Asp Val Pro Leu Ile Gly Phe Ile Gly Arg
                405                 410             415

Leu Asp Tyr Gln Lys Gly Ile Asp Leu Ile Gln Leu Ile Ile Pro Asp
            420                 425                 430

Leu Met Arg Glu Asp Val Gln Phe Val Met Leu Gly Ser Gly Asp Pro
            435                 440             445

Glu Leu Glu Asp Trp Met Arg Ser Thr Glu Ser Ile Phe Lys Asp Lys
            450                 455             460

Phe Arg Gly Trp Val Gly Phe Ser Val Pro Val Ser His Arg Ile Thr
465                 470                 475                 480

Ala Gly Cys Asp Ile Leu Leu Met Pro Ser Arg Phe Glu Pro Cys Gly
                485                 490                 495

Leu Asn Gln Leu Tyr Ala Met Gln Tyr Gly Thr Val Pro Val Val His
            500                 505                 510

Ala Thr Gly Gly Leu Arg Asp Thr Val Glu Asn Phe Asn Pro Phe Gly
            515                 520             525

Glu Asn Gly Glu Gln Gly Thr Gly Trp Ala Phe Ala Pro Leu Thr Thr
            530                 535             540

Glu Asn Met Phe Val Asp Ile Ala Asn Cys Asn Ile Tyr Ile Gln Gly
545                 550                 555                 560

Thr Gln Val Leu Leu Gly Arg Ala Asn Glu Ala Arg His Val Lys Arg
                565                 570                 575

Leu His Val Gly Pro Cys Arg
            580

<210> SEQ ID NO 58
<211> LENGTH: 2640
<212> TYPE: DNA
<213> ORGANISM: Zea mays

<400> SEQUENCE: 58
gcgagatggc gttccgggtt tctggggcgg tgctcggtgg ggccgtaagg gctccccgac    60
tcaccggcgg cggggagggt agtctagtct tccggcacac cggcctcttc ttaactcggg   120
gtgctcgagt tggatgttcg gggacgcacg gggccatgcg cgcggcggcc gcggccagga   180
aggcggtcat ggttcctgag gcgagaatg atggcctcgc atcaagggct gactcggctc   240
aattccagtc ggatgaactg gaggtaccag acatttctga agagacaacg tgcggtgctg   300
gtgtggctga tgctcaagcc ttgaacagag ttcgagtggt ccccccacca agcgatggac   360
aaaaaatatt ccagattgac cccatgttgc aaggctataa gtaccatctt gagtatcggt   420
acagcctcta tagaagaatc cgttcagaca ttgatgaaca tgaaggaggc ttggaagcct   480
tctcccgtag ttatgagaag tttggattta atgccagcgc ggaaggtatc acatatcgag   540
aatgggctcc tggagcattt tctgcagcat tggtgggtga cgtcaacaac tgggatccaa   600
atgcagatcg tatgagcaaa aatgagtttg gtgtttggga aatttttctg cctaacaatg   660
```

```
cagatggtac atcacctatt cctcatggat ctcgtgtaaa ggtgagaatg gatactccat    720
cagggataaa ggattcaatt ccagcctgga tcaagtactc agtgcaggcc ccaggagaaa    780
taccatatga tgggatttat tatgatcctc ctgaagaggt aaagtatgtg ttcaggcatg    840
cgcaacctaa acgaccaaaa tcattgcgga tatatgaaac acatgtcgga atgagtagcc    900
cggaaccgaa gataaacaca tatgtaaact ttagggatga agtcctccca agaataaaaa    960
aacttggata caatgcagtg caaataatgg caatccaaga gcactcatat tatggaagct   1020
ttggatacca tgtaactaat tttttttgcgc caagtagtcg ttttggtacc ccagaagatt   1080
tgaagtcttt gattgataga gcacatgagc ttggtttgct agttctcatg gatgtggttc   1140
atagtcatgc gtcaagtaat actctggatg ggttgaatgg ttttgatggt acagatacac   1200
attactttca cagtggtcca cgtggccatc actggatgtg ggattctcgc ctatttaact   1260
atgggaactg ggaagtttta agatttcttc tctccaatgc tagatggtgg ctcgaggaat   1320
ataagtttga tggtttccgt tttgatggtg tgacctccat gatgtacact caccacggat   1380
tacaagtaac atttacgggg aacttcaatg agtattttgg ctttgccacc gatgtagatg   1440
cagtggttta cttgatgctg gtaaatgatc taattcatgg actttatcct gaggctgtaa   1500
ccattggtga gatgttagt ggaatgccta catttgccct tcctgttcac gatggtgggg    1560
taggttttga ctatcggatg catatggctg tggctgacaa atggattgac cttctcaagc   1620
aaagtgatga aacttggaag atgggtgata ttgtgcacac actgacaaat aggaggtggt   1680
tagagaagtg tgtaacttat gctgaaagtc atgatcaagc attagtcggc gacaagacta   1740
ttgcgttttg gttgatggac aaggatatgt atgatttcat ggccctcgat agaccttcaa   1800
ctcctaccat tgatcgtggg atagcattac ataagatgat tagacttatc acaatgggtt   1860
taggaggaga gggctatctt aatttcatgg gaaatgagtt tggacatcct gaatggatag   1920 atttttccaag aggtccgcaa agacttccaa gtggtaagtt tattccaggg aataacaaca   1980
gttatgacaa atgtcgtcga agatttgacc tgggtgatgc agactatctt aggtatcatg   2040
gtatgcaaga gtttgatcag gcaatgcaac atcttgagca aaaatatgaa ttcatgacat   2100
ctgatcacca gtatatttcc cggaaacatg aggaggataa ggtgattgtg ttcgaaaagg   2160
gagatttggt atttgtgttc aacttccact gcaacaacag ctattttgac taccgtattg   2220
gttgtcgaaa gcctggggtg tataaggtgg tcttggactc cgacgctgga ctatttggtg   2280
gatttagcag gatccatcac gcagccgagc acttcaccgc cgactgttcg catgataata   2340
ggccatattc attctcggtt tatacaccaa gcagaacatg tgtcgtctat gctccagtgg   2400
agtgatagcg gggtactcgt tgctgcgcgg catgtgtggg gctgtcgatg tgaggaaaaa   2460
ccttcttcca aaaccggcag atgcatgcat gcatgctaca ataaggttct gatactttaa   2520
tcgatgctgg aaagcccatg catctcgctg cgttgtcctc tctatttata taagaccttc   2580
aaggtgtcaa ttaaacatag agttttcgtt tttcgcttaa aaaaaaaaaa aaaaaactca   2640
```

<210> SEQ ID NO 59
<211> LENGTH: 799
<212> TYPE: PRT
<213> ORGANISM: Zea mays

<400> SEQUENCE: 59

```
Met Ala Phe Arg Val Ser Gly Ala Val Leu Gly Gly Ala Val Arg Ala
 1               5                   10                  15

Pro Arg Leu Thr Gly Gly Gly Glu Gly Ser Leu Val Phe Arg His Thr
```

-continued

```
                    20                  25                  30
Gly Leu Phe Leu Thr Arg Gly Ala Arg Val Gly Cys Ser Gly Thr His
            35                  40                  45
Gly Ala Met Arg Ala Ala Ala Ala Arg Lys Ala Val Met Val Pro
        50                  55                  60
Glu Gly Glu Asn Asp Gly Leu Ala Ser Arg Ala Asp Ser Ala Gln Phe
65                  70                  75                  80
Gln Ser Asp Glu Leu Glu Val Pro Asp Ile Ser Glu Thr Thr Cys
                85                  90                  95
Gly Ala Gly Val Ala Asp Ala Gln Ala Leu Asn Arg Val Arg Val Val
                100                 105                 110
Pro Pro Pro Ser Asp Gly Gln Lys Ile Phe Gln Ile Asp Pro Met Leu
            115                 120                 125
Gln Gly Tyr Lys Tyr His Leu Glu Tyr Arg Tyr Ser Leu Tyr Arg Arg
        130                 135                 140
Ile Arg Ser Asp Ile Asp Glu His Glu Gly Leu Glu Ala Phe Ser
145                 150                 155                 160
Arg Ser Tyr Glu Lys Phe Gly Phe Asn Ala Ser Ala Glu Gly Ile Thr
                165                 170                 175
Tyr Arg Glu Trp Ala Pro Gly Ala Phe Ser Ala Leu Val Gly Asp
            180                 185                 190
Val Asn Asn Trp Asp Pro Asn Ala Asp Arg Met Ser Lys Asn Glu Phe
        195                 200                 205
Gly Val Trp Glu Ile Phe Leu Pro Asn Ala Asp Gly Thr Ser Pro
        210                 215                 220
Ile Pro His Gly Ser Arg Val Lys Val Arg Met Asp Thr Pro Ser Gly
225                 230                 235                 240
Ile Lys Asp Ser Ile Pro Ala Trp Ile Lys Tyr Ser Val Gln Ala Pro
                245                 250                 255
Gly Glu Ile Pro Tyr Asp Gly Ile Tyr Tyr Asp Pro Pro Glu Val
            260                 265                 270
Lys Tyr Val Phe Arg His Ala Gln Pro Lys Arg Pro Lys Ser Leu Arg
        275                 280                 285
Ile Tyr Glu Thr His Val Gly Met Ser Ser Pro Glu Pro Lys Ile Asn
        290                 295                 300
Thr Tyr Val Asn Phe Arg Asp Glu Val Leu Pro Arg Ile Lys Lys Leu
305                 310                 315                 320
Gly Tyr Asn Ala Val Gln Ile Met Ala Ile Gln Glu His Ser Tyr Tyr
                325                 330                 335
Gly Ser Phe Gly Tyr His Val Thr Asn Phe Phe Ala Pro Ser Ser Arg
            340                 345                 350
Phe Gly Thr Pro Glu Asp Leu Lys Ser Leu Ile Asp Arg Ala His Glu
        355                 360                 365
Leu Gly Leu Leu Val Leu Met Asp Val Val His Ser His Ala Ser Ser
        370                 375                 380
Asn Thr Leu Asp Gly Leu Asn Gly Phe Asp Gly Thr Asp Thr His Tyr
385                 390                 395                 400
Phe His Ser Gly Pro Arg Gly His His Trp Met Trp Asp Ser Arg Leu
                405                 410                 415
Phe Asn Tyr Gly Asn Trp Glu Val Leu Arg Phe Leu Leu Ser Asn Ala
            420                 425                 430
Arg Trp Trp Leu Glu Glu Tyr Lys Phe Asp Gly Phe Arg Phe Asp Gly
        435                 440                 445
```

Val Thr Ser Met Met Tyr Thr His His Gly Leu Gln Val Thr Phe Thr
450                 455                 460

Gly Asn Phe Asn Glu Tyr Phe Gly Phe Ala Thr Asp Val Asp Ala Val
465                 470                 475                 480

Val Tyr Leu Met Leu Val Asn Asp Leu Ile His Gly Leu Tyr Pro Glu
                485                 490                 495

Ala Val Thr Ile Gly Glu Asp Val Ser Gly Met Pro Thr Phe Ala Leu
            500                 505                 510

Pro Val His Asp Gly Val Gly Phe Asp Tyr Arg Met His Met Ala
        515                 520                 525

Val Ala Asp Lys Trp Ile Asp Leu Leu Lys Gln Ser Asp Glu Thr Trp
530                 535                 540

Lys Met Gly Asp Ile Val His Thr Leu Thr Asn Arg Arg Trp Leu Glu
545                 550                 555                 560

Lys Cys Val Thr Tyr Ala Glu Ser His Asp Gln Ala Leu Val Gly Asp
                565                 570                 575

Lys Thr Ile Ala Phe Trp Leu Met Asp Lys Asp Met Tyr Asp Phe Met
            580                 585                 590

Ala Leu Asp Arg Pro Ser Thr Pro Thr Ile Asp Arg Gly Ile Ala Leu
        595                 600                 605

His Lys Met Ile Arg Leu Ile Thr Met Gly Leu Gly Gly Glu Gly Tyr
610                 615                 620

Leu Asn Phe Met Gly Asn Glu Phe Gly His Pro Glu Trp Ile Asp Phe
625                 630                 635                 640

Pro Arg Gly Pro Gln Arg Leu Pro Ser Gly Lys Phe Ile Pro Gly Asn
                645                 650                 655

Asn Asn Ser Tyr Asp Lys Cys Arg Arg Phe Asp Leu Gly Asp Ala
            660                 665                 670

Asp Tyr Leu Arg Tyr His Gly Met Gln Glu Phe Asp Gln Ala Met Gln
        675                 680                 685

His Leu Glu Gln Lys Tyr Glu Phe Met Thr Ser Asp His Gln Tyr Ile
690                 695                 700

Ser Arg Lys His Glu Glu Asp Lys Val Ile Val Phe Glu Lys Gly Asp
705                 710                 715                 720

Leu Val Phe Val Phe Asn Phe His Cys Asn Asn Ser Tyr Phe Asp Tyr
                725                 730                 735

Arg Ile Gly Cys Arg Lys Pro Gly Val Tyr Lys Val Val Leu Asp Ser
            740                 745                 750

Asp Ala Gly Leu Phe Gly Gly Phe Ser Arg Ile His His Ala Ala Glu
        755                 760                 765

His Phe Thr Ala Asp Cys Ser His Asp Asn Arg Pro Tyr Ser Phe Ser
770                 775                 780

Val Tyr Thr Pro Ser Arg Thr Cys Val Val Tyr Ala Pro Val Glu
785                 790                 795

<210> SEQ ID NO 60
<211> LENGTH: 2763
<212> TYPE: DNA
<213> ORGANISM: Zea mays

<400> SEQUENCE: 60
gctgtgcctc gtgtcgccct cttcctcgcc gactccgctt ccgccgccgc ggcgctctcg    60
ctcgcatgct gatcgggcgg caccgccggg gatcgcgggt ggcggcaatg tgcgcctgag   120

```
tgtgttgtct gtccagtgca aggctcgccg gtcaggggtg cggaaggtca agagcaaatt    180
cgccactgca gctactgtgc aagaagataa aactatggca actgccaaag gcgatgtcga    240
ccatctcccc atatacgacc tggaccccaa gctggagata ttcaaggacc atttcaggta    300
ccggatgaaa agattcctag agcagaaagg atcaattgaa gaaatgaggg aagtcttga    360 atcttttttct aaaggctatt tgaaatttgg gattaataca aatgaggatg aactgtata    420 tcgtgaatgg gcacctgctg cgcaggaggc agagcttatt ggtgacttca atgactggaa    480
tggtgcaaac cataagatgg agaaggataa atttggtgtt tggtcgatca aaattgacca    540
tgtcaaaggg aaacctgcca tccctcacaa ttccaaggtt aaatttcgct ttctacatgg    600
tggagtatgg gttgatcgta ttccagcatt gattcgttat gcgactgttg atgcctctaa    660
atttggagct ccctatgatg tgttcattg ggatcctcct gcttctgaaa ggtacacatt    720
taagcatcct cggccttcaa agcctgctgc tccacgtatc tatgaagccc atgtaggtat    780
gagtggtgaa aagccagcag taagcacata tagggaattt gcagacaatg tgttgccacg    840
catacgagca aataactaca acacagttca gttgatggca gttatggagc attcgtacta    900
tgcttctttc gggtaccatg tgacaaattt ctttgcggtt agcagcagat caggcacacc    960
agaggacctc aaatatcttg ttgataaggc acacagtttg ggtttgcgag ttctgatgga    1020
tgttgtccat agccatgcaa gtaataatgt cacagatggt ttaaatggct atgatgttgg    1080
acaaagcacc caagagtcct attttcatgc gggagataga ggttatcata aactttggga    1140
tagtcggctg ttcaactatg ctaactggga ggtattaagg tttcttcttt ctaacctgag    1200
atattggttg gatgaattca tgtttgatgg cttccgattt gatggagtta catcaatgct    1260
gtatcatcac catggtatca atgtgggggtt tactggaaac taccaggaat atttcagttt    1320
ggacacagct gtggatgcag ttgtttacat gatgcttgca aaccatttaa tgcacaaaact    1380 cttgccagaa gcaactgttg ttgctgaaga tgtttcaggc atgccggtcc tttgccggcc    1440
agttgatgaa ggtgggggttg ggtttgacta tcgcctggca atggctatcc ctgatagatg    1500
gattgactac ctgaagaata agatgactc tgagtggtcg atgggtgaaa tagcgcatac    1560
tttgactaac aggagatata ctgaaaaatg catcgcatat gctgagagcc atgatcagtc    1620
tattgttggc gacaaaacta ttgcatttct cctgatggac aaggaaatgt acactggcat    1680
gtcagacttg cagcctgctt cacctacaat tgatcgaggg attgcactcc aaaagatgat    1740
tcacttcatc acaatggccc ttggaggtga tggctacttg aattttatgg gaaatgagtt    1800
tggtcaccca gaatggattg actttccaag agaagggaac aactggagct atgataaatg    1860
cagacgacag tggagccttg tggacactga tcacttgcgg tacaagtaca tgaatgcgtt    1920
tgaccaagcg atgaatgcgc tcgatgagag atttttccttc ctttcgtcgt caaagcagat    1980
cgtcagcgac atgaacgatg aggaaaaggt tattgtctttt gaacgtggag atttagtttt    2040
tgttttcaat ttccatccca agaaaactta cgagggctac aaagtgggat gcgatttgcc    2100
tgggaaatac agagtagccc tggactctga tgctctggtc ttcggtggac atggaagagt    2160
tggccacgac gtggatcact tcacgtcgcc tgaagggggtg ccaggggtgc ccgaaacgaa    2220
cttcaacaac cggccgaact cgttcaaagt cctttctccg ccccgcacct gtgtggctta    2280
ttaccgtgta gacgaagcag gggctggacg acgtcttcac gcgaaagcag agacaggaaa    2340
gacgtctcca gcagagagca tcgacgtcaa agcttccaga gctagtagca aagaagacaa    2400
ggaggcaacg gctggtggca agaagggatg gaagtttgcg cggcagccat ccgatcaaga    2460
taccaaatga agccacgagt ccttggtgag gactggactg gctgccggcg ccctgttagt    2520
```

-continued

```
agtcctgctc tactggacta gccgccgctg gcgcccttgg aacggtcctt tcctgtagct    2580
tgcaggcgac tggtgtctca tcaccgagca ggcaggcact gcttgtatag cttttctaga    2640
ataataatca gggatggatg gatggtgtgt attggctatc tggctagacg tgcatgtgcc    2700
cagtttgtat gtacaggagc agttcccgtc cagaataaaa aaaaacttgt tgggggtttt    2760
ttc                                                                  2763
```

<210> SEQ ID NO 61
<211> LENGTH: 759
<212> TYPE: PRT
<213> ORGANISM: Zea mays

<400> SEQUENCE: 61

```
Ala Thr Val Gln Glu Asp Lys Thr Met Ala Thr Ala Lys Gly Asp Val
 1               5                  10                  15

Asp His Leu Pro Ile Tyr Asp Leu Asp Pro Lys Leu Glu Ile Phe Lys
            20                  25                  30

Asp His Phe Arg Tyr Arg Met Lys Arg Phe Leu Glu Gln Lys Gly Ser
        35                  40                  45

Ile Glu Glu Asn Glu Gly Ser Leu Glu Ser Phe Ser Lys Gly Tyr Leu
    50                  55                  60

Lys Phe Gly Ile Asn Thr Asn Glu Asp Gly Thr Val Tyr Arg Glu Trp
65                  70                  75                  80

Ala Pro Ala Ala Gln Glu Ala Glu Leu Ile Gly Asp Phe Asn Asp Trp
                85                  90                  95

Asn Gly Ala Asn His Lys Met Glu Lys Asp Lys Phe Gly Val Trp Ser
            100                 105                 110

Ile Lys Ile Asp His Val Lys Gly Lys Pro Ala Ile Pro His Asn Ser
        115                 120                 125

Lys Val Lys Phe Arg Phe Leu His Gly Gly Val Trp Val Asp Arg Ile
    130                 135                 140

Pro Ala Leu Ile Arg Tyr Ala Thr Val Asp Ala Ser Lys Phe Gly Ala
145                 150                 155                 160

Pro Tyr Asp Gly Val His Trp Asp Pro Pro Ala Ser Glu Arg Tyr Thr
                165                 170                 175

Phe Lys His Pro Arg Pro Ser Lys Pro Ala Ala Pro Arg Ile Tyr Glu
            180                 185                 190

Ala His Val Gly Met Ser Gly Glu Lys Pro Ala Val Ser Thr Tyr Arg
        195                 200                 205

Glu Phe Ala Asp Asn Val Leu Pro Arg Ile Arg Ala Asn Asn Tyr Asn
    210                 215                 220

Thr Val Gln Leu Met Ala Val Met Glu His Ser Tyr Tyr Ala Ser Phe
225                 230                 235                 240

Gly Tyr His Val Thr Asn Phe Phe Ala Val Ser Ser Arg Ser Gly Thr
                245                 250                 255

Pro Glu Asp Leu Lys Tyr Leu Val Asp Lys Ala His Ser Leu Gly Leu
            260                 265                 270

Arg Val Leu Met Asp Val Val His Ser His Ala Ser Asn Asn Val Thr
        275                 280                 285

Asp Gly Leu Asn Gly Tyr Asp Val Gly Gln Ser Thr Gln Glu Ser Tyr
    290                 295                 300

Phe His Ala Gly Asp Arg Gly Tyr His Lys Leu Trp Asp Ser Arg Leu
305                 310                 315                 320
```

-continued

```
Phe Asn Tyr Ala Asn Trp Glu Val Leu Arg Phe Leu Ser Asn Leu
                325                 330                 335

Arg Tyr Trp Leu Asp Glu Phe Met Phe Asp Gly Phe Arg Phe Asp Gly
            340                 345                 350

Val Thr Ser Met Leu Tyr His His Gly Ile Asn Val Gly Phe Thr
            355                 360                 365

Gly Asn Tyr Gln Glu Tyr Phe Ser Leu Asp Thr Ala Val Asp Ala Val
    370                 375                 380

Val Tyr Met Met Leu Ala Asn His Leu Met His Lys Leu Leu Pro Glu
385                 390                 395                 400

Ala Thr Val Val Ala Glu Asp Val Ser Gly Met Pro Val Leu Cys Arg
                405                 410                 415

Pro Val Asp Glu Gly Gly Val Gly Phe Asp Tyr Arg Leu Ala Met Ala
            420                 425                 430

Ile Pro Asp Arg Trp Ile Asp Tyr Leu Lys Asn Lys Asp Asp Ser Glu
            435                 440                 445

Trp Ser Met Gly Glu Ile Ala His Thr Leu Thr Asn Arg Arg Tyr Thr
    450                 455                 460

Glu Lys Cys Ile Ala Tyr Ala Glu Ser His Asp Gln Ser Ile Val Gly
465                 470                 475                 480

Asp Lys Thr Ile Ala Phe Leu Leu Met Asp Lys Glu Met Tyr Thr Gly
                485                 490                 495

Met Ser Asp Leu Gln Pro Ala Ser Pro Thr Ile Asp Arg Gly Ile Ala
            500                 505                 510

Leu Gln Lys Met Ile His Phe Ile Thr Met Ala Leu Gly Gly Asp Gly
            515                 520                 525

Tyr Leu Asn Phe Met Gly Asn Glu Phe Gly His Pro Glu Trp Ile Asp
    530                 535                 540

Phe Pro Arg Glu Gly Asn Asn Trp Ser Tyr Asp Lys Cys Arg Arg Gln
545                 550                 555                 560

Trp Ser Leu Val Asp Thr Asp His Leu Arg Tyr Lys Tyr Met Asn Ala
                565                 570                 575

Phe Asp Gln Ala Met Asn Ala Leu Asp Glu Arg Phe Ser Phe Leu Ser
            580                 585                 590

Ser Ser Lys Gln Ile Val Ser Asp Met Asn Asp Glu Glu Lys Val Ile
            595                 600                 605

Val Phe Glu Arg Gly Asp Leu Val Phe Val Phe Asn Phe His Pro Lys
    610                 615                 620

Lys Thr Tyr Glu Gly Tyr Lys Val Gly Cys Asp Leu Pro Gly Lys Tyr
625                 630                 635                 640

Arg Val Ala Leu Asp Ser Asp Ala Leu Val Phe Gly Gly His Gly Arg
                645                 650                 655

Val Gly His Asp Val Asp His Phe Thr Ser Pro Glu Gly Val Pro Gly
            660                 665                 670

Val Pro Glu Thr Asn Phe Asn Asn Arg Pro Asn Ser Phe Lys Val Leu
            675                 680                 685

Ser Pro Pro Arg Thr Cys Val Ala Tyr Tyr Arg Val Asp Glu Ala Gly
    690                 695                 700

Ala Gly Arg Arg Leu His Ala Lys Ala Glu Thr Gly Lys Thr Ser Pro
705                 710                 715                 720

Ala Glu Ser Ile Asp Val Lys Ala Ser Arg Ala Ser Ser Lys Glu Asp
                725                 730                 735

Lys Glu Ala Thr Ala Gly Gly Lys Lys Gly Trp Lys Phe Ala Arg Gln
```

```
                    740                 745                 750
Pro Ser Asp Gln Asp Thr Lys
        755

<210> SEQ ID NO 62
<211> LENGTH: 153
<212> TYPE: DNA
<213> ORGANISM: Zea mays
<220> FEATURE:
<221> NAME/KEY: CDS
<222> LOCATION: (1)..(153)

<400> SEQUENCE: 62 atg gcg acg ccc tcg gcc gtg ggc gcc gcg tgc ctc ctc ctc gcg cgg      48
Met Ala Thr Pro Ser Ala Val Gly Ala Ala Cys Leu Leu Leu Ala Arg
 1               5                  10                  15 gcc gcc tgg ccg gcc gcc gtc ggc gac cgg gcg cgc ccg cgg cgg ctc      96
Ala Ala Trp Pro Ala Ala Val Gly Asp Arg Ala Arg Pro Arg Arg Leu
             20                  25                  30 cag cgc gtg ctg cgc cgc cgg tgc gtc gcg gag ctg agc agg gag ggg     144
Gln Arg Val Leu Arg Arg Arg Cys Val Ala Glu Leu Ser Arg Glu Gly
         35                  40                  45 ccc cat atg                                                         153
Pro His Met
     50

<210> SEQ ID NO 63
<211> LENGTH: 51
<212> TYPE: PRT
<213> ORGANISM: Zea mays

<400> SEQUENCE: 63

Met Ala Thr Pro Ser Ala Val Gly Ala Ala Cys Leu Leu Leu Ala Arg
 1               5                  10                  15

Ala Ala Trp Pro Ala Ala Val Gly Asp Arg Ala Arg Pro Arg Arg Leu
             20                  25                  30

Gln Arg Val Leu Arg Arg Arg Cys Val Ala Glu Leu Ser Arg Glu Gly
         35                  40                  45

Pro His Met
     50

<210> SEQ ID NO 64
<211> LENGTH: 10
<212> TYPE: PRT
<213> ORGANISM: Zea mays

<400> SEQUENCE: 64

Cys Val Ala Glu Leu Ser Arg Glu Gly Pro
 1               5                  10

<210> SEQ ID NO 65
<211> LENGTH: 9
<212> TYPE: PRT
<213> ORGANISM: Zea mays
<220> FEATURE:
<221> NAME/KEY: MOD_RES
<222> LOCATION: (7)
<223> OTHER INFORMATION: Arg or Asp

<400> SEQUENCE: 65

Cys Val Ala Glu Leu Ser Xaa Leu Gly
 1               5
```

```
<210> SEQ ID NO 66
<211> LENGTH: 8
<212> TYPE: PRT
<213> ORGANISM: Zea mays

<400> SEQUENCE: 66

Ser Ile Val Phe Val Thr Gly Glu
 1               5

<210> SEQ ID NO 67
<211> LENGTH: 8
<212> TYPE: PRT
<213> ORGANISM: Zea mays

<400> SEQUENCE: 67

Ala Ser Ala Gly Met Asn Val Val
 1               5

<210> SEQ ID NO 68
<211> LENGTH: 8
<212> TYPE: PRT
<213> ORGANISM: Zea mays

<400> SEQUENCE: 68

Ala Glu Ala Glu Ala Gly Gly Lys
 1               5

<210> SEQ ID NO 69
<211> LENGTH: 8
<212> TYPE: PRT
<213> ORGANISM: Zea mays

<400> SEQUENCE: 69

Ala Ser Ala Gly Met Asn Val Val
 1               5

<210> SEQ ID NO 70
<211> LENGTH: 9
<212> TYPE: PRT
<213> ORGANISM: Zea mays

<400> SEQUENCE: 70

Gly Ser Val Gly Ala Ala Leu Arg Ser
 1               5

<210> SEQ ID NO 71
<211> LENGTH: 9
<212> TYPE: PRT
<213> ORGANISM: Zea mays

<400> SEQUENCE: 71

Met Asn Val Val Val Ala Ser Glu
 1               5

<210> SEQ ID NO 72
<211> LENGTH: 8
<212> TYPE: PRT
<213> ORGANISM: Zea mays

<400> SEQUENCE: 72

Ala Ser Ala Gly Met Asn Val Val
 1               5

<210> SEQ ID NO 73
<211> LENGTH: 18
```

```
<212> TYPE: PRT
<213> ORGANISM: Escherichia coli

<400> SEQUENCE: 73

Phe Ser Gly Asn Ala Tyr Met Asn Ala Pro Phe Thr Tyr Ser Ser Pro
 1               5                  10                  15
Thr Leu

<210> SEQ ID NO 74
<211> LENGTH: 31
<212> TYPE: PRT
<213> ORGANISM: Escherichia coli

<400> SEQUENCE: 74

His Asn Ser Pro Leu Ala Asn Pro Leu Pro Ser Ala Arg Ile Thr Thr
 1               5                  10                  15
Val Arg Ala Ser Thr Ser His Phe Ser Pro Leu Met Pro Ser Gly
            20                  25                  30

<210> SEQ ID NO 75
<211> LENGTH: 26
<212> TYPE: PRT
<213> ORGANISM: Escherichia coli

<400> SEQUENCE: 75

Asn Cys Val Ser Leu Thr Pro Met Ala Arg Asn Ile Ala Met Thr Cys
 1               5                  10                  15
Gln Gly Thr Val Ala Thr Phe Gly Thr Val
            20                  25

<210> SEQ ID NO 76
<211> LENGTH: 10
<212> TYPE: PRT
<213> ORGANISM: Escherichia coli

<400> SEQUENCE: 76

Cys Arg Phe Tyr Met Tyr Val Gln Arg Cys
 1               5                  10

<210> SEQ ID NO 77
<211> LENGTH: 10
<212> TYPE: PRT
<213> ORGANISM: Escherichia coli

<400> SEQUENCE: 77

Cys Arg Phe Tyr Met Tyr Val Gln Arg Cys
 1               5                  10

<210> SEQ ID NO 78
<211> LENGTH: 10
<212> TYPE: PRT
<213> ORGANISM: Escherichia coli

<400> SEQUENCE: 78

Cys Arg Phe Tyr Met Tyr Val Gln Arg Cys
 1               5                  10

<210> SEQ ID NO 79
<211> LENGTH: 32
<212> TYPE: PRT
<213> ORGANISM: Zea mays

<400> SEQUENCE: 79
```

```
Arg Val Arg Pro Ala Gly Pro Leu Ile Ser Arg Val Val Gln Arg Cys
 1               5                  10                  15

Trp Asp Ile Phe Leu Tyr Met Leu Phe Arg Leu Cys Asp Met Asp Lys
            20                  25                  30
```

<210> SEQ ID NO 80
<211> LENGTH: 66
<212> TYPE: PRT
<213> ORGANISM: Zea mays

<400> SEQUENCE: 80

```
Leu Ala Thr Arg Arg Ser Cys Arg Arg Thr Trp Thr Leu Phe Arg
 1               5                  10                  15

Arg Leu Phe Ser Leu Ala Ala Leu Met Arg Ala Ser His Leu Arg Arg
            20                  25                  30

Ala Asp Gly Arg Arg Trp Leu Ala Tyr Arg Leu Arg Arg Leu Arg Ala
        35                  40                  45

Leu Gly Ile Trp Ala Gly Thr Met Met Pro Leu Gly Thr Gly Arg Gly
    50                  55                  60

Val Val
65
```

<210> SEQ ID NO 81
<211> LENGTH: 38
<212> TYPE: PRT
<213> ORGANISM: Zea mays

<400> SEQUENCE: 81

```
Tyr Glu Thr Asp Gly Asp Gly Asp Glu Ala His Gly Ile Phe Pro Leu
 1               5                  10                  15

Ile Asn Gly Glu Leu Tyr Ala Thr Leu Ile Ser Pro Leu Leu Leu Val
            20                  25                  30

Phe Ile Leu Met Ala Ala
        35
```

<210> SEQ ID NO 82
<211> LENGTH: 14
<212> TYPE: PRT
<213> ORGANISM: Zea mays

<400> SEQUENCE: 82

```
Arg Gly Thr Arg Cys Cys Ala Ala Cys Val Gly Leu Ser Met
 1               5                  10
```

<210> SEQ ID NO 83
<211> LENGTH: 16
<212> TYPE: PRT
<213> ORGANISM: Zea mays

<400> SEQUENCE: 83

```
Gly Lys Thr Phe Phe Gln Asn Arg Gln Met His Ala Cys Met Leu Gln
 1               5                  10                  15
```

<210> SEQ ID NO 84
<211> LENGTH: 22
<212> TYPE: PRT
<213> ORGANISM: Zea mays

<400> SEQUENCE: 84

```
Gly Ser Asp Thr Leu Ile Asp Ala Gly Lys Pro Met His Leu Ala Ala
 1               5                  10                  15
```

```
Leu Ser Ser Leu Phe Ile
            20

<210> SEQ ID NO 85
<211> LENGTH: 6
<212> TYPE: PRT
<213> ORGANISM: Zea mays

<400> SEQUENCE: 85

Asp Leu Gln Gly Val Asn
 1               5

<210> SEQ ID NO 86
<211> LENGTH: 13
<212> TYPE: PRT
<213> ORGANISM: Zea mays

<400> SEQUENCE: 86

Ser Phe Arg Phe Ser Leu Lys Lys Lys Lys Lys Lys Leu
 1               5                  10
```

What is claimed is:

1. An isolated nucleic acid encoding a GlgC3 mutant adenosine diphosphate glucose pyrophophorylase protein having a sequence comprising SEQ ID NO:45.

2. A plasmid adapted for expression in a plant, said plasmid comprising the isolated nucleic acid of claim 1.

3. A plant comprising the plasmid of claim 2.

4. The plant of claim 3, selected from the group consisting of a monocot and a dicot.

5. The monocot of claim 4, selected from the group consisting of corn, wheat, barley, oats, sorghum, and milo.

6. The monocot of claim 5, which is corn.

7. The dicot of claim 4, selected from the group consisting of potatoes, sweet potato, taro, yam, lotus, cassava, peanuts, peas, soybean, bean, and chickpeas.

8. The dicot of claim 7, which is soybean.

* * * * *